(12) United States Patent
Stubenrauch et al.

(10) Patent No.: US 11,679,127 B2
(45) Date of Patent: Jun. 20, 2023

(54) ANTIGEN BINDING RECEPTORS SPECIFIC FOR MUTATED FC DOMAINS

(71) Applicant: Hoffmann-La Roche Inc., Little Falls, NJ (US)

(72) Inventors: Kay-Gunnar Stubenrauch, Penzberg (DE); Ekkehard Moessner, Schlieren (CH); Christian Klein, Schlieren (CH); Diana Darowski, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 691 days.

(21) Appl. No.: 16/576,546

(22) Filed: Sep. 19, 2019

(65) Prior Publication Data
US 2020/0093860 A1    Mar. 26, 2020

Related U.S. Application Data

(63) Continuation of application No. PCT/EP2018/057566, filed on Mar. 26, 2018.

(30) Foreign Application Priority Data

Mar. 27, 2017 (EP) .................................. 17163090

(51) Int. Cl.
| | | |
|---|---|---|
| *A61K 35/17* | (2015.01) | |
| *C07K 14/705* | (2006.01) | |
| *C07K 14/725* | (2006.01) | |
| *C07K 14/71* | (2006.01) | |
| *C07K 16/28* | (2006.01) | |
| *C07K 16/30* | (2006.01) | |
| *C07K 16/40* | (2006.01) | |
| *A61K 38/00* | (2006.01) | |

(52) U.S. Cl.
CPC .......... *A61K 35/17* (2013.01); *C07K 14/7051* (2013.01); *C07K 14/70517* (2013.01); *C07K 14/70521* (2013.01); *C07K 14/70578* (2013.01); *C07K 14/71* (2013.01); *C07K 16/283* (2013.01); *C07K 16/2887* (2013.01); *C07K 16/3007* (2013.01); *C07K 16/40* (2013.01); *A61K 38/00* (2013.01); *C07K 2317/32* (2013.01); *C07K 2317/565* (2013.01); *C07K 2317/732* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | |
|---|---|---|
| 5,500,362 A | 3/1996 | Robinson et al. |
| 5,571,894 A | 11/1996 | Wels et al. |
| 5,580,859 A | 12/1996 | Felgner et al. |
| 5,587,458 A | 12/1996 | King et al. |
| 5,589,466 A | 12/1996 | Felgner et al. |
| 5,750,373 A | 5/1998 | Garrard et al. |
| 5,821,337 A | 10/1998 | Carter et al. |
| 6,248,516 B1 | 6/2001 | Winter et al. |
| 6,737,056 B1 | 5/2004 | Presta |
| 7,332,581 B2 | 2/2008 | Presta |
| 7,785,903 B2 | 8/2010 | Bond et al. |
| 7,985,840 B2 | 7/2011 | Fuh et al. |
| 8,679,490 B2 | 3/2014 | Dennis et al. |
| 2005/0079574 A1 | 4/2005 | Bond |
| 2007/0117126 A1 | 5/2007 | Sidhu et al. |
| 2007/0237764 A1 | 10/2007 | Birtalan et al. |
| 2007/0292936 A1 | 12/2007 | Barthelemy et al. |
| 2009/0002360 A1 | 1/2009 | Chen et al. |

(Continued)

FOREIGN PATENT DOCUMENTS

| | | |
|---|---|---|
| CN | 106163547 A | 11/2016 |
| EP | 0404097 B1 | 9/1996 |

(Continued)

OTHER PUBLICATIONS

Cartellieri et al. (Journal of Biomedicine and Biotechnology, vol. 2010, Article ID 956304, 13 pages).*
Chicaybam et al. (International Reviews of Immunology, 2011, 30:294-311).*
Chu et al., "Genetic Modification of T Cells Redirected toward CS1 Enhances Eradication of Myeloma Cells," Clin Cancer Res. 20(15):3989-4000 (2014) (13 pages).
Gorchakov et al., "Chimeric antigen receptors for adoptive T-cell therapy," Russian Journal of Biotherapy. 15(1):25-26 (2016) (1 page) (English Translation).

(Continued)

*Primary Examiner* — Sharon X Wen
(74) *Attorney, Agent, or Firm* — Clark & Elbing LLP; Thomas J. Takara

(57) ABSTRACT

The present invention generally relates to antigen binding receptors capable of specific binding to mutated Fc domains with reduced Fc receptor binding and T cells expressing these antigen binding receptors. More precisely, the present invention relates to T cells, transfected/transduced with an antigen binding receptor which is recruited by specifically binding to/interacting with the mutated Fc domain of therapeutic antibodies. Furthermore, the invention relates to a kit comprising the T cells of the invention and/or nucleic acid molecules, vectors expressing antigen binding receptors of the present invention and (a) tumor targeting antibody/ antibodies comprising a mutated Fc domain. The invention also provides the production and use of T cells in a method for the treatment of particular diseases in conjunction with tumor-specific antibodies as well as pharmaceutical compositions/medicaments comprising T cells and/or therapeutic antibodies, wherein T cells are to be administered in combination with therapeutic-tumor targeting antibody/antibodies comprising a mutated Fc domain with reduced Fc receptor binding.

31 Claims, 29 Drawing Sheets

Specification includes a Sequence Listing.

(56) References Cited

U.S. PATENT DOCUMENTS

| | | | |
|---|---|---|---|
| 2011/0280894 A1 | 11/2011 | Krackhardt et al. | |
| 2015/0139943 A1* | 5/2015 | Campana | C07K 16/32 424/174.1 |
| 2016/0068613 A1* | 3/2016 | Regula | C07K 16/2863 424/134.1 |

FOREIGN PATENT DOCUMENTS

| | | |
|---|---|---|
| WO | WO-93/01161 A1 | 1/1993 |
| WO | WO-93/16185 A2 | 8/1993 |
| WO | WO-94/20627 A1 | 9/1994 |
| WO | WO-94/29469 A2 | 12/1994 |
| WO | WO-97/00957 A1 | 1/1997 |
| WO | WO-2004/056312 A2 | 7/2004 |
| WO | WO-2005/113595 A3 | 12/2005 |
| WO | WO-2006/082515 A2 | 8/2006 |
| WO | WO-2012/130831 A1 | 10/2012 |
| WO | WO-2014/177460 A1 | 11/2014 |
| WO | WO-2015/142675 A2 | 9/2015 |
| WO | WO-2015/179833 A1 | 11/2015 |
| WO | WO-2016/040441 A1 | 3/2016 |
| WO | WO-2016/090369 A1 | 6/2016 |
| WO | WO-2017/072210 A1 | 5/2017 |
| WO | WO-2018/177967 A1 | 10/2018 |

OTHER PUBLICATIONS

Klein et al., "The use of CrossMAb technology for the generation of bi- and multispecific antibodies," MAbs. 8(6):1010-20 (2016).
Morozova et al., "Prospectives of T-cells genetic programming in adoptive immunotherapy of malignancies," Sechenov Medical Journal. 3(25):23-28 (2016) (English Translation).
Yarilin, Chapter 3: Molecular and cellular basis of adaptive immunity. *Immunology Basics: Manual.* Medicina, (1999) (12 pages).
Anderson, "Human Gene Therapy," Science. 256(5058):808-13 (1992).
Bazan et al., "Phage display—a powerful technique for immunotherapy: 1. Introduction and potential of therapeutic applications," Hum Vaccin Immunother. 8(12):1817-28 (2012).
Brunger et al., "Scaffold-mediated lentiviral transduction for functional tissue engineering of cartilage," Proc Natl Acad Sci U S A. 111(9):E798-E806 (2014).
Brüggemann et al., "Comparison of the effector functions of human immunoglobulins using a matched set of chimeric antibodies," J Exp Med. 166(5):1351-61 (1987).
Campeau et al., "A Versatile Viral System for Expression and Depletion of Proteins in Mammalian Cells," Plos One. 4(8):e6529 (2009).
Cao et al., "Design of Switchable Chimeric Antigen Receptor T Cells Targeting Breast Cancer," Angew Chem Int Ed Engl. 55(26):7520-24 (2016).
Chang et al., "E1B-55 kD-Deleted Adenovirus Driven by Murine Oct-3/4 Promoter for Bladder Cancer Therapy," Mole Ther. 9(S1):S367 (2004).
Chen et al., "Retroviral Transduction of Protein Kinase C-gamma into Tumor Specific T Cells Allows Antigen-Independent Long-Term Growth in IL-2 with Retention of Functional Specificity In Vitro and Ability to Mediate Tumor Therapy In Vivo [1]," J Immunol. 153(8):3630-38 (1994).
Cherf et al., "Applications of yeast surface display for protein engineering," Methods Mol Bio. 1319:155-175 (2015).
Chothia et al., "Canonical structures for the hypervariable regions of immunoglobulins," J Mol Biol. 196(4):901-17(1987).
Chothia et al., "Conformations of immunoglobulin hypervariable regions," Nature. 342(6252):877-83 (1989).
Clackson et al., "Making antibody fragments using phage display libraries," Nature. 352(6336):624-8 (1991).
Clay et al., "Efficient transfer of a tumor antigen-reactive TCR to human peripheral blood lymphocytes confers anti-tumor reactivity," J Immunol. 163(1):507-13 (1999).
Clynes et al., "Fc receptors are required in passive and active immunity to melanoma," Proc Natl Acad Sci USA. 95(2):652-6 (1998).
Cochlovius et al., "Stable expression of a retrovirally transferred adhesion molecule in a human melanoma-specific cytotoxic T lymphocyte clone," Cancer Immunol Immunother. 46(1):61-6 (1998).
Cragg et al., "Antibody specificity controls in vivo effector mechanisms of anti-CD20 reagents," Blood. 103(7):2738-43 (2004).
Cragg et al., "Complement-mediated lysis by anti-CD20 mAb correlates with segregation into lipid rafts," Blood. 101(3):1045-52 (2003).
de Witte et al., "Requirements for Effective Antitumor Responses of TCR Transduced T Cells," J Immunol. 181(7):5128-5136 (2008).
DeSiderio, S., et al., "Rearrangement of Exogenous Immunoglobulin Vh and DJh Gene Segments after Retroviral Transduction into Immature Lymphoid Cell Lines" J Exp Med. 167(2):372-388 (1988).
Dudley et al., "Adoptive Cell Therapy for Patients With Metastatic Melanoma: Evaluation of Intensive Myeloablative Chemoradiation Preparative Regimens," J Clin Oncol. 26(32):5233-5239 (2008).
Dudley et al., "Generation of Tumor-Infiltrating Lymphocyte Cultures for Use in Adoptive Transfer Therapy for Melanoma Patients," J Immunother. 26(4):332-342 (2003).
Duewell et al., "RIG-I-like helicases induce immunogenic cell death of pancreatic cancer cells and sensitize tumors toward killing by CD8+ T cells," Cell Death Differ. 21(12):1825-37 (2014).
Duewell et al., Erratum: "RIG-I-like helicases induce immunogenic cell death of pancreatic cancer cells and sensitize tumors toward killing by CD8+ T cells," Cell Death Differ. 21(12):161 (2014).
Ekkens et al., "Th1 and Th2 Cells Help CD8 T-Cell Responses" Infect Immun. 75(5):2291-6 (2007).
Engels et al., "Retroviral vectors for high-level transgene expression in T lymphocytes," Hum Gene Ther. 14(12):1155-68 (2003).
Fellouse et al., "Synthetic antibodies from a four-amino-acid code: A dominant role for tyrosine in antigen recognition," Proc Natl Acad Sci U S A. 101(34):12467-72 (2004).
Frenzel et al., "Phage display-derived human antibodies in clinical development and therapy," MABS. 8(7):1177-1194 (2016).
Gallardo et al., "Recombinant Retroviruses Pseudotyped With the Vesicular Stomatitis Virus G Glycoprotein Mediate Both Stable Gene Transfer and Pseudotransduction in Human Peripheral Blood Lymphocytes," Blood. 90(3):952-957 (1997).
Gazzano-Santoro et al., "A non-radioactive complement-dependent cytotoxicity assay for anti-CD20 monoclonal antibody," J Immunol Methods. 202(2):163-71 (1997).
Ge et al., "Homeostatic T cell proliferation in a T cell-dendritic cell coculture system," Proc Natl Acad Sci U S A. 99(5):2983-2988 (2002).
Gerdes et al., "Green flourescent protein: application in cell biology," Febs Lett. 389(1):44-47 (1996).
Giacomin et al., "Expression of a PAL1 promoter luciferase gene fusion in *Arabidopsis thaliana* in response to infection by phytopathogenic bacteria," Plant Sci. 116(1):59-72 (1996).
Gilham et al., "Primary Polyclonal Human T Lymphocytes Targeted to Carcino-Embryonic Antigens and Neural Cell Adhesion Molecule Tumor Antigens by CD3zeta-Based Chimeric Immune Receptors," J Immunother. 25(2):139-151 (2002).
Giordano et al., "Intracoronary gene transfer of fibroblast growth factor-5 increases blood flow and contractile function in an ischemic region of the heart," Nat Med. 2(5):534-539 (1996).
Grevys et al., "Fc Engineering of Human IgG1 for Altered Binding to the Neonatal Fc Receptor Affects Fc Effector Functions," J Immunol. 194(11):5497-5508 (2015).
Griffiths et al., "Human anti-self antibodies with high specificity from phage display libraries," EMBO J. 12(2):725-34 (1993).
Grupp et al., "Chimeric Antigen Receptor-Modified T Cells for Acute Lymphoid Leukemia," New England J Med. 368(16):1509-1518 (2013).
Hanes et al., "In vitro selection and evolution of functional proteins by using ribosome display," Proc Natl Acad Sci USA. 94(10):4937-42 (1997).
Hartman et al., "Two dominant-acting selectable markers for gene transfer studies in mammalian cells," Proc Natl Acad Sci U S A. 85(21):8047-51 (1988).

(56) References Cited

OTHER PUBLICATIONS

He et al., "Antibody-ribosome-mRNA (ARM) complexes as efficient selection particles for in vitro display and evolution of antibody combining sites," Nucleic Acids Res. 25(24):5132-5134 (1997).

Heeley et al., "Mutations Flanking the Polyglutamine Repeat in the Modulatory Domain of Rat Glucocorticoid Receptor Lead to an Increase in Affinity for Hormone," Endocr Res. 28(3):217-229 (2002).

Heemskerk et al., "Inhibition of T-Cell nad Promotion of Natural Killer Cell Development by the Dominant Negative Helix Loop Helix Factor Id3," J Exp Med. 186(9):1597-1602 (1997).

Hellström et al., "Antitumor effects of L6, an IgG2a antibody that reacts with most human carcinomas," Proc Natl Acad Sci USA. 83(18):7059-63 (1986).

Herrera-Estrella et al., "Chimeric genes as dominant selectable markers in plant cells," EMBO J. 2(6):987-995 (1983).

Holliger et al., "'Diabodies': Small bivalent and bispecific antibody fragments," Proc Natl Acad Sci USA. 90(14):6444-8 (1993).

Hoogenboom et al., "By-passing immunisation. Human antibodies from synthetic repertoires of germline VH gene segments rearranged in vitro," J Mol Biol. 227(2):381-388 (1992).

Hoogenboom et al., "Overview of antibody phage-display technology and its applications," Methods Mol Biol. 178:1-37 (2002).

Hotta et al., "Isolation of human iPS cells using EOS lentiviral vectors to select for pluripotency," Nat Methods. 6(5):370-378 (2009).

Hu et al., "Fibulin-3 Is Uniquely Upregulated in Malignant Gliomas and Promotes Tumor Cell Motility and Invasion," Mol Cancer Res. 7(11):1756-1770 (2009).

Hudson et al., "Engineered Antibodies," *Nat Med.* 9(1):129-134 (2003).

Isner et al., "Clinical evidence of angiogenesis after arterial gene transfer of phVEGF$_{165}$ in patient with ischaemic limb," Lancet. 348(9024):370-374 (1996).

Jefferson et al., "GUS fusions: beta-glucuronidase as a sensitive and versatile gene fusion marker in higher plants," Embo J. 6(13):3901-7 (1987).

Kang et al., "Simultaneous Profiling of 194 Distinct Receptor Transcripts in Human Cells," SCI Signal. 6(297):rs13 (2013).

Kantoff et al., "Correction of adenosine deaminase deficiency in cultured human T and B celss by retrovirus-mediated gene transfer," Proc Natl Acad Sci U S A. 83(17):6563-67 (1986).

Kasid et al., "Human gene transfer: Characterization of human tumor-infiltrating lymphocytes as vehicles for retroviral-mediated gene transfer in man," Proc Natl Acad Sci USA. 87(1):473-7 (1990).

Keiler et al., "C-terminal specific protein degradation: Activity and substrate specificity of the Tsp protease," Protein Sci. 4(8):1507-15 (1995).

Kim et al., "Redirection of Genetically Engineered CAR-T Cells Using Bifunctional Small Molecules," J Am Chem Soc. 137(8):2832-2835 (2015).

Kindt et al., "Antigens and Antibodies," Chapter 4, Kuby Immunology. 91 (2007).

Kochenderfer et al., "Chemotherapy-Refractory Diffuse Large B-Cell Lymphoma and Indolent B-Cell Malignancies Can Be Effectively Treated ith Autologous T Cells Expressin an Anti-CD19 Chimeric Antigen Receptor," J Clin Oncol. 33(6):540-9 (2015).

Krutzik et al., "Chapter 9: Phospho Flow Cytometry Methods for the Analysis of Kinase Signaling in Cell Lines and Primary Human Blood Samples," Methods Mol Biol. 699:179-202 (2011).

Laver et al., "Epitopes on Protein Antigens: Misconceptions and Realities," Cell. 61(4):553-6 (1990).

Lazebnik et al., "Determination and Functional Analysis of the Consensus Binding Site for TFII-I Family Member BEN, Implicated in William-Bueren Syndrome," J Biol Chem. 283(17):11078-82 (2008).

Lee et al., "Bivalent antibody phage display mimics natural immunoglobulin," J Immunol Methods. 284(1-2):119-32 (2004).

Lee et al., "High-affinity human antibodies from phage-displayed synthetic fab libraries with a single framework scaffold", *J Mol Biol.* 340(5):1073-1093 (2004).

Lemoine et al., "Efficient transduction and selection of human T-lymphocytes with bicistronic Thy1/HSV1-TK retroviral vector produced by a human packaging cell line," J Gene Med. 6(4):374-86 (2004).

Lerner, "Combinatorial antibody libraries: new advances, new immunological insights," Nat Rev Immunol. 16(8):498-508 (2016).

Liljeblad et al., "Analysis of agalacto-IgG in rheumatoid arthritis using surface plasmon resonance," Glycoconj J. 17(5):323-29 (2000).

Lois et al., "Germline transmission and tissue-specific expression of transgenes delivered by lentiviral vectors," Science. 295(5556):868-72 (2002).

Ma et al., "Versatile strategy for controlling the specificity and activity of engineered T cells," Proc Natl Acad Sci USA. 113(4):E450-E458 (2016).

Mack et al., "A small biospecific antibody construct expressed as a functional single-chain molecule with high tumor cell cytotoxicity," Proc Natl Acad Sci U S A. 92(15):7021-25 (1995).

Marks et al., "By-passing immunization, human antibodies from V-gene libraries displayed on phage," J Mol Biol. 222(3): 581-97 (1991).

Marks et al., "Selection of Human Antibodies from Phage Display Libraries," Methods Mol Biol. 248:161-176 (2004).

Marr et al., "Neprilysin Regulates Amyloid Beta Peptide Levels," J Mol Neurosci. 22(1-2):5-11 (2004).

Marsch et al., "The pIC plasmid and phage vectors with versatile cloning sites for recombinant selection by insertional inactivation," Gene. 32(3):481-85 (1984).

Maude et al., Chimeric Antigen Receptor T Cells for Sustained Remissions in Leukemia, N Engl J Med. 317(16):1507-17 (2014).

McCafferty et al., "Phage antibodies: filamentous phage displaying antibody variable domains," Nature. 348(6301):552-4 (1990).

Miyoshi et al., "Development of a self-inactivating lentivirus vector," J Virol. 72(10):8150-7 (1998).

Morgan et al., "High efficiency TCR gene transfer into primary human lymphocytes affords avid recognition of melanoma tumor antigen glycoprotein 100 and does not alter the recognition of autologous melanoma antigens," J Immunol. 171(6):3287-95 (2003).

Muhlhauser et al., "VEGF165 Expressed by a Replication-Deficient Recombinant Adenovirus Vector Induces Angiogenesis In Vivo," Circ Res. 77(6):1077-86 (1995).

Mullen et al., "Molecular Analysis of T Lymphocyte-Directed Gene Therapy for Adenosine Deaminase Deficiency: Long-Term Expression in Vivo of Genes Introduced with a Retroviral Vector," Hum Gene Ther. 7(9):1123-29 (1996).

Nabel et al., "In Vivo Gene Transfer: A Biological Tool," Ann NY Acad Sci. 811:289-292 (1997).

Neil et al., "Transduction and rearrangement of the myc gene by feline leukaemia virus in naturally occurring T-cell leukaemias," Nature. 308(5962):814-20 (1984).

Onodera et al., "Successful Peripheral T-Lymphocyte-Directed Gene Transfer for a Patient With Severe Combined Immune Deficiency Caused by Adenosine Deaminase," Blood. 91(1):30-6 (1998).

Pluckthun et al., "Chapter 11: Antibodies from *Escherichia coli*," The Pharmacology of Monoclonal Antibodies. 113:269-315 (1994).

Qin et al., "Systematic Comparison of Constitutive Promoters and the Doxycycline-Inducible Promoter," Plos One. 5(5):e10611 (2010).

Raissi et al., "Sema4D localizes to synapses and regulates GABAergic synapse development as a membrane-bound molecule in the mammalian hippocampus," Mol Cell Neurosci. 57:23-32 (2013).

Raum et al., "Anti-self antibodies selected from a human IgD heavy chain repertoire: a novel approach to generate therapeutic human antibodies against tumor-associated differentiation antigens," Cancer Immunol Immunother. 50(3):141-50 (2001).

Reiss et al., "A family of binary gene vectors with low intertransformant variation," Plant Physiol Life Sci Adv. 13:143-49 (1994).

Ritz-Laser et al., "Ectopic expression of the beta-cell specific trnscription factor Pdx1 inhibits glucagon gene transcription," Diabetologia. 46(6):810-21 (2003).

(56) References Cited

OTHER PUBLICATIONS

Rodgers et al., "Switch-mediated activation and retargeting of CAR-T cells for B-cell malignancies," Proc Natl Acad Sci U S A. 113(4):E459-E468 (2016).

Rosenberg et al., "Adoptive cell transfer as personalized immunotherapy for human cancer," Science. 348(6230):62-8 (2015).

Schaper et al., "Molecular Mechanisms of Coronary Collateral Vessel Growth," Circ Res. 79(5):911-19 (1996).

Schlothauer et al., "Novel Human IgG1 and IgG4 Fc-engineered Antibodies with Completely Abolished Immune Effector Functions," Protein Engineering, Design & Selection. 29(10):457-466 (2016).

Sela, "Antigenicity: Some Molecular Aspects," Science. 166(3911):1365-74 (1969).

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 276(9):6591-604 (2001).

Sidhu et al., "Phage-displayed antibody libraries of synthetic heavy chain complementarity determining regions," J Mol Biol. 338(2):299-310 (2004).

Solomon et al., "Frequent truncating mutations of STAG2 in bladder cancer," Nat Genet. 45(12):1428-30 (2013).

Srikantha et al., "The Sea Pansy Renilla reinformis Luciferase Serves as a Sensitive Bioluminescent Reporter for Differential Gene Expression in Candida albicans," J Bacteriol. 178(1):121-29 (1996).

Sun et al., "Construction of Retroviral Vectors Carrying Human CD3gamma cDNA and Reconstitution of CD3gamma Expression and T Cell Receptor Surface Expression and Function in a CD3gamma-Deficient Mutant T Cell Line," Hum Gene Ther. 8(9):1041-48 (1997).

Tamada et al., "Redirecting Gene-Modified T Cells toward Various Cancer Types Using Tagged Antibodies," Clin Cancer Res. 18(23):6436-45 (2012).

Tamura et al., "Blasticidin S Deaminase Gene (BSD): a New Selection Marker Gene for Transformation of *Arabidopsis thaliana* and Nicotiana tabacum," Biosci Biotechnol Biochem. 59(12):2336-38 (1995).

Taylor et al., "Reconstitution of T Cell Receptor Signaling in ZAP-70-deficient Cells by Retroviral Transduction of the ZAP-70 Gene," J Exp Med. 184(5):2031-36 (1996).

Thakur et al., "Real time monitoring of the cell viability during treatment with tumor-targeted toxins and saponins using impedance measurement," Biosens Bioelectron. 35(1):503-6 (2012).

Tiberghien et al., "Ganciclovir Treatment of Herpes Simplex Thymidine Kinase-Transduced Primary T Lymphocytes: An Approach for Specific In Vivo Donor T-Cell Depletion After Bone Marrow Transplantation?," Blood. 84(4):1333-41 (1994).

Verma et al., "Gene therapy—promises, problems and prospects," Nature 389(6648): 239-42 (1997).

Verma et al., "Gene transfer into human umbilical cord blood-derived CD34+ cells by particle-mediated gene transfer," Gene Ther. 5(5):692-9 (1998).

Verzeletti et al., "Herpes simplex virus thymidine kinase gene transfer for controlled graft-versus-host disease and graft-versus-leukemia: clinical follow-up and improved new vectors," Hum Gene Ther. 9(15):2243-51 (1998).

Vieillard et al., "Interferon β transduction of peripheral blood lymphocytes from HIV-infected donors increases Th1-type cytokine production and improves the proliferative response to recall antigens," Proc Natl Acad Sci U S A. 94(21):11595-11600 (1997).

Wang et al., "A time- and matrix-dependent TGFBR3-JUND-KRT5 regulatory circuit in single breast epithelial cells and basal-like premalignancies," Nat Cell Biol. 16(4):345-56 (2014).

Wang et al., "Second-generation adenovirus vectors," Nat Med. 2(6):714-16 (1996).

Weijtens et al., "A retroviral vector system 'STITCH' in combination with an optimized single chain antibody chimeric receptor gene structure allows efficient gene transduction and expression in human T lymphocytes," Gene Ther. 5(9):1195-1203 (1998).

Winter et al., "Making antibodies by phage display technology," Annu Rev Immunol. 12:433-55 (1994).

Wu et al., "Improvement of Gene Transduction Efficiency in T Lymphocytes Using Retroviral Vectors," Hum Gene Ther. 10(6):977-82 (1999).

Wu et al., "Isolation and characterization of the murine Nanog gene promoter," Cell Res. 15(5):317-24 (2005).

Xie et al., "Akt isoforms differentially protect against stroke-induced neuronal injury by regulating mTOR activities," J Cereb Blood F Metab. 33(12):1875-85 (2013).

Zhao et al., "High-efficiency transfection of primary human and mouse T lymphocytes using RNA electroporation," Mol Ther. 13(1):151-9 (2006).

Zhao et al., "Phage antibody display libraries: a powerful antibody discovery platform for immunotherapy," Crit Rev Biotechnol. 36(2):276-89 (2016).

Zhao et al., "Primary human lymphocytes transduced with NY-ESO-1 antigen-specific TCR genes recognize and kill diverse human tumor cell lines," J Immunol. 174(7):4415-23 (2005).

Zhao et al., "Chapter 5: Yeast Display of Engineered Antibody Domains," *Methods Mol Biol*. 899:73-84 (2012).

International Preliminary Report on Patentability for International Application No. PCT/EP2018/057566, dated Oct. 1, 2019 (10 pages).

International Search Report for International Application No. PCT/EP2018/057566, dated May 11, 2018 (7 pages).

\* cited by examiner

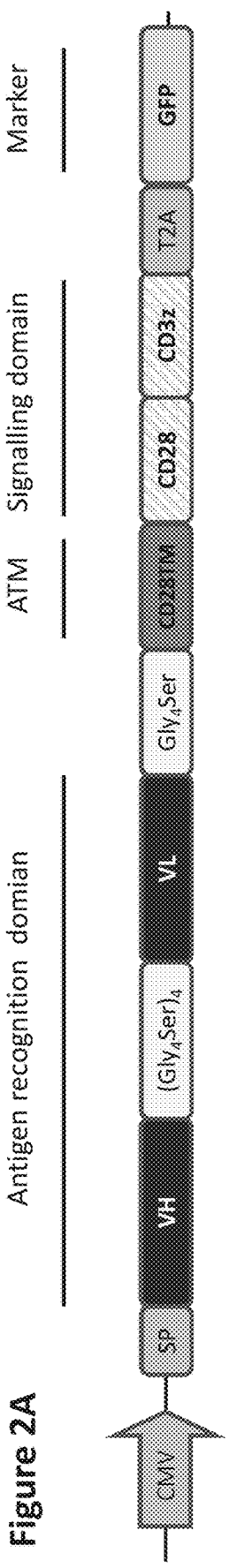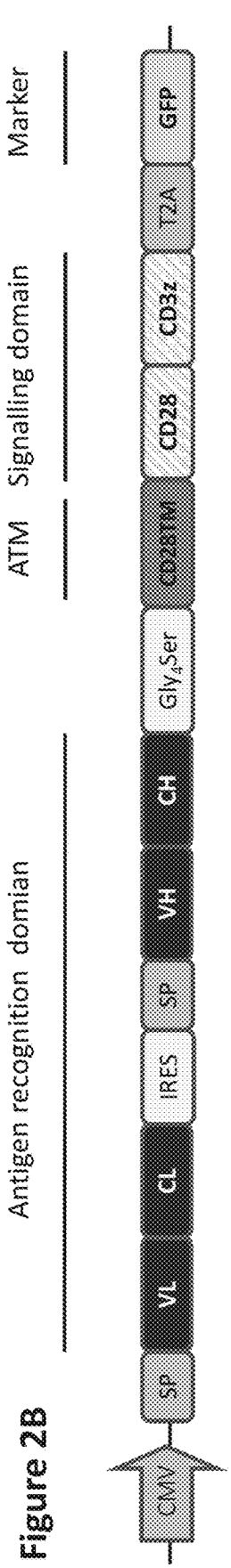

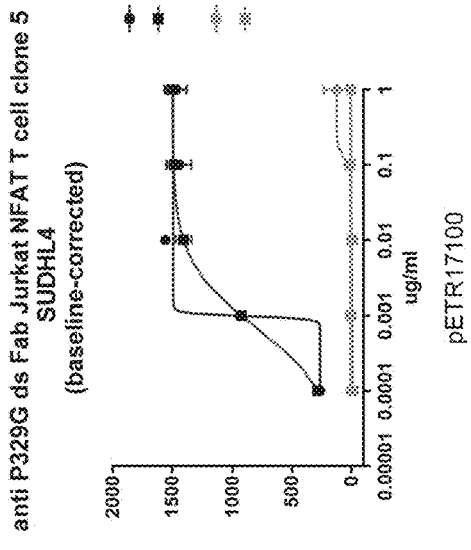
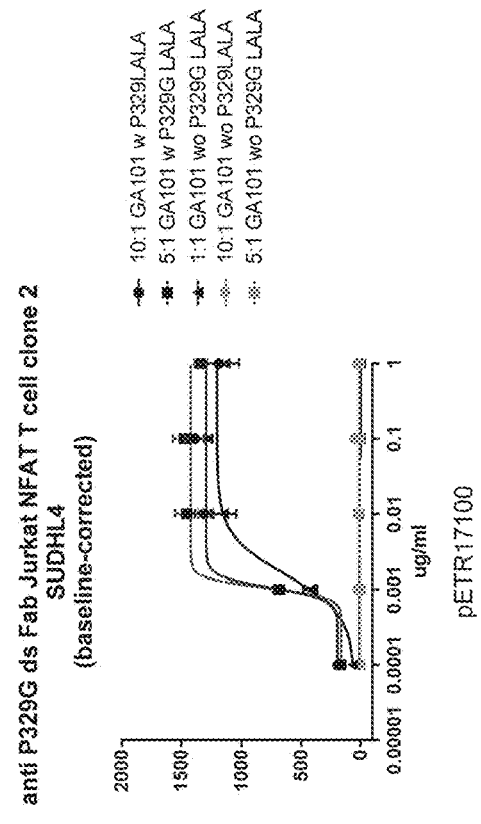
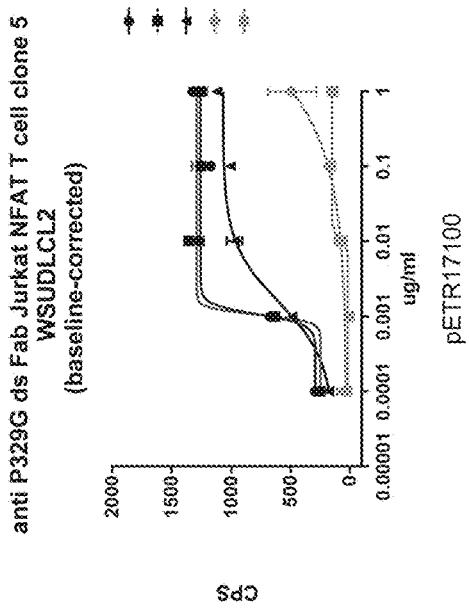
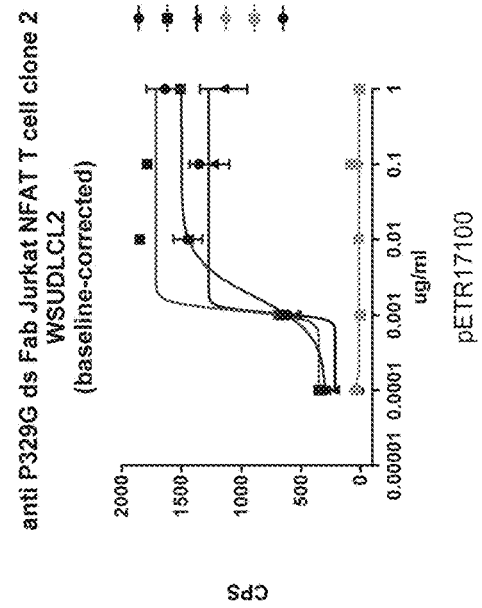

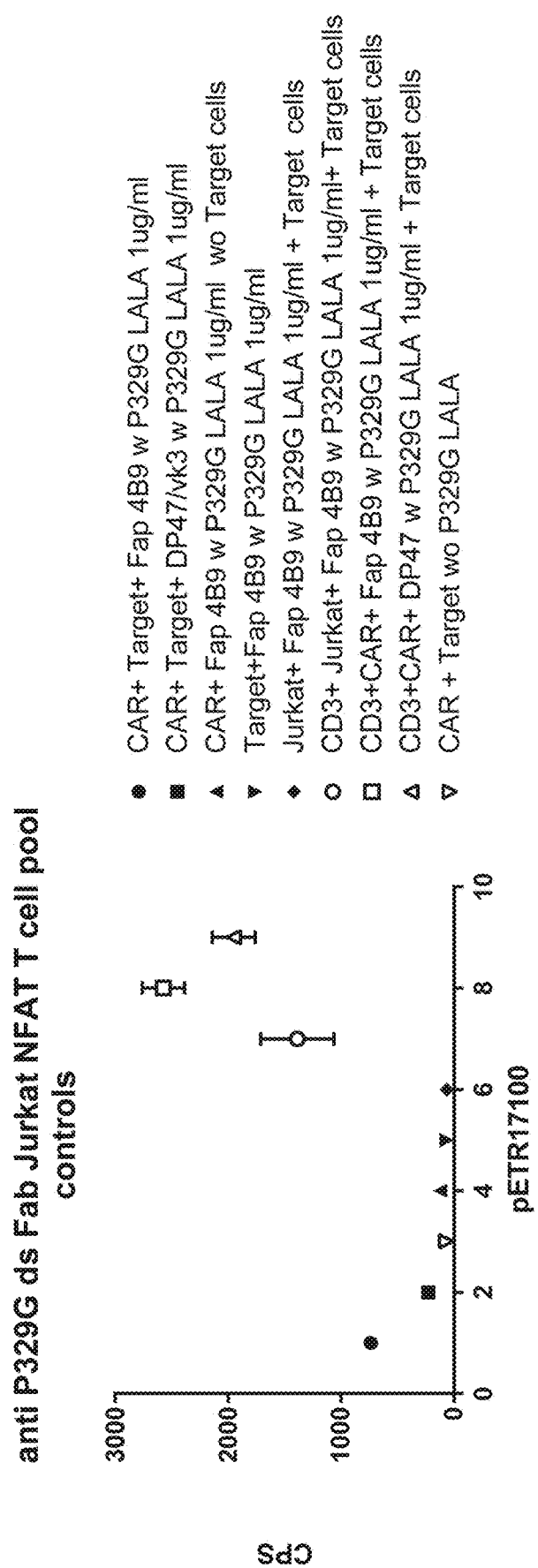

ANTIGEN BINDING RECEPTORS SPECIFIC FOR MUTATED FC DOMAINS

CROSS REFERENCE TO RELATED APPLICATIONS

This application is a continuation of International Application No. PCT/EP2018/057566, filed Mar. 26, 2018, the content of which is herein incorporated by reference in its entirety, which claims priority to EP Application No. 17163090.8 filed Mar. 27, 2017.

SEQUENCE LISTING

This application contains a Sequence Listing which has been submitted electronically in ASCII format and is hereby incorporated by reference in its entirety. Said ASCII copy, created on Sep. 17, 2019, is named "P34178-US_sequence_listing.txt" and is 206,541 bytes in size.

FIELD OF THE INVENTION

The present invention generally relates to antigen binding receptors capable of specific binding to mutated Fc domains with reduced Fc receptor binding and T cells expressing these antigen binding receptors. More precisely, the present invention relates to T cells, transfected/transduced with an antigen binding receptor which is recruited by specifically binding to/interacting with the mutated Fc domain of therapeutic antibodies. Furthermore, the invention relates to a kit comprising the T cells of the invention and/or nucleic acid molecules, vectors expressing antigen binding receptors of the present invention and (a) tumor targeting antibody/antibodies comprising a mutated Fc domain. The invention also provides the production and use of T cells in a method for the treatment of particular diseases in conjunction with tumor-specific antibodies as well as pharmaceutical compositions/medicaments comprising T cells and/or therapeutic antibodies, wherein T cells are to be administered in combination with therapeutic-tumor targeting antibody/antibodies comprising a mutated Fc domain with reduced Fc receptor binding.

BACKGROUND

Adoptive T cell therapy (ACT) is a powerful treatment approach using cancer-specific T cells (Rosenberg and Restifo, Science 348(6230) (2015), 62-68). ACT may use naturally occurring tumor-specific cells or T cells rendered specific by genetic engineering using T cell or chimeric antigen receptors (Rosenberg and Restifo, Science 348 (6230) (2015), 62-68). ACT can successfully treat and induce remission in patients suffering even from advanced and otherwise treatment refractory diseases such as acute lymphatic leukemia, non-hodgkins lymphoma or melanoma (Dudley et al., J Clin Oncol 26(32) (2008), 5233-5239; Grupp et al., N Engl J Med 368 (16) (2013), 1509-1518; Kochenderfer et al., J Clin Oncol. (2015) 33(6):540-549, doi: 10.1200/JCO.2014.56.2025. Epub 2014 Aug. 25).

However, despite impressive clinical efficacy, ACT is limited by treatment-related toxicities. The specificity, and resulting on-target and off-target effects, of engineered T cells used in ACT is mainly driven by the tumor targeting antigen binding moiety implemented in the chimeric antigen receptor (CAR). Non-exclusive expression of the tumor antigen or temporal difference in the expression level can result with serious side effects or even abortion of ACT due to non-tolerable toxicity of the treatment.

Additionally, the availability of tumor-specific T cells for efficient tumor cells lysis is dependent on the long-term survival and proliferation capacity of engineered T cells in vivo. On the other hand, in vivo survival and proliferation of T cells may result with unwanted long-term effects due to the persistence of an uncontrolled CAR-T response (Grupp et al. 2013 N Engl J Med 368(16):1509-18, Maude et al. 2014 2014 N Engl J Med 371(16):1507-17).

One approach for limiting serious treatment-related toxicities and to improve safety of ACT is to restrict the activation and proliferation of CAR-T cells by introducing adaptor molecules in the immunological synapse. Such adaptor molecules comprise small molecular bimodular switches as e.g. recently described folate-FITC switch (Kim et al. J Am Chem Soc 2015; 137:2832-2835). A further approach included artificially modified antibodies comprising a tag to guide and direct the specificity of CAR-T cells to target tumor cells (Ma et al. PNAS 2016; 113(4):E450-458, Cao et al. Angew Chem 2016; 128:1-6, Rogers et al. PNAS 2016; 113(4):E459-468, Tamada et al. Clin Cancer Res 2012; 18(23):6436-6445).

However, existing approaches have several limitations. Immunological synapses relying on molecular switches require introduction of additional elements which might elicit an immune response or result with non-specific off-target effects. Furthermore, the complexity of such multi-component systems may limit treatment efficacy and tolerability. On the other hand, the introduction of tag structure in existing therapeutic monoclonal antibodies may affect the efficacy and safety profile of these constructs.

Accordingly, the targeted tumor therapy, particularly the adoptive T cell therapy needs to be improved in order to suffice the needs of the cancer patients. Thus, there is still a need to provide improved means having the potential to improve safety and efficacy of ACT and overcome the above disadvantages.

SUMMARY OF THE INVENTION

The present invention generally relates to antigen binding receptors capable of specific binding to mutated Fc domains with reduced Fc receptor binding and T cells expressing these antigen binding receptors.

In one aspect the invention relates to an antigen binding receptor comprising an anchoring transmembrane domain and an extracellular domain comprising an antigen binding moiety, wherein the antigen binding moiety is capable of specific binding to a mutated fragment crystallizable (Fc) domain but not capable of specific binding to the non-mutated parent Fc domain, wherein the mutated Fc domain comprises at least one amino acid substitution compared to the non-mutated parent Fc domain.

In one embodiment, Fc receptor binding of the mutated Fc domain is reduced compared to Fc receptor binding of the non-mutated parent Fc domain, particularly wherein the Fc receptor is a Fcγ receptor or neonatal Fc receptor (FcRn). In one embodiment, Fc receptor binding is measured by Surface Plasmon Resonance (SPR) at 25° C.

In one embodiment, the antigen binding moiety is a scFv, a Fab, a crossFab, or a scFab. In a preferred embodiment, the antigen binding moiety is a scFv. In another preferred embodiment, the antigen binding moiety is a Fab or a crossFab.

In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof.

In one embodiment, the anchoring transmembrane domain is the CD28 transmembrane domain, in particular wherein the anchoring transmembrane domain comprises the amino acid sequence of SEQ ID NO:11.

In one embodiment, the antigen binding receptor further comprises at least one stimulatory signaling domain and/or at least one co-stimulatory signaling domain. In one embodiment, the at least one stimulatory signaling domain is individually selected from the group consisting of the intracellular domain of CD3z, of FCGR3A and of NKG2D, or fragments thereof. In one embodiment, the at least one stimulatory signaling domain is a fragment of the intracellular domain of CD3z, in particular wherein the at least one stimulatory signaling domain comprises the amino acid sequence of SEQ ID NO:13. In one embodiment, the at least one co-stimulatory signaling domain is individually selected from the group consisting of the intracellular domain of CD27, of CD28, of CD137, of OX40, of ICOS, of DAP10 and of DAP12, or fragments thereof. In one embodiment, the at least one co-stimulatory signaling domain is a fragment of the CD28 intracellular domain. In one embodiment, the antigen binding receptor comprises one stimulatory signaling domain comprising the intracellular domain of CD3z, or a fragment thereof, and wherein the antigen binding receptor comprises one co-stimulatory signaling domain comprising the intracellular domain of CD28, or a fragment thereof. In one embodiment, the stimulatory signaling domain comprises the amino acid sequence of SEQ ID NO:13 and the co-stimulatory signaling domain comprises the amino acid sequence of SEQ ID NO:12.

In one embodiment, the extracellular domain is connected to the anchoring transmembrane domain, optionally through a peptide linker. In one embodiment, the peptide linker comprises the amino acid sequence GGGGS (SEQ ID NO:17). In one embodiment, the anchoring transmembrane domain is connected to a co-signaling domain or to a signaling domain, optionally through a peptide linker. In one embodiment, the signaling and/or co-signaling domains are connected, optionally through at least one peptide linker.

In one embodiment, the antigen binding moiety is a scFv fragment, wherein the scFv fragment is connected at the C-terminus to the N-terminus of the anchoring transmembrane domain, optionally through a peptide linker.

In one embodiment, the antigen binding moiety is a Fab fragment or a crossFab fragment, wherein the Fab or crossFab fragment is connected at the C-terminus of the heavy chain to the N-terminus of the anchoring transmembrane domain, optionally through a peptide linker.

In one embodiment, the antigen binding receptor comprises one co-signaling domain, wherein the co-signaling domain is connected at the N-terminus to the C-terminus of the anchoring transmembrane domain. In one embodiment, the antigen binding receptor comprises one stimulatory signaling domain, wherein the stimulatory signaling domain is connected at the N-terminus to the C-terminus of the co-stimulatory signaling domain.

In one embodiment, the non-mutated parent Fc domain is an IgG1 or an IgG4 Fc domain, particularly a human IgG1 Fc domain. In one embodiment, the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.

In one embodiment, the mutated Fc domain comprises at least one amino acid mutation at a position selected from the group consisting of L234, L235 and P329 according to EU numbering, in particular the amino acid mutations L234A, L235A and P329G ("PGLALA").

In one embodiment, the mutated Fc domain comprises the amino acid mutation P329G according to EU numbering, wherein Fcγ receptor binding of the mutated Fc domain is reduced compared to Fcγ receptor binding of the non-mutated parent Fc domain, in particular wherein the Fcγ receptor is human FcγRIIIa and/or FcγRIIa.

In one embodiment, the mutated Fc domain comprises at least one amino acid mutation at a position selected from the group consisting of I253, H310 and H435 according to EU numbering, in particular the amino acid mutations I253A, H310A and H435A ("AAA"), wherein FcRn binding of the mutated Fc domain is reduced compared to FcRn binding of the non-mutated parent Fc domain.

In one embodiment, the at least one antigen binding moiety is capable of specific binding to a mutated Fc domain comprising the P329G mutation but not capable of specific binding to the non-mutated parent Fc domain, wherein the antigen binding moiety comprises:
  (i) a heavy chain variable region (VH) comprising
    (a) the heavy chain complementarity-determining region (CDR H) 1 amino acid sequence RYWMN (SEQ ID NO:1);
    (b) the CDR H2 amino acid sequence EITPDSSTINYTPSLKD (SEQ ID NO:2); and
    (c) the CDR H3 amino acid sequence PYDYGAWFAS (SEQ ID NO:3); and
  (ii) a light chain variable region (VL) comprising
    (d) the light chain complementarity-determining region (CDR L) 1 amino acid sequence RSSTGAVTTSNYAN (SEQ ID NO:4);
    (e) the CDR L2 amino acid sequence GTNKRAP (SEQ ID NO:5); and
    (f) the CDR L3 amino acid sequence ALWYSNHWV (SEQ ID NO:6).

In one embodiment, the at least one antigen binding moiety is capable of specific binding to a mutated Fc domain comprising the P329G mutation but not capable of specific binding to the non-mutated parent Fc domain, wherein the antigen binding moiety comprises a heavy chain variable region (VH) comprising an amino acid sequence that is at least about 95%, 96%, 97%, 98%, 99% or 100% identical to an amino acid sequence selected from the group consisting of SEQ ID NO:8 and SEQ ID NO:32, and a light chain variable region (VL) comprising an amino acid sequence that is at least about 95%, 96%, 97%, 98%, 99% or 100% identical to an amino acid sequence selected from the group consisting of SEQ ID NO:9 and SEQ ID NO:33.

In one embodiment, the at least one antigen binding moiety comprises the heavy chain variable region (VH) of SEQ ID NO:8 and the light chain variable region (VL) of SEQ ID NO:9.

In one embodiment, the at least one antigen binding moiety is a scFv capable of specific binding to a mutated Fc domain comprising the P329G mutation but not capable of specific binding to the non-mutated parent Fc domain, wherein the antigen binding receptor comprises an amino acid sequence that is at least about 95%, 96%, 97%, 98%, 99% or 100% identical to an amino acid sequence selected from the group consisting of SEQ ID NO:7 and SEQ ID NO:31. In one embodiment, the antigen binding receptor comprises the amino acid sequence of SEQ ID NO:7.

In one embodiment, the at least one antigen binding moiety is a Fab fragment capable of specific binding to a mutated Fc domain comprising the P329G mutation but not capable of specific binding to the non-mutated parent Fc domain, wherein the antigen binding receptor comprises
 a) a heavy chain fusion polypeptide that is at least about 95%, 96%, 97%, 98%, 99% or 100% identical to an amino acid sequence selected from the group consisting of SEQ ID NO:39 and SEQ ID NO:48; and
 b) a light chain polypeptide that is at least about 95%, 96%, 97%, 98%, 99% or 100% identical to an amino acid sequence selected from the group consisting of SEQ ID NO:41 and SEQ ID NO:50.

In one embodiment, the antigen binding receptor comprises
 a) the heavy chain fusion polypeptide of SEQ ID NO:39; and
 b) the light chain polypeptide of SEQ ID NO:41.

In one embodiment, the at least one antigen binding moiety is capable of specific binding to a mutated Fc domain comprising the I253A, H310A and H435A ("AAA") mutations but not capable of specific binding to the non-mutated parent Fc domain, wherein the antigen binding moiety comprises:
 (i) a heavy chain variable region (VH) comprising
 (a) the heavy chain complementarity-determining region (CDR H) 1 amino acid sequence SYGMS (SEQ ID NO:53);
 (b) the CDR H2 amino acid sequence SSGGSY (SEQ ID NO:54); and
 (c) the CDR H3 amino acid sequence LGMITTGYAMDY (SEQ ID NO:55); and
 (ii) a light chain variable region (VL) comprising
 (d) the light chain complementary-determining region (CDR L) 1 amino acid sequence RSSQTIVH-STGHTYLE (SEQ ID NO:56);
 (e) the CDR L2 amino acid sequence KVSNRFS (SEQ ID NO:57); and
 (f) the CDR L3 amino acid sequence FQGSHVPYT (SEQ ID NO:58).

In one embodiment, the at least one antigen binding moiety is capable of specific binding to a mutated Fc domain comprising the I253A, H310A and H435A ("AAA") mutations but not capable of specific binding to the non-mutated parent Fc domain, wherein the antigen binding moiety comprises a heavy chain variable region (VH) comprising an amino acid sequence that is at least about 95%, 96%, 97%, 98%, 99% or 100% identical to the amino acid sequence of SEQ ID NO:61 and a light chain variable region (VL) comprising an amino acid sequence that is at least about 95%, 96%, 97%, 98%, 99% or 100% identical to the amino acid sequence of SEQ ID NO:62.

In one embodiment, the at least one antigen binding moiety comprises
 a) the heavy chain variable region (VH) of SEQ ID NO:61; and
 b) the light chain variable region (VL) of SEQ ID NO:62.

In one embodiment, the at least one antigen binding moiety is a scFv capable of specific binding to a mutated Fc domain comprising the I253A, H310A and H435A ("AAA") mutations but not capable of specific binding to the non-mutated parent Fc domain, wherein the antigen binding receptor comprises an amino acid sequence that is at least about 95%, 96%, 97%, 98%, 99% or 100% identical to the amino acid sequence of SEQ ID NO:59. In one embodiment, the antigen binding receptor comprises the amino acid sequence of SEQ ID NO:59.

In one embodiment, the at least one antigen binding moiety is a Fab fragment capable of specific binding to a mutated Fc domain comprising the P329G mutation but not capable of specific binding to the non-mutated parent Fc domain, wherein the antigen binding receptor comprises
 a) a heavy chain fusion polypeptide that is at least about 95%, 96%, 97%, 98%, 99% or 100% identical to the amino acid sequence of SEQ ID NO:39; and
 b) a light chain polypeptide that is at least about 95%, 96%, 97%, 98%, 99% or 100% identical to the amino acid sequence of SEQ ID NO:41.

In one embodiment, the antigen binding receptor comprises
 a) the heavy chain fusion polypeptide of SEQ ID NO:39; and
 b) the light chain polypeptide of SEQ ID NO:41.

In one embodiment, provided is an isolated polynucleotide encoding the antigen binding receptor as described herein. In one embodiment, provided is an isolated polynucleotide encoding a heavy chain fusion polypeptide or a light chain polypeptide of the antigen binding receptor as described herein. In one embodiment, provided is a composition encoding the antigen binding receptor as described herein, comprising a first isolated polynucleotide encoding a heavy chain fusion polypeptide, and a second isolated polynucleotide encoding a light chain polypeptide.

In one embodiment, provided is a polypeptide encoded by the polynucleotide as described herein or by the composition as described herein.

In one embodiment, provided is a vector, particularly an expression vector, comprising the polynucleotide(s) as described herein.

In one embodiment, provided is a transduced T cell comprising the polynucleotide(s) as described herein or the vector as described herein. In one embodiment, provided is a transduced T cell capable of expressing the antigen binding receptor as described herein. In one embodiment, provided is the transduced T cell as described herein, wherein the transduced T cell is co-transduced with a T cell receptor (TCR) capable of specific binding of a target antigen. In one embodiment, provided is a kit comprising
 (A) a transduced T cell capable of expressing the antigen binding receptor as described herein; and
 (B) an antibody comprising a mutated Fc domain;
 wherein the antigen binding receptor is capable of specific binding to the mutated Fc domain but not capable of specific binding to the non-mutated parent Fc domain.

In one embodiment, provided is a kit comprising
 (A) an isolated polynucleotide encoding the antigen binding receptor as described herein; and
 (B) an antibody comprising a mutated Fc domain;
 wherein the antigen binding receptor is capable of specific binding to the mutated Fc domain but not capable of specific binding to the non-mutated parent Fc domain.

In one embodiment, provided is a kit comprising
 (A) the composition or the vector as described herein encoding the antigen binding receptor as described herein; and
 (B) an antibody comprising a mutated Fc domain;
 wherein the antigen binding receptor is capable of specific binding to the mutated Fc domain but not capable of specific binding to the non-mutated parent Fc domain.

In one embodiment, the non-mutated parent Fc domain is an IgG1 or an IgG4 Fc domain, particularly a human IgG1

Fc domain. In one embodiment, provided is a mutated Fc domain comprising at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A. In one embodiment, the mutated Fc domain comprises at least one amino acid mutation at a position selected from the group consisting of L234, L235 and P329 according to EU numbering, in particular the amino acid mutations L234A, L235A and P329G ("PGLALA").

In one embodiment, the mutated Fc domain comprises the amino acid mutation P329G according to EU numbering. In one embodiment, the mutated Fc domain comprises at least one amino acid mutation at a position selected from the group consisting of I253, H310 and H435 according to EU numbering, in particular the amino acid mutations I253A, H310A and H435A ("AAA").

In one embodiment, the antibody comprising the mutated Fc domain is capable of specific binding to an antigen on the surface of a tumor cell, in particular wherein the antigen is selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX, and/or to a peptide bound to a molecule of the human major histocompatibility complex (MHC).

In one embodiment, the antibody comprising the mutated Fc domain is capable of specific binding to an antigen selected from the group consisting of fibroblast activation protein (FAP), carcinoembryonic antigen (CEA), mesothelin (MSLN), CD20, folate receptor 1 (FOLR1) and tenascin (TNC).

In one embodiment, provided is the kit as described herein for use as a medicament.

In one embodiment, provided is the antigen binding receptor or the transduced T cell as described herein for use as a medicament, wherein the transduced T cell expressing the antigen binding receptor is administered before, simultaneously with or after administration of an antibody comprising a mutated Fc domain wherein the antigen binding receptor is capable of specific binding to the mutated Fc domain but not capable of specific binding to the non-mutated parent Fc domain.

In one embodiment, provided is the kit as described herein for use in the treatment of a malignant disease. In one embodiment, provided is the antigen binding receptor or the transduced T cell as described herein for use in the treatment of a malignant disease, wherein the treatment comprises administration of a transduced T cell expressing the antigen binding receptor before, simultaneously with or after administration of an antibody comprising a mutated Fc domain wherein the antigen binding receptor is capable of specific binding to the mutated Fc domain but not capable of specific binding to the non-mutated parent Fc domain.

In one embodiment, said malignant disease is selected from cancer of epithelial, endothelial or mesothelial origin and cancer of the blood.

In one embodiment, the transduced T cell is derived from a cell isolated from the subject to be treated. In one embodiment, the transduced T cell is not derived from a cell isolated from the subject to be treated.

In one embodiment, provided is a method of treating a disease in a subject, comprising administering to the subject a transduced T cell capable of expressing the antigen binding receptor as described herein and administering before, simultaneously with or after administration of the transduced T cell a therapeutically effective amount of an antibody comprising a mutated Fc domain, wherein the antigen binding receptor is capable of specific binding to the mutated Fc domain but not capable of specific binding to the non-mutated parent Fc domain. In one embodiment, the T cell is additionally isolated from the subject and the transduced T cell is generated by transducing the isolated T cell with the polynucleotide, the composition or the vector as described herein. In one embodiment, the T cell is transduced with a retroviral or lentiviral vector construct or with a non-viral vector construct. In one embodiment, the non-viral vector construct is a sleeping beauty minicircle vector.

In one embodiment, the transduced T cell is administered to the subject by intravenous infusion. In one embodiment, the transduced T cell is contacted with anti-CD3 and/or anti-CD28 antibodies prior to administration to the subject. In one embodiment, the transduced T cell is contacted with at least one cytokine prior to administration to the subject, preferably with interleukin-2 (IL-2), interleukin-7 (IL-7), interleukin-15 (IL-15), and/or interleukin-21, or variants thereof.

In one embodiment, the disease is a malignant disease. In one embodiment, the malignant disease is selected from cancer of epithelial, endothelial or mesothelial origin and cancer of the blood.

In one embodiment, provided is a method for inducing lysis of a target cell, comprising contacting the target cell with a transduced T cell capable of expressing the antigen binding receptor as described herein in the presence of an antibody comprising a mutated Fc domain wherein the antigen binding receptor is capable of specific binding to the mutated Fc domain but not capable of specific binding to the non-mutated parent Fc domain.

In one embodiment, the target cell is a cancer cell. In one embodiment, the target cell expresses an antigen selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX. In one embodiment, the target cell expresses an antigen selected from the group consisting of carcinoembryonic antigen (CEA), mesothelin (MSLN), CD20, folate receptor 1 (FOLR1), and tenascin (TNC).

In one embodiment, the polynucleotides or the transduced T cell as described herein is used for the manufacture of a medicament. In one embodiment, the medicament is for treatment of a malignant disease.

SHORT DESCRIPTION OF THE FIGURES

FIGS. 1A and 1B depict the architecture of exemplary antigen binding receptors according to the invention. FIG. 1A shows the architecture of the anti-P329G-scFv-CD28ATD-CD28CSD-CD3zSSD format and anti-P329G-ds-scFv-CD28ATD-CD28CSD-CD3zSSD format. Depicted is the extracellular domain comprising an antigen binding moiety capable of specific binding to a mutated Fc domain comprising the P329G mutation. The antigen binding moiety consists of a variable heavy and a variable light chain. Both are connected by a $(Gly_4Ser)_4$ linker. Attached to the variable light chain, a $Gly_4Ser$ linker connects the antigen recognition domain with the CD28 transmembrane domain (TM) which is fused to the intracellular co-stimulatory signaling domain (CSD) of CD28 which in turn is fused to the stimulatory signaling domain (SSD) of CD3z. FIG. 1B shows the architecture of the anti-P329G-Fab-CD28ATD-CD28CSD-CD3zSSD and anti-P329G-ds-Fab-CD28ATD-CD28CSD-CD3zSSD format. Depicted is the extracellular domain comprising an antigen binding moiety capable of specific binding to a mutated Fc domain comprising the P329G mutation. The antigen binding moiety consists of an Ig heavy chain and an Ig light chain. Attached to the heavy chain, a Gly$_4$Ser linker connects the antigen recognition domain with the CD28 transmembrane domain which is fused to the intracellular co-stimulatory signaling domain of CD28 which in turn is fused to the stimulatory signaling domain of CD3z.

FIGS. 2A and 2B depict a schematic representation illustrating the modular composition of exemplary expression constructs encoding antigen binding receptors of the invention. FIG. 2A depicts a P392G-targeted scFv format. FIG. 2B depicts a P392G-targeted Fab format.

Figure 5:
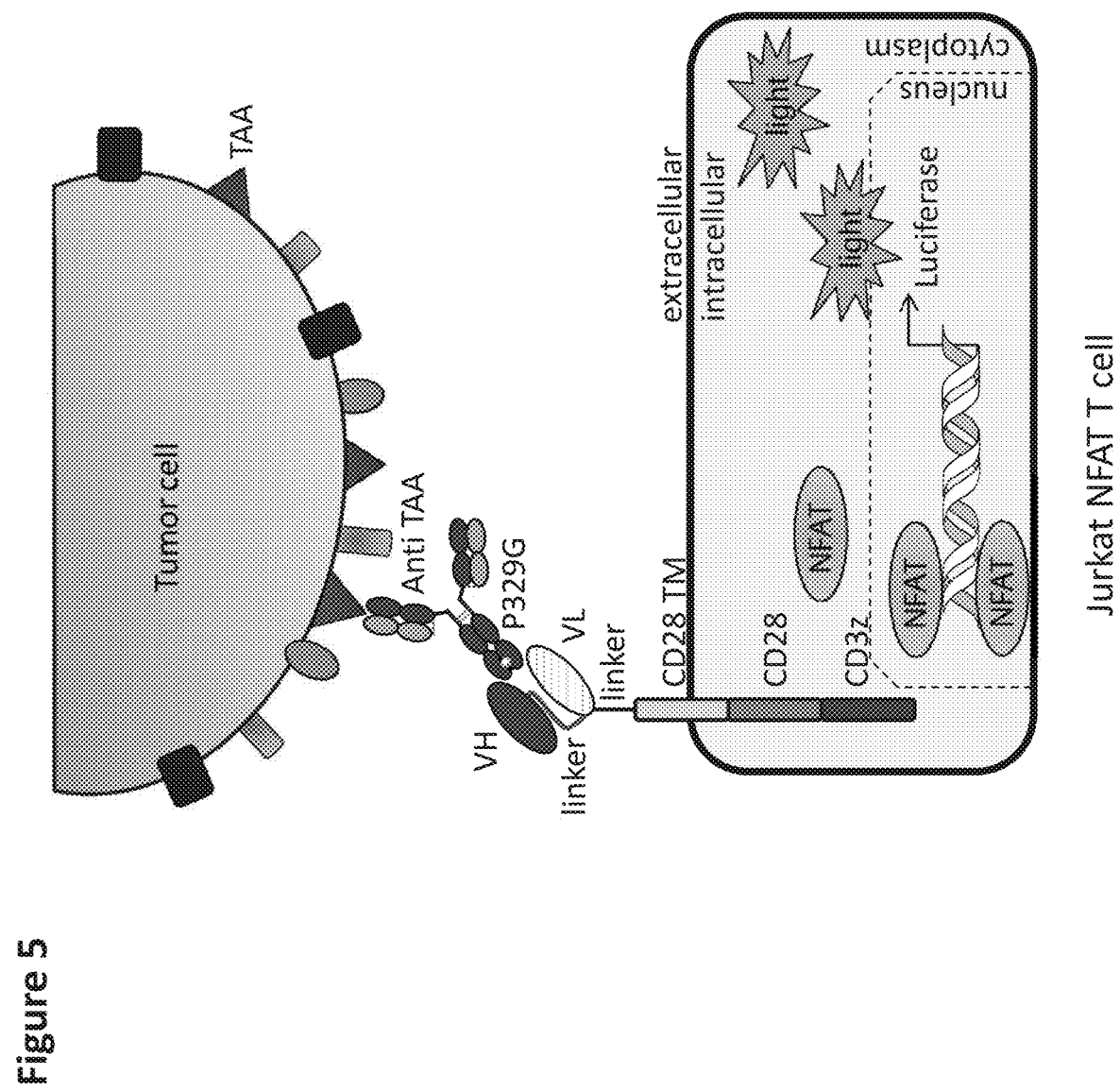

FIG. 5 shows a schematic representation of a Jurkat NFAT T cell reporter assay. TAA bound IgG harboring the P329G mutation can be recognized by the anti-P329G antigen binding receptor expressing Jurkat NFAT T cell. This recognition leads to the activation of the cell which can be detected by measuring luminescence (cps).

Figure 6A:
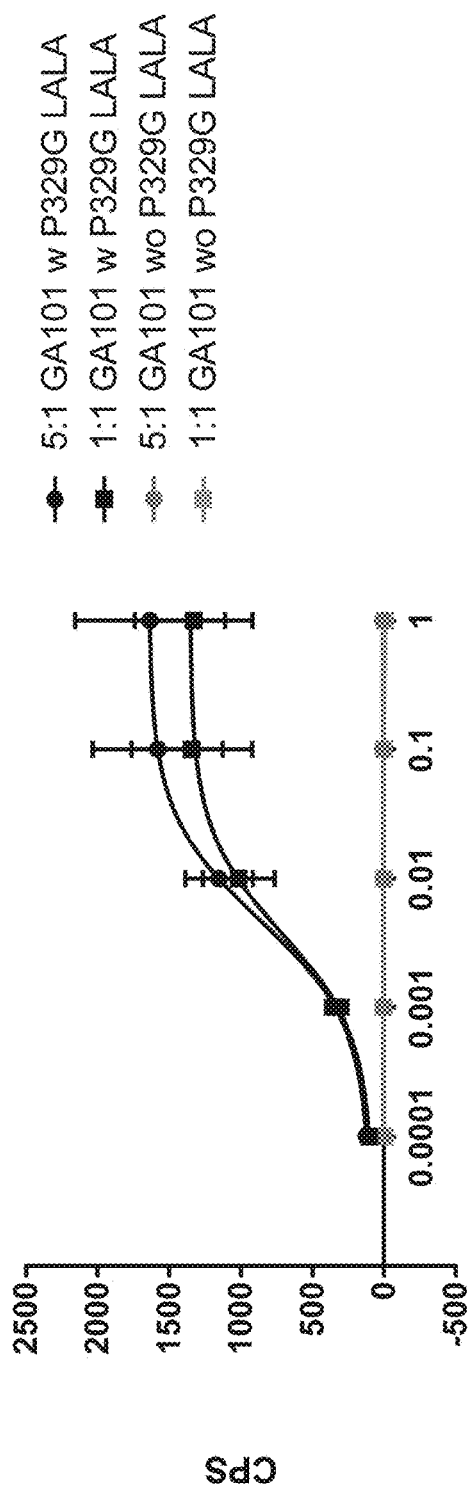
Figure 6B:
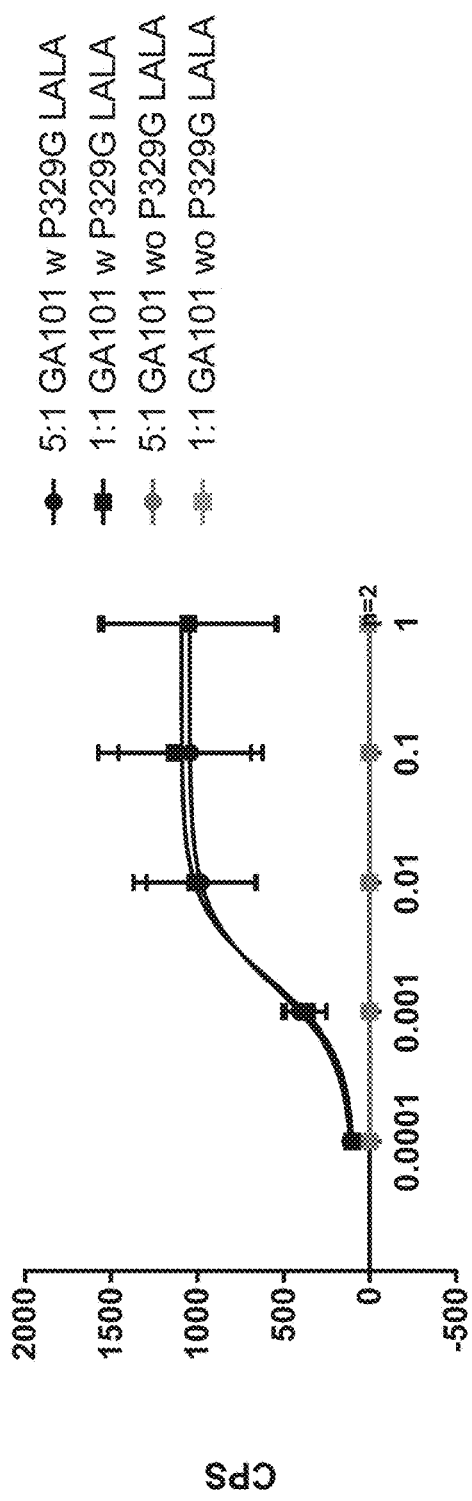

FIGS. 6A and 6B depict the Jurkat NFAT T cell reporter assay using CD20 expressing SUDHDL4 tumor cells as target cells. An anti-CD20 IgG antibody (GA101) harboring the P329G mutation was used, which on one hand recognizes the tumor associated antigen and on the other hand is recognized by Jurkat NFAT T cells expressing antigen binding receptors according to the invention. In FIG. 6A a sorted pool of anti-P329G-ds-Fab-CD28ATD-CD28CSD-CD3zSSD expressing Jurkat NFAT T cells was used as as effector cells. In FIG. 6B a sorted pool of anti-P329G-ds-scFv-CD28ATD-CD28CSD-CD3zSSD expressing Jurkat NFAT T cells was used as effector cells.

FIGS. 7A to 7D depict the Jurkat NFAT T cell reporter assay using CD20 tumor cells as target cells. An anti-CD20 IgG antibody (GA101) harboring the P329G mutation was used which recognizes the tumor associated antigen and is recognized by the Jurkat NFAT T cells expressing antigen binding receptors according to the invention. In FIG. 7A the single clone 5 of anti-P329G-ds-Fab-CD28ATD-CD28CSD-CD3zSSD expressing Jurkat NFAT T cells were used as effector cells and WSUDLCL2 cells as tumor cells. In FIG. 7B the single clone 2 of anti-P329G-ds-Fab-CD28ATD-CD28CSD-CD3zSSD expressing Jurkat NFAT T cells were used as effector cells and WSUDLCL2 cells as tumor cells. In FIG. 7C the single clone 5 of anti-P329G-ds-Fab-CD28ATD-CD28CSD-CD3zSSD expressing Jurkat NFAT T cells were used as effector cells and SUDHL4 cells as tumor cells. In FIG. 7D the single clone 2 of anti-P329G-ds-Fab-CD28ATD-CD28CSD-CD3zSSD expressing Jurkat NFAT T cells were used as effector cells and SUDHL4 as tumor cells.

Figure 8A:
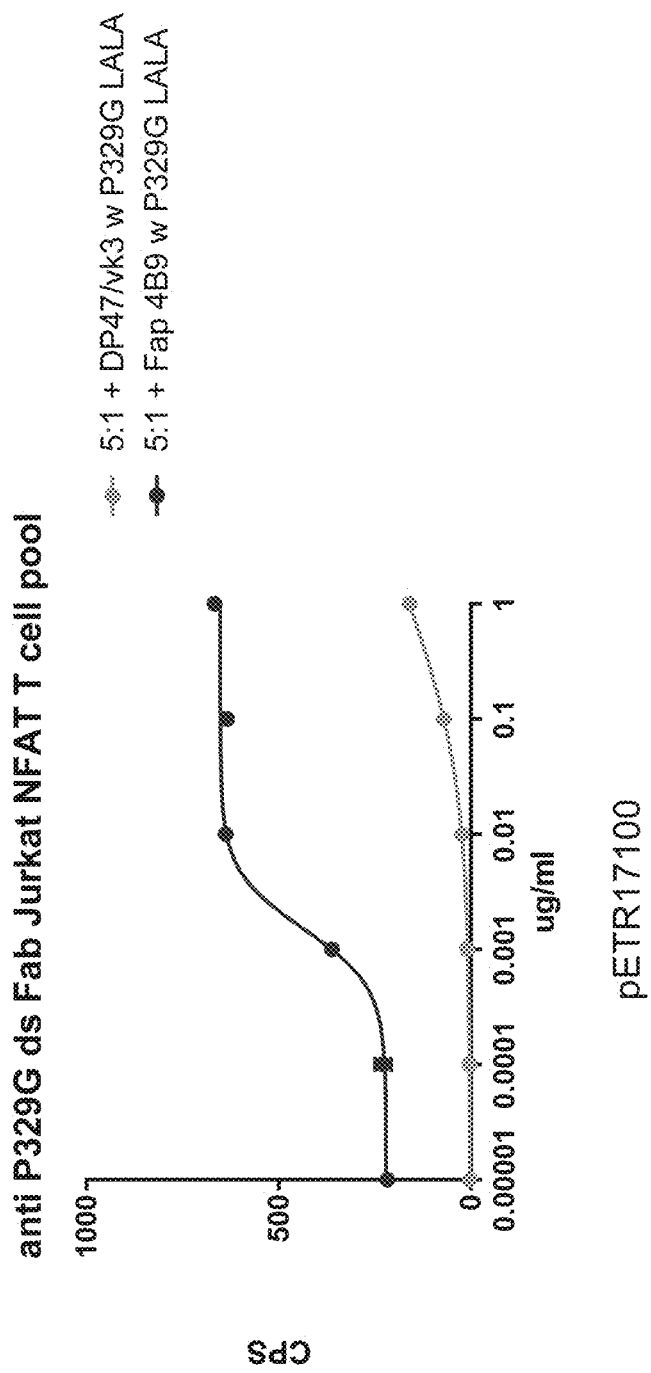
Figure 8B:
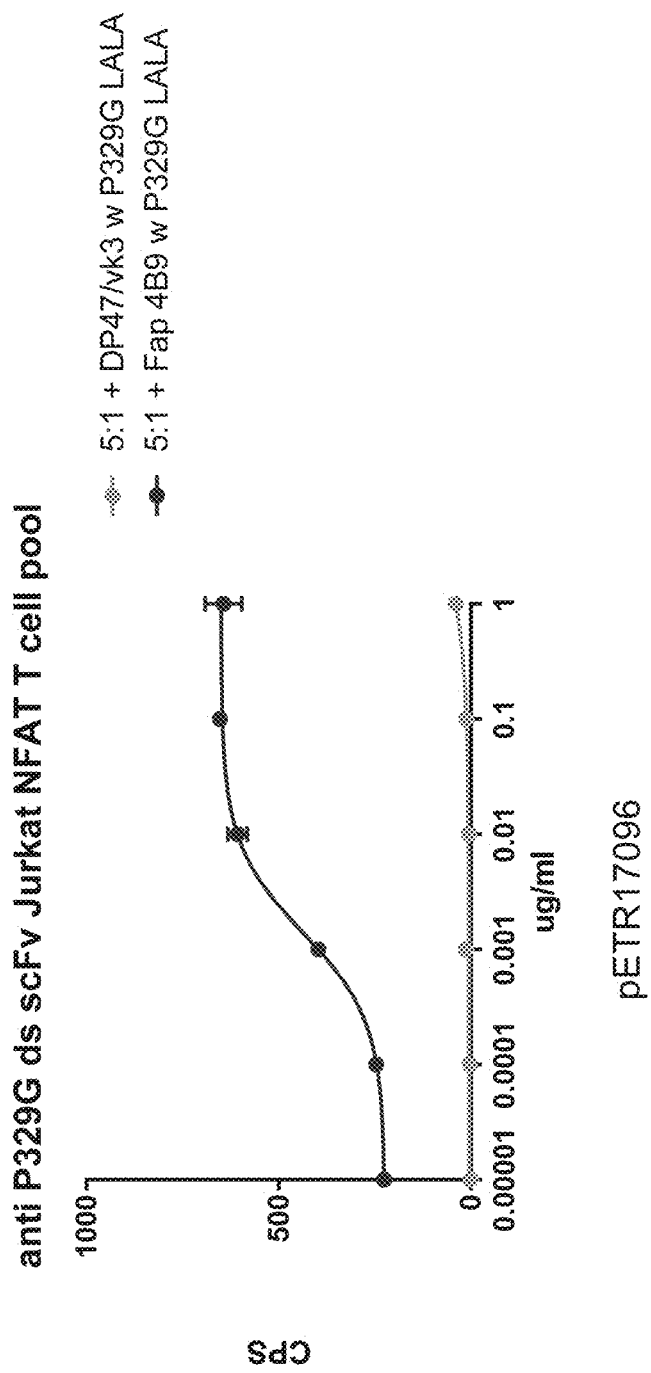
Figure 8D:
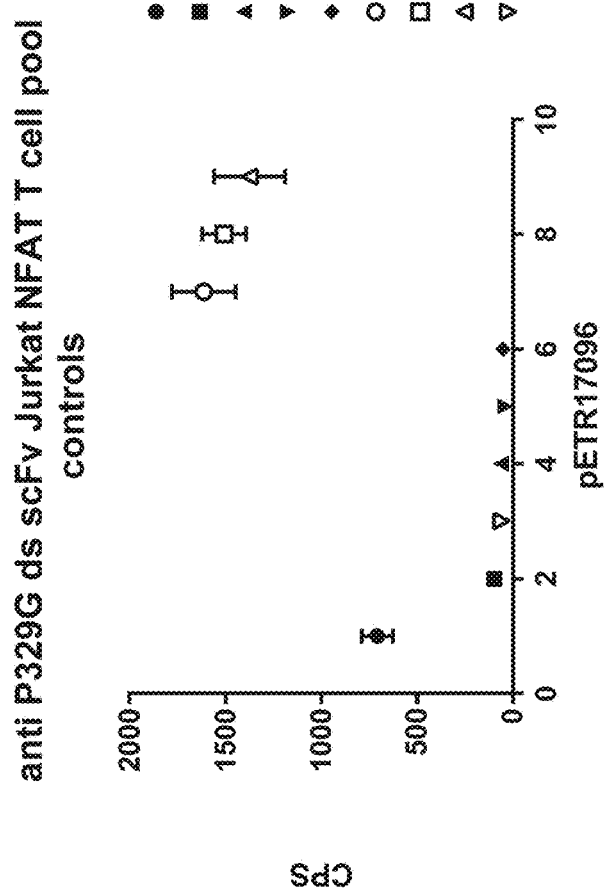
Figure 9A:
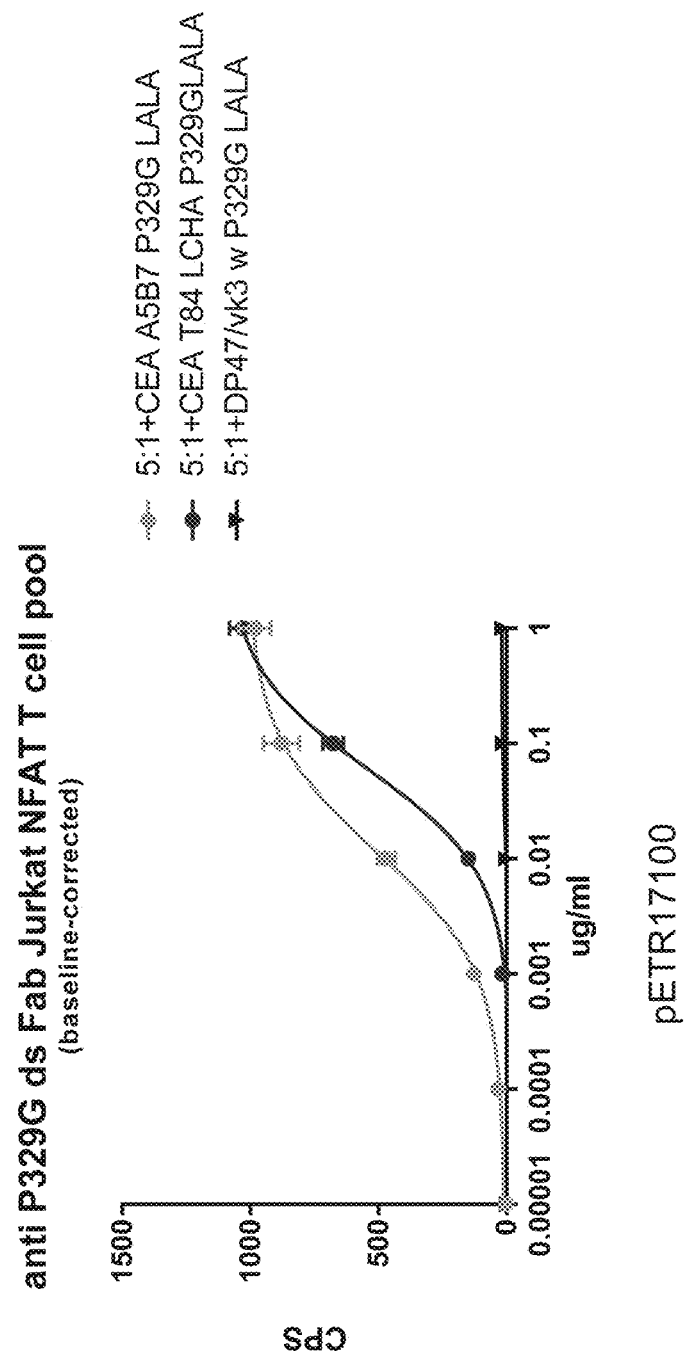

FIGS. 8A to 8D depict the Jurkat NFAT T cell reporter assay performed using adherent FAP expressing NIH/3T3-huFAP cl 19 tumor cells as target cells. The anti-FAP IgG antibody clone 4B9 harboring the P329G mutation was used which recognizes the tumor associated antigen and is recognized by the Jurkat NFAT T cells expressing antigen binding receptors according to the invention. IgG DP47/vk3 harboring P329G mutation was included as isotype control. In FIG. 8A a sorted pool of anti-P329G-ds-Fab-CD28ATD-CD28CSD-CD3zSSD expressing Jurkat NFAT T cells was used as effector cells. In FIG. 8B a sorted pool of anti-P329G-ds-scFv-CD28ATD-CD28CSD-CD3zSSD expressing Jurkat NFAT T cells was used as effector cells. In FIG. 8C a sorted pool of anti-P329G-ds-Fab-CD28ATD-CD28CSD-CD3zSSD expressing Jurkat NFAT T cells was used as effector cells. In FIG. 8D a sorted pool of anti-P329G-ds-scFv-CD28ATD-CD28CSD-CD3zSSD expressing Jurkat NFAT T cells was used as effector cells FIGS. 9A to 9D depict the Jurkat NFAT T cell reporter assay using adherent CEA expressing MKN45 tumor cells as target cells. Either the anti-CEA IgG clone A5B7 or the anti-CEA IgG clone T84 LCHA both harboring the P329G mutation were used which recognize the tumor associated antigen and are recognized by the Jurkat NFAT T cells expressing antigen binding receptors according to the invention. Further IgG DP47/vk3 harboring the P329G mutation was included as isotype control. In FIG. 9A and in FIG. 9B a sorted pool of anti-P329G-ds-Fab-CD28ATD-CD28CSD-CD3zSSD expressing NFAT T cells was used as effector cells. In FIG. 9C and in FIG. 9D a sorted pool of anti-P329G-ds-scFv-CD28ATD-CD28CSD-CD3zSSD expressing NFAT T cells was used as effector cells.

Figure 10A:
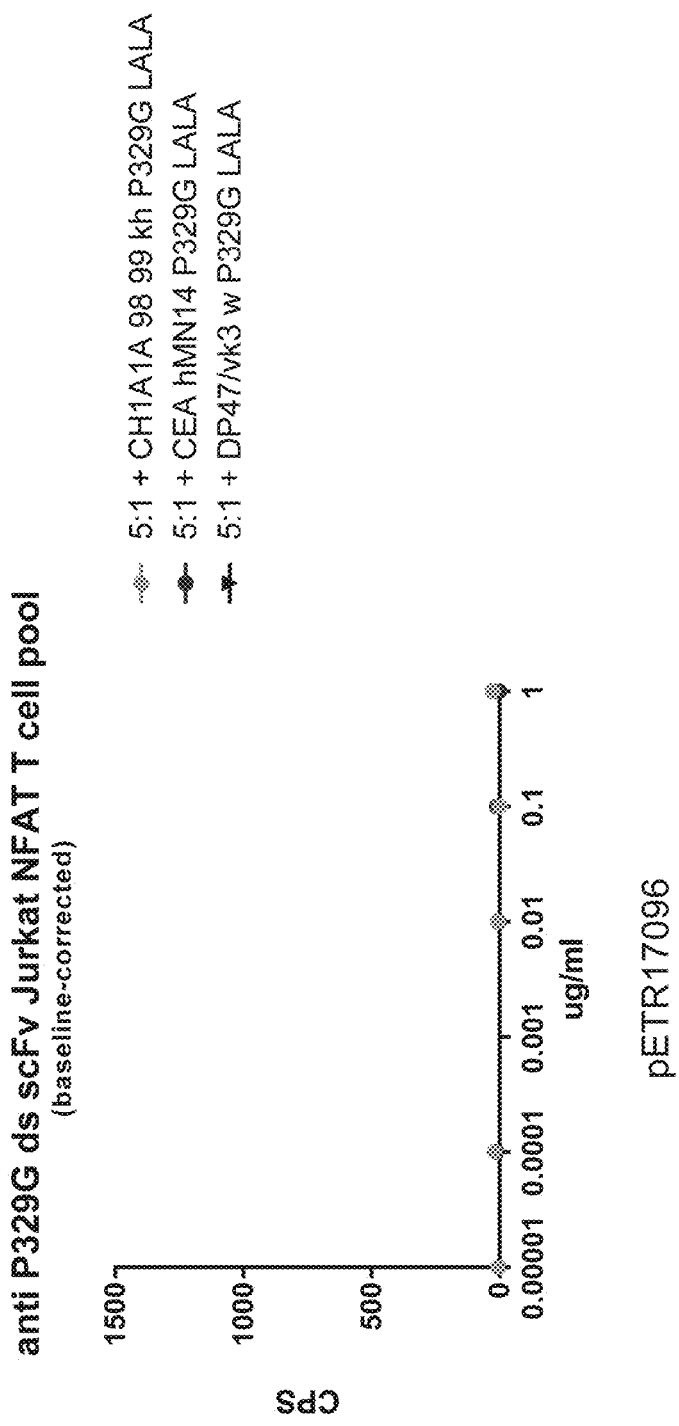
Figure 10B:
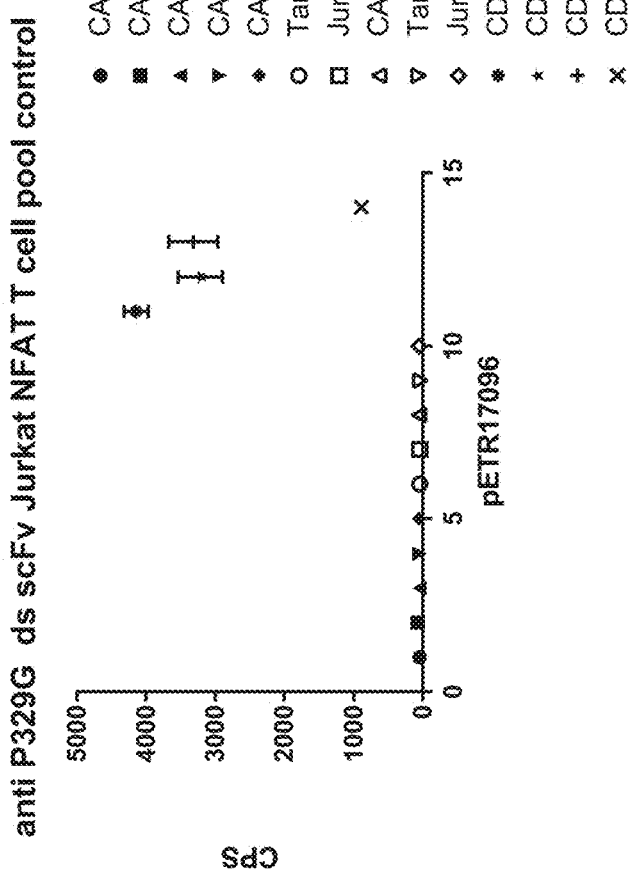
Figure 10C:
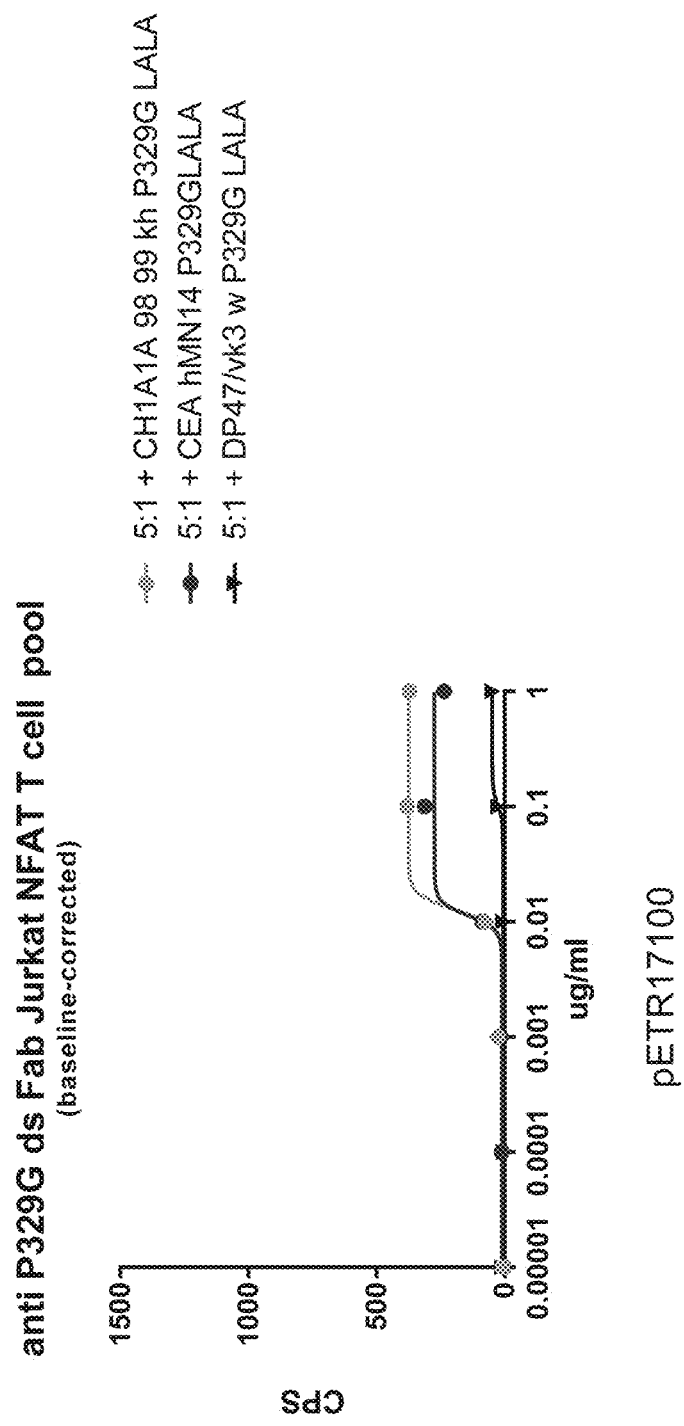

FIGS. 10A to 10D depict the Jurkat NFAT T cell reporter assay using adherent CEA expressing MKN45 tumor cells as target cells. Either the anti-CEA clone CH1A1A 98 99 or the anti-CEA IgG clone hMN14 IgG both harboring the P329G mutation were used which recognize the tumor associated antigen and are recognized by the Jurkat NFAT T cells expressing antigen binding receptors according to the invention. Further IgG DP47/vk3 harboring P329G mutation was included as isotype control. In FIG. 10A and in FIG. 10B a sorted pool of anti-P329G-ds-scFv-CD28ATD-CD28CSD-CD3zSSD expressing NFAT T cells was used as effector cells. In FIG. 10C and in FIG. 10D a sorted pool of anti-P329G-ds-Fab-CD28ATD-CD28CSD-CD3zSSD expressing NFAT T cells was used as effector cells.

Figure 11A:
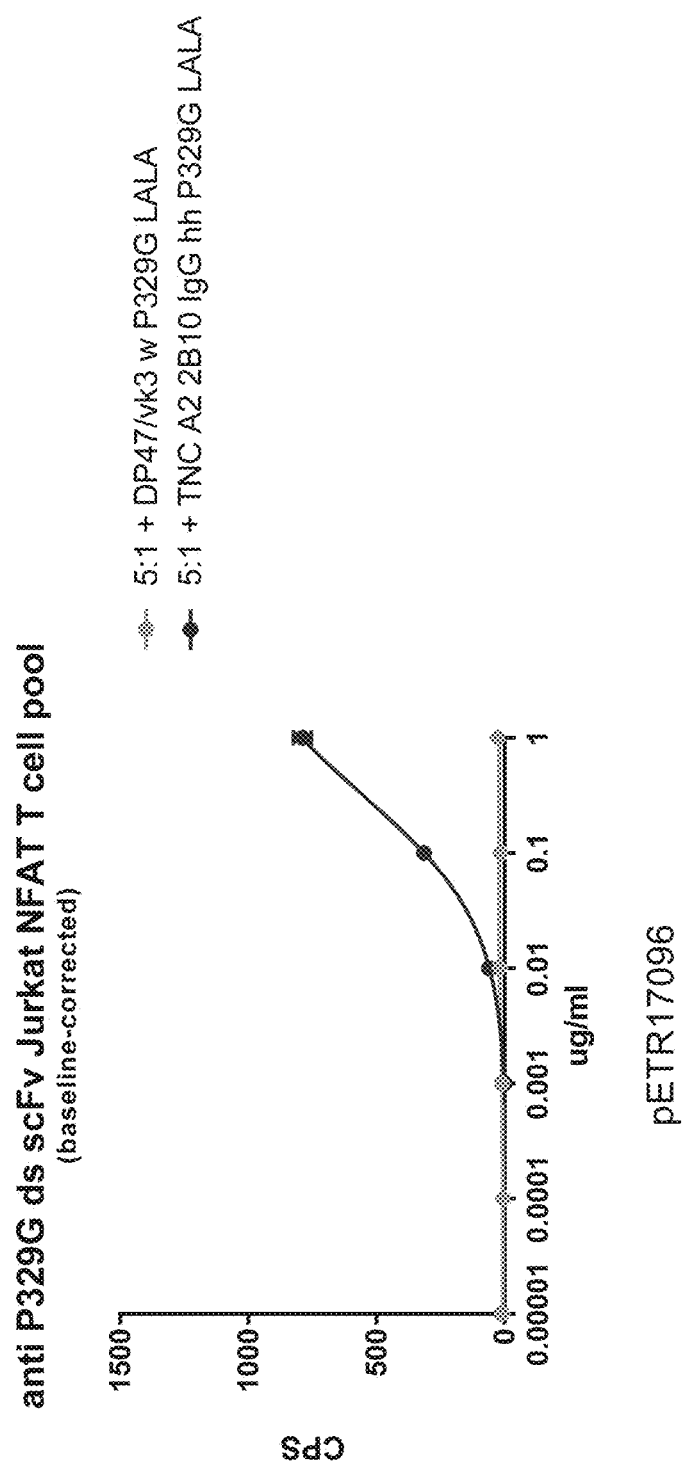
Figure 11B:
Figure 11C:
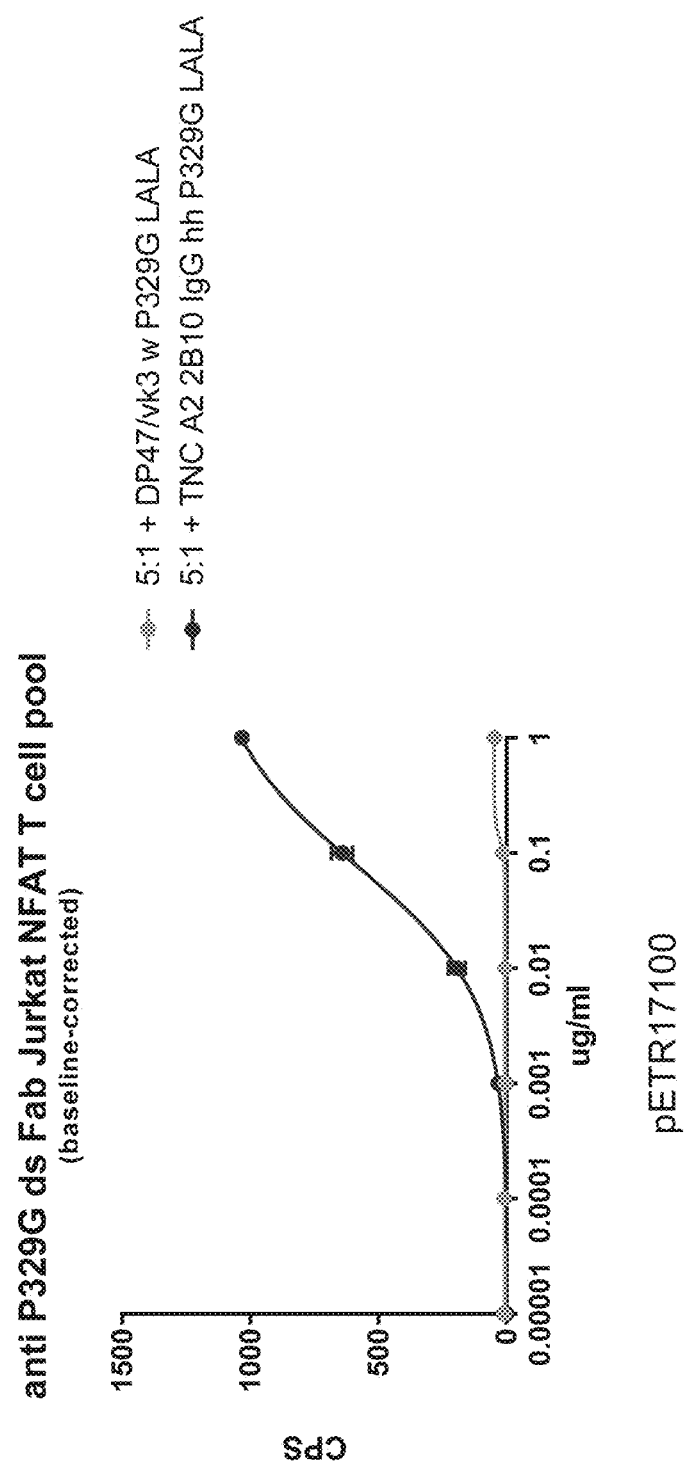

FIGS. 11A to 11D depict the Jurkat NFAT T cell reporter assay using adherent TNC expressing CT26TNC cl 19 tumor cells as target cells. The anti-TNC IgG clone A2B10 harboring the P329G mutation was used as IgG antibody which recognizes the tumor associated antigen and is recognized by the Jurkat NFAT T cells expressing antigen binding receptors according to the invention. Further IgG DP47/vk3 harboring P329G mutation was included as isotype control. In FIG. 11A and in FIG. 11B a sorted pool of anti-P329G-ds-scFv-CD28ATD-CD28CSD-CD3zSSD expressing NFAT T cells was used as effector cells. In FIG. 11C and in FIG. 11D a sorted pool of anti-P329G-ds-Fab-CD28ATD-CD28CSD-CD3zSSD expressing NFAT T cells was used as effector cells FIG. 12A and FIG. 12B depict the Jurkat NFAT T cell reporter assay using adherent TNC expressing CT26TNC cl 19 tumor cells as target cells. The anti-TNC IgG clone A2B10 harboring the P329G mutation was used which recognizes the tumor associated antigen and is recognized by the Jurkat NFAT T cells expressing antigen binding receptors according to the invention. Further IgG DP47/vk3 harboring P329G mutation was included as isotype control. A sorted pool of anti-P329G-Fab-CD28ATD-CD28CSD-CD3zSSD expressing Jurkat NFAT T cells was used as effector cells.

Figure 13A:
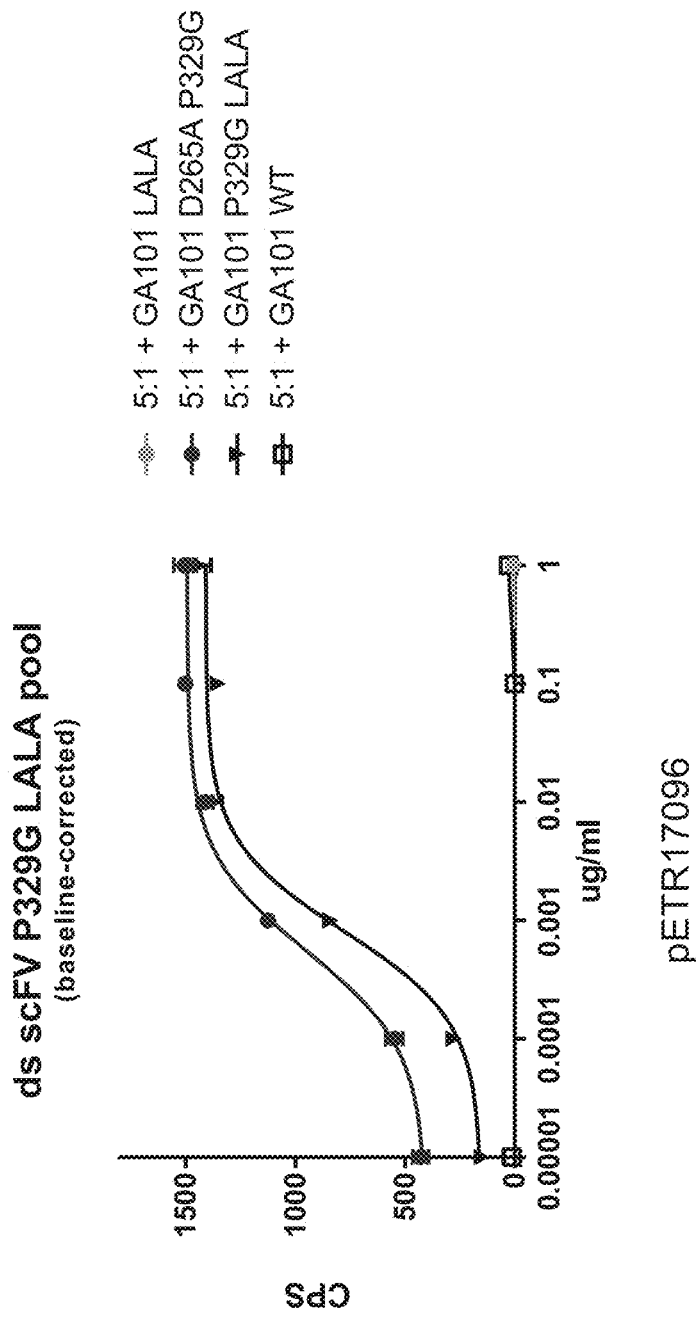
Figure 13B:
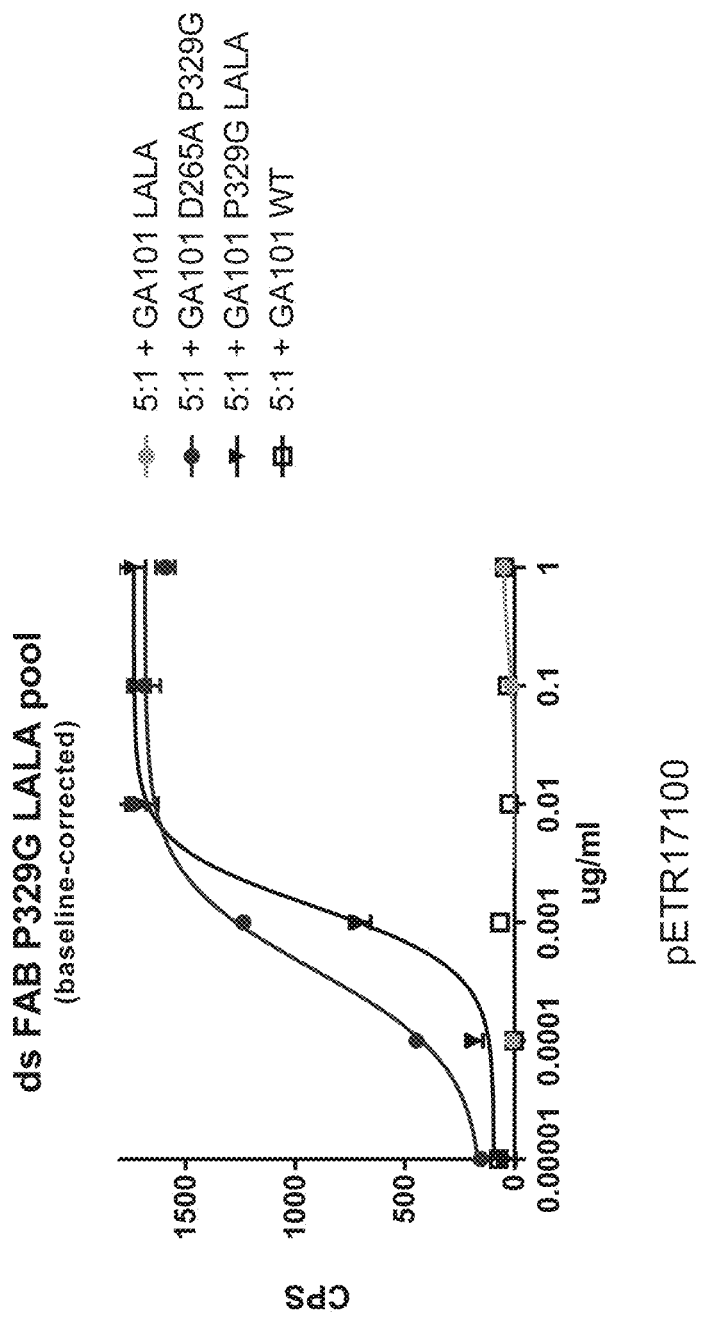

FIGS. 13A and 13B depict the Jurkat NFAT T cell reporter assay using CD20 tumor cells as target cells. Either an anti-CD20 IgG antibody (GA101) harboring the P329G and the LALA mutation mutation, a P329G and D265A mutation, the LALA mutation alone or no mutation at all were used in order to detect the tumor associated antigen and is recognized by the Jurkat NFAT T cells expressing antigen binding receptors according to the invention. In FIG. 13A the pool of cells of anti-P329G-ds-scFv-CD28ATD-CD28CSD-CD3zSSD expressing Jurkat NFAT T cells were used as effector cells and SUDHL4 cells as tumor cells. In FIG. 13B the pool of cells of anti-P329G-ds-Fab-CD28ATD-CD28CSD-CD3zSSD expressing Jurkat NFAT T cells were used as effector cells and SUDHL4 cells as tumor cells.

Figure 14A:
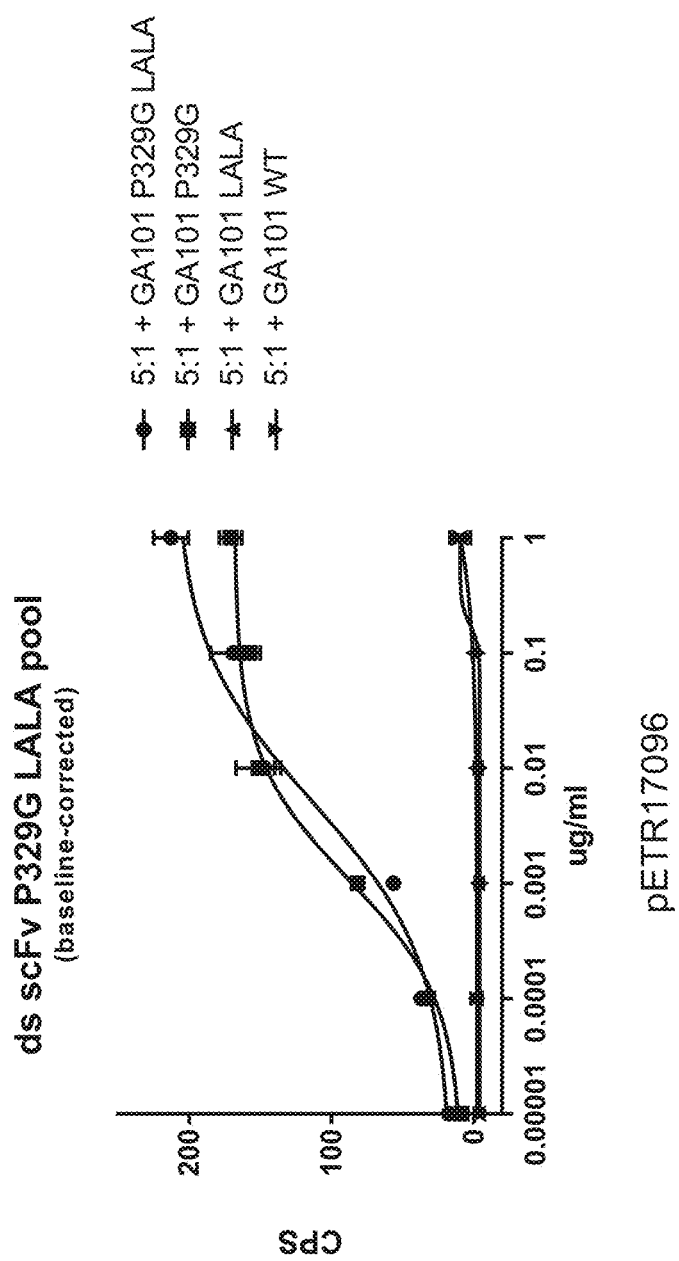
Figure 14B:
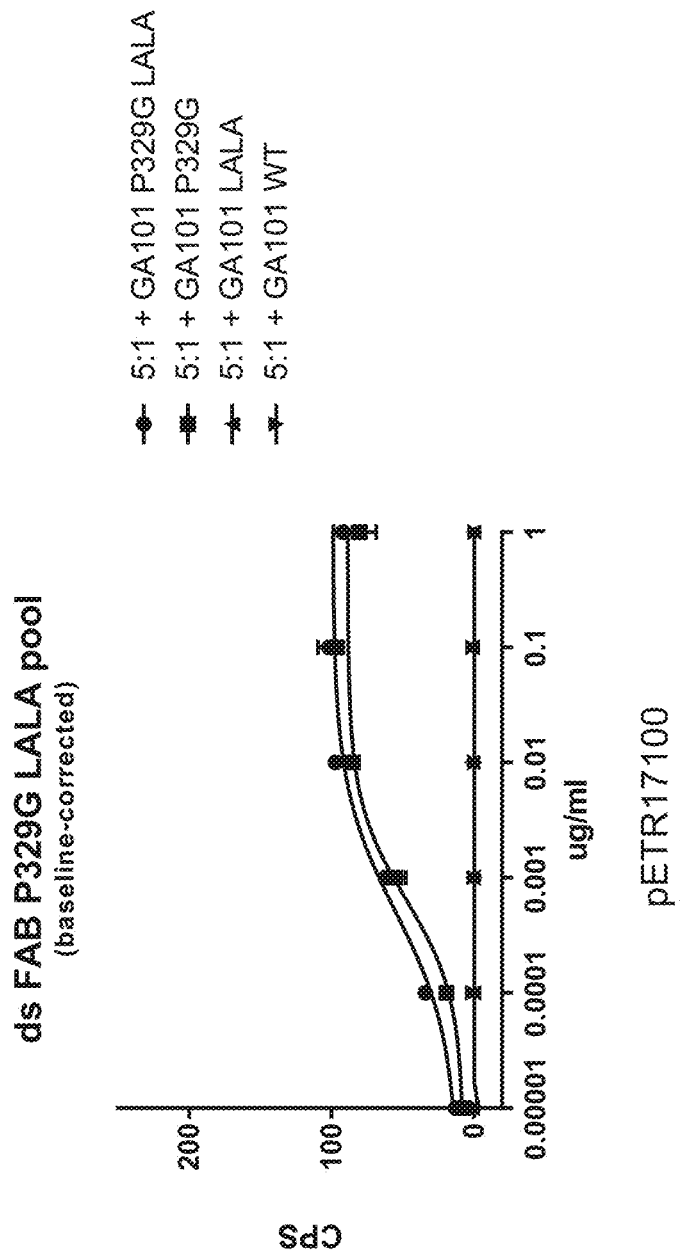

FIGS. 14A and 14B depict the Jurkat NFAT T cell reporter assay using CD20 tumor cells as target cells. Either an anti-CD20 IgG antibody (GA101) harboring the P329G and the LALA mutation mutation, a P329G mutation alone, the LALA mutation alone or no mutation at all were used in order to detect the tumor associated antigen and is recognized by the Jurkat NFAT T cells expressing antigen binding receptors according to the invention. In FIG. 14A the pool of cells of anti-P329G-ds-scFv-CD28ATD-CD28CSD-CD3zSSD expressing Jurkat NFAT T cells were used as effector cells and SUDHL4 cells as tumor cells. In FIG. 14B the pool of cells of anti-P329G-ds-Fab-CD28ATD-CD28CSD-CD3zSSD expressing Jurkat NFAT T cells were used as effector cells and SUDHL4 cells as tumor cells.

DETAILED DESCRIPTION

Definitions

Terms are used herein as generally used in the art, unless otherwise defined in the following.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity ("ADCC") is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been mutated. For example the reduction in ADCC mediated by an antibody comprising in its Fc domain an amino acid mutation that reduces ADCC, is relative to the ADCC mediated by the same antibody without this amino acid mutation in the Fc domain. Suitable assays to measure ADCC are well known in the art (see e.g., PCT publication no. WO 2006/082515 or PCT publication no. WO 2012/130831).

An "effective amount" of an agent (e.g., an antibody) refers to the amount that is necessary to result in a physiological change in the cell or tissue to which it is administered.

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen and/or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A preferred method for measuring affinity is Surface Plasmon Resonance (SPR) and a preferred temperature for the measurement is 25° C.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g. hydroxyproline, γ-carboxyglutamate, and O-phosphoserine. Amino acid analogs refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor. Amino acid sequence deletions and insertions include amino- and/or carboxy-terminal deletions and insertions of amino acids. Particular amino acid mutations are amino acid substitutions. For the purpose of altering e.g., the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

The term "antibody" herein is used in the broadest sense and encompasses various antibody structures, including but not limited to monoclonal antibodies, polyclonal antibodies, and antibody fragments so long as they exhibit the desired antigen-binding activity. Accordingly, in context of the present invention, the term antibody relates to full immunoglobulin molecules as well as to parts of such immunoglobulin molecules. Furthermore, the term relates, as discussed herein, to modified and/or altered antibody molecules, in particular to mutated antibody molecules. The term also relates to recombinantly or synthetically generated/synthesized antibodies. In the context of the present invention the term antibody is used interchangeably with the term immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g., scFv), and single-domain antibodies. For a review of certain antibody fragments, see Hudson et al., Nat Med 9, 129-134 (2003). For a review of scFv fragments, see e.g., Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody (Domantis, Inc., Waltham, Mass.; see e.g., U.S. Pat. No. 6,248,516 B1). Antibody fragments can be made by various techniques, including but not limited to proteolytic digestion of an intact antibody as well as production by recombinant host cells (e.g., E. coli or phage), as described herein.

As used herein, the term "antigen binding molecule" refers in its broadest sense to a molecule that specifically binds an antigenic determinant. Examples of antigen binding molecules are immunoglobulins and derivatives, e.g., fragments, thereof as well as antigen binding receptors and derivatives thereof.

As used herein, the term "antigen binding moiety" refers to a polypeptide molecule that specifically binds to an antigenic determinant. In one embodiment, an antigen binding moiety is able to direct the entity to which it is attached (e.g., an immunoglobulin or an antigen binding receptor) to a target site, for example to a specific type of tumor cell or tumor stroma bearing the antigenic determinant or to an immunoglobulin binding to the antigenic determinant on a tumor cell. In another embodiment an antigen binding moiety is able to activate signaling through its target antigen, for example signaling is activated upon binding of an antigenic determinant to an antigen binding receptor on a T cell. In the context of the present invention, antigen binding moieties may be included in antibodies and fragments thereof as well as in antigen binding receptors and fragments thereof as further defined herein. Antigen binding moieties include an antigen binding domain, comprising an immunoglobulin heavy chain variable region and an immunoglobulin light chain variable region. In certain embodiments, the antigen binding moieties may comprise immunoglobulin constant regions as further defined herein and known in the art. Useful heavy chain constant regions include any of the five isotypes: α, δ, ε, γ, or μ. Useful light chain constant regions include any of the two isotypes: κ and λ.

In the context of the present invention the term "antigen binding receptor" relates to an antigen binding molecule comprising an anchoring transmembrane domain and an extracellular domain comprising at least one antigen binding moiety. An antigen binding receptor can be made of polypeptide parts from different sources. Accordingly, it may be also understood as a "fusion protein" and/or a "chimeric protein". Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins. Recombinant fusion proteins are created artificially by recombinant DNA technology for use in biological research or therapeutics. Further details on the antigen binding receptors of the present invention are described herein below. In the context of the present invention a CAR (chimeric antigen receptor) is understood to be an antigen binding receptor comprising an extracellular portion comprising an antigen binding moiety fused by a spacer sequence to an anchoring transmembrane domain which is itself fused to the intracellular signaling domains of CD3z and CD28.

An "antigen binding site" refers to the site, i.e. one or more amino acid residues, of an antigen binding molecule which provides interaction with the antigen. For example, the antigen binding site of an antibody or an antigen binding receptor comprises amino acid residues from the complementarity determining regions (CDRs). A native immunoglobulin molecule typically has two antigen binding sites, a Fab or a scFv molecule typically has a single antigen binding site.

The term "antigen binding domain" refers to the part of an antibody or an antigen binding receptor that comprises the area which specifically binds to and is complementary to part or all of an antigen. An antigen binding domain may be provided by, for example, one or more immunoglobuling variable domains (also called variable regions). Particularly, an antigen binding domain comprises an immunoglobulin light chain variable region (VL) and an immunoglobulin heavy chain variable region (VH).

The term "variable region" or "variable domain" refers to the domain of an immunoglobulin heavy or light chain that is involved in binding the antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co, page 91 (2007). A single VH or VL domain is usually sufficient to confer antigen-binding specificity.

The term "ATD" as used herein refers to "anchoring transmembrane domain" which defines a polypeptide stretch capable of integrating in (the) cellular membrane(s) of a cell. The ATM can be fused to further extracellular and/or intracellular polypeptide domains wherein these extracellular and/or intracellular polypeptide domains will be confined to the cell membrane as well. In the context of the antigen binding receptors of the present invention the ATM confers membrane attachment and confinement of the antigen binding receptor of the present invention. The antigen binding receptors of the present invention comprise at least one ATM and an extracellular domain comprising an antigen binding moiety. Additionally, the ATM may be fused to further intracellular signaling domains.

The term "binding to" as used in the context of the antigen binding receptors of the present invention defines a binding (interaction) of an "antigen-interaction-site" and an antigen with each other. The term "antigen-interaction-site" defines, in accordance with antigen binding receptors of the present invention, a motif of a polypeptide which shows the capacity of specific interaction with a specific antigen or a specific group of antigens (i.e. mutated Fc domains). Said binding/interaction is also understood to define a "specific recognition". The term "specifically recognizing" means in accordance with this invention that the antigen binding receptor is capable of specifically interacting with and/or binding to a modified molecule as defined herein whereas the non-modified molecule is not recognized. The antigen binding moiety of an antigen binding receptor can recognize, interact and/or bind to different epitopes on the same molecule. This term relates to the specificity of the antigen binding receptor, i.e., to its ability to discriminate between the specific regions of a modified molecule, i.e. a mutated Fc domain, as defined herein. The specific interaction of the antigen-interaction-site with its specific antigen may result in an initiation of a signal, e.g. due to the induction of a change of the conformation of the polypeptide comprising the antigen, an oligomerization of the polypeptide comprising the antigen, an oligomerization of the antigen binding receptor, etc. Thus, a specific motif in the amino acid sequence of the antigen-interaction-site and the antigen bind to each other as a result of their primary, secondary or tertiary structure as well as the result of secondary modifications of said structure. Accordingly, the term binding to does not only relate to a linear epitope but may also relate to a conformational epitope, a structural epitope or a discontinuous epitope consisting of two regions of the target molecules or parts thereof. In the context of this invention, a conformational epitope is defined by two or more discrete amino acid sequences separated in the primary sequence which comes together on the surface of the molecule when the polypeptide folds to the native protein (Sela, Science 166 (1969), 1365 and Laver, Cell 61 (1990), 553-536). Moreover, the term "binding to" is interchangeably used in the context of the present invention with the term "interacting with". The ability of the antigen binding moiety (e.g. a Fab or scFv domain) of an antigen binding receptor or an antibody to bind to a specific target antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of a antigen binding moiety to an unrelated protein is less than about 10% of the binding of the antigen binding moiety to the target antigen as measured, in particular by SPR. In certain embodiments, an antigen binding moiety that binds to the target antigen, has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). The term "specific binding" as used in accordance with the present invention means that the molecules of the invention do not or do not essentially cross-react with (poly-) peptides of similar structures, i.e. with a non-mutated parent Fc domain wherein an antigen binding receptor of the invention is capable of specific binding to a mutated Fc domain. Accordingly, the antigen binding receptor of the invention specifically binds to/interacts with a mutated Fc domain. Cross-reactivity of a panel of constructs under investigation may be tested, for example, by assessing binding of a panel of antigen binding moieties under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the mutated Fc domain of interest as well as to parent non-mutated Fc domain. Only those constructs (i.e. Fab fragments, scFvs and the like) that bind to the mutated Fc domain of interest but do not or do not essentially bind to a non-mutated parent Fc domain are considered specific for the mutated Fc domain of interest and selected for further studies in accordance with the method provided herein. These methods may comprise, inter alia, binding studies, blocking and competition studies with structurally and/or functionally closely related Fc domains. The binding studies also comprise FACS analysis, surface plasmon resonance (SPR, e.g. with BIAcore®), analytical ultracentrifugation, isothermal titration calorimetry, fluorescence anisotropy, fluorescence spectroscopy or by radiolabeled ligand binding assays.

The term "CDR" as employed herein relates to "complementary determining region", which is well known in the art. The CDRs are parts of immunoglobulins or antigen binding receptors that determine the specificity of said molecules and make contact with a specific ligand. The CDRs are the most variable part of the molecule and contribute to the antigen binding diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in "Kabat" (Sequences of Proteins of Immunological Interest", 5th edit. NIH Publication no. 91-3242 U.S. Department of Health and Human Services (1991); Chothia J. Mol. Biol. 196 (1987), 901-917) or "Chothia" (Nature 342 (1989), 877-883).

The term "CD3z" refers to T-cell surface glycoprotein CD3 zeta chain, also known as "T-cell receptor T3 zeta chain" and "CD247".

The term "chimeric antigen receptor" or "chimeric receptor" or "CAR" refers to an antigen binding receptor constituted of an extracellular portion of an antigen binding moiety (e.g. a single chain antibody domain) fused by a spacer sequence to the intracellular signaling domains of CD3z and CD28. The invention additionally provides antigen binding receptors wherein the antigen binding moiety is a Fab or a crossFab fragment. The term "CAR" is understood in its broadest form to comprise antigen binding receptors constituted of an extracellular portion comprising an antigen binding moiety fused to CD3z and fragment thereof and to CD28 and fragments thereof, optionally through one or several peptide linkers.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

By a "crossover Fab molecule" (also termed "crossFab" or "crossover Fab fragment") is meant a Fab molecule wherein either the variable regions or the constant regions of the Fab heavy and light chain are exchanged, i.e. the crossFab fragment comprises a peptide chain composed of the light chain variable region and the heavy chain constant region, and a peptide chain composed of the heavy chain variable region and the light chain constant region. For clarity, in a crossFab fragment wherein the variable regions of the Fab light chain and the Fab heavy chain are exchanged, the peptide chain comprising the heavy chain constant region is referred to herein as the heavy chain of the crossover Fab molecule. Conversely, in a crossFab fragment wherein the constant regions of the Fab light chain and the Fab heavy chain are exchanged, the peptide chain comprising the heavy chain variable region is referred to herein as the heavy chain of the crossFab fragment. Accordingly, a crossFab fragment comprises a heavy or light chain composed of the heavy chain variable and the light chain constant regions (VH-CL), and a heavy or light chain composed of the light chain variable and the heavy chain constant regions (VL-CH1). In contrast thereto, by a "conventional Fab" molecule is meant a Fab molecule in its natural format, i.e. comprising a heavy chain composed of the heavy chain variable and constant regions (VH-CH1), and a light chain composed of the light chain variable and constant regions (VL-CL).

The term "CSD" as used herein refers to co-stimulatory signaling domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

As used herein, the terms "engineer", "engineered", "engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode antigen binding molecules of the invention or fragments thereof.

A "Fab molecule" refers to a protein consisting of the VH and CH1 domain of the heavy chain (the "Fab heavy chain") and the VL and CL domain of the light chain (the "Fab light chain") of an antigen binding molecule.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the "EU numbering" system, also called the EU index, as described in Kabat et al., Sequences of Proteins of Immunological Interest, 5th Ed. Public Health Service, National Institutes of Health, Bethesda, Md., 1991. A subunit of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody consisting of two "full length antibody heavy chains" and two "full length antibody light chains". A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE.) The full length antibodies used according to the invention can be from a single species e.g. human, or they can be chimerized or humanized antibodies. In some embodiments, the full length antibodies used according to the invention, i.e. a therapeutic antibody comprising a mutated Fc domain, comprise two antigen binding sites each formed by a pair of VH and VL, which both specifically bind to the same antigen. In further embodiments, the full length antibodies used according to the invention comprise two antigen binding sites each formed by a pair of VH and VL, wherein the two antigen binding sites bind to different antigens, e.g. wherein the antibodies are bispecific. The C-terminus of the heavy or light chain of said full length antibody denotes the last amino acid at the C-terminus of said heavy or light chain.

By "fused" is meant that the components (e.g., a Fab and a transmembrane domain) are linked by peptide bonds, either directly or via one or more peptide linkers.

The terms "host cell", "host cell line" and "host cell culture" are used interchangeably and refer to cells into which exogenous nucleic acid has been introduced, including the progeny of such cells. Host cells include "transformants" and "transformed cells" which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate an antibody used according to the present invention. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody and/or an antigen binding receptor or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |

TABLE 1-continued

| CDR Definitions[1] | | | |
|---|---|---|---|
| CDR | Kabat | Chothia | AbM[2] |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of Kabat numbering to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antigen binding moiety variable region are according to the Kabat numbering system. The polypeptide sequences of the sequence listing are not numbered according to the Kabat numbering system. However, it is well within the ordinary skill of one in the art to convert the numbering of the sequences of the Sequence Listing to Kabat numbering.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human.

By "isolated nucleic acid" molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed below for polypeptides (e.g., ALIGN-2).

By an "isolated polypeptide" or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "nucleic acid molecule" relates to the sequence of bases comprising purine- and pyrimidine bases which are comprised by polynucleotides, whereby said bases represent the primary structure of a nucleic acid molecule. Herein, the term nucleic acid molecule includes DNA, cDNA, genomic DNA, RNA, synthetic forms of DNA and mixed polymers comprising two or more of these molecules. In addition, the term nucleic acid molecule includes both, sense and antisense strands. Moreover, the herein described nucleic acid molecule may contain non-natural or derivatized nucleotide bases, as will be readily appreciated by those skilled in the art.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical composition" refers to a preparation which is in such form as to permit the biological activity of an active ingredient contained therein to be effective, and which contains no additional components which are unacceptably toxic to a subject to which the formulation would be administered. A pharmaceutical composition usually comprises one or more pharmaceutically acceptable carrier(s).

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative. As used herein, term "polypeptide" refers to a molecule composed of monomers (amino acids) linearly linked by amide bonds (also known as peptide bonds). The term polypeptide refers to any chain of two or more amino acids, and does not refer to a specific length of the product. Thus, peptides, dipeptides, tripeptides, oligopeptides, protein, amino acid chain, or any other term used to refer to a chain of two or more amino acids, are included within the definition of polypeptide, and the term polypeptide may be used instead of, or interchangeably with any of these terms. The term polypeptide is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term nucleic acid molecule refers to any one or more nucleic acid segments, e.g., DNA or RNA fragments, present in a polynucleotide.

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

The term "regulatory sequence" refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

As used herein, the term "single-chain" refers to a molecule comprising amino acid monomers linearly linked by peptide bonds. In certain embodiemtns, one of the antigen binding moieties is a scFv fragment, i.e. a VH domain and a VL domain connected by a peptide linker. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

The term "SSD" as used herein refers to stimulatory signaling domain.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, cell expressing antigen binding receptors of the invention are used together with therapeutic antibodies comprising a mutated Fc domain to delay development of a disease or to slow the progression of a disease.

As used herein, the term "target antigenic determinant" is synonymous with "target antigen", "target epitope" and "target cell antigen" and refers to a site (e.g., a contiguous stretch of amino acids or a conformational configuration made up of different regions of non-contiguous amino acids) on a polypeptide macromolecule to which an antibody binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g., CD20, CEA, FAP, TNC) can be any native form of the proteins from any vertebrate source, including mammals such as primates (e.g., humans) and rodents (e.g., mice and rats), unless otherwise indicated. In a particular embodiment the target antigen is a human protein. Where reference is made to a specific target protein herein, the term encompasses the "full-length", unprocessed target protein as well as any form of the target protein that results from processing in the target cell. The term also encompasses naturally occurring variants of the target protein, e.g., splice variants or allelic variants. Exemplary human target proteins useful as antigens include, but are not limited to: CD20, CEA, FAP, TNC, MSLN, FolR1, HER1 and HER2. The ability of an antibody to bind to a specific target antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of the antibody to an unrelated protein is less than about 10% of the binding of the antibody to the target antigen as measured, e.g., by SPR. In certain embodiments, the antibody binds to the target antigen with an affinity dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

"Antibodies comprising a mutated Fc domain" according to the present invention, i.e. therapeutic antibodies may have one, two, three or more binding domains and may be monospecific, bispecific or multispecific. The antibodies can be full length from a single species, or be chimerized or humanized. For an antibody with more than two antigen binding domains, some binding domains may be identical and/or have the same specificity.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The antigen binding receptors of the invention are capable of inducing T cell activation. Suitable assays to measure T cell activation are known in the art described herein. In accordance with this invention, the term "T cell receptor" or "TCR" is commonly known in the art. In particular, herein the term "T cell receptor" refers to any T cell receptor, provided that the following three criteria are fulfilled: (i) tumor specificity, (ii) recognition of (most) tumor cells, which means that an antigen or target should be expressed in (most) tumor cells and (iii) that the TCR matches to the HLA-type of the subjected to be treated. In this context, suitable T cell receptors which fulfill the above mentioned three criteria are known in the art such as receptors recognizing NY-ESO-1 (for sequence information(s) see, e.g., PCT/GB2005/001924) and/or HER2neu (for sequence information(s) see WO-A1 2011/0280894).

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode antigen binding receptors of the invention or fragments thereof.

Antigen Binding Receptors Capable of Specific Binding to (a) Mutated Fc Domain(s)

The present invention relates to antigen binding receptors capable of specific binding to the mutated Fc domain of an antibody, i.e. a therapeutic antibody targeting a cancer cell. In particular, the present invention relates to antigen binding receptors comprising an extracellular domain comprising at least one antigen binding moiety capable of specific binding to a mutated Fc domain but not capable of specific binding to the parent non-mutated Fc domain. In preferred embodiments, the mutated Fc domain comprises at least one amino acid substitution compared to the non-mutated parent Fc domain, wherein Fc receptor binding by the mutated Fc domain is reduced compared to Fc receptor binding by the non-mutated Fc domain. In particular embodiments, the present invention relates to antigen binding receptors comprising an extracellular domain comprising at least one antigen binding moiety capable of specific binding to a mutated Fc domain, wherein the at least one antigen binding moiety is not capable of specific binding to the parent non-mutated Fc domain, wherein the mutated Fc domain comprises at least one amino acid substitution selected from the group consisting of L234, L235, I253, H310, P331, P329 and H435, in particular wherein the amino acid mutation is L234A, L235A, I253A, N297A, H310A, P329G and/or H435A, compared to the non-mutated parent Fc domain, wherein Fc receptor binding by the mutated Fc domain is reduced compared to Fc receptor binding by the non-mutated Fc domain. In one preferred embodiment, the amino acid mutation is P329G wherein binding to Fcγ receptor is reduced as measured by SPR at 25° C. In a further preferred embodiment, the amino acid mutations are I253A, H310A and H435A wherein binding to the neonatal Fc receptor (FcRn) is reduced as measured by SPR at 25° C.

The present invention further relates to the transduction of T cells, such as CD8+ T cells, CD4+ T cells, CD3+ T cells, γδ T cells or natural killer (NK) T cells, preferably CD8+ T cells, with an antigen binding receptor as described herein and their targeted recruitment, e.g., to a tumor, by an antibody molecule, e.g. a therapeutic antibody, comprising a mutated Fc domain. In one embodiment, the antibody is capable of specific binding to a tumor-specific antigen that is naturally occurring on the surface of a tumor cell.

As shown in the appended Examples, as a proof of the inventive concept, the antigen binding receptor comprising an anchoring transmembrane domain and an extracellular domain according to the invention pETR17096 (SEQ ID NO:7 as encoded by the DNA sequence shown in SEQ ID NO:19) was constructed which is capable of specific binding to a therapeutic antibody (represented by the anti-CD20 antibody comprising a heavy chain of SEQ ID NO ID: 112 and a light chain of SEQ ID NO:113) comprising the P329G mutation. Transduced T cells (Jurkat NFAT T cells) expressing the Anti-P329G-scFv-CD28ATD-CD28CSD-CD3zSSD protein (SEQ ID NO:7 as encoded by the DNA sequence shown in SEQ ID NO:19) could be strongly activated by co-incubation with the anti-CD20 antibody comprising the P329G mutation in the Fc domain together with CD20 positive tumor cells. The inventors further provided multiple formats of the antigen binding receptor capable of specific binding to a mutated Fc domain but not capable of specific binding to the non-mutated parent Fc domain to support the proof of the inventive concept.

The treatment of tumor cells by the combination of an antibody directed against a tumor antigen wherein the antibody comprises the P329G mutation together with transduced T cells expressing the Anti-P329G-Fab-ds-CD28ATD-CD28CSD-CD3zSSD protein (SEQ ID NOs: 44 (DNA) and 39, 41 (protein)) surprisingly leads to stronger activation of the transduced T cell compared to the transduced T cells expressing the Anti-P329G-scFv-CD28ATD-CD28CSD-CD3zSSD (SEQ ID NOs: 19 (DNA) and 7 (protein)) fusion protein. (see e.g. FIGS. 6 and 8 to 11).

Accordingly, it was surprisingly and unexpectedly found that T cells, preferably CD8+ T cells, that were transduced with an antigen binding receptor of the present invention can be specifically stimulated by the use of a tumor-specific antibody comprising a mutated Fc domain and recruited by the tumor-specific antibody as linking element to the tumor cell. Thus, it was surprisingly and unexpectedly shown in the present invention that pairing a tumor-specific antibody, i.e. a therapeutic antibody, comprising a mutated Fc domain with T cells transduced with an antigen binding receptor which comprise/consist of an extracellular domain comprising an antigen binding moiety capable of specific binding to the mutated Fc domain would result in a specific activation of the T cells and subsequent lysis of the tumor cell. This approach bears significant safety advantages over conventional T cell based approaches, as the T cell would be inert in the absence of the antibody comprising the mutated Fc domain and their availability may be controlled by the antibody molecule format chosen (i.e. smaller molecules for shorter half-life and vice-versa). Accordingly, the invention provides a versatile therapeutic platform wherein IgG type antibodies may be used to mark or label tumor cells as a guidance for T cell and wherein transduced T cells are specifically targeted toward the tumor cells by providing specificity for a mutated Fc domain of the IgG type antibody. After binding to the mutated Fc domain of the antibody on the surface of a tumor cell, the transduced T cell as described herein becomes activated and the tumor cell will subsequently be lysed. The platform is flexible and specific by allowing the use of diverse (existing or newly developed) target antibodies or co-application of multiple antibodies with different antigen specificity but comprising the same mutation in the Fc domain. The degree of T cell activation can further be adjusted by adjusting the dosage of the co-applied therapeutic antibody or by switching to different antibody specificities or formats. Transduced T cell according to the invention are inert without co-application of a targeting antibody comprising a mutated Fc domain because mutations to the Fc domain as described herein do not occur in natural or non-mutated immunoglobulins. Accordingly, in one embodiment, the mutated Fc domain does not naturally occur in wild type immunoglobulins.

Accordingly, the present invention relates to an antigen binding receptor comprising an extracellular domain comprising at least one antigen binding moiety capable of specific binding to a mutated Fc domain, wherein the at least one antigen binding moiety is not capable of specific binding to the parent non-mutated Fc domain, wherein the mutated Fc domain comprises at least one amino acid mutation compared to the non-mutated parent Fc domain, wherein Fc receptor binding by the mutated Fc domain and/or effector function induced by the mutated Fc domain is reduced compared to Fc receptor binding and/or effector function induced by the non-mutated Fc domain. It may be particularly desirable to use therapeutic antibodies with reduced effector function in cancer therapy since effector function may lead to severe side effects of antibody-based tumor therapies as further described herein.

In the context of the present invention, the antigen binding receptor comprises an extracellular domain that does not naturally occur in or on T cells. Thus, the antigen binding receptor is capable of providing tailored binding specificity to cells expressing the antigen binding receptor according to the invention. Cells, e.g. T cells, transduced with (an) antigen binding receptor(s) of the invention become capable of specific binding to a mutated Fc domain but not to the non-mutated parent Fc domain. Specificity is provided by the antigen binding moiety of the extracellular domain of the antigen binding receptor, such antigen binding moieties are considered to be specific for the mutated Fc domain as defined herein. In the context of the present invention and as explained herein, the antigen binding moiety capable of specific binding to a mutated Fc domain bind to/interact with the mutated Fc domain but not to/with the non-mutated parent Fc domain.

Antigen Binding Moieties

In an illustrative embodiment of the present invention, as a proof of concept, antigen binding receptors are provided comprising an anchoring transmembrane domain and an extracellular domain comprising at least one antigen binding moiety, wherein the at least one antigen binding moiety is capable of specific binding to a mutated Fc domain but not capable of specific binding to the non-mutated parent Fc domain, wherein the mutated Fc domain comprises at least one amino acid substitution compared to the non-mutated parent Fc.

In certain embodiment, at least one of the antigen binding moieties is a conventional Fab fragment, i.e. a Fab molecule consisting of a Fab light chain and a Fab heavy chain. In certain embodiment, at least one of the antigen binding moieties is a crossFab fragment, i.e. a Fab molecule consisting of a Fab light chain and a Fab heavy chain, wherein either the variable regions or the constant regions of the Fab heavy and light chain are exchanged. In certain embodiments, at least one of the antigen binding moieties is a scFv fragment. In a particular such embodiment, the C-terminus of the variable heavy chain (VH) is connected to the N-terminus of the variable light chain (VL) in the scFv molecule, optionally through a peptide linker. In certain embodiments, at least one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule, optionally through a peptide linker.

Accordingly, in the context of the present invention, the antigen binding moiety is capable of specific binding to a mutated Fc domain but not capable of specific binding to the non-mutated parent Fc domain, wherein the mutated Fc domain comprises at least one amino acid substitution compared to the non-mutated parent Fc domain.

Antigen binding moieties capable of specific binding to a mutated Fc domain may be generated by immunization of e.g. a mammalian immune system. Such methods are known in the art and e.g. are described in Burns in Methods in Molecular Biology 295:1-12 (2005). Alternatively, antigen binding moieties of the invention may be isolated by screening combinatorial libraries for antibodies with the desired activity or activities. Methods for screening combinatorial libraries are reviewed, e.g., in Lerner et al. in Nature Reviews 16:498-508 (2016). For example, a variety of methods are known in the art for generating phage display libraries and screening such libraries for antigen binding moieties possessing the desired binding characteristics. Such methods are reviewed, e.g., in Frenzel et al. in mAbs 8:1177-1194 (2016); Bazan et al. in Human Vaccines and Immunotherapeutics 8:1817-1828 (2012) and Zhao et al. in Critical Reviews in Biotechnology 36:276-289 (2016) as well as in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992) and in Marks and Bradbury in Methods in Molecular Biology 248:161-175 (Lo, ed., Human Press, Totowa, N.J., 2003). Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). In certain phage display methods, repertoires of VH and VL genes are separately cloned by polymerase chain reaction (PCR) and recombined randomly in phage libraries, which can then be screened for antigen-binding phage as described in Winter et al. in Annual Review of Immunology 12: 433-455 (1994). Phage typically display antibody fragments, either as single-chain Fv (scFv) fragments or as Fab fragments. Libraries from immunized sources provide high-affinity antigen binding moieties to the immunogen without the requirement of constructing hybridomas. Alternatively, the naive repertoire can be cloned (e.g., from human) to provide a single source of antigen binding moieties to a wide range of non-self and also self antigens without any immunization as described by Griffiths et al. in EMBO Journal 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in Journal of Molecular Biology 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936. and 2009/0002360. Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in Methods in Molecular Biology 503:135-56 (2012) and in Cherf et al. in Methods in Molecular biology 1319:155-175

(2015) as well as in the Zhao et al. in Methods in Molecular Biology 889:73-84 (2012). Methods for ribosome display are described, e.g., in He et al. in Nucleic Acids Research 25:5132-5134 (1997) and in Hanes et al. in PNAS 94:4937-4942 (1997).

In the context of the present invention, provided herein are antigen binding receptors comprising at least one antigen binding moiety capable of specific binding to a mutated Fc domain. Accordingly, transduced cells, i.e. T cells, expressing an antigen binding receptor according to the invention are capable of specific binding to the mutated Fc domain of an antibody, i.e. of a therapeutic antibody. The Fc domain confers to antibodies, i.e. therapeutic antibodies, favorable pharmacokinetic properties, including a long serum half-life which contributes to good accumulation in the target tissue and a favorable tissue-blood distribution ratio. At the same time it may, however, lead to undesirable targeting of therapeutic antibodies to cells expressing Fc receptors rather than to the preferred antigen-bearing cells. Moreover, the co-activation of Fc receptor signaling pathways may lead to cytokine release which, results in excessive activation of cytokine receptors and severe side effects upon systemic administration of therapeutic antibodies. Activation of (Fc receptor-bearing) immune cells other than T cells may even reduce efficacy of therapeutic antibodies due to the potential destruction of immune cells. Accordingly, therapeutic antibodies known in the art may be engineered or mutated to exhibit reduced binding affinity to an Fc receptor and/or reduced effector function, as compared to, e.g., a native IgGi Fc domain. The antigen binding receptors according to the invention may be used to target effector cells, e.g. T cells, expressing the antigen binding receptors according to the invention in vitro and/or in vivo to target cells, i.e. tumor cells, which are labeled with an antibody capable of specific binding to the target cells, wherein the antibody comprise an engineered and/or mutated Fc domain as described herein.

In an illustrative embodiment of the present invention, as a proof of concept, provided are antigen binding receptors capable of specific binding to a mutated Fc domain comprising the amino acid mutation P329G and effector cells expressing said antigen binding receptors. The P329G mutation reduces binding to Fcγ receptors and associated effector function. Accordingly, the mutated Fc domain comprising the P329G mutation binds to Fcγ receptors with reduced or abolished affinity compared to the non-mutated Fc domain. In an alternative illustrative embodiment of the present invention, as a proof of concept provided are antigen binding receptors capable of specific binding to a mutated Fc domain comprising the amino acid mutations I253A, H310A and H435A ("AAA"). The AAA mutations essentially abolishes binding to the FcRn.

However, antibodies with reduced with improved or diminished binding to Fc receptors (FcRs) and/or effector function comprising a mutated Fc domain are widely used in the art. Accordingly, herein provided are antigen binding receptors capable of specific binding to antibodies comprising a mutated Fc domain, such antibodies are herein also referred to as target antibodies. Accordingly, in one embodiment the antigen binding receptor of the present invention is capable of specific binding to a target antibody comprising a mutated Fc domain with reduced binding affinity to an Fc receptor and/or reduced effector function. Target antibodies with reduced effector function include those with mutation of one or more of Fc region residues 238, 265, 269, 270, 297, 327 and 329 (U.S. Pat. No. 6,737,056). Such Fc mutants include Fc mutants with mutations at two or more of amino acid positions 265, 269, 270, 297 and 327, including the so-called "DANA" Fc mutant with mutation of residues 265 and 297 to alanine (U.S. Pat. No. 7,332,581). Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).) In certain embodiments, an antigen binding receptor is provided capable of specific binding to an antibody variant comprises an Fc region with one or more amino acid mutations which improve ADCC, e.g., mutations at positions 298, 333, and/or 334 of the Fc region (EU numbering of residues). In certain embodiments, a target antibody variant comprises an Fc region with one or more amino acid mutations, which reduce or diminish FcRn binding, e.g., mutations at positions 253, and/or 310, and/or 435 of the Fc region (EU numbering of residues). In certain embodiments, the target antibody variant comprises an Fc region with the amino acid mutations at positions 253, 310 and 435. In one embodiment the mutations are I253A, H310A and H435A in an Fc region derived from a human IgG1 Fc region. See e.g., Grevys, A., et al., J. Immunol. 194 (2015) 5497-5508.

In certain embodiments, an antigen binding receptor is provided capable of specific binding to an antibody variant comprising an Fc region with one or more amino acid mutations, which reduced or diminished FcRn binding, e.g., mutations at one of the positions 310 and/or, 433 and/or 436 of the Fc region (EU numbering of residues). In certain embodiments, the target antibody variant comprises an Fc region with the amino acid mutations at positions 310, 433 and 436. In one embodiment the mutations are H310A, H433A and Y436A in an Fc region derived from a human IgG1 Fc region. In certain embodiments, a target antibody variant comprises an Fc region with one or more amino acid mutations, which increased FcRn binding, e.g., mutations at positions 252 and/or, 254 and/or 256 of the Fc region (EU numbering of residues). In certain embodiments, the target antibody variant comprises an Fc region with the amino acid mutations at positions 252, 254, and 256. In one embodiment the mutations are M252Y, S254T and T256E in an Fc region derived from a human IgG1 Fc region. In certain embodiments, an antigen binding receptor is provided capable of specific binding to an antibody variant comprising an Fc region with amino acid mutations, which diminish FcγR binding, e.g., mutations at positions 234, 235 and 329 of the Fc region (EU numbering of residues). In one embodiment the mutations are L234A and L235A (LALA). In certain embodiments, the target antibody variant further comprises D265A and/or P329G in an Fc region derived from a human IgG1 Fc region. In one embodiment the mutation is P329G ("PG") in an Fc region derived from a human IgG1 Fc region. In another embodiment, the mutations are I253A, H310A and H435A ("AAA") in an Fc region derived from a human IgG1 Fc region.

In one embodiment the antigen binding moiety is capable of specific binding to a mutated Fc domain composed of a first and a second subunit capable of stable association. In one embodiment the Fc domain is an IgG, specifically an $IgG_1$ or $IgG_4$, Fc domain. In one embodiment the Fc domain is a human Fc domain. In one embodiment the mutated Fc domain exhibits reduced binding affinity to an Fc receptor and/or reduced effector function, as compared to a native $IgG_1$ Fc domain. In one embodiment the Fc domain comprises one or more amino acid mutations that reduce binding to an Fc receptor and/or effector function.

In one preferred embodiment the one or more amino acid mutation is at one or more position selected from the group of L234, L235, and P329 (Kabat numbering). In one particular embodiment each subunit of the Fc domain comprises three amino acid mutations that reduce binding to an activating Fc receptor and/or effector function wherein said amino acid mutations are L234A, L235A and P329G. In one particular embodiment the Fc receptor is an Fcγ receptor. In one embodiment the effector function is antibody-dependent cell-mediated cytotoxicity (ADCC).

In a particular embodiment, the mutated Fc domain comprises the P329G mutation. Accordingly, the mutated Fc domain comprising the P329G mutation binds to Fcγ receptors with reduced or abolished affinity compared to the non-mutated Fc domain. In one embodiment, the extracellular domain of the antigen binding receptor comprises an antigen binding moiety capable of specific binding to an Fc domain comprising the P329G mutation, wherein the antigen binding moiety comprises a heavy chain variable region comprising at least one of:
  (a) a heavy chain complementarity determining region (CDR H) 1 amino acid sequence of RYWMN (SEQ ID NO:1);
  (b) a CDR H2 amino acid sequence of EITPDSSTI-NYTPSLKD (SEQ ID NO:2); and
  (c) a CDR H3 amino acid sequence of PYDYGAWFAS (SEQ ID NO:3).

In one embodiment the extracellular domain of the antigen binding receptor comprises an antigen binding moiety capable of specific binding to an Fc domain comprising the P329G mutation, wherein the antigen binding moiety comprises a light chain variable region comprising at least one of:
  (d) a light chain (CDR L)1 amino acid sequence of RSSTGAVTTSNYAN (SEQ ID NO:4);
  (e) a CDR L2 amino acid sequence of GTNKRAP (SEQ ID NO:5); and
  (f) a CDR L3 amino acid sequence of ALWYSNHWV (SEQ ID NO:6).

In one embodiment the extracellular domain of the antigen binding receptor comprises an antigen binding moiety capable of specific binding to an Fc domain comprising the P329G mutation, wherein the antigen binding moiety comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO:1, SEQ ID NO:2 and SEQ ID NO:3 and at least one light chain CDR selected from the group of SEQ ID NO:4, SEQ ID NO:5 and SEQ ID NO:6.

In one embodiment the extracellular domain of the antigen binding receptor comprises an antigen binding moiety capable of specific binding to an Fc domain comprising the P329G mutation, wherein the antigen binding moiety comprises the heavy chain complementarity determining region (CDRs) of SEQ ID NO:1, SEQ ID NO:2 and SEQ ID NO:3 and the light chain CDRs of SEQ ID NO:4, SEQ ID NO:5 and SEQ ID NO:6.

In one preferred embodiment the extracellular domain of the antigen binding receptor comprises an antigen binding moiety capable of specific binding to an Fc domain comprising the P329G mutation, wherein the antigen binding moiety comprises a heavy chain variable region comprising:
  (a) a heavy chain complementarity determining region (CDR H) 1 amino acid sequence of RYWMN (SEQ ID NO:1);
  (b) a CDR H2 amino acid sequence of EITPDSSTI-NYTPSLKD (SEQ ID NO:2);
  (c) a CDR H3 amino acid sequence of PYDYGAWFAS (SEQ ID NO:3);

and a light chain variable region comprising:
  (d) a light chain (CDR L)1 amino acid sequence of RSSTGAVTTSNYAN (SEQ ID NO:4);
  (e) a CDR L2 amino acid sequence of GTNKRAP (SEQ ID NO:5); and
  (f) a CDR L3 amino acid sequence of ALWYSNHWV (SEQ ID NO:6).

In one embodiment the extracellular domain of the antigen binding receptor comprises an antigen binding moiety capable of specific binding to an Fc domain comprising the P329G mutation, wherein the antigen binding moiety comprises a heavy chain variable region (VH) comprising an amino acid sequence that is at least about 95%, 96%, 97%, 98%, 99% or 100% identical to an amino acid sequence selected from SEQ ID NO:8 and SEQ ID NO:32 and a light chain variable region (VL) comprising an amino acid sequence that is at least about 95%, 96%, 97%, 98%, 99% or 100% identical to an amino acid sequence selected from SEQ ID NO:9 and SEQ ID NO:33.

In one embodiment the extracellular domain of the antigen binding receptor comprises an antigen binding moiety capable of specific binding to an Fc domain comprising the P329G mutation, wherein the antigen binding moiety comprises a heavy chain variable region (VH) comprising an amino acid sequence selected from SEQ ID NO:8 and SEQ ID NO:32, and a light chain variable region (VL) comprising an amino acid sequence selected from SEQ ID NO:9 and SEQ ID NO:33.

In one embodiment the extracellular domain of the antigen binding receptor comprises an antigen binding moiety capable of specific binding to an Fc domain comprising the P329G mutation, wherein the antigen binding moiety comprises a heavy chain variable region (VH) comprising the amino acid sequence of SEQ ID NO:32 and a light chain variable region (VL) comprising the amino acid sequence of SEQ ID NO:33.

In one preferred embodiment the extracellular domain of the antigen binding receptor comprises an antigen binding moiety capable of specific binding to an Fc domain comprising the P329G mutation, wherein the antigen binding moiety comprises a heavy chain variable region (VH) comprising the amino acid sequence of SEQ ID NO:8 and a light chain variable region (VL) comprising the amino acid sequence of SEQ ID NO:9.

In one embodiment, the at least one antigen binding moiety is a scFv, a Fab, a crossFab or a scFab fragment. In one embodiment the extracellular domain of the antigen binding receptor comprises an antigen binding moiety capable of specific binding to an Fc domain comprising the P329G mutation, wherein the antigen binding moiety is a Fab fragment.

In a preferred embodiment the extracellular domain of the antigen binding receptor comprises an antigen binding moiety capable of specific binding to an Fc domain comprising the P329G mutation, wherein the Fab fragment comprising a heavy chain of SEQ ID NO:40 and a light chain of SEQ ID NO:41.

In one embodiment the extracellular domain of the antigen binding receptor comprises an antigen binding moiety capable of specific binding to an Fc domain comprising the P329G mutation, wherein the at least one antigen binding moiety is a scFv fragment which is a polypeptide consisting of an heavy chain variable domain (VH), an light chain variable domain (VL) and a linker, wherein said variable domains and said linker have one of the following configurations in N-terminal to C-terminal direction: a) VH-linker- VL or b) VL-linker-VH. In a preferred embodiment, the scFv fragment has the configuration VH-linker-VL.

In a preferred embodiment the extracellular domain of the antigen binding receptor comprises an antigen binding moiety capable of specific binding to an Fc domain comprising the P329G mutation, wherein the scFv fragment comprises the amino acid sequence of SEQ ID NO:10.

In an alternative particular embodiment, the mutated Fc domain comprises the I253A, H310A and H435A ("AAA") mutations. The AAA mutations reduce binding to the neonatal Fc receptor (FcRn). Accordingly, the mutated Fc domain comprising the AAA mutations binds to FcRn with reduced or abolished affinity compared to the non-mutated Fc domain.

Accordingly, in one embodiment, the extracellular domain of the antigen binding receptor comprises an antigen binding moiety capable of specific binding to an Fc domain comprising the I253A, H310A and H435A mutations, wherein the antigen binding moiety comprises a heavy chain variable region comprising at least one of:
  (a) a heavy chain complementarity determining region (CDR H) 1 amino acid sequence of SYGMS (SEQ ID NO:53);
  (b) a CDR H2 amino acid sequence of SSGGSY (SEQ ID NO:54); and
  (c) a CDR H3 amino acid sequence of LGMITTG-YAMDY (SEQ ID NO:55).

In one embodiment the extracellular domain of the antigen binding receptor comprises an antigen binding moiety capable of specific binding to an Fc domain comprising the I253A, H310A and H435A mutations, wherein the antigen binding moiety comprises a light chain variable region comprising at least one of:
  (d) a light chain (CDR L)1 amino acid sequence of RSSQTIVHSTGHTYLE (SEQ ID NO:56);
  (e) a CDR L2 amino acid sequence of KVSNRFS (SEQ ID NO:57); and
  (f) a CDR L3 amino acid sequence of FQGSHVPYT (SEQ ID NO:58).

In one embodiment the extracellular domain of the antigen binding receptor comprises an antigen binding moiety capable of specific binding to an Fc domain comprising the I253A, H310A and H435A mutations, wherein the antigen binding moiety comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO:53, SEQ ID NO:54 and SEQ ID NO:55 and at least one light chain CDR selected from the group of SEQ ID NO:56, SEQ ID NO:57 and SEQ ID NO:58.

In one embodiment the extracellular domain of the antigen binding receptor comprises an antigen binding moiety capable of specific binding to an Fc domain comprising the P329G mutation, wherein the antigen binding moiety comprises the heavy chain complementarity determining region (CDRs) of SEQ ID NO:53, SEQ ID NO:54 and SEQ ID NO:55 and the light chain CDRs of SEQ ID NO:56, SEQ ID NO:57 and SEQ ID NO:58.

In a preferred embodiment the extracellular domain of the antigen binding receptor comprises an antigen binding moiety capable of specific binding to an Fc domain comprising the I253A, H310A and H435A mutations, wherein the antigen binding moiety comprises a heavy chain variable region comprising:
  (a) a heavy chain complementarity determining region (CDR H) 1 amino acid sequence of SYGMS (SEQ ID NO:53);
  (b) a CDR H2 amino acid sequence of SSGGSY (SEQ ID NO:54);
  (c) a CDR H3 amino acid sequence of LGMITTG-YAMDY (SEQ ID NO:55); and a light chain variable region comprising:
  (d) a light chain (CDR L)1 amino acid sequence of RSSQTIVHSTGHTYLE (SEQ ID NO:56);
  (e) a CDR L2 amino acid sequence of KVSNRFS (SEQ ID NO:57); and
  (f) a CDR L3 amino acid sequence of FQGSHVPYT (SEQ ID NO:58).

In one embodiment the extracellular domain of the antigen binding receptor comprises an antigen binding moiety capable of specific binding to an Fc domain comprising the I253A, H310A and H435A mutations, wherein the antigen binding moiety comprises a heavy chain variable region (VH) comprising an amino acid sequence that is at least about 95%, 96%, 97%, 98%, 99% or 100% identical to the amino acid sequence of SEQ ID NO:61 and a light chain variable region (VL) comprising an amino acid sequence that is at least about 95%, 96%, 97%, 98%, 99% or 100% identical to the amino acid sequence selected of SEQ ID NO:62.

In one embodiment the extracellular domain of the antigen binding receptor comprises an antigen binding moiety capable of specific binding to an Fc domain comprising the I253A, H310A and H435A mutations, wherein the antigen binding moiety comprises a heavy chain variable region (VH) comprising the amino acid sequence of SEQ ID NO:61, and a light chain variable region (VL) comprising the amino acid sequence of SEQ ID NO:62.

In one embodiment, the at least one antigen binding moiety is a scFv, a Fab, a crossFab or a scFab fragment. In one embodiment the extracellular domain of the antigen binding receptor comprises an antigen binding moiety capable of specific binding to an Fc domain comprising the I253A, H310A and H435A mutations, wherein the at least the antigen binding moiety is a Fab fragment. In a particular embodiment the extracellular domain of the antigen binding receptor comprises an antigen binding moiety capable of specific binding to an Fc domain comprising the I253A, H310A and H435A mutations, wherein the Fab fragment comprising a heavy chain of SEQ ID NO:64 and a light chain of SEQ ID NO:65.

In one embodiment the extracellular domain of the antigen binding receptor comprises an antigen binding moiety capable of specific binding to an Fc domain comprising the I253A, H310A and H435A mutations, wherein the at least one antigen binding moiety is a scFv fragment. In a particular embodiment the extracellular domain of the antigen binding receptor comprises an antigen binding moiety capable of specific binding to an Fc domain comprising the I253A, H310A and H435A mutations, wherein the scFv fragment comprises the amino acid sequence of SEQ ID NO:60.

In further embodiments according to the invention the antigen binding moiety comprised in the extracellular domain is a single chain Fab fragment or scFab.

Fab and scFab fragments are stabilized via the natural disulfide bond between the CL domain and the CH1 domain. Antigen binding moieties comprising a heavy chain variable domain (VH) and a light chain variable domain (VL), such as the Fab, crossFab, scFv and scFab fragments as described herein might be further stabilized by introducing interchain disulfide bridges between the VH and the VL domain. Accordingly, in one embodiment, the Fab fragment(s), the crossFab fragment(s), the scFv fragment(s) and/or the scFab fragment(s) comprised in the antigen binding receptors according to the invention might be further stabilized by generation of interchain disulfide bonds via insertion of cysteine residues (e.g., position 44 in the variable heavy chain and position 100 in the variable light chain according to Kabat numbering). Such stabilized antigen binding moieties are referred to by the term "ds" within the appended examples and Figures.

Anchoring Transmembrane Domain

In the context of the present invention, the anchoring transmembrane domain of the antigen binding receptors of the present invention may be characterized by not having a cleavage site for mammalian proteases. In the context of the present invention, proteases refer to proteolytic enzymes that are able to hydrolyze the amino acid sequence of a transmembrane domain comprising a cleavage site for the protease. The term proteases include both endopeptidases and exopeptidases. In the context of the present invention any anchoring transmembrane domain of a transmembrane protein as laid down among others by the CD-nomenclature may be used to generate the antigen binding receptors of the invention, which activate T cells, preferably CD8+ T cells, upon binding to a mutated Fc domain as defined herein.

Accordingly, in the context of the present invention, the anchoring transmembrane domain may comprise part of a murine/mouse or preferably of a human transmembrane domain. An example for such an anchoring transmembrane domain is a transmembrane domain of CD28, for example, having the amino acid sequence as shown herein in SEQ ID NO:11 (as encoded by the DNA sequence shown in SEQ ID NO:24). In the context of the present invention, the transmembrane domain of the antigen binding receptor of the present invention may comprise/consist of an amino acid sequence as shown in SEQ ID NO:11 (as encoded by the DNA sequence shown in SEQ ID NO:24).

In an illustrative embodiment of the present invention, as a proof of concept, an antigen binding receptor is provided which comprises an antigen binding moiety comprising an amino acid sequence of SEQ ID NO:10 (as encoded by the DNA sequence shown in SEQ ID NO:22), and a fragment/polypeptide part of CD28 (the Uniprot Entry number of the human CD28 is P10747 (with the version number 173 and version 1 of the sequence)) as shown herein as SEQ ID NO:71 (as encoded by the DNA sequence shown in SEQ ID NO:70). Alternatively, any protein having a transmembrane domain, as provided among others by the CD nomenclature, may be used as an anchoring transmembrane domain of the antigen binding receptor protein of the invention. As described above, the herein provided antigen binding receptor may comprise the anchoring transmembrane domain of CD28 which is located at amino acids 153 to 179, 154 to 179, 155 to 179, 156 to 179, 157 to 179, 158 to 179, 159 to 179, 160 to 179, 161 to 179, 162 to 179, 163 to 179, 164 to 179, 165 to 179, 166 to 179, 167 to 179, 168 to 179, 169 to 179, 170 to 179, 171 to 179, 172 to 179, 173 to 179, 174 to 179, 175 to 179, 176 to 179, 177 to 179 or 178 to 179 of the human full length CD28 protein as shown in SEQ ID NO:71 (as encoded by the cDNA shown in SEQ ID NO:70). Accordingly, in context of the present invention the anchoring transmembrane domain may comprise or consist of an amino acid sequence as shown in SEQ ID NO:11 (as encoded by the DNA sequence shown in SEQ ID NO:24).

In one embodiment provided is an antigen binding receptor comprising an anchoring transmembrane domain and an extracellular domain comprising a Fab fragment capable of specific binding to an Fc domain comprising the I253A, H310A and H435A mutations, wherein antigen binding receptor comprises a
(a) a heavy chain comprising the amino acid sequence of SEQ ID NO:64 fused at the C-terminus to the N-terminus of the anchoring transmembrane domain of SEQ ID NO:11, optionally through the peptide linker of SEQ ID NO:17; and
(b) a light chain comprising the amino acid sequence of SEQ ID NO:65.

In one embodiment provided is an antigen binding receptor comprising an anchoring transmembrane domain and an extracellular domain comprising a Fab fragment capable of specific binding to an Fc domain comprising the P329G mutation, wherein the antigen binding receptor comprises a
(a) a heavy chain comprising an amino acid sequence selected from SEQ ID NO:40 and SEQ ID NO:49 fused at the C-terminus to the N-terminus of the anchoring transmembrane domain of SEQ ID NO:11, optionally through the peptide linker of SEQ ID NO:17; and
(b) a light chain comprising an amino acid sequence selected from SEQ ID NO:41 and SEQ ID NO:50.

In one embodiment provided is an antigen binding receptor comprising an anchoring transmembrane domain and an extracellular domain comprising a Fab fragment capable of specific binding to an Fc domain comprising the P329G mutation, wherein the antigen binding receptor comprises a
(a) a heavy chain comprising the amino acid sequence of SEQ ID NO:40 fused at the C-terminus to the N-terminus of the anchoring transmembrane domain of SEQ ID NO:11, optionally through the peptide linker of SEQ ID NO:17; and
(b) a light chain comprising the amino acid sequence of SEQ ID NO:41.

In one preferred embodiment provided is an antigen binding receptor comprising an anchoring transmembrane domain and an extracellular domain comprising a Fab fragment capable of specific binding to an Fc domain comprising the P329G mutation, wherein the antigen binding receptor comprises a
(a) a heavy chain comprising the amino acid sequence of SEQ ID NO:49 fused at the C-terminus to the N-terminus of the anchoring transmembrane domain of SEQ ID NO:11, optionally through the peptide linker of SEQ ID NO:17; and
(b) a light chain comprising the amino acid sequence of SEQ ID NO:50.

In one embodiment provided is an antigen binding receptor comprising an anchoring transmembrane domain and an extracellular domain comprising a scFv fragment capable of specific binding to an Fc domain comprising the I253A, H310A and H435A mutations but not capable of specific binding to the non-mutated parent Fc domain, wherein the antigen binding receptor comprises the amino acid of SEQ ID NO:60 fused at the C-terminus to the N-terminus of the anchoring transmembrane domain of SEQ ID NO:11, optionally through the peptide linker of SEQ ID NO:17.

In one embodiment provided is an antigen binding receptor comprising an anchoring transmembrane domain and an extracellular domain comprising a scFv fragment capable of specific binding to an Fc domain comprising the P329G mutation but not capable of specific binding to the non-mutated parent Fc domain, wherein the antigen binding receptor comprises an amino acid sequence selected from SEQ ID NO:10 and SEQ ID NO:34 fused at the C-terminus to the N-terminus of the anchoring transmembrane domain of SEQ ID NO:11, optionally through the peptide linker of SEQ ID NO:17.

In one preferred embodiment provided is an antigen binding receptor comprising an anchoring transmembrane domain and an extracellular domain comprising a scFv fragment capable of specific binding to an Fc domain comprising the P329G mutation but not capable of specific binding to the non-mutated parent Fc domain, wherein the antigen binding receptor comprises the amino acid sequence of SEQ ID NO:10 fused at the C-terminus to the N-terminus of the anchoring transmembrane domain of SEQ ID NO:11, optionally through a peptide linker of SEQ ID NO:17.

In one embodiment provided is an antigen binding receptor comprising an anchoring transmembrane domain and an extracellular domain comprising a scFab fragment capable of specific binding to an Fc domain comprising the P329G mutation but not capable of specific binding to the non-mutated parent Fc domain, wherein the scFv fragment comprises the amino acid sequence of SEQ ID NO:34 fused at the C-terminus to the N-terminus of the anchoring transmembrane domain of SEQ ID NO:11, optionally through a peptide linker of SEQ ID NO:17.

Stimulatory Signaling Domain (SSD) and Co-Stimulatory Signaling Domain (CSD)

Preferably, the antigen binding receptor of the present invention comprises at least one stimulatory signaling domain and/or at least one co-stimulatory signaling domain. Accordingly, the herein provided antigen binding receptor preferably comprises a stimulatory signaling domain, which provides T cell activation. The herein provided antigen binding receptor may comprise a stimulatory signaling domain which is a fragment/polypeptide part of murine/mouse or human CD3z (the UniProt Entry of the human CD3z is P20963 (version number 177 with sequence number 2; the UniProt Entry of the murine/mouse CD3z is P24161 (primary citable accession number) or Q9D3G3 (secondary citable accession number) with the version number 143 and the sequence number 1)), FCGR3A (the UniProt Entry of the human FCGR3A is P08637 (version number 178 with sequence number 2)), or NKG2D (the UniProt Entry of the human NKG2D is P26718 (version number 151 with sequence number 1); the UniProt Entry of the murine/mouse NKG2D is O54709 (version number 132 with sequence number 2)).

Thus, the stimulatory signaling domain which is comprised in the herein provided antigen binding receptor may be a fragment/polypeptide part of the full length of CD3z, FCGR3A or NKG2D. The amino acid sequences of the murine/mouse full length of CD3z, or NKG2D are shown herein as SEQ ID NOs: 96 (CD3z), 100 (FCGR3A) or 104 (NKG2D) (murine/mouse as encoded by the DNA sequences shown in SEQ ID NOs:97 (CD3z), 101 (FCGR3A) or 105 (NKG2D). The amino acid sequences of the human full length CD3z, FCGR3A or NKG2D are shown herein as SEQ ID NOs:94 (CD3z), 98 (FCGR3A) or 102 (NKG2D) (human as encoded by the DNA sequences shown in SEQ ID NOs:95 (CD3z), 99 (FCGR3A) or 103 (NKG2D)). The antigen binding receptor of the present invention may comprise fragments of CD3z, FCGR3A or NKG2D as stimulatory domain, provided that at least one signaling domain is comprised. In particular, any part/fragment of CD3z, FCGR3A, or NKG2D is suitable as stimulatory domain as long as at least one signaling motive is comprised. However, more preferably, the antigen binding receptor of the present invention comprises polypeptides which are derived from human origin. Thus, more preferably, the herein provided antigen binding receptor comprises the amino acid sequences as shown herein as SEQ ID NOs:94 (CD3z), 98 (FCGR3A) or 102 (NKG2D) (human as encoded by the DNA sequences shown in SEQ ID NOs:95 (CD3z), 99 (FCGR3A) or 103 (NKG2D)). For example, the fragment/polypeptide part of the human CD3z which may be comprised in the antigen binding receptor of the present invention may comprise or consist of the amino acid sequence shown in SEQ ID NO:13 (as encoded by the DNA sequence shown in SEQ ID NO:26). Accordingly, in one embodiment the antigen binding receptor comprises the sequence as shown in SEQ ID NO:13 or a sequence which has up to 1, 2, 3, 4, 5, 6, 7, 8, 9, 10, 11, 12, 13, 14, 15, 16, 17, 18, 19, 20, 21, 22, 23, 23, 24, 25, 26, 27, 28, 29 or 30 substitutions, deletions or insertions in comparison to SEQ ID NO:13 and which is characterized by having a stimulatory signaling activity. Specific configurations of antigen binding receptors comprising a stimulatory signaling domain (SSD) are provided herein below and in the Examples and Figures. The stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

Furthermore, the herein provided antigen binding receptor preferably comprises at least one co-stimulatory signaling domain which provides additional activity to the T cell. The herein provided antigen binding receptor may comprise a co-stimulatory signaling domain which is a fragment/polypeptide part of murine/mouse or human CD28 (the UniProt Entry of the human CD28 is P10747 (version number 173 with sequence number 1); the UniProt Entry of the murine/mouse CD28 is P31041 (version number 134 with sequence number 2)), CD137 (the UniProt Entry of the human CD137 is Q07011 (version number 145 with sequence number 1); the UniProt Entry of murine/mouse CD137 is P20334 (version number 139 with sequence number 1)), OX40 (the UniProt Entry of the human OX40 is P23510 (version number 138 with sequence number 1); the UniProt Entry of murine/mouse OX40 is P43488 (version number 119 with sequence number 1)), ICOS (the UniProt Entry of the human ICOS is Q9Y6W8 (version number 126 with sequence number 1)); the UniProt Entry of the murine/mouse ICOS is Q9WV40 (primary citable accession number) or Q9JL17 (secondary citable accession number) with the version number 102 and sequence version 2)), CD27 (the UniProt Entry of the human CD27 is P26842 (version number 160 with sequence number 2); the Uniprot Entry of the murine/mouse CD27 is P41272 (version number 137 with sequence version 1)), 4-1-BB (the UniProt Entry of the murine/mouse 4-1-BB is P20334 (version number 140 with sequence version 1); the UniProt Entry of the human 4-1-BB is Q07011 (version number 146 with sequence version)), DAP10 (the UniProt Entry of the human DAP10 is Q9UBJ5 (version number 25 with sequence number 1); the UniProt entry of the murine/mouse DAP10 is Q9QUJO (primary citable accession number) or Q9R1E7 (secondary citable accession number) with the version number 101 and the sequence number 1)) or DAP12 (the UniProt Entry of the human DAP12 is O43914 (version number 146 and the sequence number 1); the UniProt entry of the murine/mouse DAP12 is O054885 (primary citable accession number) or Q9R1E7 (secondary citable accession number) with the version number 123 and the sequence number 1). In certain embodiments of the present invention the antigen binding receptor of the present invention may comprise one or more, i.e. 1, 2, 3, 4, 5, 6 or 7 of the herein defined co-stimulatory signaling domains.

Accordingly, in the context of the present invention, the antigen binding receptor of the present invention may comprise a fragment/polypeptide part of a murine/mouse or preferably of a human CD28 as first co-stimulatory signaling domain and the second co-stimulatory signaling domain is selected from the group consisting of the murine/mouse or preferably of the human CD27, CD28, CD137, OX40, ICOS, DAP10 and DAP12, or fragments thereof. Preferably, the antigen binding receptor of the present invention comprises a co-stimulatory signaling domain which is derived from a human origin. Thus, more preferably, the co-stimulatory signaling domain(s) which is (are) comprised in the antigen binding receptor of the present invention may comprise or consist of the amino acid sequence as shown in SEQ ID NO:12 (as encoded by the DNA sequence shown in SEQ ID NO:25).

Thus, the co-stimulatory signaling domain which may be optionally comprised in the herein provided antigen binding receptor is a fragment/polypeptide part of the full length CD27, CD28, CD137, OX40, ICOS, DAP10 and DAP12. The amino acid sequences of the murine/mouse full length CD27, CD28, CD137, OX40, ICOS, CD27, DAP10 or DAP12 are shown herein as SEQ ID NOs:69 (CD27), 73 (CD28), 77 (CD137), 81 (OX40), 85 (ICOS), 89 (DAP10) or 93 (DAP12) (murine/mouse as encoded by the DNA sequences shown in SEQ ID NOs:68 (CD27), 72 (CD28), 76 (CD137), 80 (OX40), 84 (ICOS), 88 (DAP10) or 92 (DAP12)). However, because human sequences are most preferred in the context of the present invention, the co-stimulatory signaling domain which may be optionally comprised in the herein provided antigen binding receptor protein is a fragment/polypeptide part of the human full length CD27, CD28, CD137, OX40, ICOS, DAP10 or DAP12. The amino acid sequences of the human full length CD27, CD28, CD137, OX40, ICOS, DAP10 or DAP12 are shown herein as SEQ ID NOs: 67(CD27), 71 (CD28), 75 (CD137), 79 (OX40), 83 (ICOS), 87 (DAP10) or 91 (DAP12) (human as encoded by the DNA sequences shown in SEQ ID NOs: 66 (CD27), 70 (CD28), 74 (CD137), 78 (OX40), 82 (ICOS), 86 (DAP10) or 90 (DAP12)).

In one preferred embodiment, the antigen binding receptor comprises CD28 or a fragment thereof as co-stimulatory signaling domain. The herein provided antigen binding receptor may comprise a fragment of CD28 as co-stimulatory signaling domain, provided that at least one signaling domain of CD28 is comprised. In particular, any part/fragment of CD28 is suitable for the antigen binding receptor of the invention as long as at least one of the signaling motives of CD28 is comprised. For example, the CD28 polypeptide which is comprised in the antigen binding receptor protein of the present invention may comprise or consist of the amino acid sequence shown in SEQ ID NO:12 (as encoded by the DNA sequence shown in SEQ ID NO:25). In the present invention the intracellular domain of CD28, which functions as a co-stimulatory signaling domain, may comprise a sequence derived from the intracellular domain of the CD28 polypeptide having the sequence(s) YMNM (SEQ ID NO:106) and/or PYAP (SEQ ID NO:107). Preferably, the antigen binding receptor of the present invention comprises polypeptides which are derived from human origin. For example, the fragment/polypeptide part of the human CD28 which may be comprised in the antigen binding receptor of the present invention may comprise or consist of the amino acid sequence shown in SEQ ID NO:12 (as encoded by the DNA sequence shown in SEQ ID NO:25). Accordingly, in the context of the present invention the antigen binding receptor comprises the sequence as shown in SEQ ID NO:12 or a sequence which has up to 1, 2, 3, 4, 5, 6, 7, 8, 9 or 10 substitutions, deletions or insertions in comparison to SEQ ID NO:12 and which is characterized by having a co-stimulatory signaling activity. Specific configurations of antigen binding receptors comprising a co-stimulatory signaling domain (CSD) are provided herein below and in the Examples and Figures. The co-stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

As mentioned above, in an embodiment of the present invention, the co-stimulatory signaling domain of the antigen binding receptor may be derived from the human CD28 gene (Uni Prot Entry No: P10747 (accession number with the entry version: 173 and version 1 of the sequence)) and provides CD28 activity, defined as cytokine production, proliferation and lytic activity of the transduced cell described herein, like a transduced T cell. CD28 activity can be measured by release of cytokines by ELISA or flow cytometry of cytokines such as interferon-gamma (IFN-γ) or interleukin 2 (IL-2), proliferation of T cells measured e.g. by ki67-measurement, cell quantification by flow cytometry, or lytic activity as assessed by real time impedence measurement of the target cell (by using e.g. an ICELLligence instrument as described e.g. in Thakur et al., Biosens Bioelectron. 35(1) (2012), 503-506; Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Düwell et al., Cell Death Differ. 21(12) (2014), 1825-1837, Erratum in: Cell Death Differ. 21(12) (2014), 161). The co-stimulatory signaling domains PYAP (AA 208 to 211 of SEQ ID NO:107) and YMNM (AA 191 to 194 of SEQ ID NO:106) are beneficial for the function of the CD28 polypeptide and the functional effects enumerated above. The amino acid sequence of the YMNM domain is shown in SEQ ID NO:106; the amino acid sequence of the PYAP domain is shown in SEQ ID NO:107. Accordingly, in the antigen binding receptor of the present invention, the CD28 polypeptide preferably comprises a sequence derived from intracellular domain of a CD28 polypeptide having the sequences YMNM (SEQ ID NO:106) and/or PYAP (SEQ ID NO:107). In the context of the present invention an intracellular domain of a CD28 polypeptide having the sequences YMNM (SEQ ID NO:106) and/or PYAP (SEQ ID NO:107) characterized by a CD28 activity, defined as cytokine production, proliferation and lytic activity of a transduced cell described herein, like e.g. a transduced T cell. Accordingly, in the context of the present invention the co-stimulatory signaling domain of the antigen binding receptors of the present invention has the amino acid sequence of SEQ ID NO:12 (human) (as encoded by the DNA sequence shown in SEQ ID NO:25). However, in the antigen binding receptor of the present invention, one or both of these domains may be mutated to FMNM (SEQ ID NO:108) and/or AYAA (SEQ ID NO:109), respectively. Either of these mutations reduces the ability of a transduced cell comprising the antigen binding receptor to release cytokines without affecting its ability to proliferate and can advantageously be used to prolong the viability and thus the therapeutic potential of the transduced cells. Or, in other words, such a non-functional mutation preferably enhances the persistence of the cells which are transduced with the herein provided antigen binding receptor in vivo.

These signaling motives may, however, be present at any site within the intracellular domain of the herein provided antigen binding receptor.

Linker and Signal Peptides

Moreover, the herein provided antigen binding receptor may comprise at least one linker (or "spacer"). A linker is usually a peptide having a length of up to 20 amino acids. Accordingly, in the context of the present invention the linker may have a length of 1, 2, 3, 4, 5, 6, 7, 8, 9, 10, 11, 12, 13, 14, 15, 16, 17, 18, 19 or 20 amino acids. For example, the herein provided antigen binding receptor may comprise a linker between the extracellular domain comprising at least one antigen binding moiety capable of specific binding to a mutated Fc domain, the anchoring transmembrane domain, the co-stimulatory signaling domain and/or the stimulatory signaling domain. Such linkers have the advantage that they increase the probability that the different polypeptides of the antigen binding receptor (i.e. the extracellular domain comprising at least one antigen binding moiety capable of specific binding to a mutated Fc domain, the anchoring transmembrane domain, the co-stimulatory signaling domain and/or the stimulatory signaling domain) fold independently and behave as expected. Thus, in the context of the present invention, the extracellular domain comprising at least one antigen binding moiety capable of specific binding to a mutated Fc domain, the anchoring transmembrane domain that does not have a cleavage site for mammalian proteases, the co-stimulatory signaling domain and the stimulatory signaling domain may be comprised in a single-chain multi-functional polypeptide. A single-chain fusion construct e.g. may consist of (a) polypeptide(s) comprising (an) extracellular domain(s) comprising at least one antigen binding moiety capable of specific binding to a mutated Fc domain, (an) anchoring transmembrane domain(s), (a) co-stimulatory signaling domain(s) and/or (a) stimulatory signaling domain(s). In alternative embodiments, the antigen binding receptor comprises a antigen binding moiety which is not a single chain fusion construct, i.e. the antigen binding moiety is a Fab or a crossFab fragment. In such embodiments the antigen binding receptor is not a single chain fusion construct comprising only one polypeptide chain. Preferably such constructs will comprise a single chain heavy chain fusion polypeptide combined with an immunoglobulin light chain as described herein, e.g., heavy chain fusion polypeptide comprises (an) immunoglobulin heavy chain(s), (an) anchoring transmembrane domain(s), (a) co-stimulatory signaling domain(s) and/or (a) stimulatory signaling domain(s) and is combined with (an) immunoglobulin light chain(s). Accordingly, the antigen binding moiety, the anchoring transmembrane domain, the co-stimulatory signaling domain and the stimulatory signaling domain may be connected by one or more identical or different peptide linker as described herein. For example, in the herein provided antigen binding receptor the linker between the extracellular domain comprising at least one antigen binding moiety capable of specific binding to a mutated Fc domain and the anchoring transmembrane domain may comprise or consist of the amino and amino acid sequence as shown in SEQ ID NO:17. Accordingly, the anchoring transmembrane domain, the co-stimulatory signaling domain and/or the stimulatory signaling domain may be connected to each other by peptide linkers or alternatively, by direct fusion of the domains.

In some embodiments according to the invention the antigen binding moiety comprised in the extracellular domain is a single-chain variable fragment (scFv) which is a fusion protein of the variable regions of the heavy (VH) and light chains (VL) of an antibody, connected with a short linker peptide often to about 25 amino acids. The linker is usually rich in glycine for flexibility, as well as serine or threonine for solubility, and can either connect the N-terminus of the VH with the C-terminus of the VL, or vice versa. For example, in the herein provided antigen binding receptor the linker may have the amino and amino acid sequence as shown in SEQ ID NO:16. The scFv antigen binding moiety as described herein retains the specificity of the original antibody, despite removal of the constant regions and the introduction of the linker. scFv antibodies are, e.g. described in Houston, J. S., Methods in Enzymol. 203 (1991) 46-96).

In some embodiments according to the invention the antigen binding moiety comprised in the extracellular domain is a single chain Fab fragment or scFab which is a polypeptide consisting of an heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain.

In some embodiments according to the invention the antigen binding moiety comprised in the extracellular domain is a crossover single chain Fab fragment which is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids.

The herein provided antigen binding receptor or parts thereof may comprise a signal peptide. Such a signal peptide will bring the protein to the surface of the T cell membrane. For example, in the herein provided antigen binding receptor the signal peptide may have the amino and amino acid sequence as shown in SEQ ID NO:110 (as encoded by the DNA sequence shown in SEQ ID NO:111).

T Cell Activating Antigen Binding Receptors Capable of Specific Binding to Mutated Fc Domains The components of the antigen binding receptors as described herein can be fused to each other in a variety of configurations to generate T cell activating antigen binding receptors.

In some embodiments, the antigen binding receptor comprises an extracellular domain composed of a heavy chain variable domain (VH) and a light chain variable domain (VL) connected to an anchoring transmembrane domain. In some embodiments, the VH domain is fused at the C-terminus to the N-terminus of the VL domain, optionally through a peptide linker. In other embodiments, the antigen binding receptor further comprises a stimulatory signaling domain and/or a co-stimulatory signaling domain. In a specific such embodiment, the antigen binding receptor essentially consists of a VH domain and a VL domain, an anchoring transmembrane domain, and optionally a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain. Optionally, the antigen binding receptor further comprises a co-stimulatory signaling domain. In one such specific embodiment, the antigen binding receptor essentially consists of a VH domain and a VL domain, an anchoring transmembrane domain, a stimulatory signaling domain and a co-stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain, wherein the stimulatory signaling domain is fused at the C-terminus to the N-terminus of the co-stimulatory signaling domain. In an alternative embodiment, the co-stimulatory signaling domain is connected to the anchoring transmembrane domain instead of the stimulatory signaling domain. In a preferred embodiment, the antigen binding receptor essentially consists of a VH domain and a VL domain, an anchoring transmembrane domain, a co-stimulatory signaling domain and a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the co-stimulatory signaling domain, wherein the co-stimulatory signaling domain is fused at the C-terminus to the N-terminus of the stimulatory signaling domain.

In preferred embodiments, one of the binding moieties is a Fab fragment or a crossFab fragment. In one preferred embodiment, the antigen binding moiety is fused at the C-terminus of the Fab or crossFab heavy chain to the N-terminus of the anchoring transmembrane domain, optionally through a peptide linker. In an alternative embodiment, the antigen binding moiety is fused at the C-terminus of the Fab or crossFab light chain to the N-terminus of the anchoring transmembrane domain, optionally through a peptide linker. In other embodiments, the antigen binding receptor further comprises a stimulatory signaling domain and/or a co-stimulatory signaling domain. In a specific such embodiment, the antigen binding receptor essentially consists of a Fab or crossFab fragment, an anchoring transmembrane domain, and optionally a stimulatory signaling domain connected by one or more peptide linkers, wherein the Fab or crossFab fragment is fused at the C-terminus of the heavy or light chain to the N-terminus of the anchoring transmembrane domain, wherein the anchoring transmembrane domain is fused at the C-terminus to the N-terminus of the stimulatory signaling domain. Preferably, the antigen binding receptor further comprises a co-stimulatory signaling domain. In one such embodiment, the antigen binding receptor essentially consists of a Fab or crossFab fragment, an anchoring transmembrane domain, a stimulatory signaling domain and a co-stimulatory signaling domain connected by one or more peptide linkers, wherein the Fab or crossFab fragment is fused at the C-terminus of the heavy or light chain to the N-terminus of the anchoring transmembrane domain, wherein the stimulatory signaling domain is fused at the C-terminus to the N-terminus of the co-stimulatory signaling domain. In a preferred embodiment, the co-stimulatory signaling domain is connected to the anchoring transmembrane domain instead of the stimulatory signaling domain. In a most preferred embodiment, the antigen binding receptor essentially consists of a Fab or crossFab fragment, an anchoring transmembrane domain, a co-stimulatory signaling domain and a stimulatory signaling domain, wherein the Fab or crossFab fragment is fused at the C-terminus of the heavy chain to the N-terminus of the anchoring transmembrane domain through a peptide linker, wherein the anchoring transmembrane domain is fused at the C-terminus to the N-terminus of the co-stimulatory signaling domain, wherein the co-stimulatory signaling domain is fused at the C-terminus to N-terminus of the stimulatory signaling domain.

The antigen binding moiety, the anchoring transmembrane domain and the stimulatory signaling and/or co-stimulatory signaling domains may be fused to each other directly or through one or more peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers, wherein "n" is generally a number between 1 and 10, typically between 2 and 4. A preferred peptide linker for connecting the antigen binding moiety and the anchoring transmembrane moiety is GGGGS ($G_4S$) according to SEQ ID NO 17. An exemplary peptide linker suitable for connecting variable heavy chain (VH) and the variable light chain (VL) is GGGSGGGSGGGSGGGS $(G_4S)_4$ according to SEQ ID NO 16.

Additionally, linkers may comprise (a portion of) an immunoglobulin hinge region. Particularly where an antigen binding moiety is fused to the N-terminus of an anchoring transmembrane domain, it may be fused via an immunoglobulin hinge region or a portion thereof, with or without an additional peptide linker.

As described herein, the antigen binding receptors of the present invention comprise an extracellular domain comprising at least one antigen binding moiety. An antigen binding receptor with a single antigen binding moiety capable of specific binding to a target cell antigen is useful and preferred, particularly in cases where high expression of the antigen binding receptor is needed. In such cases, the presence of more than one antigen binding moiety specific for the target cell antigen may limit the expression efficiency of the antigen binding receptor.

In other cases, however, it will be advantageous to have an antigen binding receptor comprising two or more antigen binding moieties specific for a target cell antigen, for example to optimize targeting to the target site or to allow crosslinking of target cell antigens.

In one particular embodiment, the antigen binding receptor comprises one antigen binding moiety capable of specific binding to a mutated Fc domain, in particular an IgG1 Fc domain, comprising the P329G mutation. In one embodiment, the antigen binding moiety capable of specific binding to a mutated Fc domain but not capable of specific binding to the non-mutated parent Fc domain is a scFv, a Fab or a crossFab.

In one embodiment, the antigen binding moiety is fused at the C-terminus of the scFv fragment or at the C-terminus of the Fab or crossFab heavy chain to the N-terminus of an anchoring transmembrane domain, optionally through a peptide linker. In one embodiment the peptide linker comprises the amino acid sequence GGGGS (SEQ ID NO:16). In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof. In a preferred embodiment, the anchoring transmembrane domain is the CD28 transmembrane domain or a fragment thereof. In a particular embodiment, the anchoring transmembrane domain comprises or consist of the amino acid sequence of FWVLVVVGGVLACYSLL-VTVAFIIFWV (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, of CD28, of CD137, of OX40, of ICOS, of DAP10 and of DAP12, or fragments thereof as described herein before. In a preferred embodiment, the co-stimulatory signaling domain is the intracellular domain of CD28 or a fragment thereof. In a particular embodiment the co-stimulatory signaling domain comprises or consists of the sequence RSKRSRLLHSDYMNMTPRRPGPTRKHYQPYAPPRD-FAAYRS (SEQ ID NO:12). In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof. In a particular embodiment the co-stimulatory signaling domain comprises or consists of the sequence:

```
                                            (SEQ ID NO: 13)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.
```

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGD-VEENPGP (T2A) according to SEQ ID NO:18.

In a particular embodiment, the antigen binding receptor comprises an anchoring transmembrane domain and an extracellular domain comprising at least one antigen binding moiety, wherein the at least one antigen binding moiety is a scFv fragment capable of specific binding to a mutated Fc domain but not capable of specific binding to the non-mutated parent Fc domain, wherein the mutated Fc domain comprises the P329G mutation. The P329G mutation reduces Fcγ receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration scFv-ATD-CSD-SSD. In a preferred embodiment, the antigen binding receptor has the configuration scFv-G₄S-ATD-CSD-SSD, wherein G₄S is a linker comprising the sequence GGGGS of SEQ ID NO:17. Optionally, a reporter protein can be added to the C-terminus of the antigen binding receptor, optionally through a peptide linker.

In a particular embodiment, the antigen binding moiety is a scFv fragment capable of specific binding to a mutated Fc domain comprising the P329G mutation, wherein the antigen binding moiety comprises at least one heavy chain complementarity determining region (CDR) selected from the group consisting of SEQ ID NO:1, SEQ ID NO:2 and SEQ ID NO:3 and at least one light chain CDR selected from the group of SEQ ID NO:4, SEQ ID NO:5, SEQ ID NO:6.

In a preferred embodiment, the antigen binding moiety is a scFv capable of specific binding to a mutated Fc domain comprising the P329G mutation, wherein the antigen binding moiety comprises the complementarity determining region (CDR H) 1 amino acid sequence RYWMN (SEQ ID NO:1), the CDR H2 amino acid sequence EITPDSSTI-NYTPSLKD (SEQ ID NO:2), the CDR H3 amino acid sequence PYDYGAWFAS (SEQ ID NO:3), the light chain complementary-determining region (CDR L) 1 amino acid sequence RSSTGAVTTSNYAN (SEQ ID NO:4), the CDR L2 amino acid sequence GTNKRAP (SEQ ID NO:5) and the CDR L3 amino acid sequence ALWYSNHWV (SEQ ID NO:6).

In one embodiment the present invention provides an antigen binding receptor comprising in order from the N-terminus to the C-terminus:

(i) an antigen binding moiety which is a scFv fragment capable of specific binding to a mutated Fc domain comprising the P329G mutation, wherein the scFv fragment comprises a heavy chain variable region (VH) comprising the heavy chain complementarity determining region (CDR) 1 of SEQ ID NO:1, the heavy chain CDR 2 of SEQ ID NO:2, the heavy chain CDR 3 of SEQ ID NO:3, and a light chain variable region (VH) comprising the light chain CDR 1 of SEQ ID NO:4, the light chain CDR 2 of SEQ ID NO:5 and the light chain CDR 3 of SEQ ID NO:6;

(ii) a peptide linker, in particular the peptide linker of SEQ ID NO:17;

(iii) an anchoring transmembrane domain, in particular the anchoring transmembrane domain of SEQ ID NO:11;

(iii) a co-stimulatory signaling domain, in particular the co-stimulatory signaling domain of SEQ ID NO:12; and (iv) a stimulatory signaling domain, in particular the stimulatory signaling domain of SEQ ID NO:13.

In one embodiment, the present invention provides an antigen binding receptor comprising in order from the N-terminus to the C-terminus:

(i) an antigen binding moiety which is a scFv molecule capable of specific binding to a mutated Fc domain comprising the P329G mutation, wherein the scFv comprises a heavy chain variable domain (VH) selected from SEQ ID NO:8 and SEQ ID NO:32 and the light chain variable domain (VL) selected from SEQ ID NO:9 and SEQ ID NO:33;

(ii) a peptide linker, in particular the peptide linker of SEQ ID NO:17;

(iii) an anchoring transmembrane domain, in particular the anchoring transmembrane domain of SEQ ID NO:11;

(iii) a co-stimulatory signaling domain, in particular the co-stimulatory signaling domain of SEQ ID NO:12; and (iv) a stimulatory signaling domain, in particular the stimulatory signaling domain of SEQ ID NO:13.

In a preferred embodiment, the present invention provides an antigen binding receptor comprising in order from the N-terminus to the C-terminus (i) an antigen binding moiety which is a scFv molecule capable of specific binding to a mutated Fc domain comprising the P329G mutation, wherein the scFv comprises the heavy chain variable domain (VH) SEQ ID NO:8 and the light chain variable domain (VL) SEQ ID NO:9;

(ii) a peptide linker, in particular the peptide linker of SEQ ID NO:17;

(iii) an anchoring transmembrane domain, in particular the anchoring transmembrane domain of SEQ ID NO:11;

(iii) a co-stimulatory signaling domain, in particular the co-stimulatory signaling domain of SEQ ID NO:12; and (iv) a stimulatory signaling domain, in particular the stimulatory signaling domain of SEQ ID NO:13.

In a preferred embodiment, the present invention provides an antigen binding receptor comprising in order from the N-terminus to the C-terminus (i) an antigen binding moiety which is a scFv molecule capable of specific binding to a mutated Fc domain comprising the P329G mutation, wherein the scFv comprises an amino acid sequence of SEQ ID NO:10 or SEQ ID NO:34;

(ii) a peptide linker, in particular the peptide linker of SEQ ID NO:17;

(iii) an anchoring transmembrane domain, in particular the anchoring transmembrane domain of SEQ ID NO:11;

(iii) a co-stimulatory signaling domain, in particular the co-stimulatory signaling domain of SEQ ID NO:12; and (iv) a stimulatory signaling domain, in particular the stimulatory signaling domain of SEQ ID NO:13.

In a particular embodiment, the antigen binding moiety is capable of specific binding to a mutated Fc domain comprising the P329G mutation, wherein the antigen binding receptor comprises an amino acid sequence that is at least about 95%, 96%, 97%, 98%, 99% or 100% identical to the amino acid sequence of: SEQ ID NO:31.

In a preferred embodiment, the antigen binding moiety is capable of specific binding to a mutated Fc domain comprising the P329G mutation, wherein the antigen binding receptor comprises the amino acid sequence of: SEQ ID NO:31

In a preferred embodiment, the antigen binding moiety is a Fab fragment. In one embodiment, the antigen binding moiety is fused at the C-terminus of the Fab heavy chain to the N-terminus of an anchoring transmembrane domain. In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof. In a preferred embodiment, the anchoring transmembrane domain is the CD28 transmembrane domain or a fragment thereof.

In a particular embodiment, the anchoring transmembrane domain is FWVLVVVGGVLACYSLLVTVAFIIFWV (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, CD28, CD137, OX40, ICOS, DAP10 and DAP12, or fragments thereof as described herein before. In a preferred embodiment, the co-stimulatory signaling domain is the intracellular domain of CD28 or a fragment thereof. In a particular embodiment the co-stimulatory signaling domain comprises or consists of the sequence: RSKRSRLLHSDYMNMT-PRRPGPTRKHYQPYAPPRDFAAYRS (SEQ ID NO:12). In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof. In a particular embodiment the co-stimulatory signaling domain comprises or consists of the sequence:

(SEQ ID NO: 13)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGD-VEENPGP (T2A) of SEQ ID NO:18.

In a particular embodiment, the antigen binding receptor comprises an anchoring transmembrane domain and an extracellular domain comprising at least one antigen binding moiety, wherein the at least one antigen binding moiety is a Fab fragment capable of specific binding to a mutated Fc domain but not capable of specific binding to the non-mutated parent Fc domain, wherein the mutated Fc domain comprises the P329G mutation, wherein the P329G mutation reduces Fcγ receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration Fab-ATD-CSD-SSD. In a preferred embodiment, the antigen binding receptor has the configuration Fab-$G_4$S-ATD-CSD-SSD, wherein $G_4$S is a linker comprising the sequence GGGGS of SEQ ID NO:17. Optionally, a reporter protein can be added to the C-terminus of the antigen binding receptor, optionally through a peptide linker. In a particular embodiment, the antigen binding moiety is capable of specific binding to a mutated Fc domain comprising the P329G mutation, wherein the antigen binding moiety is a Fab fragment comprising at least one heavy chain complementarity determining region (CDR) selected from the group consisting of SEQ ID NO:1, SEQ ID NO:2 and SEQ ID NO:3 and at least one light chain CDR selected from the group of SEQ ID NO:4, SEQ ID NO:5, SEQ ID NO:6.

In a preferred embodiment, the antigen binding moiety is a Fab fragment capable of specific binding to a mutated Fc domain comprising the P329G mutation, wherein the antigen binding moiety comprises the complementarity determining region (CDR H) 1 amino acid sequence RYWMN (SEQ ID NO:1), the CDR H2 amino acid sequence EITPDSSTINYTPSLKD (SEQ ID NO:2), the CDR H3 amino acid sequence PYDYGAWFAS (SEQ ID NO:3), the light chain complementary-determining region (CDR L) 1 amino acid sequence RSSTGAVTTSNYAN (SEQ ID NO:4), the CDR L2 amino acid sequence GTNKRAP (SEQ ID NO:5) and the CDR L3 amino acid sequence ALWYSNHWV (SEQ ID NO:6).

In one embodiment the present invention provides an antigen binding receptor comprising in order from the N-terminus to the C-terminus
(i) an antigen binding moiety which is a Fab molecule capable of specific binding to a mutated Fc domain comprising the P329G mutation, comprising the heavy chain complementarity determining region (CDR) 1 of SEQ ID NO:1, the heavy chain CDR 2 of SEQ ID NO:2, the heavy chain CDR 3 of SEQ ID NO:3, the light chain CDR 1 of SEQ ID NO:4, the light chain CDR 2 of SEQ ID NO:5 and the light chain CDR 3 of SEQ ID NO:6;
(ii) a peptide linker, in particular the peptide linker of SEQ ID NO:17;
(iii) an anchoring transmembrane domain, in particular the anchoring transmembrane domain of SEQ ID NO:11;
(iii) a co-stimulatory signaling domain, in particular the co-stimulatory signaling domain of SEQ ID NO:12; and
(iv) a stimulatory signaling domain, in particular the stimulatory signaling domain of SEQ ID NO:13.

In one embodiment the present invention provides an antigen binding receptor comprising:
a) a heavy chain fusion polypeptide comprising in order from the N-terminus to the C-terminus;
(i) a heavy chain comprising the heavy chain complementarity determining region (CDR) 1 of SEQ ID NO:1, the heavy chain CDR 2 of SEQ ID NO:2, the heavy chain CDR 3 of SEQ ID NO:3;
(ii) a peptide linker, in particular the peptide linker of SEQ ID NO:17;
(iii) an anchoring transmembrane domain, in particular the anchoring transmembrane domain of SEQ ID NO:11;
(iii) a co-stimulatory signaling domain, in particular the co-stimulatory signaling domain of SEQ ID NO:12; and
(iv) a stimulatory signaling domain, in particular the stimulatory signaling domain of SEQ ID NO:13 and
b) a light chain comprising the light chain CDR 1 of SEQ ID NO:4, the light chain CDR 2 of SEQ ID NO:5 and the light chain CDR 3 of SEQ ID NO:6.

In one embodiment the present invention provides an antigen binding receptor comprising:
a) a heavy chain fusion polypeptide comprising in order from the N-terminus to the C-terminus;
(i) the heavy chain variable domain (VH) SEQ ID NO: 8;
(ii) a peptide linker, in particular the peptide linker of SEQ ID NO:17;
(iii) an anchoring transmembrane domain, in particular the anchoring transmembrane domain of SEQ ID NO:11;
(iii) a co-stimulatory signaling domain, in particular the co-stimulatory signaling domain of SEQ ID NO:12; and
(iv) a stimulatory signaling domain, in particular the stimulatory signaling domain of SEQ ID NO:13 and
b) the light chain variable domain (VL) SEQ ID NO:9.

In one embodiment the antigen binding moiety is a Fab fragment comprising a heavy chain comprising or consisting of an amino acid sequence of SEQ ID NO:40 or SEQ ID NO:49, and a light chain comprising or consisting of the amino acid sequence of SEQ ID NO:41 or SEQ ID NO:50.

In a preferred embodiment the antigen binding moiety is a Fab fragment comprising a heavy chain comprising or consisting of an amino acid sequence of SEQ ID NO:40 and a light chain comprising or consisting of the amino acid sequence of SEQ ID NO:41.

In a particular embodiment, the antigen binding moiety is a Fab fragment capable of specific binding to a mutated Fc domain comprising the P329G mutation, wherein the antigen binding receptor comprises a heavy chain fusion polypeptide comprising an amino acid sequence that is at least about 95%, 96%, 97%, 98%, 99% or 100% identical to an amino acid sequence selected from the group of SEQ ID NO:39 and SEQ ID NO:48 and a light chain polypeptide comprising an amino acid sequence that is at least about 95%, 96%, 97%, 98%, 99% or 100% identical to an amino acid sequence selected from the group of SEQ ID NO:41 and SEQ ID NO:50.

In a preferred embodiment, the antigen binding moiety is a Fab fragment capable of specific binding to a mutated Fc domain comprising the P329G mutation, wherein the antigen binding receptor comprises a heavy chain fusion polypeptide comprising the amino acid sequence of SEQ ID NO:39 and a light chain polypeptide comprising the amino acid sequence of SEQ ID NO:41.

In an alternative embodiment, the antigen binding receptor comprises one antigen binding moiety capable of specific binding to a mutated Fc domain, in particular an IgG1 Fc domain, comprising the mutations I253A, H310A and H435A ("AAA"), In one embodiment, antigen binding moiety capable of specific binding to a mutated Fc domain but not capable of specific binding to the non-mutated parent Fc domain is a scFv, a Fab or a crossFab.

In one embodiment, the antigen binding moiety is fused at the C-terminus of the scFv fragment or at the C-terminus of the Fab or crossFab heavy chain to the N-terminus of an anchoring transmembrane domain, optionally through a peptide linker. In one embodiment the peptide linker comprises the amino acid sequence GGGGS (SEQ ID NO:16). In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof. In a preferred embodiment, the anchoring transmembrane domain is the CD28 transmembrane domain or a fragment thereof. In a particular embodiment, the anchoring transmembrane domain comprises or consist of the amino acid sequence of FWVLVVVGGVLACYSLL-VTVAFIIFWV (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, of CD28, of CD137, of OX40, of ICOS, of DAP10 and of DAP12, or fragments thereof as described herein before. In a preferred embodiment, the co-stimulatory signaling domain is the intracellular domain of CD28 or a fragment thereof. In a particular embodiment the co-stimulatory signaling domain comprises or consists of the sequence: RSKRSRLLHSDYMNMTPRRPGPTRKHYQPYAPPRD-FAAYRS (SEQ ID NO:12). In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof. In a particular embodiment the co-stimulatory signaling domain comprises or consists of the sequence:

```
                                          (SEQ ID NO: 13)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.
```

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGD-VEENPGP (T2A) according to SEQ ID NO:18.

In a particular embodiment, the antigen binding receptor comprises an anchoring transmembrane domain and an extracellular domain comprising at least one antigen binding moiety, wherein the at least one antigen binding moiety is a scFv fragment capable of specific binding to a mutated Fc domain but not capable of specific binding to the non-mutated parent Fc domain, wherein the mutated Fc domain comprises the I253A, H310A and H435A mutations. The I253A, H310A and H435A mutations reduce FcRn receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration scFv-ATD-CSD-SSD. In a preferred embodiment, the antigen binding receptor has the configuration scFv-$G_4S$-ATD-CSD-SSD, wherein $G_4S$ is a linker comprising the sequence GGGGS of SEQ ID NO:17. Optionally, a reporter protein can be added to the C-terminus of the antigen binding receptor, optionally through a peptide linker.

In a particular embodiment, the antigen binding moiety is a scFv fragment capable of specific binding to a mutated Fc domain comprising the I253A, H310A and H435A mutations, wherein the antigen binding moiety comprises at least one heavy chain complementarity determining region (CDR) selected from the group consisting of SEQ ID NO:53, SEQ ID NO:54 and SEQ ID NO:55 and at least one light chain CDR selected from the group of SEQ ID NO:56, SEQ ID NO:57, SEQ ID NO:58.

In a preferred embodiment, the antigen binding moiety is a scFv capable of specific binding to a mutated Fc domain comprising the I253A, H310A and H435A mutations, wherein the antigen binding moiety comprises the complementarity determining region (CDR H) 1 amino acid sequence SYGMS (SEQ ID NO:53), the CDR H2 amino acid sequence SSGGSY (SEQ ID NO:54), the CDR H3 amino acid sequence LGMITTGYAMDY (SEQ ID NO:55), the light chain complementarity-determining region (CDR L) 1 amino acid sequence RSSQTIVHSTGHTYLE (SEQ ID NO:56), the CDR L2 amino acid sequence KVSNRFS (SEQ ID NO:57) and the CDR L3 amino acid sequence FQGSHVPYT (SEQ ID NO:58).

In one embodiment the present invention provides an antigen binding receptor comprising in order from the N-terminus to the C-terminus:
(i) an antigen binding moiety which is a scFv fragment capable of specific binding to a mutated Fc domain comprising the I253A, H310A and H435A mutations, wherein the scFv fragment comprises a heavy chain variable region (VH) comprising the heavy chain complementarity determining region (CDR) 1 of SEQ ID NO:53, the heavy chain CDR 2 of SEQ ID NO:54, the heavy chain CDR 3 of SEQ ID NO:55, and a light chain variable region (VH) comprising the light chain CDR 1 of SEQ ID NO:56, the light chain CDR 2 of SEQ ID NO:57 and the light chain CDR 3 of SEQ ID NO:58;
(ii) a peptide linker, in particular the peptide linker of SEQ ID NO:17;
(iii) an anchoring transmembrane domain, in particular the anchoring transmembrane domain of SEQ ID NO:11;
(iii) a co-stimulatory signaling domain, in particular the co-stimulatory signaling domain of SEQ ID NO:12; and
(iv) a stimulatory signaling domain, in particular the stimulatory signaling domain of SEQ ID NO:13.

In one embodiment, the present invention provides an antigen binding receptor comprising in order from the N-terminus to the C-terminus:
(i) an antigen binding moiety which is a scFv molecule capable of specific binding to a mutated Fc domain comprising the I253A, H310A and H435A mutations, wherein the scFv comprises the heavy chain variable domain (VH) of SEQ ID NO:61 and the light chain variable domain (VL) of SEQ ID NO:62;
(ii) a peptide linker, in particular the peptide linker of SEQ ID NO:17;
(iii) an anchoring transmembrane domain, in particular the anchoring transmembrane domain of SEQ ID NO:11;
(iii) a co-stimulatory signaling domain, in particular the co-stimulatory signaling domain of SEQ ID NO:12; and
(iv) a stimulatory signaling domain, in particular the stimulatory signaling domain of SEQ ID NO:13.

In one embodiment, the present invention provides an antigen binding receptor comprising in order from the N-terminus to the C-terminus:
(i) an antigen binding moiety which is a scFv molecule capable of specific binding to a mutated Fc domain comprising the I253A, H310A and H435A mutations, wherein the scFv comprises the amino acid sequence of SEQ ID NO:60;
(ii) a peptide linker, in particular the peptide linker of SEQ ID NO:17;
(iii) an anchoring transmembrane domain, in particular the anchoring transmembrane domain of SEQ ID NO:11;
(iii) a co-stimulatory signaling domain, in particular the co-stimulatory signaling domain of SEQ ID NO:12; and
(iv) a stimulatory signaling domain, in particular the stimulatory signaling domain of SEQ ID NO:13.

In a particular embodiment, the antigen binding moiety is capable of specific binding to a mutated Fc domain comprising the I253A, H310A and H435A mutations, wherein the antigen binding receptor comprises an amino acid sequence that is at least about 95%, 96%, 97%, 98%, 99% or 100% identical to the amino acid sequence of: SEQ ID NO:59.

In a preferred embodiment, the antigen binding moiety is capable of specific binding to a mutated Fc domain comprising the I253A, H310A and H435A mutations, wherein the antigen binding receptor comprises the amino acid sequence of: SEQ ID NO:595

In a preferred embodiment, the antigen binding moiety is a Fab fragment. In one embodiment, the antigen binding moiety is fused at the C-terminus of the Fab heavy chain to the N-terminus of an anchoring transmembrane domain. In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof. In a preferred embodiment, the anchoring transmembrane domain is the CD28 transmembrane domain or a fragment thereof.

In a particular embodiment, the anchoring transmembrane domain is FWVLVVVGGVLACYSLLVTVAFIIFWV (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, CD28, CD137, OX40, ICOS, DAP10 and DAP12, or fragments thereof as described herein before. In a preferred embodiment, the co-stimulatory signaling domain is the intracellular domain of CD28 or a fragment thereof. In a particular embodiment the co-stimulatory signaling domain comprises or consists of the sequence RSKRSRLLHSDYMNMT-PRRPGPTRKHYQPYAPPRDFAAYRS (SEQ ID NO:12). In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof. In a particular embodiment the co-stimulatory signaling domain comprises or consists of the sequence:

```
                                          (SEQ ID NO: 13)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.
```

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGD-VEENPGP (T2A) of SEQ ID NO:18.

In a particular embodiment, the antigen binding receptor comprises an anchoring transmembrane domain and an extracellular domain comprising at least one antigen binding moiety, wherein the at least one antigen binding moiety is a Fab fragment capable of specific binding to a mutated Fc domain but not capable of specific binding to the non-mutated parent Fc domain, wherein the mutated Fc domain comprises the I253A, H310A and H435A mutations, wherein the I253A, H310A and H435A mutations reduce FcRn receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration Fab-ATD-CSD-SSD. In a preferred embodiment, the antigen binding receptor has the configuration Fab-G$_4$S-ATD-CSD-SSD, wherein G$_4$S is a linker comprising the sequence GGGGS of SEQ ID NO:17. Optionally, a reporter protein can be added to the C-terminus of the antigen binding receptor, optionally through a peptide linker.

In a particular embodiment, the antigen binding moiety is capable of specific binding to a mutated Fc domain comprising the I253A, H310A and H435A mutations, wherein the antigen binding moiety is a Fab fragment comprising at least one heavy chain complementarity determining region (CDR) selected from the group consisting of SEQ ID NO:53, SEQ ID NO:54 and SEQ ID NO:55 and at least one light chain CDR selected from the group of SEQ ID NO:56, SEQ ID NO:57, SEQ ID NO:58.

In a preferred embodiment, the antigen binding moiety is a Fab fragment capable of specific binding to a mutated Fc domain comprising the I253A, H310A and H435A mutations, wherein the antigen binding moiety comprises the complementarity determining region (CDR H) 1 amino acid sequence SYGMS (SEQ ID NO:53), the CDR H2 amino acid sequence SSGGSY (SEQ ID NO:54), the CDR H3 amino acid sequence LGMITTGYAMDY (SEQ ID NO:55), the light chain complementary-determining region (CDR L) 1 amino acid sequence RSSQTIVHSTGHTYLE (SEQ ID NO:56), the CDR L2 amino acid sequence KVSNRFS (SEQ ID NO:57) and the CDR L3 amino acid sequence FQGSHVPYT (SEQ ID NO:58).

In one embodiment the present invention provides an antigen binding receptor comprising in order from the N-terminus to the C-terminus (i) an antigen binding moiety which is a Fab molecule capable of specific binding to a mutated Fc domain comprising the I253A, H310A and H435A mutations, comprising the heavy chain complementarity determining region (CDR) 1 of SEQ ID NO:53, the heavy chain CDR 2 of SEQ ID NO:54, the heavy chain CDR 3 of SEQ ID NO:55, the light chain CDR 1 of SEQ ID NO:56, the light chain CDR 2 of SEQ ID NO:57 and the light chain CDR 3 of SEQ ID NO:58;

(ii) a peptide linker, in particular the peptide linker of SEQ ID NO:17;

(iii) an anchoring transmembrane domain, in particular the anchoring transmembrane domain of SEQ ID NO:11;

(iii) a co-stimulatory signaling domain, in particular the co-stimulatory signaling domain of SEQ ID NO:12; and (iv) a stimulatory signaling domain, in particular the stimulatory signaling domain of SEQ ID NO:13.

In one embodiment the present invention provides an antigen binding receptor comprising:

a) a heavy chain fusion polypeptide comprising in order from the N-terminus to the C-terminus;
  (i) a heavy chain comprising the heavy chain complementarity determining region (CDR) 1 of SEQ ID NO:53, the heavy chain CDR 2 of SEQ ID NO:54, the heavy chain CDR 3 of SEQ ID NO:55;
  (ii) a peptide linker, in particular the peptide linker of SEQ ID NO:17;
  (iii) an anchoring transmembrane domain, in particular the anchoring transmembrane domain of SEQ ID NO:11;
  (iii) a co-stimulatory signaling domain, in particular the co-stimulatory signaling domain of SEQ ID NO:12; and (iv) a stimulatory signaling domain, in particular the stimulatory signaling domain of SEQ ID NO:13 and
b) a light chain comprising the light chain CDR 1 of SEQ ID NO:56, the light chain CDR 2 of SEQ ID NO:57 and the light chain CDR 3 of SEQ ID NO:58.

In one embodiment the present invention provides an antigen binding receptor comprising:
a) a heavy chain fusion polypeptide comprising in order from the N-terminus to the C-terminus;
 (i) the heavy chain variable domain (VH) SEQ ID NO:61;
 (ii) a peptide linker, in particular the peptide linker of SEQ ID NO:17;
 (iii) an anchoring transmembrane domain, in particular the anchoring transmembrane domain of SEQ ID NO:11;
 (iii) a co-stimulatory signaling domain, in particular the co-stimulatory signaling domain of SEQ ID NO:12; and
 (iv) a stimulatory signaling domain, in particular the stimulatory signaling domain of SEQ ID NO:13 and
b) the light chain variable domain (VL) SEQ ID NO:62.

In one particular embodiment the antigen binding moiety is a Fab fragment comprising a heavy chain comprising or consisting of the amino acid sequence of SEQ ID NO:64 and a light chain comprising or consisting of the amino acid sequence of SEQ ID NO:65.

In a particular embodiment, the antigen binding moiety is a Fab fragment capable of specific binding to a mutated Fc domain comprising the I253A, H310A and H435A mutations, wherein the antigen binding receptor comprises a heavy chain fusion polypeptide comprising an amino acid sequence that is at least about 95%, 96%, 97%, 98%, 99% or 100% identical to the amino acid sequence of SEQ ID NO:63 and a light chain polypeptide comprising an amino acid sequence that is at least about 95%, 96%, 97%, 98%, 99% or 100% identical to the amino acid sequence of SEQ ID NO:65.

In a preferred embodiment, the antigen binding moiety is a Fab fragment capable of specific binding to a mutated Fc domain comprising the I253A, H310A and H435A mutations, wherein the antigen binding receptor comprises a heavy chain fusion polypeptide comprising the amino acid sequence of SEQ ID NO:63 and a light chain polypeptide comprising the amino acid sequence of SEQ ID NO:65.

In certain alternative embodiments, the antigen binding receptor of the invention, the Fab light chain polypeptide and the Fab heavy chain fusion polypeptide are fused to each other, optionally via a linker peptide. Fusion of the Fab heavy and light chains can improve pairing of Fab heavy and light chains, and also reduces the number of plasmids needed for expression of some of the antigen binding receptor of the invention. An alternative strategy to reduce the number of plasmids needed for expression of the antigen binding receptor is the use of an internal ribosomal entry side to enable expression of both heavy and light chain constructs from the same plasmid as illustrated e.g. in FIG. 2.

In certain embodiments the antigen binding receptor comprises a polypeptide wherein the Fab light chain variable region of the antigen binding moiety shares a carboxy-terminal peptide bond with the Fab heavy chain constant region of the antigen binding moiety (i.e. a the antigen binding moiety comprises a crossFab heavy chain, wherein the heavy chain variable region is replaced by a light chain variable region), which in turn shares a carboxy-terminal peptide bond with the anchoring transmembrane domain ($VL_{(1)}$-$CH1_{(1)}$-ATD). In some embodiments the antigen binding receptor further comprises a polypeptide wherein the Fab heavy chain variable region of the first antigen binding moiety shares a carboxy-terminal peptide bond with the Fab light chain constant region of the first antigen binding moiety ($VH_{(1)}$-$CL_{(1)}$). In certain embodiments the polypeptides are covalently linked, e.g., by a disulfide bond. In alternative embodiments the antigen binding receptor comprises a polypeptide wherein the Fab heavy chain variable region of the antigen binding moiety shares a carboxy-terminal peptide bond with the Fab light chain constant region of the antigen binding moiety (i.e. the antigen binding moiety comprises a crossFab heavy chain, wherein the heavy chain constant region is replaced by a light chain constant region), which in turn shares a carboxy-terminal peptide bond with an anchoring transmembrane domain ($VH_{(1)}$-$CL_{(1)}$-ATD). In some embodiments the antigen binding receptor further comprises a polypeptide wherein the Fab light chain variable region of the antigen binding moiety shares a carboxy-terminal peptide bond with the Fab heavy chain constant region of the antigen binding moiety ($VL_{(1)}$-$CH1_{(1)}$) In certain embodiments the polypeptides are covalently linked, e.g., by a disulfide bond.

According to any of the above embodiments, components of the antigen binding receptor (e.g., VH and VL, antigen binding moiety, anchoring transmembrane domain, co-stimulatory signaling domain, stimulatory signaling domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally a number between 1 and 10, preferably between 1 and 4.

Exemplary T Cell Activating Antigen Binding Receptors

Figure 1B:
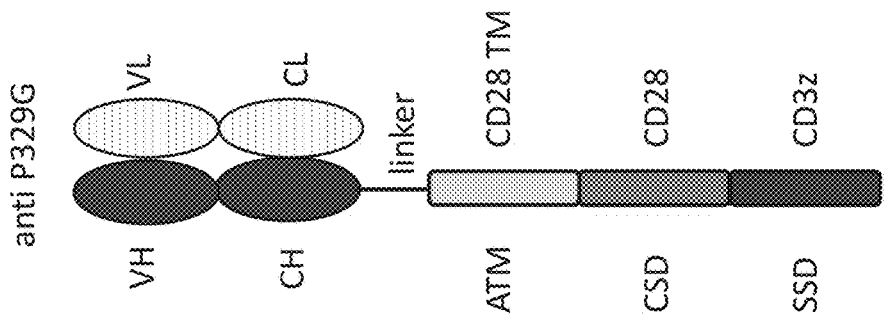
Figure 1A:
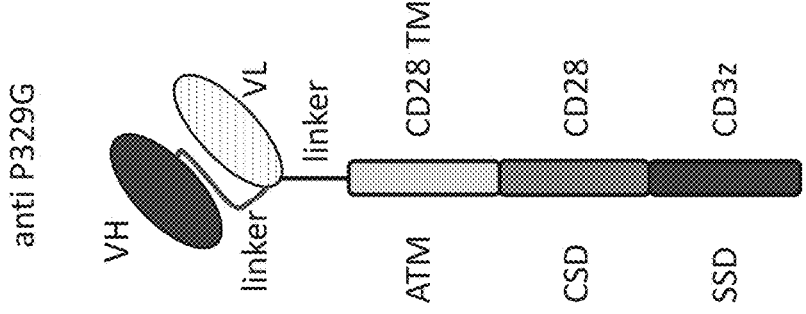
Figure 3:
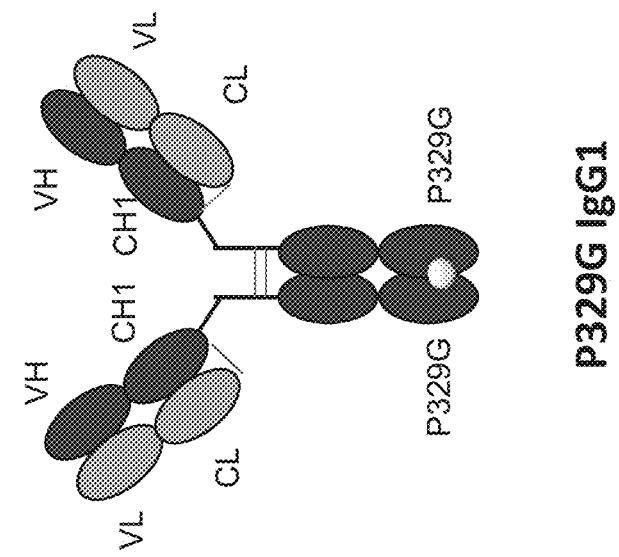
FIG. 3 depicts an exemplary IgG1 molecule harboring the P329G mutation in the Fc domain which is recognized by an anti-P329G antigen binding receptor of the invention.
Figure 4:
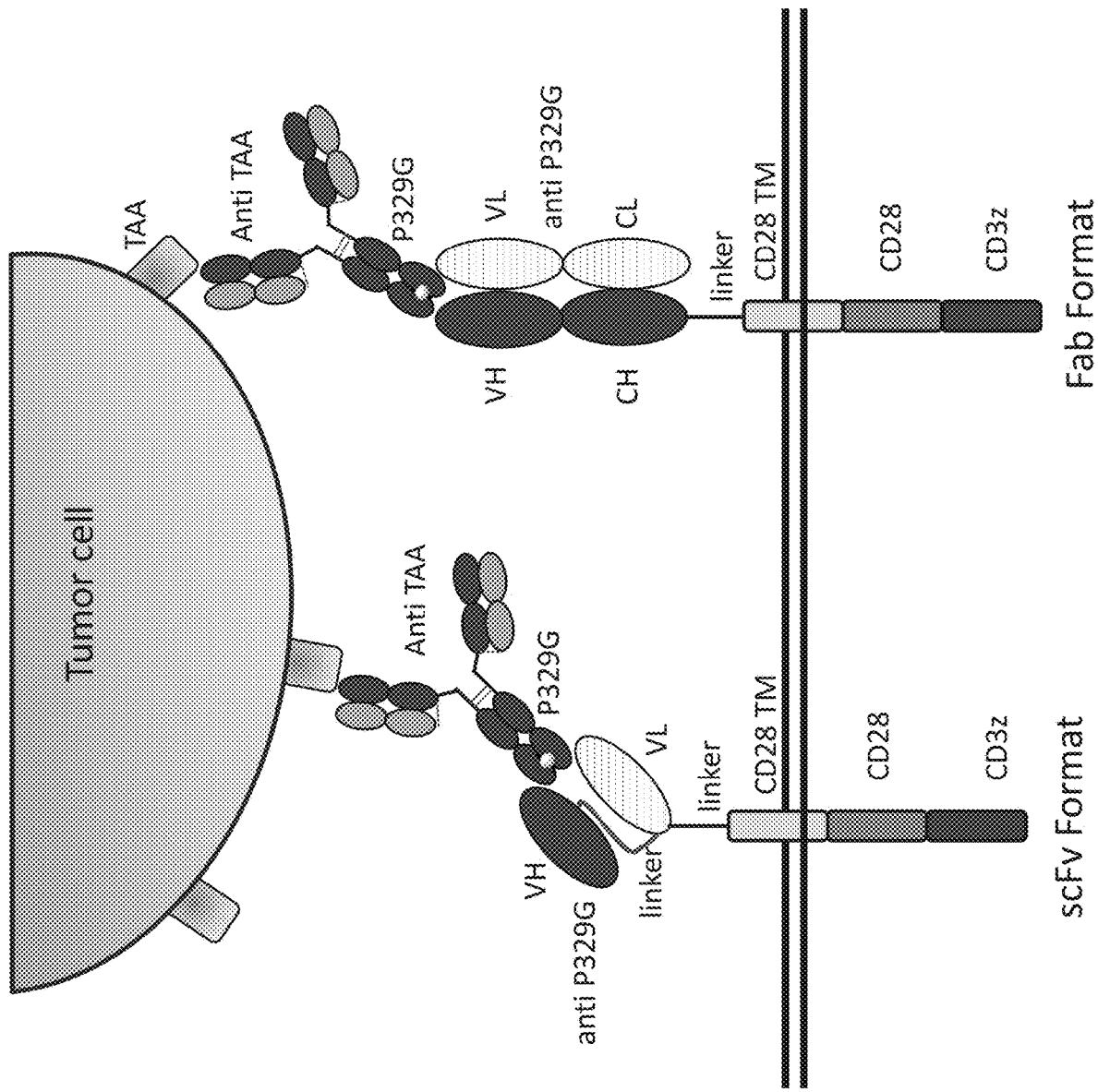
FIG. 4 depicts a schematic representation of a tumor associated antigen (TAA) bound IgG harboring the P329G mutation. This antibody can in turn be recognized by an anti-P329G antigen binding receptor expressing T cell, whereby the T cell gets activated.

As illustratively shown in the appended Examples and in FIG. 1A, as a proof of concept of the present invention, the antigen binding receptor "Anti-P329G-ds-scFv-CD28ATD-CD28CSD-CD3zSSD pETR17096" (SEQ ID NO:7) was constructed which comprises one stabilized scFv antigen binding moiety binding to/directed against/interacting with or on an antibody comprising the P329G mutation in the Fc domain. The construct further comprises the CD28 transmembrane domain, a fragment of CD28 as co-stimulatory signaling domain and a fragment of CD3z as stimulatory signaling domain. The sequences (amino acid and cDNA) of the antibody binding molecule "Anti-P329G-ds-scFv-CD28ATD-CD28CSD-CD3zSSD pETR17096" are shown in Tables 2 and 3.

Furthermore, as illustrated in FIG. 1B, as a further proof of concept of the present invention, the antigen binding receptor "Anti-P329G-ds-Fab-CD28ATD-CD28CSD-CD3zSSD pETR17100" (SEQ ID NOs: 39, 41) was constructed which comprises one stabilized Fab antigen binding moiety binding to/directed against/interacting with or on an antibody comprising the P329G mutations in the Fc domain. The construct further comprises the CD28 transmembrane domain, a fragment of CD28 as co-stimulatory signaling domain and a fragment of CD3z as stimulatory signaling domain. The sequences (amino acid and DNA) of the antigen binding receptor "Anti-P329G-ds-Fab-CD28ATD-CD28CSD-CD3zSSD pETR17100" are shown in Tables 4 and 5.

As a further proof of concept of the present invention, the antigen binding receptor "Anti-P329G-Fab-CD28ATD-CD28CSD-CD3zSSD pETR17594" (SEQ ID NOs: 48, 50) was constructed which comprises one Fab antigen binding moiety binding to/directed against/interacting with or on an antibody comprising the P329G mutations in the Fc domain. The construct further comprises the CD28 transmembrane domain, a fragment of CD28 as co-stimulatory signaling domain and a fragment of CD3z as stimulatory signaling domain. The sequences (amino acid and DNA) of the antigen binding receptor "Anti-P329G-Fab-CD28ATD-CD28CSD-CD3zSSD pETR17594" are shown in Tables 6 and 7.

As a further proof of concept of the present invention, the antigen binding receptor "Anti-AAA scFv" (SEQ ID NO:59) was constructed which comprises one scFv antigen binding moiety binding to/directed against/interacting with or on an antibody comprising the I253A, H310A and H435A mutations in the Fc domain. The construct further comprises the CD28 transmembrane domain, a fragment of CD28 as co-stimulatory signaling domain and a fragment of CD3z as stimulatory signaling domain. The sequences (amino acid and cDNA) of the antibody binding molecule "Anti-AAA scFv" are shown below in Tables 8 and 9.

As a further proof of concept of the present invention, the antigen binding receptor "Anti-AAA Fab" (SEQ ID NOs: 63, 65) was constructed which comprises one Fab antigen binding moiety binding to/directed against/interacting with or on an antibody comprising the I253A, H310A and H435A mutations in the Fc domain. The construct further comprises the CD28 transmembrane domain, a fragment of CD28 as co-stimulatory signaling domain and a fragment of CD3z as stimulatory signaling domain. The sequences (amino acid and cDNA) of the antibody binding molecule "Anti-AAA scFv" are shown below in Tables 10 and 11.

The invention also provides (a) nucleic acid molecule(s) encoding antigen binding receptors of the invention as described herein. Also encompassed by the present invention are (a) nucleic acid molecule(s) encoding the antigen binding receptors of the present invention and kits comprising nucleic acid molecule(s) according to the invention as further described herein.

Kits

A further aspect of the present invention are kits comprising or consisting of a nucleic acid encoding an antigen binding receptor of the invention and/or cells, preferably T cells transduced with antigen binding receptors of the invention and, optionally, (an) antibody/antibodies comprising a mutated Fc domain, wherein the antigen binding receptor is capable of specific binding to the mutated Fc domain.

Accordingly, provided is a kit comprising (A) a transduced T cell capable of expressing an antigen binding receptor of the invention; and (B) an antibody comprising a mutated Fc domain;

wherein the antigen binding receptor is capable of specific binding to the mutated Fc domain but not capable of specific binding to the non-mutated parent Fc domain.

Further provided is a kit comprising (A) an isolated polynucleotide and/or a vector encoding an antigen binding receptor of the invention; and (B) an antibody comprising a mutated Fc domain;

wherein the antigen binding receptor is capable of specific binding to the mutated Fc domain but not capable of specific binding to the non-mutated parent Fc domain.

In the context of the present invention, the kits of the present invention may comprise transduced T cells, isolated polynucleotides and/or vectors and one or more antibodies comprising a mutated Fc domain. In particular embodiments, the antibody is a therapeutic antibody, e.g. a tumor specific antibody. Tumor specific antigens are known in the art and described herein. In the context of the present invention, the antibody is administered before, simultaneously with or after administration of transduced T cell expressing an antigen binding receptor of the invention. The kits according to the present invention comprise transduced T cells or polynucleotides/vectors to generate transduced T cells. In this context, the transduced T cells are universal T cells since they are not specific for a given tumor but can be targeted to any tumor depending on the therapeutic antibody comprising the mutated Fc domain. Herein provided are examples of antibodies comprising a mutated Fc domain, however, any antibody comprising a mutated Fc domain as described herein may be included in the herein provided kits. In particular embodiments the mutated Fc domain of the antibodies exhibits reduced binding affinity to an Fc receptor and/or reduced effector function, as compared to a native $IgG_1$ Fc domain. In one such embodiment the mutated Fc domain (or the antibody comprising said Fc mutated domain) exhibits less than 50%, preferably less than 20%, more preferably less than 10% and most preferably less than 5% of the binding affinity to an Fc receptor, as compared to a native $IgG_1$ Fc domain (or an antibody comprising a native $IgG_1$ Fc domain), and/or less than 50%, preferably less than 20%, more preferably less than 10% and most preferably less than 5% of the effector function, as compared to a native $IgG_1$ Fc domain (or an antibody comprising a native $IgG_1$ Fc domain). In one embodiment, the mutated Fc domain (or the antibody comprising said mutated Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the mutated Fc domain exhibits substantially altered binding affinity to neonatal Fc receptor (FcRn), as compared to a native $IgG_1$ Fc domain. In one embodiment the antibody comprising mutated Fc domain exhibits less than 20%, particularly less than 10%, more particularly less than 5% of the binding affinity to an Fc receptor as compared to a antibody comprising a non-engineered Fc domain. In a particular embodiment the Fc receptor is an Fcγ receptor. In some embodiments the Fc receptor is a human Fc receptor.

In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced.

In certain embodiments the Fc domain of the antibody is mutated to have reduced effector function, as compared to a non-mutated Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or an antibody comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329. In a more specific embodiment the Fc domain comprises an amino acid substitution at a position selected from the group of L234, L235 and P329. In some embodiments the Fc domain comprises the amino acid substitutions L234A and L235A.

In one such embodiment, the Fc domain is an IgG$_1$ Fc domain, particularly a human IgG$_1$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In one embodiment the Fc domain comprises the amino acid mutations L234A, L235A and P329G ("P329G LALA"). In one such embodiment, the Fc domain is an IgG$_1$ Fc domain, particularly a human IgG$_1$ Fc domain. The "P329G LALA" combination of amino acid substitutions almost completely abolishes Fcγ receptor (as well as complement) binding of a human IgG$_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

In a particular embodiment the Fc domain exhibiting reduced binding affinity to an Fc receptor and/or reduced effector function, as compared to a native IgG$_1$ Fc domain, is a human IgG$_1$ Fc domain comprising the amino acid mutations L234A, L235A and optionally P329G, or a human IgG$_4$ Fc domain comprising the amino acid mutations S228P, L235E and optionally P329G.

In certain embodiments N-glycosylation of the Fc domain has been eliminated. In one such embodiment the Fc domain comprises an amino acid mutation at position N297, particularly an amino acid mutation replacing asparagine by alanine (N297A) or aspartic acid (N297D).

In addition to the Fc domains described hereinabove and in PCT publication no. WO 2012/130831, Fc domains with reduced Fc receptor binding and/or effector function also include those with mutation of one or more of Fc domain residues 238, 265, 269, 270, 297, 327 and 329 (U.S. Pat. No. 6,737,056). Such Fc mutants include Fc mutants with mutations at two or more of amino acid positions 265, 269, 270, 297 and 327, including the so-called "DANA" Fc mutant with mutation of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g., by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or an antibody comprising an Fc domain, can be measured by methods known in the art. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the antibody is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In one embodiment binding affinity to neonatal Fc receptor (FcRn) is reduced. In particular embodiments a mutated Fc domain according to the invention exhibits reduced binding affinity to FcRn receptor, as compared to a native IgG$_1$ Fc domain. In one such embodiment the Fc domain (or the antibody comprising said Fc domain) exhibits less than 50%, preferably less than 20%, more preferably less than 10% and most preferably less than 5% of the binding affinity to neonatal Fc receptor, as compared to a native IgG$_1$ Fc domain (or an antibody comprising a native IgG$_1$ Fc domain), and/or less than 50%, preferably less than 20%, more preferably less than 10% and most preferably less than 5% of the effector function, as compared to a native IgG$_1$ Fc domain (or an antibody comprising a native IgG$_1$ Fc domain). In one embodiment, the mutated Fc domain (or the antibody comprising said mutated Fc domain) does not substantially bind to neonatal Fc receptor. In a particular embodiment the Fc receptor is an FcRn receptor. In one embodiment the Fc receptor is a human FcRn receptor. In particular embodiments the Fc domain comprises amino acid substitutions at positions I253, H310 and H435. In more particular embodiments the Fc domain comprises the amino acid mutations I253A, H310A and H435A ("AAA"). In one such embodiment, the Fc domain is an IgGi Fc domain, particularly a human IgGi Fc domain. The "AAA" combination of amino acid substitutions almost completely abolishes FcRn receptor binding of a human $IgG_1$ Fc domain.

In a specific embodiment, the antibody comprising the mutated Fc region is capable of specific binding to CD20 and comprises the heavy chain sequence of SEQ ID NO:112, and the light chain sequence of SEQ ID NO:113. In one embodiment, the antibody comprising the mutated Fc region is capable of specific binding to FAP and comprises the heavy chain sequence of SEQ ID NO:114, and the light chain sequence of SEQ ID NO:115. In one embodiment, the antibody comprising the mutated Fc region is capable of specific binding to CEA and comprises the heavy chain sequence of SEQ ID NO:116 and the light chain sequence of SEQ ID NO:117, the heavy chain sequence of SEQ ID NO:118 and the light chain sequence of SEQ ID NO:119, the heavy chain sequence of SEQ ID NO:120 and the light chain sequence of SEQ ID NO:121, or the heavy chain sequence of SEQ ID NO:122 and the light chain sequence of SEQ ID NO:123.

In further embodiments, the antibody comprising the mutated Fc region is capable of specific binding to tenascin (TNC) and comprises the heavy chain sequence of SEQ ID NO:124, and the light chain sequence of SEQ ID NO:125.

In a further embodiment, the antibody comprising the mutated Fc region is a bispecific antibody, e.g. a T-cell activating bispecific antibody. In one such embodiment the bispecific antibody comprises a first binding moiety capable of specific binding to a T-cell activating target, in particular CD3, and a second binding moiety capable of specific binding to a tumor antigen as described herein.

In one embodiment, the antibody comprising the mutated Fc region is bispecific and capable of specific binding to Her2, wherein the bispecific antibody comprises a first heavy chain sequence of SEQ ID NO:126, a first light chain sequence of SEQ ID NO:127, a second heavy chain sequence of SEQ ID NO:128 and a second light chain sequence of SEQ ID NO:129.

In and illustrative embodiment of the present invention, as a proof of concept, a kit is provided comprising an amino acid sequence as shown in SEQ ID NO:7 ("Anti-P329G-ds-scFv-CD28ATD-CD28CSD-CD3zSSD" (as encoded by the DNA sequence shown in SEQ ID NO:19)) combined with the antibody comprising a heavy chain of SEQ ID NO:112 and a light chain of SEQ ID NO:113. Alternatively, the kit may comprise an amino acid sequence as shown in SEQ ID NO:31 ("Anti-P329G-scFv-CD28ATD-CD28CSD-CD3zSSD" (as encoded by the DNA sequence shown in SEQ ID NO:35)) combined with the antibody comprising a heavy chain of SEQ ID NO:112 and a light chain of SEQ ID NO:113. Moreover, in the context of the present invention the kit may comprise an amino acid sequence as shown in SEQ ID NO:39 ("Anti-P329G-ds-Fab-CD28ATD-CD28CSD-CD3zSSD" (as encoded by the DNA sequence shown in SEQ ID NO:44)) combined with the antibody comprising a heavy chain of SEQ ID NO:112 and a light chain of SEQ ID NO:113. Alternatively, the kit may comprise an amino acid sequence as shown in SEQ ID NO:48 ("Anti-P329G-Fab-CD28ATD-CD28CSD-CD3zSSD" (as encoded by the DNA sequence shown in SEQ ID NO:51)) combined with an antibody comprising a heavy chain of SEQ ID NO:112 and a light chain of SEQ ID NO:113. Alternatively, the kit may comprise an amino acid sequence as shown in SEQ ID NO:59 ("Anti-AAA-scFv-CD28ATD-CD28CSD-CD3zSSD") combined with an antibody comprising a heavy chain of SEQ ID NO:112 and a light chain of SEQ ID NO:113. Moreover, in the context of the present invention the kit may comprise an amino acid sequence as shown in SEQ ID NO:63 ("Anti-AAA-Fab-CD28ATD-CD28C SD-CD3zSSD") combined with an antibody comprising a heavy chain of SEQ ID NO:112 and a light chain of SEQ ID NO:113. Moreover, in the context of the present invention the kit may comprise at least one antibody molecule comprising a heavy chain and a light chain selected from the group consisting of SEQ ID NO:112 and SEQ ID NO:113, SEQ ID NO:114 and SEQ ID NO:115, SEQ ID NO:116 and SEQ ID NO:117, SEQ ID NO:118 and SEQ ID NO:119, SEQ ID NO:120 and SEQ ID NO:121, SEQ ID NO:122 and SEQ ID NO:123, and SEQ ID NO:124 and SEQ ID NO:125. Moreover, in the context of the present invention the kit may comprise a bispecific antibody molecule, in particular a bispecific antibody comprising a first heavy chain of SEQ ID NO:128, a first light chain of SEQ ID NO:129, a second heavy chain of SEQ ID NO:130 and a second light chain of SEQ ID NO:131.

Furthermore, parts of the kit of the invention can be packaged individually in vials or bottles or in combination in containers or multicontainer units. Additionally, the kit of the present invention may comprise a (closed) bag cell incubation system where patient cells, preferably T cells as described herein, can be transduced with (an) antigen binding receptor(s) of the invention and incubated under GMP (good manufacturing practice, as described in the guidelines for good manufacturating practice published by the European Commission under http://ec.europa.eu/health/documents/eudralex/index_en.htm) conditions. Furthermore, the kit of the present invention comprises a (closed) bag cell incubation system where isolated/obtained patients T cells can be transduced with (an) antigen binding receptor(s) of the invention and incubated under GMP. Furthermore, in the context of the present invention, the kit may also comprise a vector encoding (the) antigen binding receptor(s) as described herein. The kit of the present invention may be advantageously used, inter alia, for carrying out the method of the invention and could be employed in a variety of applications referred herein, e.g., as research tools or medical tools. The manufacture of the kits preferably follows standard procedures which are known to the person skilled in the art.

In this context, patient derived cells, preferably T cells, can be transduced with an antigen binding receptor of the invention capable of specific binding to a mutated Fc domain as described herein using the kit as described above. The extracellular domain comprising an antigen binding moiety capable of specific binding to a mutated Fc domain does not naturally occur in or on T cells. Accordingly, the patient derived cells transduced with the kits of the invention will acquire the capability of specific binding to a mutated Fc domain of an antibody, e.g. a therapeutic antibody and will become capable of inducing elimination/lysis of target cells via interaction with a therapeutic antibody comprising the mutated Fc domain, wherein the therapeutic antibody is able to bind to a tumor-specific antigen naturally occurring (that is endogenously expressed) on the surface of a tumor cell. Binding of the extracellular domain of the antigen binding receptor as described herein activates that T cell and brings it into physical contact with the tumor cell through the therapeutic antibody comprising the mutated Fc domain.

Non-transduced or endogenous T cells (e.g. CD8+ T cells) are unable to bind to the mutated Fc domain of the therapeutic antibody comprising the mutated Fc domain. The transduced T cells expressing the antigen binding receptor comprising the extracellular domain capable of specific binding to a mutated Fc domain remain unaffected by a therapeutic antibody not comprising the mutations in the Fc domain as described herein. Accordingly, T cells expressing the inventive antigen binding receptor molecule have the ability to lyse target cells in the presence of an antibody comprising the mutations in the Fc domain as described herein in vivo and/or in vitro. Corresponding target cells comprise cells expressing a surface molecule, i.e. a tumor-specific antigen naturally occurring on the surface of a tumor cell, which is recognized by at least one, preferably two, binding domains of the therapeutic antibody as described herein. Such surface molecules are characterized herein below.

Lysis of the target cell can be detected by methods known in the art. Accordingly, such methods comprise, inter alia, physiological in vitro assays. Such physiological assays may monitor cell death, for example by loss of cell membrane integrity (e.g. FACS based propidium Iodide assay, trypan blue influx assay, photometric enzyme release assays (LDH), radiometric 51Cr release assay, fluorometric Europium release and CalceinAM release assays). Further assays comprise monitoring of cell viability, for example by photometric MTT, XTT, WST-1 and alamarBlue assays, radiometric 3H-Thd incorporation assay, clonogenic assay measuring cell division activity, and fluorometric Rhodamine123 assay measuring mitochondrial transmembrane gradient. In addition, apoptosis may be monitored for example by FACS-based phosphatidylserin exposure assay, ELISA-based TUNEL test, caspase activity assay (photometric, fluorometric or ELISA-based) or analyzing changed cell morphology (shrinking, membrane blebbing).

Transduced T Cells Capable of Expressing Antigen Binding Receptors of the Invention A further aspect of the present invention are transduced T cells capable of expressing an antigen binding receptor of the present invention. The antigen binding receptors as described herein relate to molecules which are naturally not comprised in and/or on the surface of T cells and which are not (endogenously) expressed in or on normal (non-transduced) T cells. Thus, the antigen binding receptor of the invention in and/or on T cells is artificially introduced into T cells. In the context of the present invention said T cells, preferably CD8+ T cells, may be isolated/obtained from a subject to be treated as defined herein. Accordingly, the antigen binding receptors as described herein which are artificially introduced and subsequently presented in and/or on the surface of said T cells comprise domains comprising one or more antigen binding moiety accessible (in vitro or in vivo) to (Ig-derived) immunoglobulins, preferably antibodies, in particular to the Fc domain of the antibodies. In the context of the present invention, these artificially introduced molecules are presented in and/or on the surface of said T cells after (retroviral or lentiviral) transduction as described herein below. Accordingly, after transduction, T cells according to the invention can be activated by immunoglobulins, preferably (therapeutic) antibodies comprising specific mutations in the Fc domain as described herein.

The invention also relates to transduced T cells expressing an antigen binding receptor encoded by (a) nucleic acid molecule(s) encoding the antigen binding receptor of the present invention. Accordingly, in the context of the present invention, the transduced cell may comprise a nucleic acid molecule encoding the antigen binding receptor of the present invention or a vector of the present invention which expresses an antigen binding receptor of the present invention.

In the context of the present invention, the term "transduced T cell" relates to a genetically modified T cell (i.e. a T cell wherein a nucleic acid molecule has been introduced deliberately). The herein provided transduced T cell may comprise the vector of the present invention. Preferably, the herein provided transduced T cell comprises the nucleic acid molecule encoding the antigen binding receptor of the present invention and/or the vector of the present invention. The transduced T cell of the invention may be a T cell which transiently or stably expresses the foreign DNA (i.e. the nucleic acid molecule which has been introduced into the T cell). In particular, the nucleic acid molecule encoding the antigen binding receptor of the present invention can be stably integrated into the genome of the T cell by using a retroviral or lentiviral transduction. By using mRNA transfection, the nucleic acid molecule encoding the antigen binding receptor of the present invention may be expressed transiently. Preferably, the herein provided transduced T cell has been genetically modified by introducing a nucleic acid molecule in the T cell via a viral vector (e.g. a retroviral vector or a lentiviral vector). Accordingly, the expression of the antigen binding receptors may be constitutive and the extracellular domain of the antigen binding receptor may be detectable on the cell surface. This extracellular domain of the antigen binding receptor may comprise the complete extracellular domain of an antigen binding receptor as defined herein but also parts thereof. The minimal size required being the antigen binding site of the antigen binding moiety in the antigen binding receptor.

The expression may also be conditional or inducible in the case that the antigen binding receptor is introduced into T cells under the control of an inducible or repressible promoter. Examples for such inducible or repressible promoters can be a transcriptional system containing the alcohol dehydrogenase I (alcA) gene promoter and the transactivator protein AlcR. Different agricultural alcohol-based formulations are used to control the expression of a gene of interest linked to the alcA promoter. Furthermore, tetracycline-responsive promoter systems can function either to activate or repress gene expression system in the presence of tetracycline. Some of the elements of the systems include a tetracycline repressor protein (TetR), a tetracycline operator sequence (tetO) and a tetracycline transactivator fusion protein (tTA), which is the fusion of TetR and a herpes simplex virus protein 16 (VP16) activation sequence. Further, steroid-responsive promoters, metal-regulated or pathogenesis-related (PR) protein related promoters can be used.

The expression can be constitutive or constitutional, depending on the system used. The antigen binding receptors of the present invention can be expressed on the surface of the herein provided transduced T cell. The extracellular portion of the antigen binding receptor (i.e. the extracellular domain of the antigen binding receptor can be detected on the cell surface, while the intracellular portion (i.e. the co-stimulatory signaling domain(s) and the stimulatory signaling domain) are not detectable on the cell surface. The detection of the extracellular domain of the antigen binding receptor can be carried out by using an antibody which specifically binds to this extracellular domain or by the mutated Fc domain which the extracellular domain is capable to bind. The extracellular domain can be detected using these antibodies or Fc domains by flow cytometry or microscopy.

The transduced cells of the present invention may be any immune cell. These include but are not limited to B-cells, T cells, Natural Killer (NK) cells, Natural Killer (NK) T cells, γδ T cells, innate lymphoid cells, macrophages, monocytes, dendritic cells, or neutrophils. Preferentially, said immune cell would be a lymphocyte, preferentially a NK or T cells. The said T cells include CD4 T cells and CD8 T cells. Triggering of the antigen binding receptor of the present invention on the surface of the leukocyte will render the cell cytotoxic against a target cell in conjunction with a therapeutic antibody comprising a mutated Fc domain irrespective of the lineage the cell originated from. Cytotoxicity will happen irrespective of the stimulatory signaling domain or co-stimulatory signaling domain chosen for the antigen binding receptor and is not dependent on the exogenous supply of additional cytokines. Accordingly, the transduced cell of the present invention may be, e.g., a CD4+ T cell, a CD8+-T cell, a γδ T cell, a Natural Killer (NK) T cell, a Natural Killer (NK) cell, a tumor-infiltrating lymphocyte (TIL) cell, a myeloid cell, or a mesenchymal stem cell. Preferably, the herein provided transduced cell is a T cell (e.g. an autologous T cell), more preferably, the transduced cell is a CD8+ T cell. Accordingly, in the context of the present invention, the transduced cell is a CD8+ T cell. Further, in the context of the present invention, the transduced cell is an autologous T cell. Accordingly, in the context of the present invention, the transduced cell is preferably an autologous CD8+ T cell. In addition to the use of autologous cells (e.g. T cells) isolated from the subject, the present invention also comprehends the use of allogeneic cells. Accordingly, in the context of the present invention the transduced cell may also be an allogeneic cell, such as an allogeneic CD8+ T cell. The use of allogeneic cells is based on the fact that cells, preferably T cells can recognize a specific antigen epitope presented by foreign antigen-presenting cells (APC), provided that the APC express the MHC molecule, class I or class II, to which the specific responding cell population, i.e. T cell population is restricted, along with the antigen epitope recognized by the T cells. Thus, the term allogeneic refers to cells from an unrelated coming from an unrelated donor individual/subject which is human leukocyte antigen (HLA) compatible to the individual/subject which will be treated by e.g. the herein described antigen binding receptor expressing transduced cell. Autologous cells refer to cells which are isolated/obtained as described herein above from the subject to be treated with the transduced cell described herein. The transduced cell of the invention may be co-transduced with further nucleic acid molecules, e.g. with a nucleic acid molecule encoding a T cell receptor.

The present invention also relates to a method for the production of a transduced T cell expressing an antigen binding receptor of the invention, comprising the steps of transducing a T cell with a vector of the present invention, culturing the transduced T cell under conditions allowing the expressing of the antigen binding receptor in or on said transduced cell and recovering said transduced T cell.

In the context of the present invention, the transduced cell of the present invention is preferably produced by the following process: cells (e.g., T cells, preferably CD8+ T cells) are isolated/obtained from a subject (preferably a human patient). Methods for isolating/obtaining cells (e.g. T cells, preferably CD8+ T cells) from patients or from donors are well known in the art and in the context of the present the cells (e.g. T cells, preferably CD8+ T cells) from patients or from donors may be isolated by blood draw or removal of bone marrow. After isolating/obtaining cells as a sample of the patient, the cells (e.g. T cells) are separated from the other ingredients of the sample. Several methods for separating cells (e.g. T cells) from the sample are known and include, without being limiting, e.g. leukapheresis for obtaining cells from the peripheral blood sample from a patient or from a donor, isolating/obtaining cells by using a FACSort apparatus, picking living of dead cells from fresh biopsy specimens harboring living cells by hand or by using a micromanipulator (see, e.g., Dudley, Immunother. 26 (2003), 332-342; Robbins, Clin. Oncol. 29 (201 1), 917-924 or Leisegang, J. Mol. Med. 86 (2008), 573-58). The isolated/obtained cells T cells, preferably CD8+ T cells, are subsequently cultivated and expanded, e.g., by using an anti-CD3 antibody, by using anti-CD3 and anti-CD28 monoclonal antibodies and/or by using an anti-CD3 antibody, an anti-CD28 antibody and interleukin-2 (IL-2) (see, e.g., Dudley, Immunother. 26 (2003), 332-342 or Dudley, Clin. Oncol. 26 (2008), 5233-5239).

In a subsequent step the cells (e.g. T cells) are artificially/genetically modified/transduced by methods known in the art (see, e.g., Lemoine, J Gene Med 6 (2004), 374-386). Methods for transducing cells (e.g. T cells) are known in the art and include, without being limited, in a case where nucleic acid or a recombinant nucleic acid is transduced, for example, an electroporation method, calcium phosphate method, cationic lipid method or liposome method. The nucleic acid to be transduced can be conventionally and highly efficiently transduced by using a commercially available transfection reagent, for example, Lipofectamine (manufactured by Invitrogen, catalogue no.: 11668027). In a case where a vector is used, the vector can be transduced in the same manner as the above-mentioned nucleic acid as long as the vector is a plasmid vector (i.e. a vector which is not a viral vector In the context of the present invention, the methods for transducing cells (e.g. T cells) include retroviral or lentiviral T cell transduction, non-viral vectors (e.g., sleeping beauty minicircle vector) as well as mRNA transfection. "mRNA transfection" refers to a method well known to those skilled in the art to transiently express a protein of interest, like in the present case the antigen binding receptor of the present invention, in a cell to be transduced. In brief cells may be electroporated with the mRNA coding for the antigen binding receptor of the present by using an electroporation system (such as e.g. Gene Pulser, Bio-Rad) and thereafter cultured by standard cell (e.g. T cell) culture protocol as described above (see Zhao et al., Mol Ther. 13(1) (2006), 151-159.) The transduced cell of the invention is a T cell, most preferably a CD8+ T cell, and is generated by lentiviral, or most preferably retroviral T cell transduction.

In this context, suitable retroviral vectors for transducing T cells are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum. Gene Ther. 8 (1997), 1041-1048), SFG (Gallardo et al., Blood 90

(1997), and LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). In the context of the present invention, suitable lentiviral vector for transducing cells (e.g. T cells) are, e.g. PL-SIN lentiviral vector (Hotta et al., Nat Methods. 6(5) (2009), 370-376), p156RRL-sinPPT-CMV-GFP-PRE/NheI (Campeau et al., PLoS One 4(8) (2009), e6529), pCMVR8.74 (Addgene Catalogoue No.: 22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rs13), pHR-IG (Xie et al., J Cereb Blood Flow Metab. 33(12) (2013), 1875-85), pRRLSIN (Addgene Catalogoue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Marr et al., J Mol Neurosci. 22(1-2) (2004), 5-11), or pLEX (Addgene Catalogue No.: 27976).

The transduced T cell/T cells of the present invention is/are preferably grown under controlled conditions, outside of their natural environment. In particular, the term "culturing" means that cells (e.g. the transduced cell(s) of the invention) which are derived from multi-cellular eukaryotes (preferably from a human patient) are grown in vitro. Culturing cells is a laboratory technique of keeping cells alive which are separated from their original tissue source. Herein, the transduced cell of the present invention is cultured under conditions allowing the expression of the antigen binding receptor of the present invention in or on said transduced cells. Conditions which allow the expression or a transgene (i.e. of the antigen binding receptor of the present invention) are commonly known in the art and include, e.g., agonistic anti-CD3- and anti-CD28 antibodies and the addition of cytokines such as interleukin 2 (IL-2), interleukin 7 (IL-7), interleukin 12 (IL-12) and/or interleukin 15 (IL-15). After expression of the antigen binding receptor of the present invention in the cultured transduced cell (e.g., a CD8+ T), the transduced cell is recovered (i.e. re-extracted) from the culture (i.e. from the culture medium). Accordingly, also encompassed by the invention is a transduced cell, preferably a T cell, in particular a CD8+ T expressing an antigen binding receptor encoded by a nucleic acid molecule of the invention obtainable by the method of the present invention.

Nucleic Acid Molecules

A further aspect of the present invention are nucleic acids and vectors encoding one or several antigen binding receptors of the present invention. Exemplary nucleic acid molecules encoding the antigen binding receptors of the present invention are shown in SEQ ID NOs:19, 30, 35, 38, 44, 47, 51 and 52. The nucleic acid molecules of the invention may be under the control of regulatory sequences. For example, promoters, transcriptional enhancers and/or sequences which allow for induced expression of the antigen binding receptor of the invention may be employed. In the context of the present invention, the nucleic acid molecules are expressed under the control of constitutive or inducible promoter. Suitable promoters are e.g. the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACT5C promoter (Qin et al., PLoS One 5(5) (2010), e10611), the TRE promoter (Qin et al., PLoS One. 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24). The present invention therefore also relates to (a) vector(s) comprising the nucleic acid molecule(s) described in the present invention. Herein the term vector relates to a circular or linear nucleic acid molecule which can autonomously replicate in a host cell (i.e. in a transduced cell) into which it has been introduced. Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322, pGA18 and pGBT9. Typical expression vectors include pTRE, pCAL-n-EK, pESP-1, pOP13CAT.

The invention also relates to (a) vector(s) comprising (a) nucleic acid molecule(s) which is (are) a regulatory sequence operably linked to said nucleic acid molecule(s) encoding an antigen binding receptor as defined herein. In the context of the present invention the vector can be polycistronic. Such regulatory sequences (control elements) are known to the skilled person and may include a promoter, a splice cassette, translation initiation codon, translation and insertion site for introducing an insert into the vector(s). In the context of the present invention, said nucleic acid molecule(s) is (are) operatively linked to said expression control sequences allowing expression in eukaryotic or prokaryotic cells. It is envisaged that said vector(s) is (are) an expression vector(s) comprising the nucleic acid molecule(s) encoding the antigen binding receptor as defined herein. Operably linked refers to a juxtaposition wherein the components so described are in a relationship permitting them to function in their intended manner. A control sequence operably linked to a coding sequence is ligated in such a way that expression of the coding sequence is achieved under conditions compatible with the control sequences. In case the control sequence is a promoter, it is obvious for a skilled person that double-stranded nucleic acid is preferably used.

In the context of the present invention the recited vector(s) is (are) an expression vector(s). An expression vector is a construct that can be used to transform a selected cell and provides for expression of a coding sequence in the selected cell. An expression vector(s) can for instance be cloning (a) vector(s), (a) binary vector(s) or (a) integrating vector(s). Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in E. coli, and examples of regulatory elements permitting expression in eukaryotic host cells are the AOX1 or GAL1 promoter in yeast or the CMV-, SV40, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences encoding signal peptides capable of directing the polypeptide to a cellular compartment or secreting it into the medium may be added to the coding sequence of the recited nucleic acid sequence and are well known in the art; see also, e.g., appended Examples.

The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode an antigen binding receptor including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (Invitrogene), pEF-DHFR, pEF-ADA or pEF-neo (Raum et al. Cancer Immunol Immunother 50 (2001), 141-150) or pSPORT1 (GIBCO BRL).

In the context of the present invention, the expression control sequences will be eukaryotic promoter systems in vectors capable of transforming or transfecting eukaryotic cells, but control sequences for prokaryotic cells may also be used. Once the vector has been incorporated into the appropriate cell, the cell is maintained under conditions suitable for high level expression of the nucleotide sequences, and as desired. Additional regulatory elements may include transcriptional as well as translational enhancers. Advantageously, the above-described vectors of the invention comprise a selectable and/or scorable marker. Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149), npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from Aspergillus terreus which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule(s) can be used alone or as part of (a) vector(s) to express the antigen binding receptors of the invention in cells, for, e.g., adoptive T cell therapy but also for gene therapy purposes. The nucleic acid molecules or vector(s) containing the DNA sequence(s) encoding any one of the herein described antigen binding receptors is introduced into the cells which in turn produce the polypeptide of interest. Gene therapy, which is based on introducing therapeutic genes into cells by ex-vivo or in-vivo techniques is one of the most important applications of gene transfer. Suitable vectors, methods or gene-delivery systems for in methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91 (1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957; U.S. Pat. Nos. 5,580,859; 5,589,466; or Schaper, Current Opinion in Biotechnology 7 (1996), 635-640. The recited nucleic acid molecule(s) and vector(s) may be designed for direct introduction or for introduction via liposomes, or viral vectors (e.g., adenoviral, retroviral) into the cell. In the context of the present invention, said cell is a T cells, such as CD8+ T cells, CD4+ T cells, CD3+ T cells, γδ T cells or natural killer (NK) T cells, preferably CD8+ T cells.

In accordance with the above, the present invention relates to methods to derive vectors, particularly plasmids, cosmids and bacteriophages used conventionally in genetic engineering that comprise a nucleic acid molecule encoding the polypeptide sequence of an antigen binding receptor defined herein. In the context of the present invention, said vector is an expression vector and/or a gene transfer or targeting vector. Expression vectors derived from viruses such as retroviruses, vaccinia virus, adeno-associated virus, herpes virus, or bovine papilloma virus, may be used for delivery of the recited polynucleotides or vector into targeted cell populations. Methods which are well known to those skilled in the art can be used to construct (a) recombinant vector(s); see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra. The recited vector may, inter alia, be the pEF-DHFR, pEF-ADA or pEF-neo. The vectors pEF-DHFR, pEF-ADA and pEF-neo have been described in the art, e.g. in Mack et al. Proc. Natl. Acad. Sci. USA 92 (1995), 7021-7025 and Raum et al. Cancer Immunol Immunother 50 (2001), 141-150.

The invention also provides for a T cell transformed or transfected with a vector as described herein. Said T cell may be produced by introducing at least one of the above described vector or at least one of the above described nucleic acid molecules into the T cell or its precursor cell. The presence of said at least one vector or at least one nucleic acid molecule in the T cell may mediate the expression of a gene encoding the above described antigen binding receptor comprising an extracellular domain comprising an antigen binding moiety capable of specific binding to a mutated Fc domain. The vector of the present invention can be polycistronic.

The described nucleic acid molecule(s) or vector(s) which is (are) introduced in the T cell or its precursor cell may either integrate into the genome of the cell or it may be maintained extrachromosomally.

Tumor Specific Antigens

As mentioned above, the (Ig-derived) domain(s) of the herein-described antibody comprising a mutated Fc domain may comprise an antigen-interaction-site with specificity for a cell surface molecule, i.e. a tumor-specific antigen that naturally occurs on the surface of a tumor cell. In the context of the present invention, such antibodies will bring transduced T cells as described herein comprising the antigen binding receptor of the invention in physical contact with a tumor cell, wherein the transduced T cell becomes activated. Activation of transduced T cells of the present invention can result with lysis of the tumor cell as described herein.

Examples of tumor markers that naturally occur on the surface of tumor cells are given herein below and comprise, but are not limited to FAP (fibroblast activation protein), CEA (carcinoembryonic antigen), p95 (p95HER2), BCMA (B-cell maturation antigen), EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD19, CD20, CD22, CD33, CD38, CD52Flt3, folate receptor 1 (FOLR1), human trophoblast cell-surface antigen 2 (Trop-2) cancer antigen 12-5 (CA-12-5), human leukocyte antigen-antigen D related (HLA-DR), MUC-1 (Mucin-1), A33-antigen, PSMA (prostate-specific membrane antigen), FMS-like tyrosine kinase 3 (FLT-3), PSMA (prostate specific membrane antigen), PSCA (prostate stem cell antigen), transferrin-receptor, TNC (tenascin), carbon anhydrase IX (CA-IX), and/or peptides bound to a molecule of the human major histocompatibility complex (MHC).

Accordingly, in the context of the present invention, the antigen binding receptor as described herein binds to the mutated Fc domain of an antibody, i.e. a therapeutic antibody capable of specific binding to an antigen/marker that naturally occurs on the surface of tumor cells selected from the group consisting of FAP (fibroblast activation protein), CEA (carcinoembryonic antigen), p95 (p95HER2), BCMA (B-cell maturation antigen), EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD19, CD20, CD22, CD33, CD38, CD52Flt3, folate receptor 1 (FOLR1), human trophoblast cell-surface antigen 2 (Trop-2) cancer antigen 12-5 (CA-12-5), human leukocyte antigen-antigen D related (HLA-DR), MUC-1 (Mucin-1), A33-antigen, PSMA (prostate-specific membrane antigen), FMS-like tyrosine kinase 3 (FLT-3), PSMA (prostate specific membrane antigen), PSCA (prostate stem cell antigen), transferrin-receptor, TNC (tenascin), carbon anhydrase IX (CA-IX), and/or peptides bound to a molecule of the human major histocompatibility complex (MHC).

The sequence(s) of the (human) members of the A33-antigen, BCMA (B-cell maturation antigen), cancer antigen 12-5 (CA-12-5), carbon anhydrase IX (CA-IX), CD19, CD20, CD22, CD33, CD38, CEA (carcinoembryonic antigen), EpCAM (epithelial cell adhesion molecule), FAP (fibroblast activation protein), FMS-like tyrosine kinase 3 (FLT-3), folate receptor 1 (FOLR1), HER-1 (human epidermal growth factor 1), HER-2 (human epidermal growth factor 2), HER-3 (human epidermal growth factor 3), human leukocyte antigen-antigen D related (HLA-DR), MSLN (mesothelin), MCSP (melanoma chondroitin sulfate proteoglycan), MUC-1 (Mucin-1), PSMA (prostate specific membrane antigen), PSMA (prostate-specific membrane antigen), PSCA (prostate stem cell antigen), p95 (p95HER2), transferrin-receptor, TNC (tenascin), human trophoblast cell-surface antigen 2 (Trop-2) are available in the UniProtKB/Swiss-Prot database and can be retrieved from http://www.uniprot.org/uniprot/?query=reviewed %3Ayes. These (protein) sequences also relate to annotated modified sequences. The present invention also provides techniques and methods wherein homologous sequences, and also genetic allelic variants and the like of the concise sequences provided herein are used. Preferably such variants and the like of the concise sequences herein are used. Preferably, such variants are genetic variants. The skilled person may easily deduce the relevant coding region of these (protein) sequences in these databank entries, which may also comprise the entry of genomic DNA as well as mRNA/cDNA. The sequence(s) of the (human) FAP (fibroblast activation protein) can be obtained from the Swiss-Prot database entry Q12884 (entry version 168, sequence version 5); The sequence(s) of the (human) CEA (carcinoembryonic antigen) can be obtained from the Swiss-Prot database entry P06731 (entry version 171, sequence version 3); the sequence(s) of the (human) EpCAM (Epithelial cell adhesion molecule) can be obtained from the Swiss-Prot database entry P16422 (entry version 117, sequence version 2); the sequence(s) of the (human) MSLN (mesothelin) can be obtained from the UniProt Entry number Q13421 (version number 132; sequence version 2); the sequence(s) of the (human) FMS-like tyrosine kinase 3 (FLT-3) can be obtained from the Swiss-Prot database entry P36888 (primary citable accession number) or Q13414 (secondary accession number) with the version number 165 and the sequence version 2; the sequences of (human) MCSP (melanoma chondroitin sulfate proteoglycan) can be obtained from the UniProt Entry number Q6UVK1 (version number 118; sequence version 2); the sequence(s) of the (human) folate receptor 1 (FOLR1) can be obtained from the UniProt Entry number P15328 (primary citable accession number) or Q53EW2 (secondary accession number) with the version number 153 and the sequence version 3; the sequence(s) of the (human) trophoblast cell-surface antigen 2 (Trop-2) can be obtained from the UniProt Entry number P09758 (primary citable accession number) or Q15658 (secondary accession number) with the version number 172 and the sequence version 3; the sequence(s) of the (human) PSCA (prostate stem cell antigen) can be obtained from the UniProt Entry number O43653 (primary citable accession number) or Q6UW92 (secondary accession number) with the version number 134 and the sequence version 1; the sequence(s) of the (human) HER-1 (Epidermal growth factor receptor) can be obtained from the Swiss-Prot database entry P00533 (entry version 177, sequence version 2); the sequence(s) of the (human) HER-2 (Receptor tyrosine-protein kinase erbB-2) can be obtained from the Swiss-Prot database entry P04626 (entry version 161, sequence version 1); the sequence(s) of the (human) HER-3 (Receptor tyrosine-protein kinase erbB-3) can be otained from the Swiss-Prot database entry P21860 (entry version 140, sequence version 1); the sequence(s) of the (human) CD20 (B-lymphocyte antigen CD20) can be obtained from the Swiss-Prot database entry P11836 (entry version 117, sequence version 1); the sequence(s) of the (human) CD22 (B-lymphocyte antigen CD22) can be obtained from the Swiss-Prot database entry P20273 (entry version 135, sequence version 2); the sequence(s) of the (human) CD33 (B-lymphocyte antigen CD33) can be obtained from the Swiss-Prot database entry P20138 (entry version 129, sequence version 2); the sequence(s) of the (human) CA-12-5 (Mucin 16) can be obtained from the Swiss-Prot database entry Q8WXI7 (entry version 66, sequence version 2); the sequence(s) of the (human) HLA-DR can be obtained from the Swiss-Prot database entry Q29900 (entry version 59, sequence version 1); the sequence(s) of the (human) MUC-1 (Mucin-1) can be obtained from the Swiss-Prot database entry P15941 (entry version 135, sequence version 3); the sequence(s) of the (human) A33 (cell surface A33 antigen) can be obtained from the Swiss-Prot database entry Q99795 (entry version 104, sequence version 1); the sequence(s) of the (human) PSMA (Glutamate carboxypeptidase 2) can be obtained from the Swiss-Prot database entry Q04609 (entry version 133, sequence version 1), the sequence(s) of the (human) transferrin receptor can be obtained from the Swiss-Prot database entries Q9UP52 (entry version 99, sequence version 1) and P02786 (entry version 152, sequence version 2); the sequence of the (human) TNC (tenascin) can be obtained from the Swiss-Prot database entry P24821 (entry version 141, sequence version 3); or the sequence(s) of the (human) CA-IX (carbonic anhydrase IX) can be obtained from the Swiss-Prot database entry Q16790 (entry version 115, sequence version 2).

Therapeutic Use and Methods of Treatment

The molecules or constructs (i.e., antigen binding receptors, transduced T cells and kits) provided herein are particularly useful in medical settings, in particular for treatment of a malignant disease. For examples a tumor may be treated with a transduced T cell expressing an antigen binding receptor of the present invention in conjunction with a therapeutic antibody specific to the tumor cell and comprising a mutated Fc domain. Accordingly, in certain embodiments, the antigen binding receptor, the transduced T cell or the kit are used in the treatment of a malignant disease, in particular wherein the malignant disease is selected from cancer of epithelial, endothelial or mesothelial origin and cancer of the blood.

The tumor specificity of the treatment is provided by the therapeutic antibody comprising a mutated Fc domain, wherein the antibody is administered before, simultaneously with or after administration of transduced T cell expressing an antigen binding receptor of the invention. In this context, the transduced T cells are universal T cells since they are not specific for a given tumor but can be targeted to any tumor depending on the therapeutic antibody comprising the mutated Fc domain used according to the invention.

In this context the malignant disease may be a cancer/carcinoma of epithelial, endothelial or mesothelial origin or a cancer of the blood. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitourinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

For example, tumorous diseases and/or lymphomas may be treated with a specific construct directed against these medical indication(s). The indication for a transduced T cell of the present invention combined with a therapeutic antibody comprising a mutated Fc domain is given by specificity of the therapeutic antibody to a tumor antigen. For example, gastrointestinal cancer, pancreatic cancer, cholangiocellular cancer, lung cancer, breast cancer, ovarian cancer, skin cancer and/or oral cancer may be treated with an antibody comprising a mutated Fc domain wherein the antibody is directed against (human) EpCAM (as the tumor-specific antigen naturally occurring on the surface of a tumor cell).

Gastrointestinal cancer, pancreatic cancer, cholangiocellular cancer, lung cancer, breast cancer, ovarian cancer, skin cancer and/or oral cancer may be treated with a transduced T cell of the present invention administered before, simultaneously with or after administration of a therapeutic antibody comprising a mutated Fc domain wherein the antibody is directed against HER1, preferably human HER1. Furthermore, gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against MCSP, preferably human MCSP. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against FOLR1, preferably human FOLR1. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against Trop-2, preferably human Trop-2. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against PSCA, preferably human PSCA. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against EGFRvIII, preferably human EGFRvIII. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against MSLN, preferably human MSLN. Gastric cancer, breast cancer and/or cervical cancer may be treated with a transduced T cell of the present invention administered before, simultaneously with or after administration of a therapeutic antibody comprising a mutated Fc domain wherein the antibody is directed against HER2, preferably human HER2. Gastric cancer and/or lung cancer may be treated with a transduced T cell of the present invention administered before, simultaneously with or after administration of a therapeutic antibody comprising a mutated Fc domain wherein the antibody is directed against HER3, preferably human HER3. B-cell lymphoma and/or T cell lymphoma may be treated with a transduced T cell of the present invention administered before, simultaneously with or after administration of a therapeutic antibody comprising a mutated Fc domain wherein the antibody is directed against CD20, preferably human CD20. B-cell lymphoma and/or T cell lymphoma may be treated with a transduced T cell of the present invention administered before, simultaneously with or after administration of a therapeutic antibody comprising a mutated Fc domain wherein the antibody is directed against CD22, preferably human CD22. Myeloid leukemia may be treated with a transduced T cell of the present invention administered before, simultaneously with or after administration of a therapeutic antibody comprising a mutated Fc domain wherein the antibody is directed against CD33, preferably human CD33. Ovarian cancer, lung cancer, breast cancer and/or gastrointestinal cancer may be treated with a transduced T cell of the present invention administered before, simultaneously with or after administration of a therapeutic antibody comprising a mutated Fc domain wherein the antibody is directed against CA12-5, preferably human CA12-5. Gastrointestinal cancer, leukemia and/or nasopharyngeal carcinoma may be treated with a transduced T cell of the present invention administered before, simultaneously with or after administration of a therapeutic antibody comprising a mutated Fc domain wherein the antibody is directed against HLA-DR, preferably human HLA-DR. Colon cancer, breast cancer, ovarian cancer, lung cancer and/or pancreatic cancer may be with a transduced T cell of the present invention administered before, simultaneously with or after administration of a therapeutic antibody comprising a mutated Fc domain wherein the antibody is directed against MUC-1, preferably human MUC-1. Colon cancer may be treated with a transduced T cell of the present invention administered before, simultaneously with or after administration of a therapeutic antibody comprising a mutated Fc domain wherein the antibody is directed against A33, preferably human A33. Prostate cancer may be treated with a transduced T cell of the present invention administered before, simultaneously with or after administration of a therapeutic antibody comprising a mutated Fc domain wherein the antibody is directed against PSMA, preferably human PSMA. Gastrointestinal cancer, pancreatic cancer, cholangiocellular cancer, lung cancer, breast cancer, ovarian cancer, skin cancer and/or oral cancer may be treated with a transduced T cell of the present invention administered before, simultaneously with or after administration of a therapeutic antibody comprising a mutated Fc domain wherein the antibody is directed against the transferrin receptor, preferably the human transferring receptor. Pancreatic cancer, lunger cancer and/or breast cancer may be treated with a transduced T cell of the present invention administered before, simultaneously with or after administration of a therapeutic antibody comprising a mutated Fc domain wherein the antibody is directed against the transferrin receptor, preferably the human transferring receptor. Renal cancer may be with a transduced T cell of the present invention administered before, simultaneously with or after administration of a therapeutic antibody comprising a mutated Fc domain wherein the antibody is directed against CA-IX, preferably human CA-IX.

Accordingly, the invention also relates to a method for the treatment of a disease, a malignant disease such as cancer of epithelial, endothelial or mesothelial origin and/or cancer of blood. In the context of the present invention, said subject is a human.

In the context of the present invention a particular method for the treatment of a disease comprises the steps of (a) isolating T cells, preferably CD8+ T cells, from a subject;
(b) transducing said isolated T cells, preferably CD8+ T cells, with an antigen binding receptor as described herein; and
(c) administering the transduced T cells, preferably CD8+ T cells, to said subject.

In the context of the present invention, said transduced T cells, preferably CD8+ T cells, and/or therapeutic antibody/antibodies are co-administered to said subject by intravenous infusion. Moreover, in the context of the present invention the present invention, provides a method for the treatment of a disease comprising the steps of (a) isolating T cells, preferably CD8+ T cells, from a subject;
(b) transducing said isolated T cells, preferably CD8+ T cells, with an antigen binding receptor as described herein;
(c) optionally co-transducing said isolated T cells, preferably CD8+ T cells, with a T cell receptor;
(d) expanding the T cells, preferably CD8+ T cells, by anti-CD3 and anti-CD28 antibodies; and
(e) administering the transduced T cells, preferably CD8+ T cells, to said subject.

The above mentioned step (d) (referring to the expanding step of the T cells such as TIL by anti-CD3 and/or anti-CD28 antibodies) may also be performed in the presence of (stimulating) cytokines such as interleukin-2 and/or interleukin-15 (IL-15). In the context of the present invention, the above mentioned step (d) (referring to the expanding step of the T cells such as TIL by anti-CD3 and/or anti-CD28 antibodies) may also be performed in the presence of interleukin-12 (IL-12), interleukin-7 (IL-7) and/or interleukin-21 (IL-21).

The method for the treatment, in addition, comprise the administration of the antibody used according to the present invention. Said antibody may be administered before, simultaneously with or after the transduced T cells are to be administered. In the context of the present invention the administration of the transduced T cells will be performed by intravenous infusion. In the context of the present invention that transduced T cells are isolated/obtained from the subject to be treated.

Compositions

Furthermore, the invention provides compositions (medicaments) comprising (an) antibody molecule(s) with (a) mutated Fc domain(s), (a) transduced T cell(s) comprising an antigen binding receptor of the invention, (a) nucleic acid molecule(s) and (a) vector(s) encoding the antigen binding receptors according to the invention, and/or and kits comprising one or more of said compositions. In the context of the present invention, the composition is a pharmaceutical composition further comprising, optionally, suitable formulations of carrier, stabilizers and/or excipients. Accordingly, in the context of the present invention a pharmaceutical composition (medicament) is provided that comprises an antibody molecule comprising a mutated Fc domain as defined herein which is to be administered in combination with a transduced T cell comprising an antigen binding receptor as described herein and/or a composition comprising said transduced T cell, wherein said antibody molecule is to be administered before, simultaneously with or after administration of transduced T cells comprising an antigen binding receptor of the invention.

In accordance with this invention, the term "pharmaceutical composition" relates to a composition for administration to a patient, preferably a human patient. Furthermore, in the context of the present invention that patient suffers from a disease, wherein said disease is a malignant disease, especially cancers/carcinomas of epithelial, endothelial or mesothelial origin or a cancer of the blood. In the context of the present invention the cancers/carcinomas is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

In a preferred embodiment, the pharmaceutical composition/medicament comprises an antibody and/or a transduced T cell as defined herein for parenteral, transdermal, intraluminal, intraarterial, intravenous, intrathecal administration or by direct injection into the tissue or tumor. In the context of the present invention the composition/medicament comprises an antibody comprising a mutated Fc domain as defined herein that is to be administered before, simultaneously with or after administration of transduced T cells comprising an antigen binding receptor as defined herein. In the context of the present invention the pharmaceutical composition/medicament comprising an antibody as defined herein is to be administered in combination with a composition/medicament comprising a transduced T cell comprising an antigen binding receptor as defined herein, wherein said T cell was obtained from a subject to be treated.

The use of the term "in combination" does not restrict the order in which the components of the treatment regimen are to be administered to the subject. Accordingly, the pharmaceutical composition/medicament described herein encompass the administration of an antibody as defined herein before, simultaneously with or after administration of transduced T cells comprising an antigen binding receptor of the present invention. "In combination" as used herein also does not restrict the timing between the administration of an antibody as defined herein before and the transduced T cells comprising an antigen binding receptor as defined herein. Thus, when the two components are not administered simultaneously with/concurrently, the administrations may be separated by 1 minute, 5 minutes, 15 minutes, 30 minutes, 45 minutes, 1 hour, 2 hours, 4 hours, 6 hours, 12 hours, 24 hours, 48 hours or 72 hours or by any suitable time differential readily determined by one of skill in art and/or described herein.

In the context of the present invention the term "in combination" also encompasses the situation where the antibody as defined herein and the transduced T cells comprising an antigen binding receptor according to the invention are pre-incubated together before administration to the subject. Thus, the two components may be pre-incubated before administration, for example, for 1 minute, 5 minutes, 10 minutes, 15 minutes, 30 minutes, 45 minutes or 1 hour or for any suitable time readily determined by one skilled in the art. The invention, in another preferred embodiment, relates to a treatment regimen, in which the antibody as defined herein and the transduced T cells comprising an antigen binding receptor as defined herein, are to be administered simultaneously with/concurrently. In the context of the present invention, the antibody as defined herein may be administered after the transduced T cells comprising an antigen binding receptor has been administered.

Further, "in combination" as used herein does not restrict the disclosed treatment regimens to the administration of an antibody as defined herein and transduced T cells, preferably CD8+ T cells, comprising an antigen binding receptor of the invention in immediate sequence (i.e., the administration of one of the two components, followed (after a certain time interval) by the administration of the other without the administration and/or practice of any other treatment protocol in between. Therefore, the present treatment regimens also encompass the separate administration of an antibody molecule as defined herein and transduced T cells, preferably CD8+ T cells, comprising an antigen binding receptor according to the invention, wherein the administrations are separated by one or more treatment protocols necessary and/or suitable for the treatment or prevention of the disease, or a symptom thereof. Examples of such intervening treatment protocols include but are not limited to, administration of pain medications; administration of chemotherapeutics, surgical handling of the disease or a symptom thereof. Accordingly, the treatment regimens as disclosed herein encompass the administration of an antibody as defined herein and transduced T cells, preferably CD8+ T cells, comprising an antigen binding receptor as defined herein together with none, one, or more than one treatment protocol suitable for the treatment or prevention of a disease, or a symptom thereof, as described herein or as known in the art.

It is particular envisaged, that said pharmaceutical composition(s)/medicament(s) is (are) to be administered to a patient via infusion or injection. In the context of the present invention the transduced T cells comprising an antigen binding receptor as described herein is to be administered to a patient via infusion or injection. Administration of the suitable compositions/medicaments may be effected by different ways, intravenous, intraperitoneal, subcutaneous, intramuscular, topical or intradermal administration.

The pharmaceutical composition/medicament of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 µg to 5 g units per day. However, a more preferred dosage for continuous infusion might be in the range of 0.01 µg to 2 mg, preferably 0.01 µg to 1 mg, more preferably 0.01 µg to 100 µg, even more preferably 0.01 µg to 50 µg and most preferably 0.01 µg to 10 µg units per kilogram of body weight per hour. Particularly preferred dosages are recited herein below. Progress can be monitored by periodic assessment. Dosages will vary but a preferred dosage for intravenous administration of DNA is from approximately $10^6$ to $10^{12}$ copies of the DNA molecule.

The compositions of the invention may be administered locally or systematically. Administration will generally be parenterally, e.g., intravenously; transduced T cells may also be administered directed to the target site, e.g., by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. It is envisaged that the pharmaceutical composition of the invention might comprise, in addition to the proteinaceous antibody constructs or nucleic acid molecules or vectors encoding the same (as described in this invention), and/or cells, further biologically active agents, depending on the intended use of the pharmaceutical composition. Such agents might be drugs acting on the gastro-intestinal system, drugs acting as cytostatica, drugs preventing hyperurikemia, drugs inhibiting immunereactions (e.g. corticosteroids), drugs acting on the circulatory system and/or agents such as T cell co-stimulatory molecules or cytokines known in the art.

Possible indication for administration of the composition(s)/medicament(s) of the invention are malignant diseases such as cancer of epithelial, endothelial or mesothelial origin and cancer of the blood, especially epithelial cancers/carcinomas such as breast cancer, colon cancer, prostate cancer, head and neck cancer, skin cancer (melanoma), cancers of the genitor-urinary tract, e.g., ovarial cancer, testis cancer, endothelial cancer, cervix cancer and kidney cancer, lung cancer, gastric cancer, cancer of the bile duct, esophagus cancer, cancer of the salivatory glands and cancer of the thyroid gland or other tumorous diseases like haematological tumors, gliomas, sarcomas or osteosarcomas.

The invention further envisages the co-administration protocols with other compounds, e.g., molecules capable of providing an activation signal for immune effector cells, for cell proliferation or for cell stimulation. Said molecule may be, e.g., a further primary activation signal for T cells (e.g. a further costimulatory molecule: molecules of B7 family, Ox40L, 4.1 BBL, CD40L, anti-CTLA-4, anti-PD-1), or a further cytokine interleukin (e.g., IL-2).

The composition of the invention as described above may also be a diagnostic composition further comprising, optionally, means and methods for detection.

Accordingly, in preferred embodiments, provided are the kit, the antigen binding receptors or the transduced T cell as described herein for use as a medicament. In the context of the present invention, the antigen binding receptor according to the invention for use as a medicament is provided, wherein one or more antibodies comprising a mutated Fc domain as described herein is/are to be administered before, simultaneously with or after administration of transduced T cells, preferably CD8+ T cells, comprising and/or expressing an antigen binding receptor as defined herein and wherein said T cells, preferably CD8+ T cells, were obtained from a subject to be treated. Said medicament may be employed in a method of treatment of malignant diseases especially cancers/carcinomas of epithelial, endothelial or mesothelial origin or of the blood. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

Furthermore, in the context of the present invention the antibody as described herein comprising a mutated Fc domain binds to a tumor-specific antigen naturally occurring on the surface of a tumor cell, wherein said antibody molecule is to be administered before, simultaneously with or after administration of transduced T cells, preferably CD8+ T cells, from said subject comprising an antigen binding receptor as defined herein. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

Furthermore, in accordance to the invention, a molecule or construct (i.e., an antibody molecule described herein) comprising one or two binding domains directed to/binding to/interacting with a tumor antigen, preferably a human tumor antigen, (as the tumor-specific antigen naturally occurring on the surface of a tumor cell) and comprising a mutated Fc domain, wherein the herein defined extracellular domains of the antigen binding receptor of the present invention is directed to/binding to/interacting with the mutated Fc domain, is provided for in the treatment of gastrointestinal cancer, pancreatic cancer, cholangiocellular cancer, lung cancer, breast cancer, ovarian cancer, skin cancer and/or oral cancer. Thus, in the context of the present invention an antibody molecule comprising two binding domains directed to/binding to/interacting with a tumor antigen, preferably a human tumor antigen, and comprising a mutated Fc domain, wherein the herein defined extracellular domains of the antigen binding receptor is directed to/binding to/interacting with the mutated Fc domain, for use in the treatment of epithelial, endothelial or mesothelial origin and cancer of the blood is provided.

In one embodiment, provided is (i) an antibody, comprising two binding domains directed to/binding to/interacting with a tumor antigen, preferably a human tumor antigen, and a mutated Fc domain; and (ii) the antigen binding receptor according to the invention directed to/binding to/interacting with the mutated Fc domain, for use in the treatment of gastrointestinal cancer, pancreatic cancer, cholangiocellular cancer, lung cancer, breast cancer, ovarian cancer, skin cancer and/or oral cancer.

In one embodiment, provided is (i) an antibody, comprising one or two binding domain(s) against HER1, preferably human HER1, and a mutated Fc domain, and (ii) the antigen binding receptor according to the invention directed to/binding to/interacting with the mutated Fc domain, for use in the treatment of gastrointestinal cancer, pancreatic cancer, cholangiocellular cancer, lung cancer, breast cancer, ovarian cancer, skin cancer and/or oral cancer.

In one embodiment, provided is (i) an antibody, comprising one or two binding domain(s) against HER2, preferably human HER2, and a mutated Fc domain, and (ii) the antigen binding receptor according to the invention directed to/binding to/interacting with the mutated Fc domain, for use in the treatment of gastric cancer, breast cancer and/or cervical cancer.

In one embodiment, provided is (i) an antibody, comprising one or two binding domain(s) against HER3, preferably human HER3, and a mutated Fc domain, and (ii) the antigen binding receptor according to the invention directed to/binding to/interacting with the mutated Fc domain, for use in the treatment of gastric cancer and/or lung cancer.

In one embodiment, provided is (i) an antibody, comprising one or two binding domain(s) against CEA, preferably human CEA, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against p95, preferably human p95, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against BCMA, preferably human BCMA, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against MSLN, preferably human MSLN, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against MCSP, preferably human MCSP, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against CD19, preferably human CD19, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against CD20, preferably human CD20, and a mutated Fc domain, and (ii) the antigen binding receptor according to the invention directed to/binding to/interacting with the mutated Fc domain, for use in the treatment of B-cell lymphoma and/or T cell lymphoma.

In one embodiment, provided is (i) an antibody, comprising one or two binding domain(s) against CD22, preferably human CD22, and a mutated Fc domain, and (ii) the antigen binding receptor according to the invention directed to/binding to/interacting with the mutated Fc domain, for use in the treatment of B-cell lymphoma and/or T cell lymphoma.

In one embodiment, provided is (i) an antibody, comprising one or two binding domain(s) against CD38, preferably human CD38, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against CD52Flt3, preferably human CD52Flt3, and a mutated Fc domain; and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against FolR1, preferably human FolR1, and a mutated Fc domain; and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against Trop-2, preferably human Trop-2, and a mutated Fc domain; and (ii) the antigen binding receptor according to the invention directed to/binding to/interacting with the mutated Fc domain, for use in the treatment of gastrointestinal cancer, pancreatic cancer, cholangiocellular cancer, lung cancer, breast cancer, ovarian cancer, skin cancer, glioblastoma and/or oral cancer.

In one embodiment, provided is (i) an antibody, comprising one or two binding domain(s) against CA-12-5, preferably human CA-12-5, and a mutated Fc domain; and (ii) the antigen binding receptor according to the invention directed to/binding to/interacting with the mutated Fc domain, for use in the treatment of ovarian cancer, lung cancer, breast cancer and/or gastrointestinal cancer.

In one embodiment, provided is (i) an antibody, comprising one or two binding domain(s) against HLA-DR, preferably human HLA-DR, and a mutated Fc domain; and (ii) the antigen binding receptor according to the invention directed to/binding to/interacting with the mutated Fc domain, for use in the treatment of gastrointestinal cancer, leukemia and/or nasopharyngeal carcinoma.

In one embodiment, provided (i) is an antibody, comprising one or two binding domain(s) against MUC-1, preferably human MUC-1, and a mutated Fc domain; and (ii) the antigen binding receptor according to the invention directed to/binding to/interacting with the mutated Fc domain, for use in the treatment cancer of colon cancer, breast cancer, ovarian cancer, lung cancer and/or pancreatic cancer.

In one embodiment, provided is (i) an antibody molecule, comprising one or two binding domain(s) against A33, preferably human A33, and a mutated Fc domain; and (ii) the antigen binding receptor according to the invention directed to/binding to/interacting with the mutated Fc domain, for use in the treatment of colon cancer.

In one embodiment, provided is (i) an antibody, comprising one or two binding domain(s) against PSMA, preferably human PSMA, and a mutated Fc domain; and (ii) the antigen binding receptor according to the invention directed to/binding to/interacting with the mutated Fc domain, for use in the treatment of prostate cancer.

In one embodiment, provided is (i) an antibody molecule, comprising one or two binding domain(s) against PSCA, preferably human PSCA, and a mutated Fc domain; and (ii) the antigen binding receptor according to the invention directed to/binding to/interacting with the mutated Fc domain, for use in the treatment cancer of epithelial, endothelial or mesothelial origin and cancer of the blood.

In one embodiment, provided is (i) an antibody molecule, comprising one or two binding domain(s) against transferrin-receptor, preferably human transferring-receptor, and a mutated Fc domain; and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against tenascin, preferably human tenascin, and a mutated Fc domain; and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody molecule, comprising one or two binding domain(s) against CA-IX, preferably human XA-IX, and a mutated Fc domain; and (ii) the antigen binding receptor according to the invention directed to/binding to/interacting with the mutated Fc domain, for use in the treatment of renal cancer.

Exemplary Embodiments

1. An antigen binding receptor comprising an anchoring transmembrane domain and an extracellular domain comprising an antigen binding moiety, wherein the antigen binding moiety is capable of specific binding to a mutated fragment crystallizable (Fc) domain but not capable of specific binding to the non-mutated parent Fc domain, wherein the mutated Fc domain comprises at least one amino acid substitution compared to the non-mutated parent Fc domain.

2. The antigen binding receptor of embodiment 1, wherein Fc receptor binding of the mutated Fc domain is reduced compared to Fc receptor binding of the non-mutated parent Fc domain, particularly wherein the Fc receptor is a Fcγ receptor or neonatal Fc receptor (FcRn).

3. The antigen binding receptor of any one of embodiments 1 or 2, wherein Fc receptor binding is measured by Surface Plasmon Resonance (SPR) at 25° C.

4. The antigen binding receptor of any one of embodiments 1 to 3, wherein the antigen binding moiety is a scFv, a Fab, crossFab or a scFab.

5. The antigen binding receptor of any one of embodiments 1 to 4, wherein the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof.

6. The antigen binding receptor of any one of embodiments 1 to 5, wherein the anchoring transmembrane domain is the CD28 transmembrane domain, in particular wherein the anchoring transmembrane domain comprises the amino acid sequence of SEQ ID NO:11.

7. The antigen binding receptor of any one of embodiments 1 to 6 further comprising at least one stimulatory signaling domain and/or at least one co-stimulatory signaling domain.

8. The antigen binding receptor of any one of embodiments 1 to 7, wherein the at least one stimulatory signaling domain is individually selected from the group consisting of the intracellular domain of CD3z, of FCGR3A and of NKG2D, or fragments thereof.

9. The antigen binding receptor of any one of embodiments 1 to 8, wherein the at least one stimulatory signaling domain is the intracellular domain of CD3z or a fragment thereof, in particular wherein the at least one stimulatory signaling domain comprises the amino acid sequence of SEQ ID NO:13.

10. The antigen binding receptor of any one of embodiments 1 to 9, wherein the at least one co-stimulatory signaling domain is individually selected from the group consisting of the intracellular domain of CD27, of CD28, of CD137, of OX40, of ICOS, of DAP10 and of DAP12, or fragments thereof.

11. The antigen binding receptor of any one of embodiments 1 to 10, wherein the at least one co-stimulatory signaling domain is the CD28 intracellular domain or a fragment thereof, in particular, wherein the at least one co-stimulatory signaling domain comprises the amino acid sequence of SEQ ID NO:12.

12. The antigen binding receptor of any one of embodiments 1 to 11, wherein the antigen binding receptor comprises one stimulatory signaling domain comprising the intracellular domain of CD3z, or a fragment thereof, and wherein the antigen binding receptor comprises one co-stimulatory signaling domain comprising the intracellular domain of CD28, or a fragment thereof.

13. The antigen binding receptor of embodiment 12, wherein the stimulatory signaling domain comprises the amino acid sequence of SEQ ID NO:13 and the co-stimulatory signaling domain comprises the amino acid sequence of SEQ ID NO:12.

14. The antigen binding receptor of any one of embodiments 1 to 13, wherein the extracellular domain is connected to the anchoring transmembrane domain, optionally through a peptide linker.

15. The antigen binding receptor of embodiment 14, wherein the peptide linker comprises the amino acid sequence GGGGS (SEQ ID NO:17).

16. The antigen binding receptor of any one of embodiments 1 to 15, wherein the anchoring transmembrane domain is connected to a co-signaling domain or to a signaling domain, optionally through a peptide linker.

17. The antigen binding receptor of any one of embodiments 1 to 16, wherein the signaling and/or co-signaling domains are connected, optionally through at least one peptide linker.

18. The antigen binding receptor of any one of embodiments 1 to 17, wherein the antigen binding moiety is a scFv fragment, wherein the scFv fragment is connected at the C-terminus to the N-terminus of the anchoring transmembrane domain, optionally through a peptide linker.

19. The antigen binding receptor of any one of embodiments 1 to 17, wherein the antigen binding moiety is a Fab fragment or a crossFab fragment, wherein the Fab or crossFab fragment is connected at the C-terminus of the heavy chain to the N-terminus of the anchoring transmembrane domain, optionally through a peptide linker.

20. The antigen binding receptor of any one of embodiments 7 to 19, wherein the antigen binding receptor comprises one co-signaling domain, wherein the co-signaling domain is connected at the N-terminus to the C-terminus of the anchoring transmembrane domain.

21. The antigen binding receptor of embodiment 20, wherein the antigen binding receptor additionally comprises one stimulatory signaling domain, wherein the stimulatory signaling domain is connected at the N-terminus to the C-terminus of the co-stimulatory signaling domain.

22. The antigen binding receptor of any one of embodiments 1 to 21, wherein the non-mutated parent Fc domain is an IgG1 or an IgG4 Fc domain, particularly a human IgG1 Fc domain.

23. The antigen binding receptor of any one of embodiments 1 to 22, wherein the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.

24 The antigen binding receptor of any one of embodiments 1 to 23, wherein the mutant Fc domain comprises an amino acid substitution at a position selected from the group consisting of residue 117, 118, 136, 180, 193, 212, 214, and 318 of human IgG1 Fc (SEQ ID NO: 130), in particular wherein the amino acid mutation is L117A, L118A, I136A, N180A, H193A, P212G, P214G and/or H318A.

25. The antigen binding receptor of any one of embodiments 1 to 24, wherein the mutated Fc domain comprises at least one amino acid mutation at a position selected from the group consisting of L234, L235 and P329 according to EU numbering, in particular the amino acid mutations L234A, L235A and P329G ("PGLALA").

26. The antigen binding receptor of any one of embodiments 1 to 25, wherein the mutated Fc domain comprises the amino acid mutation P329G according to EU numbering, wherein Fcγ receptor binding of the mutated Fc domain is reduced compared to Fcγ receptor binding of the non-mutated parent Fc domain, in particular wherein the Fcγ receptor is human FcγRIIIa and/or FcγRIIa.

27 The antigen binding receptor of any one of embodiments 1 to 26, wherein the mutant Fc domain comprises an amino acid substitution at position 212 of human IgG1 Fc (SEQ ID NO: 130), in particular wherein the amino acid mutation is P212G.

28. The antigen binding receptor of any one of embodiments 1 to 24, wherein the mutated Fc domain comprises at least one amino acid mutation at a position selected from the group consisting of I253, H310 and H435 according to EU numbering, in particular the amino acid mutations I253A, H310A and H435A ("AAA"), wherein FcRn binding of the mutated Fc domain is reduced compared to FcRn binding of the non-mutated parent Fc domain.

29 The antigen binding receptor of any one of embodiments 1 to 24 or 28, wherein the mutant Fc domain comprises an amino acid substitution at positions 136, 193, and 318 of human IgG1 Fc (SEQ ID NO: 130), in particular wherein the amino acid mutation is I136A, H193A, and H318A ("AAA").

30. The antigen binding receptor of any one of embodiments 1 to 27, wherein the at least one antigen binding moiety is capable of specific binding to a mutated Fc domain comprising the P329G mutation but not capable of specific binding to the non-mutated parent Fc domain, wherein the antigen binding moiety comprises:
(i) a heavy chain variable region (VH) comprising
    (a) the heavy chain complementarity-determining region (CDR H) 1 amino acid sequence RYWMN (SEQ ID NO:1);
    (b) the CDR H2 amino acid sequence EITPDSSTINYTPSLKD (SEQ ID NO:2); and
    (c) the CDR H3 amino acid sequence PYDYGAWFAS (SEQ ID NO:3); and
(ii) a light chain variable region (VL) comprising
    (d) the light chain complementarity-determining region (CDR L) 1 amino acid sequence RSSTGAVTTSNYAN (SEQ ID NO:4);
    (e) the CDR L2 amino acid sequence GTNKRAP (SEQ ID NO:5); and
    (f) the CDR L3 amino acid sequence ALWYSNHWV (SEQ ID NO:6).

31. The antigen binding receptor of any one of embodiments 1 to 27 or 30, wherein the at least one antigen binding moiety is capable of specific binding to a mutated Fc domain comprising the P329G mutation but not capable of specific binding to the non-mutated parent Fc domain, wherein the antigen binding moiety comprises a heavy chain variable region (VH) comprising an amino acid sequence that is at least about 95%, 96%, 97%, 98%, 99% or 100% identical to an amino acid sequence selected from the group consisting of SEQ ID NO:8 and SEQ ID NO:32, and a light chain variable region (VL) comprising an amino acid sequence that is at least about 95%, 96%, 97%, 98%, 99% or 100% identical to an amino acid sequence selected from the group consisting of SEQ ID NO:9 and SEQ ID NO:33.

32. The antigen binding receptor of embodiment 1 to 27, 30 or 31, wherein the at least one antigen binding moiety comprises the heavy chain variable region (VH) of SEQ ID NO:8 and the light chain variable region (VL) of SEQ ID NO:9.

33. The antigen binding receptor of any one of embodiments 1 to 27 or 30 to 32, wherein the at least one antigen binding moiety is a scFv capable of specific binding to a mutated Fc domain comprising the P329G mutation but not capable of specific binding to the non-mutated parent Fc domain, wherein the antigen binding receptor comprises an amino acid sequence that is at least about 95%, 96%, 97%, 98%, 99% or 100% identical to an amino acid sequence selected from the group consisting of SEQ ID NO:7 and SEQ ID NO:31.

34. The antigen binding receptor of embodiment 33, comprising the amino acid sequence of SEQ ID NO:7.

35. The antigen binding receptor of any one of embodiments 1 to 27 or 30 to 32, wherein the at least one antigen binding moiety is a Fab fragment capable of specific binding to a mutated Fc domain comprising the P329G mutation but not capable of specific binding to the non-mutated parent Fc domain, wherein the antigen binding receptor comprises
   a) a heavy chain fusion polypeptide that is at least about 95%, 96%, 97%, 98%, 99% or 100% identical to an amino acid sequence selected from the group consisting of SEQ ID NO:39 and SEQ ID NO:48; and
   b) a light chain polypeptide that is at least about 95%, 96%, 97%, 98%, 99% or 100% identical to an amino acid sequence selected from the group consisting of SEQ ID NO:41 and SEQ ID NO:50.

36. The antigen binding receptor of embodiment 35, comprising
   a) the heavy chain fusion polypeptide of SEQ ID NO:39; and
   b) the light chain polypeptide of SEQ ID NO:41.

37. The antigen binding receptor of any one of embodiments 1 to 24 or 28 to 29, wherein the at least one antigen binding moiety is capable of specific binding to a mutated Fc domain comprising the I253A, H310A and H435A ("AAA") mutations but not capable of specific binding to the non-mutated parent Fc domain, wherein the antigen binding moiety comprises:
   (i) a heavy chain variable region (VH) comprising
      (a) the heavy chain complementarity-determining region (CDR H) 1 amino acid sequence SYGMS (SEQ ID NO:53);
      (b) the CDR H2 amino acid sequence SSGGSY (SEQ ID NO:54); and
      (c) the CDR H3 amino acid sequence LGMITTGYAMDY (SEQ ID NO:55); and
   (ii) a light chain variable region (VL) comprising
      (d) the light chain complementarity-determining region (CDR L) 1 amino acid sequence RSSQTIVHSTGHTYLE (SEQ ID NO:56);
      (e) the CDR L2 amino acid sequence KVSNRFS (SEQ ID NO:57); and
      (f) the CDR L3 amino acid sequence FQGSHVPYT (SEQ ID NO:58).

38. The antigen binding receptor of any one of embodiments 1 to 24, 28, 29 or 37, wherein the at least one antigen binding moiety is capable of specific binding to a mutated Fc domain comprising the I253A, H310A and H435A ("AAA") mutations but not capable of specific binding to the non-mutated parent Fc domain, wherein the antigen binding moiety comprises a heavy chain variable region (VH) comprising an amino acid sequence that is at least about 95%, 96%, 97%, 98%, 99% or 100% identical to the amino acid sequence of SEQ ID NO:61 and a light chain variable region (VL) comprising an amino acid sequence that is at least about 95%, 96%, 97%, 98%, 99% or 100% identical to the amino acid sequence of SEQ ID NO:62.

39. The antigen binding receptor of embodiment 1 to 24, 28, 29 or 37 to 38, wherein the at least one antigen binding moiety comprises
   a) the heavy chain variable region (VH) of SEQ ID NO:61; and
   b) the light chain variable region (VL) of SEQ ID NO:62.

40. The antigen binding receptor of any one of embodiments 1 to 24, 28, 29 or 37 to 39, wherein the at least one antigen binding moiety is a scFv capable of specific binding to a mutated Fc domain comprising the I253A, H310A and H435A ("AAA") mutations but not capable of specific binding to the non-mutated parent Fc domain, wherein the antigen binding receptor comprises an amino acid sequence that is at least about 95%, 96%, 97%, 98%, 99% or 100% identical to the amino acid sequence of SEQ ID NO:59.

41. The antigen binding receptor of embodiment 40, comprising the amino acid sequence of SEQ ID NO:59.

42. The antigen binding receptor of any one of embodiments 1 to 27 or 30 to 32, wherein the at least one antigen binding moiety is a Fab fragment capable of specific binding to a mutated Fc domain comprising the P329G mutation but not capable of specific binding to the non-mutated parent Fc domain, wherein the antigen binding receptor comprises
   a) a heavy chain fusion polypeptide that is at least about 95%, 96%, 97%, 98%, 99% or 100% identical to the amino acid sequence of SEQ ID NO:39; and
   b) a light chain polypeptide that is at least about 95%, 96%, 97%, 98%, 99% or 100% identical to the amino acid sequence of SEQ ID NO:41.

43. The antigen binding receptor of embodiment 42, comprising
   a) the heavy chain fusion polypeptide of SEQ ID NO:39; and
   b) the light chain polypeptide of SEQ ID NO:41.

44. An isolated polynucleotide encoding the antigen binding receptor of any one of embodiments 1 to 43.

45. An isolated polynucleotide encoding a heavy chain fusion polypeptide or a light chain polypeptide of the antigen binding receptor of any one of embodiments 1 to 32, 35 to 39 and 42 to 43.

46. A composition encoding the antigen binding receptor of any one of embodiments 1 to 32, 35 to 39 and 42 to 43, comprising a first isolated polynucleotide encoding a heavy chain fusion polypeptide, and a second isolated polynucleotide encoding a light chain polypeptide.

47. A polypeptide encoded by the polynucleotide of any one of embodiments 44 or 45 or by the composition of embodiment 46.

48. A vector, particularly an expression vector, comprising the polynucleotide of embodiment 44 or the polynucleotides of embodiment 45.

49. A transduced T cell comprising the polynucleotide of embodiment 44, the composition of embodiment 46 or the vector of embodiment 48.

50. A transduced T cell capable of expressing the antigen binding receptor of any one of embodiments 1 to 43.

51. The transduced T cell of any one of embodiments 49 or 50, wherein the transduced T cell is co-transduced with a T cell receptor (TCR) capable of specific binding of a target antigen.

52. A kit comprising
   (A) a transduced T cell capable of expressing the antigen binding receptor of any one of embodiments 1 to 43; and
   (B) an antibody comprising a mutated Fc domain;
   wherein the antigen binding receptor is capable of specific binding to the mutated Fc domain but not capable of specific binding to the non-mutated parent Fc domain.

53. A kit comprising
   (A) an isolated polynucleotide encoding the antigen binding receptor of any one of embodiments 1 to 43; and (B) an antibody comprising a mutated Fc domain;
wherein the antigen binding receptor is capable of specific binding to the mutated Fc domain but not capable of specific binding to the non-mutated parent Fc domain.

54. A kit comprising
(A) the composition of embodiment 46 or the vector of embodiment 48 encoding the antigen binding receptor of any one of embodiments 1 to 43; and
(B) an antibody comprising a mutated Fc domain;
wherein the antigen binding receptor is capable of specific binding to the mutated Fc domain but not capable of specific binding to the non-mutated parent Fc domain.

55. The kit of any one of embodiments 52 to 54, wherein the non-mutated parent Fc domain is an IgG1 or an IgG4 Fc domain, particularly a human IgG1 Fc domain.

56. The kit of any one of embodiments 52 to 55, wherein Fc receptor binding of the mutated Fc domain is reduced compared to Fc receptor binding of the non-mutated parent Fc domain, particularly wherein the Fc receptor is a Fcγ receptor or neonatal Fc receptor (FcRn).

57. The kit of embodiment 56, wherein Fc receptor binding is measured by Surface Plasmon Resonance (SPR) at 25° C.

58. The kit of any one of embodiments 52 to 57, wherein the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.

59. The kit of any one of embodiments 52 to 58, wherein the mutated Fc domain comprises at least one amino acid mutation at a position selected from the group consisting of L234, L235 and P329 according to EU numbering, in particular the amino acid mutations L234A, L235A and P329G ("PGLALA").

60. The kit of any one of embodiments 52 to 59, wherein the mutated Fc domain comprises the amino acid mutation P329G according to EU numbering.

61. The kit of any one of embodiments 52 to 60, wherein the mutated Fc domain comprises at least one amino acid mutation at a position selected from the group consisting of I253, H310 and H435 according to EU numbering, in particular the amino acid mutations I253A, H310A and H435A ("AAA").

62. The kit of any one of embodiments 52 to 61, wherein the antibody comprising the mutated Fc domain is capable of specific binding to an antigen on the surface of a tumor cell, in particular wherein the antigen is selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX, and/or to a peptide bound to a molecule of the human major histocompatibility complex (MHC).

63. The kit of any one of embodiments 52 to 62, wherein the antibody comprising the mutated Fc domain is capable of specific binding to an antigen selected from the group consisting of fibroblast activation protein (FAP), carcinoembryonic antigen (CEA), mesothelin (MSLN), CD20, folate receptor 1 (FOLR1) and tenascin (TNC).

64. The kit of any one of embodiments 52 to 63 for use as a medicament.

65. The antigen binding receptor of any one of embodiments 1 to 43 or the transduced T cell of any one of embodiments 49 to 51 for use as a medicament, wherein a transduced T cell expressing the antigen binding receptor is administered before, simultaneously with or after administration of an antibody comprising a mutated Fc domain wherein the antigen binding receptor is capable of specific binding to the mutated Fc domain but not capable of specific binding to the non-mutated parent Fc domain.

66. The kit of any one of embodiments 52 to 63 for use in the treatment of a disease, in particular for use in the treatment of a malignant disease.

67. The antigen binding receptor of any one of embodiments 1 to 43 or the transduced T cell of any one of embodiments 49 to 51 for use in the treatment of a malignant disease, wherein the treatment comprises administration of a transduced T cell expressing the antigen binding receptor before, simultaneously with or after administration of an antibody comprising a mutated Fc domain wherein the antigen binding receptor is capable of specific binding to the mutated Fc domain but not capable of specific binding to the non-mutated parent Fc domain.

68. The antigen binding receptor, the transduced T cell or the kit for use according to embodiment 66 or 67, wherein said malignant disease is selected from cancer of epithelial, endothelial or mesothelial origin and cancer of the blood.

69. The antigen binding receptor, the transduced T cell or the kit for use according to embodiments 66 to 68, wherein the antibody comprising the mutated Fc domain is capable of specific binding to an antigen on the surface of tumor cells, in particular wherein the antigen is selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX, and/or to a peptide bound to a molecule of the human major histocompatibility complex (MHC).

70. The antigen binding receptor, the transduced T cell or the kit for use according to embodiments 66 to 69, wherein the antibody comprising the mutated Fc domain is capable of specific binding to an antigen selected from the group consisting of fibroblast activation protein (FAP), carcinoembryonic antigen (CEA), mesothelin (MSLN), CD20, folate receptor 1 (FOLR1) and tenascin (TNC).

71. The antigen binding receptor, the transduced T cell or the kit for use according to any one of embodiments 66 to 70, wherein the transduced T cell is derived from a cell isolated from the subject to be treated.

72. The antigen binding receptor, the transduced T cell or the kit for use according to any one of embodiments 66 to 70, wherein the transduced T cell is not derived from a cell isolated from the subject to be treated.

73. A method of treating a disease in a subject, comprising administering to the subject a transduced T cell capable of expressing the antigen binding receptor of any one of embodiments 1 to 43 and administering before, simultaneously with or after administration of the transduced T cell a therapeutically effective amount of an antibody comprising a mutated Fc domain, wherein the antigen binding receptor is capable of specific binding to the mutated Fc domain but not capable of specific binding to the non-mutated parent Fc domain.

74. The method of embodiment 73, additionally comprising isolating a T cell from the subject and generating the transduced T cell by transducing the isolated T cell with the polynucleotide of embodiment 44, the composition of embodiment or the vector of embodiment 48.

75. The method of embodiment 74, wherein the T cell is transduced with a retroviral or lentiviral vector construct or with a non-viral vector construct.

76. The method of embodiment 75, wherein the non-viral vector construct is a sleeping beauty minicircle vector.

77. The method of any one of embodiments 73 to 76, wherein the transduced T cell is administered to the subject by intravenous infusion.

78. The method of any one of embodiments 73 to 77, wherein the transduced T cell is contacted with anti-CD3 and/or anti-CD28 antibodies prior to administration to the subject.

79. The method of any one of embodiments 73 to 78, wherein the transduced T cell is contacted with at least one cytokine prior to administration to the subject, preferably with interleukin-2 (IL-2), interleukin-7 (IL-7), interleukin-15 (IL-15), and/or interleukin-21, or variants thereof.

80. The method of any one of embodiments 73 to 79, wherein the disease is a malignant disease.

81. The method of any one of embodiments 73 to 79, wherein the disease is selected from cancer of epithelial, endothelial or mesothelial origin and cancer of the blood.

82. A method for inducing lysis of a target cell, comprising contacting the target cell with a transduced T cell capable of expressing the antigen binding receptor of any one of embodiments 1 to 43 in the presence of an antibody comprising a mutated Fc domain wherein the antigen binding receptor is capable of specific binding to the mutated Fc domain but not capable of specific binding to the non-mutated parent Fc domain.

83. The method of embodiment 82, wherein the target cell is a cancer cell.

84. The method of any one of embodiments 82 or 83, wherein the target cell expresses an antigen selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX.

85. The method of any one of embodiments 82 to 84, wherein the target cell expresses an antigen selected from the group consisting of fibroblast activation protein (FAP), carcinoembryonic antigen (CEA), mesothelin (MSLN), CD20, folate receptor 1 (FOLR1), and tenascin (TNC).

86. Use of the antigen binding receptor of any one of embodiments 1 to 43, the polynucleotides of any one of embodiments 44 and 45 or the transduced T cell of any one of embodiments 49 to 51 for the manufacture of a medicament.

87. The use of embodiment 86, wherein the medicament is for treatment of a malignant disease.

88. The use of embodiment 86, wherein the medicament is for treatment of a disease.

89. The use of embodiment 87, characterized in that said malignant disease is selected from cancer of epithelial, endothelial or mesothelial origin and cancer of the blood.

90. The use of embodiment 88, characterized in that said disease is selected from cancer of epithelial, endothelial or mesothelial origin and cancer of the blood.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.lycos.com.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE and size exclusion chromatography (SEC).

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Antibody Production

The Pro329Gly, Leu234Ala and Leu235Ala mutations were introduced in the constant region to abrogate binding to Fc gamma receptors according to the method described in International Patent Appl. Publ. No. WO2012/130831A1. Accordingly, the I253A, H310A and H435A ("AAA") mutations were introduced in the constant region to abrogate binding to FcRn. The respective antibodies were produced by co-transfecting HEK293-EBNA cells with the mammalian expression vectors using polyethylenimine. The cells were transfected with the corresponding expression vectors for heavy and light chains in a 1:1 ratio Lentiviral Transduction of Jurkat NFAT T Cells To produce lentiviral vectors, respective DNA sequences for the correct assembly of the antigen binding receptor were cloned in frame in a lentiviral polynucleotide vector under a constitutively active human cytomegalovirus immediate early promoter (CMV). The retroviral vector contained a woodchuck hepatitis virus posttranscriptional regulatory element (WPRE), a central polypurine tract (cPPT) element, a pUC origin of replication and a gene encoding for antibiotic resistance facilitating the propagation and selection in bacteria.

To produce functional virus particles, Lipofectamine LTX™ based transfection was performed using 60-70% confluent Hek293T cells (ATCC CRL3216) and CAR containing vectors as well as pCMV-VSV-G:pRSV-REV:pCgpV transfer vectors at 3:1:1:1 ratio. After 48 h supernatant was collected, centrifuge for 5 minutes at 250 g to remove cell debris and filtrated through 0.45 or 0.22 μm polyethersulfon filter. Concentrated virus particles (Lenti-x-Concentrator, Takara) were used to transduce Jurkat NFAT cells (Signosis). Positive transduced cells were sorted as pool or single clones using FACSARIA sorter (BD Bioscience). After cell expansion to appropriate density Jurkat NFAT T cells were used for experiments.

Example 1

Described herein is a Jurkat NFAT T cell reporter assay using CD20 expressing SUDHDL4 tumor cells as target cells and a sorted pool of Anti-P329G-ds-Fab-CD28ATD-CD28CSD-CD3zSSD expressing Jurkat NFAT T cells (FIG. 6A) or a pool of Anti-P329G-ds-scFv-CD28ATD-CD28CSD-CD3zSSD expressing Jurkat NFAT T cells (FIG. 6B) as target cells. GA101 IgG with P329G LALA mutation was used as IgG, which on one hand recognizes the tumor antigen and on the other hand is recognized by the transduced Jurkat NFAT T cells. As positive control a 96 well plate (Cellstar Greiner-bio-one, CAT-No. 655185) was coated with 10 μg/ml CD3 antibody (from Biolegend®) in phosphate buffered saline (PBS) either for 4° C. over night or for at least 1 h at 37° C. The CD3 coated wells were washed twice with PBS, after the final washing step PBS was fully removed. Effector cells or Jurkat NFAT wild type cells were counted and checked for their viability using Cedex HiRes. The cell number was adjusted to 1×10⁶ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the effector cells, to 1×10⁶ viable cells/ml in growth medium. Target cells and effector cells were plated in either 5:1 or 1:1 E:T ratio (110.000 cells per well in total) in triplicates in a 96-well suspension culture plate (Greiner-bio one). As a next step a serial dilution of GA101 with P329G LALA mutation, targeting the antigen of interest, was prepared in growth medium using a 2 ml deep well plate (Axygen®). To obtain final concentrations ranging from 1 μg/ml to 0.0001 μg/ml in a final volume of 200 ul per well, a 50 μl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 μl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and effector cells in a ratio 5:1 (dots) or 1:1 (squares) for 20 h the graphs show a dose-dependent activation of Anti-P329G-ds-Fab-CD28ATD-CD28CSD-CD3zSSD expressing Jurkat NFAT T cells as well as Anti-P329G-ds-scFv-CD28ATD-CD28CSD-CD3zSSD expressing Jurkat NFAT T cells when GA101 IgG with P329G LALA mutation was used as antibody (FIGS. 6A and B, depicted in black). If the GA101 IgG without P329G LALA mutation (FIGS. 6A and B, depicted in grey) was used, no activation of the transduced Jurkat NFAT T cells was detectable. Each point represents the mean value of biological duplicates, each performed as technical duplicate. All values are depicted as baseline corrected. Standard deviation is indicated by error bars.

Example 2

Described herein is a Jurkat NFAT T cell reporter assay using CD20 expressing SUDHDL4 (FIGS. 7C and 7D) or WSUDLCL2 (FIGS. 7A and 7B) tumor cells as target cells and single clone Jurkat NFAT cells expressing Anti-P329G-ds-Fab-CD28ATD-CD28CSD-CD3zSSD as target cells. GA101 IgG with P329G LALA mutation was used as IgG which on one hand recognizes the tumor antigen and on the other hand is recognized by the Jurkat NFAT T cells. Effector cells or Jurkat NFAT wild type cells were counted and checked for their viability using Cedex HiRes. The cell number was adjusted to 1×10⁶ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the effector cells, to 1×10⁶ viable cells/ml in growth medium. Target cells and effector cells were plated in either 10:1, 5:1 or 1:1 E:T ratio (110.000 cells per well in total) in triplicates in a 96-well suspension culture plate (Greiner-bio one). As a next step a serial dilution of GA101 with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Upon co-cultivation of target and effector cells in a ratio 10:1 (dots), 5:1 (squares) or 1:1 (triangles) for 20 h the graphs show a GA101 IgG with P329G LALA dose-dependent activation of Anti-P329G-ds-Fab-CD28ATD-CD28CSD-CD3zSSD expressing Jurkat NFAT T cells (FIG. 7A-D, depicted in black). If the GA101 IgG without P329G LALA mutation (FIG. 7A-D, depicted in grey) was used, then only little activation of the transduced Jurkat NFAT T cells was detectable at the highest antibody concentration of 1 µg/ml. Each point represents the mean value of technical duplicate. All values are depicted as baseline corrected. Standard deviation is indicated by error bars.

Example 3

Described herein is a Jurkat NFAT T cell reporter assay performed using adherent FAP expressing NIH/3T3-huFAP cl 19 tumor cells as target cells. As effector cells a sorted pool of Anti-P329G-ds-Fab-CD28ATD-CD28CSD-CD3zSSD expressing Jurkat NFAT T cells (FIG. 8A) or Anti-P329G-ds-scFv-CD28ATD-CD28CSD-CD3zSSD expressing Jurkat NFAT T cells (FIG. 8C) were used. FAP 4B9 IgG with P329G LALA mutation was used as IgG which on one hand recognizes the tumor antigen and on the other hand is recognized by the Jurkat NFAT T cells. IgG DP47/vk3 harboring P329G LALA mutation was included as isotype control. As positive control wells of a 96 well plate (Greiner-bio-one, CAT-No. 655185) were coated with 10 µg/ml CD3 antibody (from Biolegend®) in phosphate buffered saline (PBS) for at least 1 h at 37° C. The CD3 coated wells were washed twice with PBS, after the final washing step PBS was fully removed. Adherent NIH/3T3-huFAP cl 19 target cells were washed once with PBS and detached using Trypsin. Detached cells were resuspended in DMEM+4.5 g LD-Glucose+L-Glutamine+25 mM HEPES+10% FCS and 1% Glutamax. Effector cells or Jurkat NFAT wild type T cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the effector cells, to $1\times10^6$ viable cells/ml in growth medium. Target cells and effector cells were plated in 5:1 E:T ratio (110,000 cells per well in total) in triplicates in a 96-well suspension culture plate (Greiner-bio one). As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml, in a final volume of 200 ul per well, a 50 µl aliquot of the different dilutions was pipetted to the respective wells. The 96-well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 µl cell suspension was transferred to a new white flat clear bottom 96-well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

FIGS. 8B and 8D, represent data of Anti-P329G-ds-Fab-CD28ATD-CD28CSD-CD3zSSD expressing Jurkat NFAT T cells (FIG. 8D) or Anti-P329G-ds-scFv-CD28ATD-CD28CSD-CD3zSSD expressing Jurkat NFAT T cells (FIG. 8B) both co-cultivated with target cells and 1 µg/ml of FAP 4B9 antibody compared to different control conditions.

Upon incubation with 1 µg/ml FAP 4B9 P329G LALA, Jurkat NFAT T cells (FIGS. 8B and 8D black triangle) as well as target cells only (FIGS. 8B and 8D upside down black triangle) do not show any detectable luminescence signal.

Also Jurkat NFAT T cells show no luminescence signal upon co-cultivation with target cells and 1 µg/ml of FAP 4B9 antibody (FIG. 8B and FIG. 8D black diamond). Whereas CD3 dependent activation of Jurkat NFAT cells co-cultivated with target cells and 1 µg/ml of FAP 4B9 antibody proofs their functionality through a detectable luminescence signal (withe dots). CD3 dependent activation of Anti-P329G-ds-Fab-CD28ATD-CD28CSD-CD3zSSD expressing Jurkat NFAT T cells (FIG. 8B white squares) and activation of Anti-P329G-ds-scFv-CD28ATD-CD28CSD-CD3zSSD expressing Jurkat NFAT T cells (FIG. 8D depicted in white squares) co-cultivated with target cells and 1 µg/ml of FAP 4B9 antibody shows the highest luminescence signals of all, since it combines the CAR mediated activation with CD3 mediated activation. CD3 mediated luminescence signal is also visible when CARs are incubated with target cells and 1 µg/ml of DP47/vk3 antibody (FIG. 8B and FIG. 8D upside down white triangles). Each point represents the mean value of technical triplicates. All values are depicted as baseline corrected. Standard deviation is indicated by error bars.

Example 4

Described herein is a Jurkat NFAT T cell reporter assay using adherent CEA expressing MKN45 tumor cells as target cells. As effector cells a sorted pool of Anti-P329G-ds-Fab-CD28ATD-CD28CSD-CD3zSSD expressing Jurkat NFAT T cells (FIG. 9A) or Anti-P329G-ds-scFv-CD28ATD-CD28CSD-CD3zSSD expressing Jurkat NFAT T cells (FIG. 9C) were used. Either CEA A5B7 IgG or CEA T84 LCHA IgG both with P329G LALA mutation were used. Further IgG DP47/vk3 harboring P329G LALA mutation was included as isotype control. As positive control wells of a 96 well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent MKN45 target cells were washed once with PBS and detached using Trypsin. Detached cells were resuspended in DMEM+4.5 g LD-Glucose+L-Glutamine+25 mM HEPES+10% FCS and 1% Glutamax.

Effector cells or Jurkat NFAT wild type cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the effector cells, to $1\times10^6$ viable cells/ml in RPMI-1640+10% FCS+1% Glutamax.

Target cells and effector cells were plated in 5:1 E:T ratio (110,000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and effector cells in a ratio 5:1 (FIGS. 9A and C, dots) for 20 h the graphs show a dose-dependent activation of Anti-P329G-ds-Fab-CD28ATD-CD28CSD-CD3zSSD expressing Jurkat NFAT T cells as well Anti-P329G-ds-scFv-CD28ATD-CD28CSD-CD3zSSD expressing Jurkat NFAT T cells when CEA A5B7 with P329G LALA mutation was used as antibody (FIGS. 9A and C grey dots). The use of CEA T84 LCHA with P329G LALA mutation showed only for Anti-P329G-ds-Fab-CD28ATD-CD28CSD-CD3zSSD expressing Jurkat NFAT T cells a dose dependent activation (FIG. 9A black dots). Whereas, when using the antibody with P329G LALA mutation an activation of Anti-P329G-ds-scFv-CD28ATD-CD28CSD-CD3zSSD expressing Jurkat NFAT T cells was detectable only at the highest antibody concentration of 1 µg/ml.

If the control antibody DP47/vk3 IgG with P329G LALA mutation (FIGS. 9A and C, black triangles) was used, no activation of Anti-P329G-ds-scFv-CD28ATD-CD28CSD-CD3zSSD Jurkat NFAT T cells or Anti-P329G-ds-Fab-CD28ATD-CD28CSD-CD3zSSD expressing Jurkat NFAT T cells was detectable. Each point represents the mean value of technical triplicates. Standard deviation is indicated by error bars.

Figure 9B:
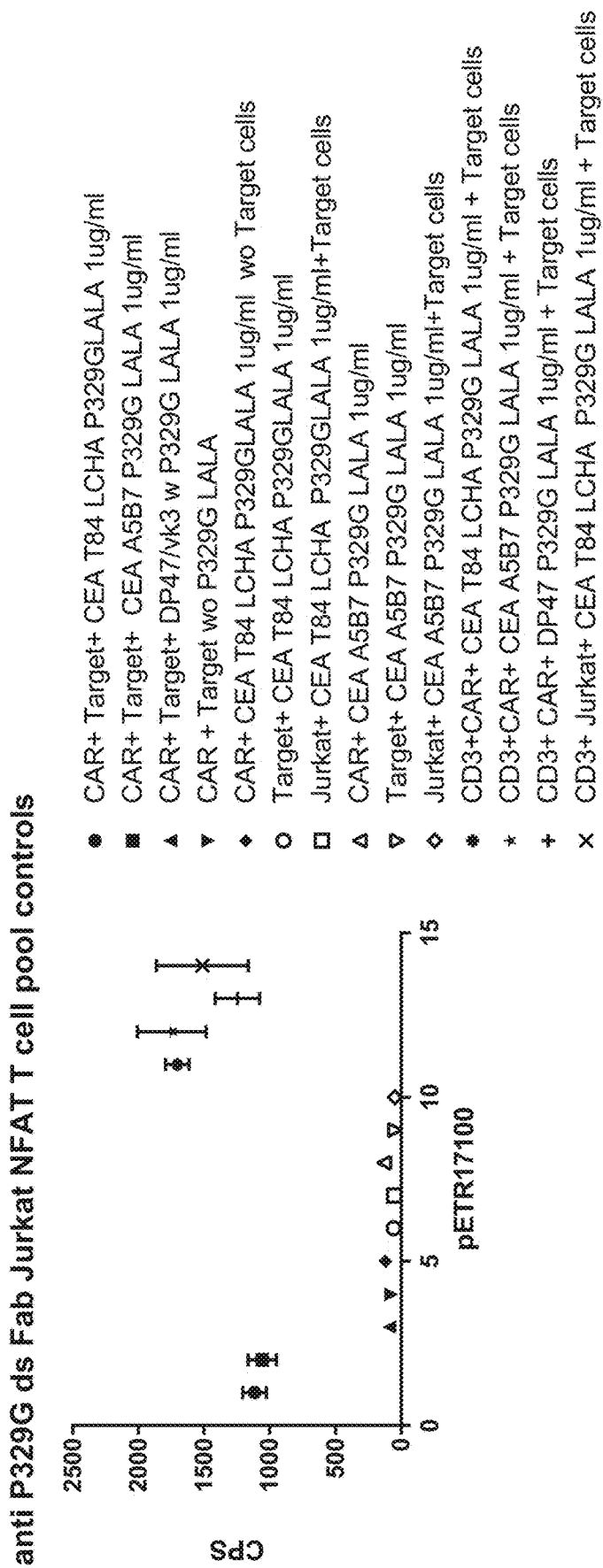
Figure 9C:
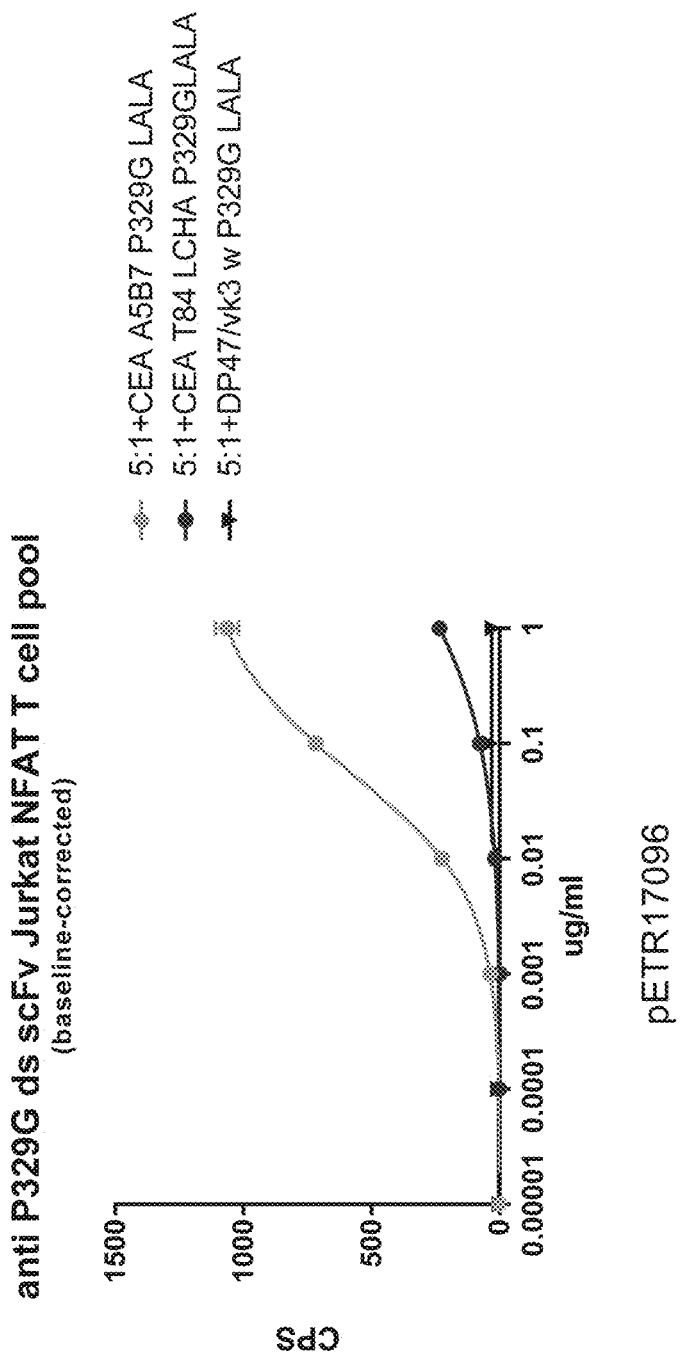
Figure 9D:
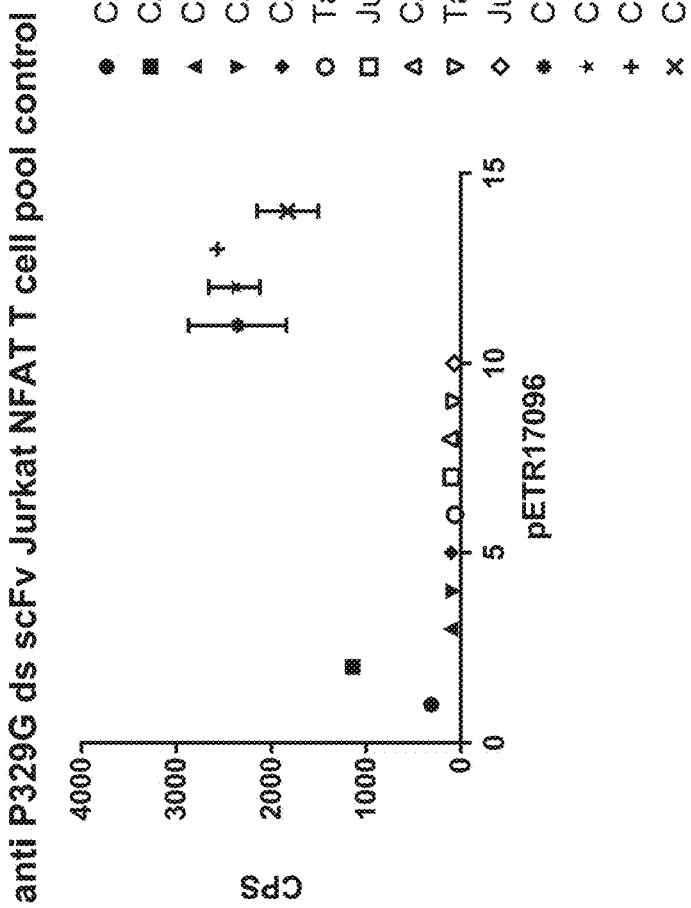

FIGS. 9B and 9D, represent data of Anti-P329G-ds-Fab-CD28ATD-CD28CSD-CD3zSSD expressing Jurkat NFAT T cells (FIG. 9B) or Anti-P329G-ds-scFv-CD28ATD-CD28CSD-CD3zSSD expressing Jurkat NFAT T cells (FIG. 9D) both co-cultivated with target cells and 1 µg/ml of CEA T8 LCHA P329G LALA or CEA A5B7 P329G LALA antibody compared to different control conditions.

Upon incubation with 1 µg/ml CEA T8 LCHA P329G LALA, Jurkat NFAT CAR T cells alone (FIGS. 9B and 9D black diamond) as well as target cells alone (FIGS. 9B and 9D white circle) do not show any detectable luminescence signal.

Also Jurkat NFAT T cells do not show a detectable luminescence signal upon co-cultivation with target cells and 1 µg/ml IgG (FIG. 9B and FIG. 9D white square and white diamond). Whereas CD3 dependent activation of Jurkat NFAT T cells co-cultivated with target cells and 1 µg/ml IgG proofs their functionality through a detectable luminescence signal (FIGS. 9B and D grey cross).

CD3 dependent activation of Anti-P329G-ds-Fab-CD28ATD-CD28CSD-CD3zSSD Jurkat NFAT T cells (FIG. 9B black star and grey star) and activation of Anti-P329G-ds-scFv-CD28ATD-CD28CSD-CD3zSSD expressing NFAT T cells (FIG. 9D black star and grey star) co-cultivated with target cells and 1 µg/ml IgG show the highest luminescence signals of all, since CAR mediated activation and CD3 mediated activation is combined. CD3 mediated luminescence signal is also visible when CARs are incubated with target cells and 1 µg/ml of DP47/vk3 antibody (FIG. 9B and FIG. 9D, grey plus). Each point represents the mean value of technical triplicates. Standard deviation is indicated by error bars.

Example 5

Described herein is a Jurkat NFAT T cell reporter assay using adherent CEA expressing MKN45 tumor cells as target cells. As effector cells, a sorted pool of Anti-P329G-ds-Fab-CD28ATD-CD28CSD-CD3zSSD expressing Jukat NFAT T cells (FIG. 10C) or Anti-P329G-ds-scFv-CD28ATD-CD28CSD-CD3zSSD expressing Jurkat NFAT T cells (FIG. 10A) were used. Either CH1A1A 98 99 or CEA hMN14 IgG both with P329G LALA mutation were used. Further IgG DP47/vk3 harboring P329G LALA mutation was included as isotype control.

As positive control wells of a 96-well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent MKN45 target cells were washed once with PBS and detached using Trypsin. Detached cells were resuspended in DMEM+4.5 g LD-Glucose+L-Glutamine+25 mM HEPES+10% FCS and 1% Glutamax.

Effector cells or Jurkat NFAT wild type cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the effector cells, to $1\times10^6$ viable cells/ml in RPMI-1640+10% FCS+1% Glutamax.

Target cells and effector cells were plated in 5:1 E:T ratio (110,000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96-well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon 20 h co-cultivation of target cells and Anti-P329G-ds-scFv-CD28ATD-CD28CSD-CD3zSSD expressing Jurkat NFAT T cells in a ratio 5:1 (FIG. 10A black and grey dots) no activation is detectable, when the CEA hMN14 antibody or the CH1A1A 98 99 antibody was used as (FIGS. 9A and B, grey dots). Anti-P329G-ds-Fab-CD28ATD-CD28CSD-CD3zSSD expressing Jurkat NFAT T cells show little activation at 0.1 and 1 µg/ml of both CEA hMN14 antibody or the CH1A1A 98 99 antibodies (FIG. 10C black and grey dots).

If the control antibody DP47/vk3 IgG with P329G LALA mutation (FIGS. 10A and C, black triangles) was used, neither the activation of Anti-P329G-ds-scFv-CD28ATD-CD28CSD-CD3zSSD expressing Jurkat NFAT T cells nor Anti-P329G-ds-Fab-CD28ATD-CD28CSD-CD3zSSD expressing Jurkat NFAT T cells was detectable. Each point represents the mean value of technical triplicates. All values are depicted as baseline corrected. Standard deviation is indicated by error bars.

Figure 10D:
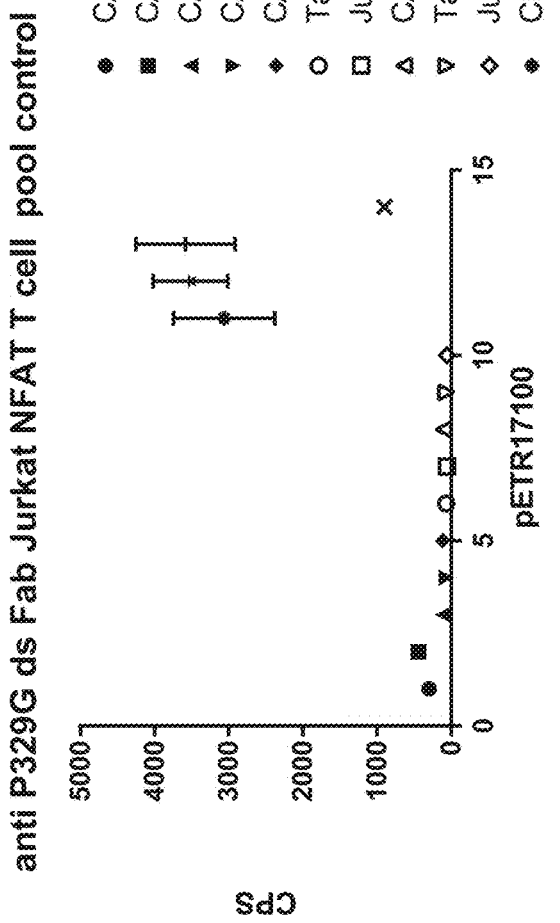

FIGS. 10B and 10D, represent data of Anti-P329G-ds-Fab-CD28ATD-CD28CSD-CD3zSSD expressing Jurkat NFAT T cells (Figure D) or Anti-P329G-ds-scFv-CD28ATD-CD28CSD-CD3zSSD expressing NFAT T cells (FIG. 9D) both co-cultivated with target cells and 1 µg/ml of CEA hMN14 antibody or the CH1A1A 98 99 antibody compared to different control conditions.

All performed control experiments do not show any detectable luminescence signal, except those were CD3 was used as an activation stimulus. Each point represents the mean value of technical triplicates. Standard deviation is indicated by error bars.

Example 6

Described herein is a Jurkat NFAT T cell reporter assay using adherent TNC expressing CT26TNC cl 19 tumor cells as target cells. As effector cells, a sorted pool of Anti-P329G-ds-Fab-CD28ATD-CD28CSD-CD3zSSD expressing Jurkat NFAT T cells (FIG. 11C) or Anti-P329G-ds-scFv-CD28ATD-CD28CSD-CD3zSSD expressing Jurkat NFAT T cells (FIG. 11A) were used. TNCA2B10 with P329G LALA mutation was used as IgG. Further IgG DP47/vk3 harboring P329G LALA mutation was included as isotype control.

As positive control wells of a 96 well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent CT26TNC cl 19 target cells were washed once with PBS and detached using Trypsin. Detached cells were resuspended in RPMI-1630+10% FCS and 1% Glutamax+ 15 µg/ml Puromycin.

Effector cells or Jurkat NFAT wild type T cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the effector cells, to $1\times10^6$ viable cells/ml in RPMI-1640+10% FCS+1% Glutamax.

Target cells and effector cells were plated in 5:1 E:T ratio (110,000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and effector cells in a ratio 5:1 (FIGS. 11A and C black dots) for 20 h the graphs show a dose-dependent activation of Anti-P329G-ds-Fab-CD28ATD-CD28CSD-CD3zSSD expressing Jurkat NFAT T cells as well as of Anti-P329G-ds-scFv-CD28ATD-CD28CSD-CD3zSSD expressing Jurkat NFAT T cells when TNC A2B10 with P329G LALA mutation was used as antibody. If the control antibody DP47/vk3 IgG with P329G LALA mutation (FIGS. 11A and C black dots) was used, neither the activation of Anti-P329G-ds-scFv-CD28ATD-CD28CSD-CD3zSSD expressing Jurkat NFAT T cells nor Anti-P329G-ds-Fab-CD28ATD-CD28CSD-CD3zSSD expressing Jurkat NFAT T cells was detectable. Each point represents the mean value of technical triplicates. All values are depicted as baseline corrected. Standard deviation is indicated by error bars.

Figure 11D:
Figure 12A:
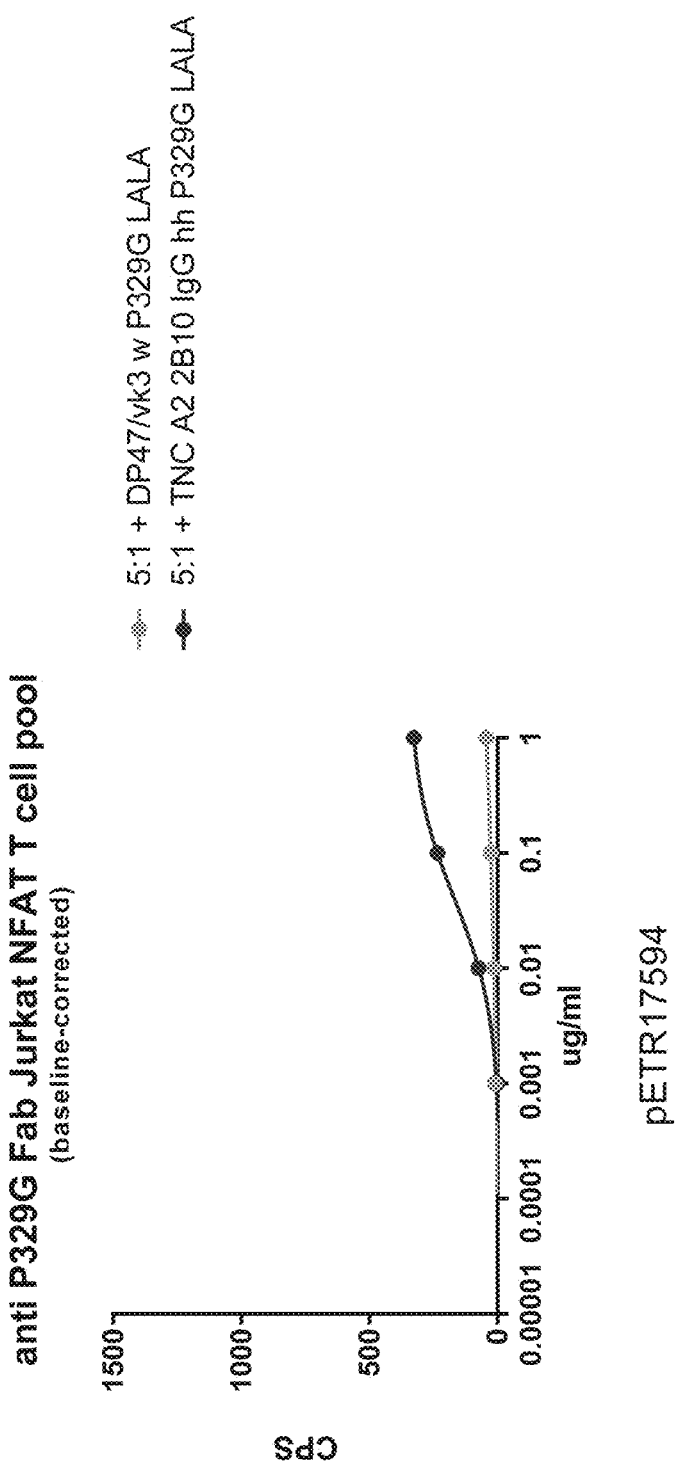
Figure 12B:
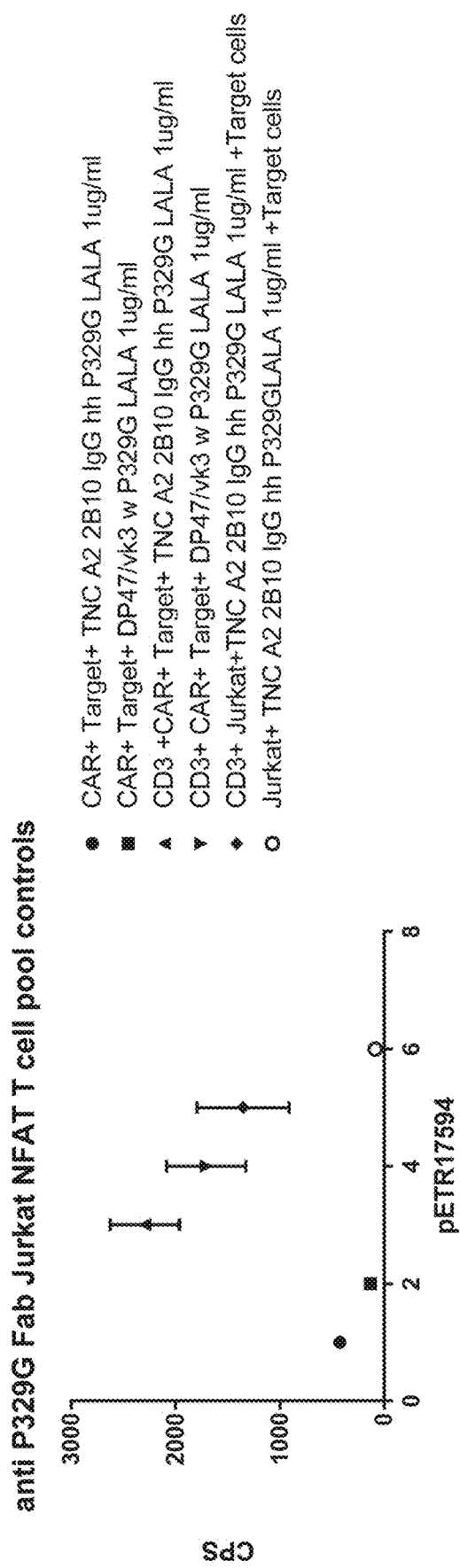

FIGS. 11B and 11D, represent data of Anti-P329G-ds-Fab-CD28ATD-CD28CSD-CD3zSSD expressing Jurkat NFAT T cells (FIG. 11D) or Anti-P329G-ds-scFv-CD28ATD-CD28CSD-CD3zSSD expressing Jurkat NFAT T cells (FIG. 11B) both co-cultivated with target cells and 1 µg/ml of TNC A2B10 compared to different control conditions.

Jurkat NFAT T cells do not show any detectable luminescence signal upon co-cultivation with target cells and 1 µg/ml IgG (FIG. 11B and FIG. 11D white triangle). Whereas CD3 dependent activation of Jurkat NFAT cells co-cultivated with target cells and 1 µg/ml IgG proofs their functionality through a detectable luminescence signal (FIG. 11B and FIG. 11D white square).

CD3 dependent activation of Anti-P329G-ds-Fab-CD28ATD-CD28CSD-CD3zSSD expressing Jurkat NFAT T cells (FIG. 11B white circle) and activation of Anti-P329G-ds-scFv-CD28ATD-CD28CSD-CD3zSSD expressing Jurkat NFAT T cells (FIG. 11D white circle) co-cultivated with target cells and 1 µg/ml IgG show the highest luminescence signals of all, since CAR mediated activation and CD3 mediated activation is combined. CD3 mediated luminescence signal is also visible when CARs are incubated with target cells and 1 μg/ml of DP47/vk3 antibody (FIG. 11B and FIG. 11D, black diamond). Each point represents the mean value of technical triplicates. Standard deviation is indicated by error bars.

Example 7

Described herein is a Jurkat NFAT T cell reporter assay using adherent TNC expressing CT26TNC cl 19 tumor cells as target cells. As effector cells, a sorted pool of Anti-P329G-Fab-CD28ATD-CD28CSD-CD3zSSD expressing Jurkat NFAT T cells (FIG. 12A) was used. TNCA2B10 with P329G LALA mutation was used as IgG. Further IgG DP47/vk3 harboring P329G LALA mutation was included as isotype control.

As positive control wells of a 96-well plate (Greiner-bio-one, CAT-No. 655185) were coated with 10 μg/ml CD3 antibody (from Biolegend®) in phosphate buffered saline (PBS) for 1 h at 37° C. The CD3 coated wells were washed twice with PBS, after the final washing step, PBS was fully removed.

Adherent CT26TNC cl 19 target cells were washed once with PBS and detached using Trypsin. Detached cells were resuspended in RPMI-1630+10% FCS and 1% Glutamax+15 μg/ml Puromycin.

Effector cells or Jurkat NFAT wild type cells were counted and checked for their viability using Cedex HiRes. The cell number was adjusted to 1×10$^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the effector cells, to 1×10$^6$ viable cells/ml in RPMI-1640+10% FCS+1% Glutamax.

Target cells and effector cells were plated in 5:1 E:T ratio (110,000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 μg/ml to 0.0001 μg/ml in a final volume of 200 ul per well, a 50 μl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 μl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and effector cells in a ratio 5:1 (FIG. 12A black dots) for 20 h the graphs show a dose-dependent activation of Anti-P329G-Fab-CD28ATD-CD28CSD-CD3zSSD expressing Jurkat NFAT T cells beginning with 0.01 μg/ml of TNC A2B10 with P329G LALA mutation. If the control antibody DP47/vk3 IgG with P329G LALA mutation (FIGS. 12A and C grey dots) was used, no activation of Anti-P329G-Fab-CD28ATD-CD28CSD-CD3zSSD expressing Jurkat NFAT T cells was detectable. Each point represents the mean value of technical triplicates. All values are depicted as baseline corrected. Standard deviation is indicated by error bars.

FIG. 12B, represents data of Anti-P329G-Fab-CD28ATD-CD28CSD-CD3zSSD expressing Jurkat NFAT T cells co-cultivated with target cells and 1 μg/ml of TNC A2B10 antibody compared to different control conditions.

Anti-P329G-Fab-CD28ATD-CD28CSD-CD3zSSD expressing Jurkat NFAT T cells incubated with target cells but without antibody (FIG. 12B black square) as well as Jurkat NFAT cells incubated with target cells and 1 μg/ml of TNC A2B10 antibody (FIG. 12B white dots) show no detectable luminescence signal. Whereas Jurkat NFAT cells co-cultured with target cells and 1 μg/ml of TNC A2B10 plated in CD3 coated wells, show a clear luminescence signal.

Further Anti-P329G-CD28ATD-CD28CSD-CD3zSSD Fab expressing Jurkat NFAT T cells incubated with target cells and either 1 μg/ml of TNC A2B10 or 1 μg/ml DP47/vk3 antibody, in CD3 coated wells, show a high luminescence signal. Each point represents the mean value of technical triplicates. Standard deviation is indicated by error bars.

Example 8

Described herein is a Jurkat NFAT T cell reporter assay using CD20 expressing SUDHDL4 tumor cells as target cells and a pool of Jurkat NFAT cells expressing anti-P329G-ds-scFv-CD28ATD-CD28CSD-CD3zSSD (FIG. 13A) or anti-P329G-ds-Fab-CD28ATD-CD28CSD-CD3zSSD as (FIG. 13B) as effector cells. Either GA101 IgG with P329G LALA, a D265A P329G mutation, a LALA mutation only or no mutation at all was used as IgG which on one hand recognizes the tumor antigen and on the other hand is recognized by the Jurkat NFAT T cells. Effector cells were counted and checked for their viability using Cedex HiRes. The cell number was adjusted to 1×10$^6$ viable cells/ml. An appropriate aliquot of the cell suspension was pelleted at 210 g for 5 min at room temperature (RT) and resuspended in fresh RPMI-160+10% FCS+1% Glutamax. Target cells expressing the antigen of interest, were counted and checked for their viability as well. The cell number was adjusted, analog as described for the effector cells, to 1×10$^6$ viable cells/ml in growth medium. Target cells and effector cells were plated in 5:1 E:T ratio (110,000 cells per well in total) in triplicates in a 96-well suspension culture plate (Greiner-bio one). As a next step a serial dilution of the different antibodies, targeting the antigen of interest, were prepared in growth medium using a 2 ml deep well plate (Axygen®). To obtain final concentrations ranging from 1 μg/ml to 10 pg/ml in a final volume of 200 μl per well, a 50 μl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 μl cell suspension was transferred to a new white flat clear bottom 96 well plate (Greiner-bio-one) and 100 μl ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. The graphs show an dose dependent activation of the target cells only when the antibodies are used that harbor a P329G mutation or the P329G and the LALA mutation but not the LALA mutation alone. Further, no activation of the effector cells is detectable if the GA101 wild type antibody is used.

Example 9

Described herein is a Jurkat NFAT T cell reporter assay using CD20 expressing SUDHDL4 tumor cells as target cells and a pool of Jurkat NFAT cells expressing anti-P329G-ds-scFv-CD28ATD-CD28CSD-CD3zSSD (FIG. 14A) or anti-P329G-ds-Fab-CD28ATD-CD28CSD-CD3zSSD as (FIG. 14B) as effector cells. Either GA101 IgG with P329G LALA, a P329G mutation alone, a LALA mutation only or no mutation at all was used as IgG which on one hand recognizes the tumor antigen and on the other hand is recognized by the Jurkat NFAT T cells. Effector cells were counted and checked for their viability using Cedex HiRes. The cell number was adjusted to $1 \times 10^6$ viable cells/ml. An appropriate aliquot of the cell suspension was pelleted at 210 g for 5 min at room temperature (RT) and resuspended in fresh RPMI-160+10% FCS+1% Glutamax. Target cells expressing the antigen of interest, were counted and checked for their viability as well. The cell number was adjusted, analog as described for the effector cells, to $1 \times 10^6$ viable cells/ml in growth medium. Target cells and effector cells were plated in 5:1 E:T ratio (110,000 cells per well in total) in triplicates in a 384-well plate. As a next step a serial dilution of the different antibodies, targeting the antigen of interest, were prepared in growth medium using a 96 well plate. To obtain final concentrations ranging from 1 μg/ml to 10 pg/ml in a final volume of 30 μl per well, a 10 μl aliquot of the different dilutions was pipetted to the respective wells. The 384 well plate was centrifuged for 2 min at 190 g and RT. Sealed with Parafilm®, the plate was incubated at 37° C. and 5% $CO_2$ in a humidity atmosphere. After 20 h incubation, 6 μl of ONE-Glo™ Luciferase Assay (Promega) was added and the readout was performed immediately using a Tecan® Spark10M plate reader, 1 sec/well as detection time. The graphs show a dose dependent activation of the target cells only when the antibodies are used that harbor a P329G mutation or the P329G and the LALA mutation but not the LALA mutation alone. Further, no activation of the effector cells is detectable if the GA101 wild type antibody is used.

Exemplary Sequences

TABLE 2

Anti-P329G-ds-scFv amino acid sequences:

| Construct | Amino acid sequence | SEQ ID NO |
|---|---|---|
| Anti-P329G CDR H1 Kabat | RYWMN | 1 |
| Anti-P329G CDR H2 Kabat | EITPDSSTINYTPSLKD | 2 |
| Anti-P329G CDR H3 Kabat | PYDYGAWFAS | 3 |
| Anti-P329G CDR L1 Kabat | RSSTGAVTTSNYAN | 4 |
| Anti-P329G CDR L2 Kabat | GTNKRAP | 5 |
| Anti-P329G CDR L3 Kabat | ALWYSNHWV | 6 |
| Anti-P329G-ds-scFv-CD28ATD-CD28CSD-CD3zSSD fusion pETR17096 | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSAGGGGSGGGGSGGGGSGGGGSQAVVTQESALT TSPGETVTLTCRSSTGAVTTSNYANWVQEKPDHLFTGL IGGTNKRAPGVPARFSGSLIGDKAALTITGAQIEDEAIY FCALWYSNHWVFGCGTKLTVLGGGGSFWVLVVVGGV LACYSLLVTVAFIIFWVRSKRSRLLHSDYMNMTPRRPG PTRKHYQPYAPPRDFAAYRSRVKFSRSADAPAYQQGQ NQLYNELNLGRREEYDVLDKRRGRDPEMGGKPRRKNP QEGLYNELQKDKMAEAYSEIGMKGERRRGKGHDGLY QGLSTATKDTYDALHMQALPPR | 7 |
| Anti-P329G-ds VH | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSA | 8 |
| Anti-P329G-ds VL | QAVVTQESALTTSPGETVTLTCRSSTGAVTTSNYANWV QEKPDHLFTGLIGGTNKRAPGVPARFSGSLIGDKAALTI TGAQTEDEAIYFCALWYSNHWVFGCGTKLTVL | 9 |
| Anti-P329G-ds-scFv | EVKLLESGGGLVQPGGSLKLSCAASGFDFSRYWMINWV RQAPGKCLEWIGEITPDSSTINYTPSLKDKFIISRDNAKN TLYLQMIKVRSEDTALYYCVRPYDYGAWFASWGQGT LVTVSAGGGGSGGGGSGGGGSGGGGSQAVVTQESALT TSPGETVTLTCRSSTGAVTTSNYANWVQEKPDHLFTGL IGGTNKRAPGVPARFSGSLIGDKAALTITGAQIEDEAIY FCALWYSNHWVFGCGTKLTVL | 10 |

TABLE 2-continued

Anti-P329G-ds-scFv amino acid sequences:

| Construct | Amino acid sequence | SEQ ID NO |
|---|---|---|
| CD28ATD | FWVLVVVGGVLACYSLLVTVAFIIFWV | 11 |
| CD28CSD | RSKRSRLLHSDYMNMTPRRPGPTRKHYQPYAPPRDFAAYRS | 12 |
| CD3zSSD | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 13 |
| CD28ATD-CD28CSD-CD3zSSD | FWVLVVVGGVLACYSLLVTVAFIIFWVRSKRSRLLHSDYMNMTPRRPGPTRKHYQPYAPPRDFAAYRSRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 14 |
| eGFP | VSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHMVLLEFVTAAGITLGMDELYK | 15 |
| (G4S)4 linker | GGGGSGGGGSGGGGSGGGGS | 16 |
| G4S linker | GGGGS | 17 |
| T2A linker | GEGRGSLLTCGDVEENPGP | 18 |

TABLE 3 anti-P329G-ds-scFv DNA sequences:

| Construct | DNA sequence | SEQ ID NO |
|---|---|---|
| Anti-P329G-ds-scFv-CD28ATD-CD28CSD-CD3zSSD fusion pETR17096 | ATGGGATGGAGCTGTATCATCCTCTTCTTGGTAGCAACAGCTACCGGTGTGCATTCCGAGGTGAAGCTGCTGGAGAGCGGCGGCGGCCTGGTGCAGCCCGGCGGCAGCCTGAAGCTGAGCTGCGCCGCCAGCGGCTTCGACTTCAGCAGGTACTGGATGAACTGGGTGAGGCAGGCCCCCGGCAAGTGTCTGGAGTGGATCGGCGAGATCACCCCCGACAGCAGCACCATCAACTACACCCCCAGCCTGAAGGACAAGTTCATCATCAGCAGGGACAACGCCAAGAACACCCTGTACCTGCAGATGATCAAGGTGAGGAGCGAGGACACCGCCCTGTACTACTGCGTGAGGGCCCTACGACTACGGCGCCTGGTTCGCCAGCTGGGGCCAGGGCACCCTGGTGACCGTGAGCGCCGGAGGGGGCGGAAGTGGTGGCGGGGGAAGCGGCGGGGGTGGCAGCGGAGGGGGCGGATCTCAGGCCGTGGTGACCCAGGAGAGCGCCCTGACCACCAGCCCCGGCGAGACCGTGACCCTGACCTGCAGGAGCAGCACCGGCGCCGTGACCACCAGCAACTACGCCAACTGGGTGCAGGAGAAGCCCGACCACCTGTTCACCGGCCTGATCGGCGGCACCAACAAGAGGGCCCCCGGCGTGCCCGCCAGGTTCAGCGGCAGCCTGATCGGCGACAAGGCCGCCCTGACCATCACCGGCGCCCAGACCGAGGACGAGGCCATCTACTTCTGCGCCCTGTGGTACAGCAACCACTGGGTGTTCGGCTGTGGCACCAAGCTGACCGTGCTGGGAGGGGCGGATCCTTCTGGGTGCTGGTGGTGGTGGGCGGCGTGCTGGCCTGCTACAGCCTGCTGGTGACCGTGGCCTTCATCATCTTCTGGGTGAGGAGCAAGAGGAGCAGGCTGCTGCACAGCGACTACATGAACATGACCCCCAGGAGGCCCGGCCCCACCAGGAAGCACTACCAGCCCTACGCCCCCCCCAGGGACTTCGCCGCCTACAGGAGCAGGGTGAAGTTCAGCAGGAGCGCCGACGCCCCCGCCTACCAGCAGGGCCAGAACCAGCTGTATAACGAGCTGAACCTGGGCAGGAGGGAGGAGTACGACGTGCTGGACAAGAGGAGGGGCAGGGACCCCGAGATGGGCGGCAAGCCCAGGAGGAAGAACCCCCAGGAGGGCCTGTATAACGAGCTGCAGAAGGACAAGATGGCCGAGGCCTACAGCGAGATCGGCATGAAGGGCGAGAGGAGGAGGGGCAAGGGCCACGACGGCCTGTACCA | 19 |

TABLE 3-continued anti-P329G-ds-scFv DNA sequences:

| Construct | DNA sequence | SEQ ID NO |
|---|---|---|
| | GGGCCTGAGCACCGCCACCAAGGACACCTACGACGC CCTGCACATGCAGGCCCTGCCCCCCAGG | |
| Anti-P329G-ds VH | GAGGTGAAGCTGCTGGAGAGCGGCGGCGGCCTGGTG CAGCCCGGCGGCAGCCTGAAGCTGAGCTGCGCCGCC AGCGGCTTCGACTTCAGCAGGTACTGGATGAACTGG GTGAGGCAGGCCCCCGGCAAGTGTCTGGAGTGGATC GGCGAGATCACCCCCGACAGCAGCACCATCAACTAC ACCCCCAGCCTGAAGGACAAGTTCATCATCAGCAGG GACAACGCCAAGAACACCCTGTACCTGCAGATGATC AAGGTGAGGAGCGAGGACACCGCCCTGTACTACTGC GTGAGGCCCTACGACTACGGCGCCTGGTTCGCCAGC TGGGGCCAGGGCACCCTGGTGACCGTGAGCGCC | 20 |
| Anti-P329G-ds VL | CAGGCCGTGGTGACCCAGGAGAGCGCCCTGACCACC AGCCCCGGCGAGACCGTGACCCTGACCTGCAGGAGC AGCACCGGCGCCGTGACCACCAGCAACTACGCCAAC TGGGTGCAGGAGAAGCCCGACCACCTGTTCACCGGC CTGATCGGCGGCACCAACAAGAGGGCCCCCGGCGTG CCCGCCAGGTTCAGCGGCAGCCTGATCGGCGACAAG GCCGCCCTGACCATCACCGGCGCCCAGACCGAGGAC GAGGCCATCTACTTCTGCGCCCTGTGGTACAGCAACC ACTGGGTGTTCGGCTGTGGCACCAAGCTGACCGTGC TG | 21 |
| Anti-P329G-ds-scFv | ATGGGATGGAGCTGTATCATCCTCTTCTTGGTAGCAA CAGCTACCGGTGTGCATTCCGAGGTGAAGCTGCTGG AGAGCGGCGGCGGCCTGGTGCAGCCCGGCGGCAGCC TGAAGCTGAGCTGCGCCGCCAGCGGCTTCGACTTCA GCAGGTACTGGATGAACTGGGTGAGGCAGGCCCCCG GCAAGTGTCTGGAGTGGATCGGCGAGATCACCCCCG ACAGCAGCACCATCAACTACACCCCCAGCCTGAAGG ACAAGTTCATCATCAGCAGGGACAACGCCAAGAACA CCCTGTACCTGCAGATGATCAAGGTGAGGAGCGAGG ACACCGCCCTGTACTACTGCGTGAGGCCCTACGACT ACGGCGCCTGGTTCGCCAGCTGGGGCCAGGGCACCC TGGTGACCGTGAGCGCCGGAGGGGGCGGAAGTGGTG GCGGGGGAAGCGGCGGGGGTGGCAGCGGAGGGGGC GGATCTCAGGCCGTGGTGACCCAGGAGAGCGCCCTG ACCACCAGCCCCGGCGAGACCGTGACCCTGACCTGC AGGAGCAGCACCGGCGCCGTGACCACCAGCAACTAC GCCAACTGGGTGCAGGAGAAGCCCGACCACCTGTTC ACCGGCCTGATCGGCGGCACCAACAAGAGGGCCCCC GGCGTGCCCGCCAGGTTCAGCGGCAGCCTGATCGGC GACAAGGCCGCCCTGACCATCACCGGCGCCCAGACC GAGGACGAGGCCATCTACTTCTGCGCCCTGTGGTAC AGCAACCACTGGGTGTTCGGCTGTGGCACCAAGCTG ACCGTGC | 22 |
| IRES EV71, internal ribosomal entry side | CCCGAAGTAACTTAGAAGCTGTAAATCAACGATCAA TAGCAGGTGTGGCACACCAGTCATACCTTGATCAAG CACTTCTGTTTCCCCGGACTGAGTATCAATAGGCTGC TCGCGCGGCTGAAGGAGAAAACGTTCGTTACCCGAC CAACTACTTCGAGAAGCTTAGTACCACCATGAACGA GGCAGGGTGTTTCGCTCAGCACAACCCCAGTGTAGA TCAGGCTGATGAGTCACTGCAACCCCCATGGGCGAC CATGGCAGTGGCTGCGTTGGCGGCCTGCCCATGGAG AAATCCATGGGACGCTCTAATTCTGACATGGTGTGA AGTGCCTATTGAGCTAACTGGTAGTCCTCCGGCCCCT GATTGCGGCTAATCCTAACTGCGGAGCACATGCTCA CAAACCAGTGGGTGGTGTGTCGTAACGGGCAACTCT GCAGCGGAACCGACTACTTTGGGTGTCCGTGTTTCCT TTTATTCCTATATTGGCTGCTTATGGTGACAATCAAA AAGTTGTTACCATATAGCTATTGGATTGGCCATCCGG TGTGCAACAGGGCAACTGTTTACCTATTTATTGGTTT TGTACCATTATCACTGAAGTCTGTGATCACTCTCAAA TTCATTTTGACCCTCAACACAATCAAAC | 23 |
| CD28ATD | TTTTGGGTGCTGGTGGTGGTTGGTGGAGTCCTGGCTT GCTATAGCTTGCTAGTAACAGTGGCCTTTATTATTTT CTGGGTG | 24 |
| CD28CSD | AGGAGTAAGAGGAGCAGGCTCCTGCACAGTGACTAC ATGAACATGACTCCCCGCCGCCCCGGGCCCACCCGC AAGCATTACCAGCCCTATGCCCCACCACGCGACTTC GCAGCCTATCGCTCC | 25 |

TABLE 3-continued anti-P329G-ds-scFv DNA sequences:

| Construct | DNA sequence | SEQ ID NO |
|---|---|---|
| CD3zSSD | AGAGTGAAGTTCAGCAGGAGCGCAGACGCCCCCGCG<br>TACCAGCAGGGCCAGAACCAGCTCTATAACGAGCTC<br>AATCTAGGACGAAGAGAGGAGTACGATGTTTTGGAC<br>AAGAGACGTGGCCGGGACCCTGAGATGGGGGGAAA<br>GCCGAGAAGGAAGAACCCTCAGGAAGGCCTGTACA<br>ATGAACTGCAGAAAGATAAGATGGCGGAGGCCTACA<br>GTGAGATTGGGATGAAAGGCGAGCGCCGGAGGGGC<br>AAGGGGCACGATGGCCTTTACCAGGGTCTCAGTACA<br>GCCACCAAGGACACCTACGACGCCCTTCACATGCAG<br>GCCCTGCCCCCTCGC | 26 |
| CD28ATD-CD28CSD-<br>CD3zSSD | TTCTGGGTGCTGGTGGTGGTGGGCGGCGTGCTGGCCT<br>GCTACAGCCTGCTGGTGACCGTGGCCTTCATCATCTT<br>CTGGGTGAGGAGCAAGAGGAGCAGGCTGCTGCACA<br>GCGACTACATGAACATGACCCCCAGGAGGCCCGGCC<br>CCACCAGGAAGCACTACCAGCCCTACGCCCCCCCA<br>GGGACTTCGCCGCCTACAGGAGCAGGGTGAAGTTCA<br>GCAGGAGCGCCGACGCCCCCGCCTACCAGCAGGGCC<br>AGAACCAGCTGTATAACGAGCTGAACCTGGGCAGGA<br>GGGAGGAGTACGACGTGCTGGACAAGAGGAGGGGC<br>AGGGACCCCGAGATGGGCGGCAAGCCCAGGAGGAA<br>GAACCCCCAGGAGGGCCTGTATAACGAGCTGCAGAA<br>GGACAAGATGGCCGAGGCCTACAGCGAGATCGGCAT<br>GAAGGGCGAGAGGAGGAGGGGCAAGGGCCACGACG<br>GCCTGTACCAGGGCCTGAGCACCGCCACCAAGGACA<br>CCTACGACGCCCTGCACATGCAGGCCCTGCCCCCCA<br>GG | 27 |
| T2A element | TCCGGAGAGGGCAGAGGAAGTCTTCTAACATGCGGT<br>GACGTGGAGGAGAATCCCGGCCCTAGG | 28 |
| eGFP | GTGAGCAAGGGCGAGGAGCTGTTCACCGGGGTGGTG<br>CCCATCCTGGTCGAGCTGGACGGCGACGTAAACGGC<br>CACAAGTTCAGCGTGTCCGGCGAGGGCGAGGGCGAT<br>GCCACCTACGGCAAGCTGACCCTGAAGTTCATCTGC<br>ACCACCGGCAAGCTGCCCGTGCCCTGGCCCACCCTC<br>GTGACCACCCTGACCTACGGCGTGCAGTGCTTCAGC<br>CGCTACCCCGACCACATGAAGCAGCACGACTTCTTC<br>AAGTCCGCCATGCCCGAAGGCTACGTCCAGGAGCGC<br>ACCATCTTCTTCAAGGACGACGGCAACTACAAGACC<br>CGCGCCGAGGTGAAGTTCGAGGGCGACACCCTGGTG<br>AACCGCATCGAGCTGAAGGGCATCGACTTCAAGGAG<br>GACGGCAACATCCTGGGGCACAAGCTGGAGTACAAC<br>TACAACAGCCACAACGTCTATATCATGGCCGACAAG<br>CAGAAGAACGGCATCAAGGTGAACTTCAAGATCCGC<br>CACAACATCGAGGACGGCAGCGTGCAGCTCGCCGAC<br>CACTACCAGCAGAACACCCCCATCGGCGACGGCCCC<br>GTGCTGCTGCCCGACAACCACTACCTGAGCACCCAG<br>TCCGCCCTGAGCAAAGACCCCAACGAGAAGCGCGAT<br>CACATGGTCCTGCTGGAGTTCGTGACCGCCGCCGGG<br>ATCACTCTCGGCATGGACGAGCTGTACAAGTGA | 29 |
| Anti-P329G-ds-scFv-<br>CD28ATD-CD28CSD-<br>CD3zSSD-<br>eGFP fusion<br>pETR17096 | ATGGGATGGAGCTGTATCATCCTCTTCTTGGTAGCAA<br>CAGCTACCGGTGTGCATTCCGAGGTGAAGCTGCTGG<br>AGAGCGGCGGCGCCCTGGTGCAGCCCGGCGGCAGCC<br>TGAAGCTGAGCTGCGCCGCCAGCGGCTTCGACTTCA<br>GCAGGTACTGGATGAACTGGGTGAGGCAGGCCCCCG<br>GCAAGTGTCTGGAGTGGATCGGCGAGATCACCCCCG<br>ACAGCAGCACCATCAACTACACCCCCAGCCTGAAGG<br>ACAAGTTCATCATCAGCAGGGACAACGCCAAGAACA<br>CCCTGTACCTGCAGATGATCAAGGTGAGGAGCGAGG<br>ACACCGCCCTGTACTACTGCGTGAGGCCCTACGACT<br>ACGGCGCCTGGTTCGCCAGCTGGGGCCAGGGCACCC<br>TGGTGACCGTGAGCGCCGGAGGGGCGGAAGTGGTG<br>GCGGGGGAAGCGGCGGGGTGGCAGCGGAGGGGGC<br>GGATCTCAGGCCGTGGTGACCCAGGAGAGCGCCCTG<br>ACCACCAGCCCCGGCGAGACCGTGACCCTGACCTGC<br>AGGAGCAGCACCGGCGCCGTGACCACCAGCAACTAC<br>GCCAACTGGGTGCAGGAGAAGCCCGACCACCTGTTC<br>ACCGGCCTGATCGGCGGCACCAACAAGAGGGCCCCC<br>GGCGTGCCCGCCAGGTTCAGCGGCAGCCTGATCGGC<br>GACAAGGCCGCCCTGACCATCACCGGCGCCCAGACC<br>GAGGACGAGGCCATCTACTTCTGCGCCCTGTGGTAC<br>AGCAACCACTGGGTGTTCGGCTGTGGCACCAAGCTG<br>ACCGTGCTGGGAGGGGGCGGATCCTTCTGGGTGCTG | 30 |

TABLE 3-continued anti-P329G-ds-scFv DNA sequences:

| Construct | DNA sequence | SEQ ID NO |
|---|---|---|
| | GTGGTGGTGGGCGGCGTGCTGGCCTGCTACAGCCTG<br>CTGGTGACCGTGGCCTTCATCATCTTCTGGGTGAGGA<br>GCAAGAGGAGCAGGCTGCTGCACAGCGACTACATGA<br>ACATGACCCCCAGGAGGCCCGGCCCCACCAGGAAGC<br>ACTACCAGCCCTACGCCCCCCCCAGGGACTTCGCCG<br>CCTACAGGAGCAGGGTGAAGTTCAGCAGGAGCGCCG<br>ACGCCCCCGCCTACCAGCAGGGCCAGAACCAGCTGT<br>ATAACGAGCTGAACCTGGGCAGGAGGGAGGAGTAC<br>GACGTGCTGGACAAGAGGAGGGGCAGGGACCCCGA<br>GATGGGCGGCAAGCCCAGGAGGAAGAACCCCCAGG<br>AGGGCCTGTATAACGAGCTGCAGAAGGACAAGATGG<br>CCGAGGCCTACAGCGAGATCGGCATGAAGGGCGAG<br>AGGAGGAGGGGCAAGGGCCACGACGGCTGTACCA<br>GGGCCTGAGCACCGCCACCAAGGACACCTACGACGC<br>CCTGCACATGCAGGCCCTGCCCCCCAGGTCCGGAGA<br>GGGCAGAGGAAGTCTTCTAACATGCGGTGACGTGGA<br>GGAGAATCCCGGCCCTAGGGTGAGCAAGGGCGAGG<br>AGCTGTTCACCGGGGTGGTGCCCATCCTGGTCGAGCT<br>GGACGGCGACGTAAACGGCCACAAGTTCAGCGTGTC<br>CGGCGAGGGCGAGGGCGATGCCACCTACGGCAAGCT<br>GACCCTGAAGTTCATCTGCACCACCGGCAAGCTGCC<br>CGTGCCCTGGCCCACCCTCGTGACCACCCTGACCTAC<br>GGCGTGCAGTGCTTCAGCCGCTACCCCGACCACATG<br>AAGCAGCACGACTTCTTCAAGTCCGCCATGCCCGAA<br>GGCTACGTCCAGGAGCGCACCATCTTCTTCAAGGAC<br>GACGGCAACTACAAGACCCGCGCCGAGGTGAAGTTC<br>GAGGGCGACACCCTGGTGAACCGCATCGAGCTGAAG<br>GGCATCGACTTCAAGGAGGACGGCAACATCCTGGGG<br>CACAAGCTGGAGTACAACTACAACAGCCACAACGTC<br>TATATCATGGCCGACAAGCAGAAGAACGGCATCAAG<br>GTGAACTTCAAGATCCGCCACAACATCGAGGACGGC<br>AGCGTGCAGCTCGCCGACCACTACCAGCAGAACACC<br>CCCATCGGCGACGGCCCCGTGCTGCTGCCCGACAAC<br>CACTACCTGAGCACCCAGTCCGCCCTGAGCAAAGAC<br>CCCAACGAGAAGCGCGATCACATGGTCCTGCTGGAG<br>TTCGTGACCGCCGCCGGGATCACTCTCGGCATGGAC<br>GAGCTGTACAAGTGA | |

TABLE 4

Anti-P329G-scFv amino acid sequences:

| Construct | Amino acid sequence | SEQ ID NO |
|---|---|---|
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-scFv-CD28ATD-CD28CSD-CD3zSSD fusion | EVKLLESGGGLVQPGGSLKLSCAASGFDFSRYWMNWV RQAPGKGLEWIGEITPDSSTINYTPSLKDKFIISRDN AKNTLYLQMIKVRSEDTALYYCVRPYDYGAWFASWGQ GTLVTVSAGGGGSGGGGSGGGGSGGGGSQAVVTQESA LTTSPGETVTLTCRSSTGAVTTSNYANWVQEKPDHLF TGLIGGTNKRAPGVPARFSGSLIGDKAALTITGAQIE DEAIYFCALWYSNHWVFGGGTKLTVLGGGGSFWVLVV VGGVLACYSLLVTVAFIIFWVRSKRSRLLHSDYMNMT PRRPGPTRKHYQPYAPPRDFAAYRSRVKFSRSADAPA YQQGQNQLYNELNLGRREEYDVLDKRRGRDPEMGGKP RRKNPQEGLYNELQKDKMAEAYSEIGMKGERRRGKGH DGLYQGLSTATKDTYDALHMQALPPR | 31 |
| Anti-P329G VH | EVKLLESGGGLVQPGGSLKLSCAASGFDFSRYWMNWV RQAPGKGLEWIGEITPDSSTINYTPSLKDKFIISRDN AKNTLYLQMIKVRSEDTALYYCVRPYDYGAWFASWGQ GTLVTVSA | 32 |
| Anti-P329G VL | QAVVTQESALTTSPGETVTLTCRSSTGAVTTSNYANW VQEKPDHLFTGLIGGTNKRAPGVPARFSGSLIGDKAA LTITGAQTEDEAIYFCALWYSNHWVFGGGTKLTVL | 33 |

TABLE 4-continued

Anti-P329G-scFv amino acid sequences:

| Construct | Amino acid sequence | SEQ ID NO |
|---|---|---|
| Anti-P329G-scFv | EVKLLESGGGLVQPGGSLKLSCAASGFDFSRYWMNWV RQAPGKGLEWIGEITPDSSTINYTPSLKDKFIISRDN AKNTLYLQMIKVRSEDTALYYCVRPYDYGAWFASWGQ GTLVTVSAGGGGSGGGGSGGGGSGGGGSQAVVTQESA LTTSPGETVTLTCRSSTGAVTTSNYANWVQEKPDHLF TGLIGGTNKRAPGVPARFSGSLIGDKAALTITGAQIE DEAIYFCALWYSNHWVFGGGTKLTVL | 34 |
| CD28ATD | see Table 2 | 11 |
| CD28CSD | see Table 2 | 12 |
| CD3zSSD | see Table 2 | 13 |
| CD28ATD-CD28CDS-CD3zSSD | see Table 2 | 14 |
| eGFP | see Table 2 | 15 |
| (G4S)4 linker | see Table 2 | 16 |
| G4S linker | see Table 2 | 17 |
| T2A linker | see Table 2 | 18 |

TABLE 5

Anti-P329G-scFv DNA sequences:

| Construct | DNA sequence | SEQ ID NO |
|---|---|---|
| Anti-P329G-scFv-CD28ATD-CD28CSD-CD3zSSD fusion | ATGGGATGGAGCTGTATCATCCTCTTCTTGGTAGCAA CAGCTACCGGTGTGCATTCCGAGGTGAAGCTGCTGG AGAGCGGCGGCGGCCTGGTGCAGCCCGGCGGCAGCC TGAAGCTGAGCTGCGCCGCCAGCGGCTTCGACTTCA GCAGGTACTGGATGAACTGGGTGAGGCAGGCCCCCG GCAAGGGTCTGGAGTGGATCGGCGAGATCACCCCCG ACAGCAGCACCATCAACTACACCCCCAGCCTGAAGG ACAAGTTCATCATCAGCAGGGACAACGCCAAGAACA CCCTGTACCTGCAGATGATCAAGGTGAGGAGCGAGG ACACCGCCCTGTACTACTGCGTGAGGCCCTACGACT ACGGCGCCTGGTTCGCCAGCTGGGGCCAGGGCACCC TGGTGACCGTGAGCGCCGGAGGGGGCGGAAGTGGTG GCGGGGGAAGCGGCGGGGGTGGCAGCGGAGGGGGC GGATCTCAGGCCGTGGTGACCCAGGAGAGCGCCCTG ACCACCAGCCCCGGCGAGACCGTGACCCTGACCTGC AGGAGCAGCACCGGCGCCGTGACCACCAGCAACTAC GCCAACTGGGTGCAGGAGAAGCCCGACCACCTGTTC ACCGGCCTGATCGGCGGCACCAACAAGAGGGCCCCC GGCGTGCCCGCCAGGTTCAGCGGCAGCCTGATCGGC GACAAGGCCGCCCTGACCATCACCGGCGCCCAGACC GAGGACGAGGCCATCTACTTCTGCGCCCTGTGGTAC AGCAACCACTGGGTGTTCGGCGGTGGCACCAAGCTG ACCGTGCTGGGAGGGGGCGGATCCTTCTGGGTGCTG GTGGTGGTGGGCGGCGTGCTGGCCTGCTACAGCCTG CTGGTGACCGTGGCCTTCATCATCTTCTGGGTGAGGA GCAAGAGGAGCAGGCTGCTGCACAGCGACTACATGA ACATGACCCCCAGGAGGCCCGGCCCCACCAGGAAGC ACTACCAGCCCTACGCCCCCCCCAGGGACTTCGCCG CCTACAGGAGCAGGGTGAAGTTCAGCAGGAGCGCCG ACGCCCCCGCCTACCAGCAGGGCCAGAACCAGCTGT ATAACGAGCTGAACCTGGGCAGGAGGGAGGAGTAC GACGTGCTGGACAAGAGGAGGGGCAGGGACCCCGA GATGGGCGGCAAGCCCAGGAGGAAGAACCCCCAGG AGGGCCTGTATAACGAGCTGCAGAAGGACAAGATGG CCGAGGCCTACAGCGAGATCGGCATGAAGGGCGAG AGGAGGAGGGGCAAGGGCCACGACGGCCTGTACCA GGGCCTGAGCACCGCCACCAAGGACACCTACGACGC CCTGCACATGCAGGCCCTGCCCCCCAGG | 35 |
| Anti-P329G VH | GAGGTGAAGCTGCTGGAGAGCGGCGGCGGCCTGGTG CAGCCCGGCGGCAGCCTGAAGCTGAGCTGCGCCGCC AGCGGCTTCGACTTCAGCAGGTACTGGATGAACTGG GTGAGGCAGGCCCCCGGCAAGGGTCTGGAGTGGATC GGCGAGATCACCCCCGACAGCAGCACCATCAACTAC ACCCCCAGCCTGAAGGACAAGTTCATCATCAGCAGG GACAACGCCAAGAACACCCTGTACCTGCAGATGATC AAGGTGAGGAGCGAGGACACCGCCCTGTACTACTGC GTGAGGCCCTACGACTACGGCGCCTGGTTCGCCAGC TGGGGCCAGGGCACCCTGGTGACCGTGAGCGCC | 36 |

TABLE 5-continued

Anti-P329G-scFv DNA sequences:

| Construct | DNA sequence | SEQ ID NO |
|---|---|---|
| Anti-P329G VL | CAGGCCGTGGTGACCCAGGAGAGCGCCCTGACCACC<br>AGCCCCGGCGAGACCGTGACCCTGACCTGCAGGAGC<br>AGCACCGGCGCCGTGACCACCAGCAACTACGCCAAC<br>TGGGTGCAGGAGAAGCCCGACCACCTGTTCACCGGC<br>CTGATCGGCGGCACCAACAAGAGGGCCCCCGGCGTG<br>CCCGCCAGGTTCAGCGGCAGCCTGATCGGCGACAAG<br>GCCGCCCTGACCATCACCGGCGCCCAGACCGAGGAC<br>GAGGCCATCTACTTCTGCGCCCTGTGGTACAGCAACC<br>ACTGGGTGTTCGGCGGTGGCACCAAGCTGACCGTGC<br>TG | 37 |
| CD28ATD | see Table 3 | 24 |
| CD28CSD | see Table 3 | 25 |
| CD3zSSD | see Table 3 | 26 |
| CD28ATD-CD28CSD-<br>CD3zSSD | see Table 3 | 27 |
| T2A element | see Table 3 | 28 |
| eGFP | see Table 3 | 29 |
| Anti-P329G-scFv-<br>CD28ATD-CD28CSD-<br>CD3zSSD-<br>eGFP fusion | ATGGGATGGAGCTGTATCATCCTCTTCTTGGTAGCAA<br>CAGCTACCGGTGTGCATTCCGAGGTGAAGCTGCTGG<br>AGAGCGGCGGCGGCCTGGTGCAGCCCGGCGGCAGCC<br>TGAAGCTGAGCTGCGCCGCCAGCGGCTTCGACTTCA<br>GCAGGTACTGGATGAACTGGGTGAGGCAGGCCCCCG<br>GCAAGGGTCTGGAGTGGATCGGCGAGATCACCCCCG<br>ACAGCAGCACCATCAACTACACCCCCAGCCTGAAGG<br>ACAAGTTCATCATCAGCAGGGACAACGCCAAGAACA<br>CCCTGTACCTGCAGATGATCAAGGTGAGGAGCGAGG<br>ACACCGCCCTGTACTACTGCGTGAGGCCCTACGACT<br>ACGGCGCCTGGTTCGCCAGCTGGGGCCAGGGCACCC<br>TGGTGACCGTGAGCGCCGAGGGGGCGGAAGTGGTG<br>GCGGGGGAAGCGGCGGGGGTGGCAGCGGAGGGGGC<br>GGATCTCAGGCCGTGGTGACCCAGGAGAGCGCCCTG<br>ACCACCAGCCCCGGCGAGACCGTGACCCTGACCTGC<br>AGGAGCAGCACCGGCGCCGTGACCACCAGCAACTAC<br>GCCAACTGGGTGCAGGAGAAGCCCGACCACCTGTTC<br>ACCGGCCTGATCGGCGGCACCAACAAGAGGGCCCCC<br>GGCGTGCCCGCCAGGTTCAGCGGCAGCCTGATCGGC<br>GACAAGGCCGCCCTGACCATCACCGGCGCCCAGACC<br>GAGGACGAGGCCATCTACTTCTGCGCCCTGTGGTAC<br>AGCAACCACTGGGTGTTCGGCGGTGGCACCAAGCTG<br>ACCGTGCTGGGAGGGGCGGATCCTTCTGGGTGCTG<br>GTGGTGGTGGGCGGCGTGCTGGCCTGCTACAGCCTG<br>CTGGTGACCGTGGCCTTCATCATCTTCTGGGTGAGGA<br>GCAAGAGGAGCAGGCTGCTGCACAGCGACTACATGA<br>ACATGACCCCCAGGAGGCCCGGCCCCACCAGGAAGC<br>ACTACCAGCCCTACGCCCCCCCCAGGGACTTCGCCG<br>CCTACAGGAGCAGGGTGAAGTTCAGCAGGAGCGCCG<br>ACGCCCCCGCCTACCAGCAGGGCCAGAACCAGCTGT<br>ATAACGAGCTGAACCTGGGCAGGAGGGAGGAGTAC<br>GACGTGCTGGACAAGAGGAGGGGCAGGGACCCCGA<br>GATGGGCGGCAAGCCCAGGAGGAAGAACCCCCAGG<br>AGGGGCCTGTATAACGAGCTGCAGAAGGACAAGATGG<br>CCGAGGCCTACAGCGAGATCGGCATGAAGGGCGAG<br>AGGAGGAGGGGCAAGGGCCACGACGGCCTGTACCA<br>GGGCCTGAGCACCGCCACCAAGGACACCTACGACGC<br>CCTGCACATGCAGGCCCTGCCCCCCAGGTCCGGAGA<br>GGGCAGAGGAAGTCTTCTAACATGCGGTGACGTGGA<br>GGGAGAATCCCGGCCCTAGGGTGAGCAAGGGCGAGG<br>AGCTGTTCACCGGGGTGGTGCCCATCCTGGTCGAGCT<br>GGACGGCGACGTAAACGGCCACAAGTTCAGCGTGTC<br>CGGCGAGGGCGAGGGCGATGCCACCTACGGCAAGCT<br>GACCCTGAAGTTCATCTGCACCACCGGCAAGCTGCC<br>CGTGCCCTGGCCCACCCTCGTGACCACCCTGACCTAC<br>GGCGTGCAGTGCTTCAGCCGCTACCCCGACCACATG<br>AAGCAGCACGACTTCTTCAAGTCCGCCATGCCCGAA<br>GGCTACGTCCAGGAGCGCACCATCTTCTTCAAGGAC<br>GACGGCAACTACAAGACCCGCGCCGAGGTGAAGTTC<br>GAGGGCGACACCCTGGTGAACCGCATCGAGCTGAAG<br>GGCATCGACTTCAAGGAGGACGGCAACATCCTGGGG<br>CACAAGCTGGAGTACAACTACAACAGCCACAACGTC | 38 |

TABLE 5-continued

| Anti-P329G-scFv DNA sequences: | | |
|---|---|---|
| Construct | DNA sequence | SEQ ID NO |
| | TATATCATGGCCGACAAGCAGAAGAACGGCATCAAG<br>GTGAACTTCAAGATCCGCCACAACATCGAGGACGGC<br>AGCGTGCAGCTCGCCGACCACTACCAGCAGAACACC<br>CCCATCGGCGACGGCCCCGTGCTGCTGCCCGACAAC<br>CACTACCTGAGCACCCAGTCCGCCCTGAGCAAAGAC<br>CCCAACGAGAAGCGCGATCACATGGTCCTGCTGGAG<br>TTCGTGACCGCCGCCGGGATCACTCTCGGCATGGAC<br>GAGCTGTACAAGTGA | |

TABLE 6

| Anti-P329G-ds-Fab amino acid sequences | | |
|---|---|---|
| Construct | Amino acid sequence | SEQ ID NO |
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-ds-Fab-heavy chain-CD28ATD-CD28CSD-CD3zSSD fusion pETR17100 | EVKLLESGGGLVQPGGSLKLSCAASGFDFSRYWMNWV<br>RQAPGKCLEWIGEITPDSSTINYTPSLKDKFIISRDNAKN<br>TLYLQMIKVRSEDTALYYCVRPYDYGAWFASWGQGT<br>LVTVSAASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCGGGGS<br>FWVLVVVGGVLACYSLLVTVAFIIFWVRSKRSRLLHSD<br>YMNMTPRRPGPTRKHYQPYAPPRDFAAYRSRVKFSRS<br>ADAPAYQQGQNQLYNELNLGRREEYDVLDKRRGRDP<br>EMGGKPRRKNPQEGLYNELQKDKMAEAYSEIGMKGE<br>RRRGKGHDGLYQGLSTATKDTYDALHMQALPPR | 39 |
| Anti-P329G-ds-Fab heavy chain | EVKLLESGGGLVQPGGSLKLSCAASGIFDFSRYWMNWV<br>RQAPGKCLEWIGEITPDSSTINYTPSLKDKFIISRDNAKN<br>TLYLQMIKVRSEDTALYYCVRPYDYGAWFASWGQGT<br>LVTVSAASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSC | 40 |
| Anti-P329G-ds-Fab light chain | QAVVTQESALTTSPGETVTLTCRSSTGAVTTSNYANWV<br>QEKPDHLFTGLIGGTNKRAPGVPARFSGSLIGDKAALTI<br>TGAQTEDEAIYFCALWYSNHWVFGCGTKLTVLRTVAA<br>PSVFIFPPSDEQLKSGTASVVCLLNNFYPREAKVQWKV<br>DNALQSGNSQESVTEQDSKDSTYSLSSTLTLSKADYEK<br>HKVYACEVTHQGLSSPVTKSFNRGEC | 41 |
| Anti-P329G-ds VL | see Table 2 | 9 |
| CL | RTVAAPSVFIFPPSDEQLKSGTASVVCLLNNFYPREAKV<br>QWKVDNALQSGNSQESVTEQDSKDSTYSLSSTLTLSKA<br>DYEKHKVYACEVTHQGLSSPVTKSFNRGEC | 42 |
| Anti-P329G-ds VH | see Table 2 | 8 |
| CH1 | ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSC | 43 |

TABLE 6-continued

Anti-P329G-ds-Fab amino acid sequences

| Construct | Amino acid sequence | SEQ ID NO |
|---|---|---|
| CD28ATD-CD28CSD-CD3zSSD | see Table 2 | 14 |

TABLE 7

Anti-P329G-ds-Fab DNA sequences:

| Construct | DNA Sequenz | SEQ ID NO |
|---|---|---|
| Anti-P329G-ds-Fab-heavy chain-CD28ATD-CD28CSD-CD3zSSD fusion pETR17100 | ATGGGATGGAGCTGTATCATCCTCTTCTTGGTAGCAA CAGCTACGGGTGTGCATTCCCAGGCCGTGGTGACCC AGGAGAGCGCCCTGACCACCAGCCCCGGCGAGACCG TGACCCTGACCTGCAGGAGCAGCACCGGCGCCGTGA CCACCAGCAACTACGCCAACTGGGTGCAGGAGAAGC CCGACCACCTGTTCACCGGCCTGATCGGCGGCACCA ACAAGAGGGCCCCCGGCGTGCCCGCCAGGTTCAGCG GCAGCCTGATCGGCGACAAGGCCGCCCTGACCATCA CCGGCGCCCAGACCGAGGACGAGGCCATCTACTTCT GCGCCCTGTGGTACAGCAACCACTGGGTGTTCGGCT GTGGCACCAAGCTGACCGTGCTGCGTACGGTGGCTG CACCATCTGTCTTCATCTTCCCGCCATCTGATGAGCA GTTGAAATCTGGAACTGCCTCTGTTGTGTGCCTGCTG AATAACTTCTATCCCAGAGAGGCCAAAGTACAGTGG AAGGTGGATAACGCCCTCCAATCGGGTAACTCCCAG GAGAGTGTCACAGAGCAGGACAGCAAGGACAGCAC CTACAGCCTCAGCAGCACCCTGACGCTGAGCAAAGC AGACTACGAGAAACACAAAGTCTACGCCTGCGAAGT CACCCATCAGGGCCTGAGCTCGCCCGTCACAAAGAG CTTCAACAGGGGAGAGTGTTAGGAATTCCCCGAAGT AACTTAGAAGCTGTAAATCAACGATCAATAGCAGGT GTGGCACACCAGTCATACCTTGATCAAGCACTTCTGT TTCCCCGGACTGAGTATCAATAGGCTGCTCGCGCGG CTGAAGGAGAAAACGTTCGTTACCCGACCAACTACT TCGAGAAGCTTAGTACCACCATGAACGAGGCAGGGT GTTTCGCTCAGCACAACCCCAGTGTAGATCAGGCTG ATGAGTCACTGCAACCCCCATGGGCGACCATGGCAG TGGCTGCGTTGGCGGCCTGCCCATGGAGAAATCCAT GGGACGCTCTAATTCTGACATGGTGTGAAGTGCCTAT TGAGCTAACTGGTAGTCCTCCGGCCCCTGATTGCGGC TAATCCTAACTGCGGAGCACATGCTCACAAACCAGT GGGTGGTGTCGTAACGGGCAACTCTGCAGCGGAA CCGACTACTTTGGGTGTCCGTGTTTCCTTTTATTCCTA TATTGGCTGCTTATGGTGACAATCAAAAAGTTGTTAC CATATAGCTATTGGATTGGCCATCCGGTGTGCAACA GGGCAACTGTTTACCTATTTATTGGTTTTGTACCATT ATCACTGAAGTCTGTGATCACTCTCAAATTCATTTTG ACCCTCAACACAATCAAACGCCACCATGGGATGGAG CTGTATCATCCTCTTCTTGGTAGCAACAGCTACCGGT GTGCACTCCGAGGTGAAGCTGCTGGAGAGCGGCGGC GGCCTGGTGCAGCCCGGCGGCAGCCTGAAGCTGAGC TGCGCCGCCAGCGGCTTCGACTTCAGCAGGTACTGG ATGAACTGGGTGAGGCAGGCCCCCGGCAAGTGTCTG GAGTGGATCGGCGAGATCACCCCCGACAGCAGCACC ATCAACTACACCCCCAGCCTGAAGGACAAGTTCATC ATCAGCAGGGACAACGCCAAGAACACCCTGTACCTG CAGATGATCAAGGTGAGGAGCGAGGACACCGCCCTG TACTACTGCGTGAGGCCCTACGACTACGGCGCCTGG TTCGCCAGCTGGGGCCAGGGCACCCTGGTGACCGTG AGCGCCGCTAGCACCAAGGGCCCCTCCGTGTTCCCC CTGGCCCCCAGCAGCAAGAGCACCAGCGGCGGCACA GCCGCTCTGGGCTGCCTGGTCAAGGACTACTTCCCCG AGCCCGTGACCGTGTCCTGGAACAGCGGAGCCCTGA CCTCCGGCGTGCACACCTTCCCCGCCGTGCTGCAGAG TTCTGGCCTGTATAGCCTGAGCAGCGTGGTCACCGTG CCTTCTAGCAGCCTGGGCACCCAGACCTACATCTGCA ACGTGAACCACAAGCCCAGCAACACCAAGGTGGACA AGAAGGTGGAGCCCAAGAGCTGCGAGGGGGCCGGA TCCTTCTGGGTGCTGGTGGTGGTGGGCGGCGTGCTGG CCTGCTACAGCCTGCTGGTGACCGTGGCCTTCATCAT CTTCTGGGTGAGGAGCAAGAGGAGCAGGCTGCTGCA CAGCGACTACATGAACATGACCCCCAGGAGGCCCGG CCCCACCAGGAAGCACTACCAGCCCTACGCCCCCCC | 44 |

TABLE 7-continued

Anti-P329G-ds-Fab DNA sequences:

| Construct | DNA Sequenz | SEQ ID NO |
|---|---|---|
| | CAGGGACTTCGCCGCCTACAGGAGCAGGGTGAAGTT<br>CAGCAGGAGCGCCGACGCCCCCGCCTACCAGCAGGG<br>CCAGAACCAGCTGTATAACGAGCTGAACCTGGGCAG<br>GAGGGAGGAGTACGACGTGCTGGACAAGAGGAGGG<br>GCAGGGACCCCGAGATGGGCGGCAAGCCCAGGAGG<br>AAGAACCCCCAGGAGGGCCTGTATAACGAGCTGCAG<br>AAGGACAAGATGGCCGAGGCCTACAGCGAGATCGG<br>CATGAAGGGCGAGAGGAGGAGGGGCAAGGGCCACG<br>ACGGCCTGTACCAGGGCCTGAGCACCGCCACCAAGG<br>ACACCTACGACGCCCTGCACATGCAGGCCCTGCCCC<br>CCAGG | |
| Anti-P329G-ds VL | see Table 3 | 21 |
| CL | CGTACGGTGGCTGCACCATCTGTCTTCATCTTCCCGC<br>CATCTGATGAGCAGTTGAAATCTGGAACTGCCTCTGT<br>TGTGTGCCTGCTGAATAACTTCTATCCCAGAGAGGCC<br>AAAGTACAGTGGAAGGTGGATAACGCCCTCCAATCG<br>GGTAACTCCCAGGAGAGTGTCACAGAGCAGGACAGC<br>AAGGACAGCACCTACAGCCTCAGCAGCACCCTGACG<br>CTGAGCAAAGCAGACTACGAGAAACACAAAGTCTAC<br>GCCTGCGAAGTCACCCATCAGGGCCTGAGCTCGCCC<br>GTCACAAAGAGCTTCAACAGGGGAGAGTGTTAG | 45 |
| Anti-P329G-ds VH | see Table 3 | 20 |
| CH1 | GCTAGCACCAAGGGCCCCTCCGTGTTCCCCCTGGCCC<br>CCAGCAGCAAGAGCACCAGCGGCGGCACAGCCGCTC<br>TGGGCTGCCTGGTCAAGGACTACTTCCCCGAGCCCGT<br>GACCGTGTCCTGGAACAGCGGAGCCCTGACCTCCGG<br>CGTGCACACCTTCCCCGCCGTGCTGCAGAGTTCTGGC<br>CTGTATAGCCTGAGCAGCGTGGTCACCGTGCCTTCTA<br>GCAGCCTGGGCACCCAGACCTACATCTGCAACGTGA<br>ACCACAAGCCCAGCAACACCAAGGTGGACAAGAAG<br>GTGGAGCCCAAGAGCTGC | 46 |
| CD28ATD-CD28CSD-<br>CD3zSSD | see Table 3 | 27 |
| Anti-P329G-ds-Fab-<br>heavy chain-<br>CD28ATD-CD28CSD-<br>CD3ZSSD-<br>eGFP fusion<br>pETR17100 | ATGGGATGGAGCTGTATCATCCTCTTCTTGGTAGCAA<br>CAGCTACGGGTGTGCATTCCCAGGCCGTGGTGACCC<br>AGGAGAGCGCCCTGACCACCAGCCCCGGCGAGACCG<br>TGACCCTGACCTGCAGGAGCAGCACCGGCGCCGTGA<br>CCACCAGCAACTACGCCAACTGGGTGCAGGAGAAGC<br>CCGACCACCTGTTCACCGGCCTGATCGGCGGCACCA<br>ACAAGAGGGCCCCCGGCGTGCCCGCCAGGTTCAGCG<br>GCAGCCTGATCGGCGACAAGGCCGCCCTGACCATCA<br>CCGGCGCCCAGACCGAGGACGAGGCCATCTACTTCT<br>GCGCCCTGTGGTACAGCAACCACTGGGTGTTCGGCT<br>GTGGCACCAAGCTGACCGTGCTGCGTACGGTGGCTG<br>CACCATCTGTCTTCATCTTCCCGCCATCTGATGAGCA<br>GTTGAAATCTGGAACTGCCTCTGTTGTGTGCCTGCTG<br>AATAACTTCTATCCCAGAGAGGCCAAAGTACAGTGG<br>AAGGTGGATAACGCCCTCCAATCGGGTAACTCCCAG<br>GAGAGTGTCACAGAGCAGGACAGCAAGGACAGCAC<br>CTACAGCCTCAGCAGCACCCTGACGCTGAGCAAAGC<br>AGACTACGAGAAACACAAAGTCTACGCCTGCGAAGT<br>CACCCATCAGGGCCTGAGCTCGCCCGTCACAAAGAG<br>CTTCAACAGGGGAGAGTGTTAGGAATTCCCCGAAGT<br>AACTTAGAAGCTGTAAATCAACGATCAATAGCAGGT<br>GTGGCACACCAGTCATACCTTGATCAAGCACTTCTGT<br>TTCCCCGGACTGAGTATCAATAGGCTGCTCGCGCGG<br>CTGAAGGAGAAAACGTTCGTTACCCGACCAACTACT<br>TCGAGAAGCTTAGTACCACCATGAACGAGGCAGGGT<br>GTTTCGCTCAGCACAACCCCAGTGTAGATCAGGCTG<br>ATGAGTCACTGCAACCCCCATGGGCGACCATGGCAG<br>TGGCTGCGTTGGCGGCCTGCCCATGGAGAAATCCAT<br>GGGACGCTCTAATTCTGACATGGTGTGAAGTGCCTAT<br>TGAGCTAACTGGTAGTCCTCCGGCCCTGATTGCGGC<br>TAATCCTAACTGCGGAGCACATGCTCACAAACCAGT<br>GGGTGGTGTGTCGTAACGGGCAACTCTGCAGCGGAA<br>CCGACTACTTTGGGTGTCCGTGTTTCCTTTTATTCCTA<br>TATTGGCTGCTTATGGTGACAATCAAAAGTTGTTAC<br>CATATAGCTATTGGATTGGCCATCCGGTGTGCAACA<br>GGGCAACTGTTTACCTATTTATTGGTTTTGTACCATT<br>ATCACTGAAGTCTGTGATCACTCTCAAATTCATTTTG | 47 |

TABLE 7-continued

Anti-P329G-ds-Fab DNA sequences:

| Construct | DNA Sequenz | SEQ ID NO |
|---|---|---|
| | ACCCTCAACACAATCAAACGCCACCATGGGATGGAG<br>CTGTATCATCCTCTTCTTGGTAGCAACAGCTACCGGT<br>GTGCACTCCGAGGTGAAGCTGCTGGAGAGCGGCGGC<br>GGCCTGGTGCAGCCCGGCGGCAGCCTGAAGCTGAGC<br>TGCGCCGCCAGCGGCTTCGACTTCAGCAGGTACTGG<br>ATGAACTGGGTGAGGCAGGCCCCCGGCAAGTGTCTG<br>GAGTGGATCGGCGAGATCACCCCCGACAGCAGCACC<br>ATCAACTACACCCCCAGCCTGAAGGACAAGTTCATC<br>ATCAGCAGGGACAACGCCAAGAACACCCTGTACCTG<br>CAGATGATCAAGGTGAGGAGCGAGGACACCGCCCTG<br>TACTACTGCGTGAGGCCCTACGACTACGGCGCCTGG<br>TTCGCCAGCTGGGGCCAGGGCACCCTGGTGACCGTG<br>AGCGCCGCTAGCACCAAGGGCCCCTCCGTGTTCCCC<br>CTGGCCCCCAGCAGCAAGAGCACCAGCGGCGGCACA<br>GCCGCTCTGGGCTGCCTGGTCAAGGACTACTTCCCCG<br>AGCCCGTGACCGTGTCCTGGAACAGCGGAGCCCTGA<br>CCTCCGGCGTGCACACCTTCCCCGCCGTGCTGCAGAG<br>TTCTGGCCTGTATAGCCTGAGCAGCGTGGTCACCGTG<br>CCTTCTAGCAGCCTGGGCACCCAGACCTACATCTGCA<br>ACGTGAACCACAAGCCCAGCAACACCAAGGTGGACA<br>AGAAGGTGGAGCCCAAGAGCTGCGGAGGGGGCGGA<br>TCCTTCTGGGTGCTGGTGGTGGTGGGCGGCGTGCTGG<br>CCTGCTACAGCCTGCTGGTGACCGTGGCCTTCATCAT<br>CTTCTGGGTGAGGAGCAAGAGGAGCAGGCTGCTGCA<br>CAGCGACTACATGAACATGACCCCCAGGAGGCCCGG<br>CCCCACCAGGAAGCACTACCAGCCCTACGCCCCCCC<br>CAGGGACTTCGCCGCCTACAGGAGCAGGGTGAAGTT<br>CAGCAGGAGCGCCGACGCCCCCGCCTACCAGCAGGG<br>CCAGAACCAGCTGTATAACGAGCTGAACCTGGGCAG<br>GAGGGAGGAGTACGACGTGCTGGACAAGAGGAGGG<br>GCAGGGACCCCGAGATGGGCGGCAAGCCCAGGAGG<br>AAGAACCCCCAGGAGGGCCTGTATAACGAGCTGCAG<br>AAGGACAAGATGGCCGAGGCCTACAGCGAGATCGG<br>CATGAAGGGCGAGAGGAGGAGGGGCAAGGGCCACG<br>ACGGCCTGTACCAGGGCCTGAGCACCGCCACCAAGG<br>ACACCTACGACGCCCTGCACATGCAGGCCCTGCCCC<br>CCAGGTCCGGAGAGGGCAGAGGAAGTCTTCTAACAT<br>GCGGTGACGTGGAGGAGAATCCCGGCCCTAGGGTGA<br>GCAAGGGCGAGGAGCTGTTCACCGGGGTGGTGCCCA<br>TCCTGGTCGAGCTGGACGGCGACGTAAACGGCCACA<br>AGTTCAGCGTGTCCGGCGAGGGCGAGGGCGATGCCA<br>CCTACGGCAAGCTGACCCTGAAGTTCATCTGCACCA<br>CCGGCAAGCTGCCCGTGCCCTGGCCCACCCTCGTGA<br>CCACCCTGACCTACGGCGTGCAGTGCTTCAGCCGCTA<br>CCCCGACCACATGAAGCAGCACGACTTCTTCAAGTC<br>CGCCATGCCCGAAGGCTACGTCCAGGAGCGCACCAT<br>CTTCTTCAAGGACGACGGCAACTACAAGACCCGCGC<br>CGAGGTGAAGTTCGAGGGCGACACCCTGGTGAACCG<br>CATCGAGCTGAAGGGCATCGACTTCAAGGAGGACGG<br>CAACATCCTGGGGCACAAGCTGGAGTACAACTACAA<br>CAGCCACAACGTCTATATCATGGCCGACAAGCAGAA<br>GAACGGCATCAAGGTGAACTTCAAGATCCGCCACAA<br>CATCGAGGACGGCAGCGTGCAGCTCGCCGACCACTA<br>CCAGCAGAACACCCCCATCGGCGACGGCCCCGTGCT<br>GCTGCCCGACAACCACTACCTGAGCACCCAGTCCGC<br>CCTGAGCAAAGACCCCAACGAGAAGCGCGATCACAT<br>GGTCCTGCTGGAGTTCGTGACCGCCGCCGGGATCAC<br>TCTCGGCATGGACGAGCTGTACAAGTGA | |

TABLE 8

Anti-P329G-Fab amino acid sequences:

| Construct | Amino acid sequence | SEQ ID NO |
|---|---|---|
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |

TABLE 8-continued

Anti-P329G-Fab amino acid sequences:

| Construct | Amino acid sequence | SEQ ID NO |
|---|---|---|
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-Fab-heavy chain-CD28ATD-CD28CSD-CD3zSSD fusion pETR17594 | EVKLLESGGGLVQPGGSLKLSCAASGFDFSRYWMNWV RQAPGKGLEWIGEITPDSSTINYTPSLKDKFIISRDNAKN TLYLQMIKVRSEDTALYYCVRPYDYGAWFASWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCGGGGS FWVLVVVGGVLACYSLLVTVAFIIFWVRSKRSLLHSD YMNMTPRRPGPTRKHYQPYAPPRDFAAYRSRVKFSRS ADAPAYQQGQNQLYNELNLGRREEYDVLDKRRGRDP EMGGKPRRKNPQEGLYNELQKDKMAEAYSEIGMKGE RRRGKGHDGLYQGLSTATKDTYDALHMQALPPR | 48 |
| Anti-P329G-Fab heavy chain | EVKLLESGGGLVQPGGSLKLSCAASGFDFSRYWMNWV RQAPGKGLEWIGEITPDSSTINYTPSLKDKFIISRDNAKN TLYLQMIKVRSEDTALYYCVRPYDYGAWFASWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSC | 49 |
| Anti-P329G-Fab light chain | QAVVTQESALTTSPGETVTLTCRSSTGAVTTSNYANWV QEKPDHLFTGLIGGTNKRAPGVPARFSGSLIGDKAALTI TGAQTEDEAIYFCALWYSNHWVFGGGTKLTVLRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC | 50 |
| Anti-P329G VL | see Table 4 | 33 |
| CL | see Table 6 | 42 |
| Anti-P329G VH | see Table 4 | 32 |
| CH1 | see Table 6 | 43 |
| CD28ATD-CD28CSD-CD3zSSD | see Table 2 | 14 |

TABLE 9

Anti-P329G-Fab DNA sequences:

| Construct | DNA Sequenz | SEQ ID NO |
|---|---|---|
| Anti-P329G-Fab-heavy chain-CD28ATD-CD28CSD-CD3zSSD fusion pETR17594 | ATGGGATGGAGCTGTATCATCCTCTTCTTGGTAGCAA CAGCTACGGGTGTGCATTCCCAGGCCGTGGTGACCC AGGAGAGCGCCCTGACCACCAGCCCCGGCGAGACCG TGACCCTGACCTGCAGGAGCAGCACCGGCGCCGTGA CCACCAGCAACTACGCCAACTGGGTGCAGGAGAAGC CCGACCACCTGTTCACCGGCCTGATCGGCGGCACCA ACAAGAGGGCCCCCGGCGTGCCCGCCAGGTTCAGCG GCAGCCTGATCGGCGACAAGGCCGCCCTGACCATCA CCGGCGCCCAGACCGAGGACGAGGCCATCTACTTCT GCGCCCTGTGGTACAGCAACCACTGGGTGTTCGGCG GTGGCACCAAGCTGACCGTGCTGCGTACGGTGGCTG CACCATCTGTCTTCATCTTCCCGCCATCTGATGAGCA GTTGAAATCTGGAACTGCCTCTGTTGTGTGCCTGCTG AATAACTTCTATCCCAGAGAGGCCAAAGTACAGTGG AAGGTGGATAACGCCCTCCAATCGGGTAACTCCCAG GAGAGTGTCACAGAGCAGGACAGCAAGGACAGCAC CTACAGCCTCAGCAGCACCCTGACGCTGAGCAAAGC AGACTACGAGAAACACAAAGTCTACGCCTGCGAAGT CACCCATCAGGGCCTGAGCTCGCCCGTCACAAAGAG CTTCAACAGGGGAGAGTGTTAGGAATTCCCCGAAGT | 51 |

TABLE 9-continued

Anti-P329G-Fab DNA sequences:

| Construct | DNA Sequenz | SEQ ID NO |
|---|---|---|
| | AACTTAGAAGCTGTAAATCAACGATCAATAGCAGGT<br>GTGGCACACCAGTCATACCTTGATCAAGCACTTCTGT<br>TTCCCCGGACTGAGTATCAATAGGCTGCTCGCGCGG<br>CTGAAGGAGAAAACGTTCGTTACCCGACCAACTACT<br>TCGAGAAGCTTAGTACCACCATGAACGAGGCAGGGT<br>GTTTCGCTCAGCACAACCCCAGTGTAGATCAGGCTG<br>ATGAGTCACTGCAACCCCATGGGCGACCATGGCAG<br>TGGCTGCGTTGGCGGCCTGCCCATGGAGAAATCCAT<br>GGGACGCTCTAATTCTGACATGGTGTGAAGTGCCTAT<br>TGAGCTAACTGGTAGTCCTCCGGCCCCTGATTGCGGC<br>TAATCCTAACTGCGGAGCACATGCTCACAAACCAGT<br>GGGTGGTGTGTCGTAACGGGCAACTCTGCAGCGGAA<br>CCGACTACTTTGGGTGTCCGTGTTTCCTTTTATTCCTA<br>TATTGGCTGCTTATGGTGACAATCAAAAAGTTGTTAC<br>CATATAGCTATTGGATTGGCCATCCGGTGTGCAACA<br>GGGCAACTGTTTACCTATTTATTGGTTTTGTACCATT<br>ATCACTGAAGTCTGTGATCACTCTCAAATTCATTTTG<br>ACCCTCAACACAATCAAACGCCACCATGGGATGGAG<br>CTGTATCATCCTCTTCTTGGTAGCAACAGCTACCGGT<br>GTGCACTCCGAGGTGAAGCTGCTGGAGAGCGGCGGC<br>GGCCTGGTGCAGCCCGGCGGCAGCCTGAAGCTGAGC<br>TGCGCCGCCAGCGGCTTCGACTTCAGCAGGTACTGG<br>ATGAACTGGGTGAGGCAGGCCCCCGGCAAGGGTCTG<br>GAGTGGATCGGCGAGATCACCCCCGACAGCAGCACC<br>ATCAACTACACCCCCAGCCTGAAGGACAAGTTCATC<br>ATCAGCAGGGACAACGCCAAGAACACCCTGTACCTG<br>CAGATGATCAAGGTGAGGAGCGAGGACACCGCCCTG<br>TACTACTGCGTGAGGCCCTACGACTACGGCGCCTGG<br>TTCGCCAGCTGGGGCCAGGGCACCCTGGTGACCGTG<br>AGCGCCGCTAGCACCAAGGGCCCCTCCGTGTTCCCC<br>CTGGCCCCCAGCAGCAAGAGCACCAGCGGCGGCACA<br>GCCGCTCTGGGCTGCCTGGTCAAGGACTACTTCCCCG<br>AGCCCGTGACCGTGTCCTGGAACAGCGGAGCCCTGA<br>CCTCCGGCGTGCACACCTTCCCCGCCGTGCTGCAGAG<br>TTCTGGCCTGTATAGCCTGAGCAGCGTGGTCACCGTG<br>CCTTCTAGCAGCCTGGGCACCCAGACCTACATCTGCA<br>ACGTGAACCACAAGCCCAGCAACACCAAGGTGGACA<br>AGAAGGTGGAGCCCAAGAGCTGCGGAGGGGGCGGA<br>TCCTTCTGGGTGCTGGTGGTGGTGGGCGGCGTGCTGG<br>CCTGCTACAGCCTGCTGGTGACCGTGGCCTTCATCAT<br>CTTCTGGGTGAGGAGCAAGAGGAGCAGGCTGCTGCA<br>CAGCGACTACATGAACATGACCCCCAGGAGGCCCGG<br>CCCCACCAGGAAGCACTACCAGCCCTACGCCCCCCC<br>CAGGGACTTCGCCGCCTACAGGAGCAGGGTGAAGTT<br>CAGCAGGAGCGCCGACGCCCCCGCCTACCAGCAGGG<br>CCAGAACCAGCTGTATAACGAGCTGAACCTGGGCAG<br>GAGGGAGGAGTACGACGTGCTGGACAAGAGGAGGG<br>GCAGGGACCCCGAGATGGGCGGCAAGCCCAGGAGG<br>AAGAACCCCCAGGAGGGCCTGTATAACGAGCTGCAG<br>AAGGACAAGATGGCCGAGGCCTACAGCGAGATCGG<br>CATGAAGGGCGAGAGGAGGAGGGGCAAGGGCCACG<br>ACGGCCTGTACCAGGGCCTGAGCACCGCCACCAAGG<br>ACACCTACGACGCCCTGCACATGCAGGCCCTGCCCC<br>CCAGG | |
| Anti-P329G VL | see Table 5 | 37 |
| CL | see Table 7 | 45 |
| Anti-P329G VH | see Table 5 | 36 |
| CH1 | see Table 7 | 46 |
| CD28ATD-CD28CSD-<br>CD3zSSD | see Table 3 | 27 |
| Anti-P329G-Fab-<br>heavy chain-<br>CD28ATD-CD28CSD-<br>CD3zSSD-<br>eGFP fusion<br>pETR17594 | ATGGGATGGAGCTGTATCATCCTCTTCTTGGTAGCAA<br>CAGCTACGGGTGTGCATTCCCAGGCCGTGGTGACCC<br>AGGAGAGCGCCCTGACCACCAGCCCCGGCGAGACCG<br>TGACCCTGACCTGCAGGAGCAGCACCGGCGCCGTGA<br>CCACCAGCAACTACGCCAACTGGGTGCAGGAGAAGC<br>CCGACCACCTGTTCACCGGCCTGATCGGCGGCACCA<br>ACAAGAGGGCCCCCGGCGTGCCCGCCAGGTTCAGCG<br>GCAGCCTGATCGGCGACAAGGCCGCCCTGACCATCA<br>CCGGCGCCCAGACCGAGGACGAGGCCATCTACTTCT<br>GCGCCCTGTGGTACAGCAACCACTGGGTGTTCGGCG | 52 |

TABLE 9-continued

Anti-P329G-Fab DNA sequences:

| Construct | DNA Sequenz | SEQ ID NO |
|---|---|---|
| | GTGGCACCAAGCTGACCGTGCTGCGTACGGTGGCTG | |
| | CACCATCTGTCTTCATCTTCCCGCCATCTGATGAGCA | |
| | GTTGAAATCTGGAACTGCCTCTGTTGTGTGCCTGCTG | |
| | AATAACTTCTATCCCAGAGAGGCCAAAGTACAGTGG | |
| | AAGGTGGATAACGCCCTCCAATCGGGTAACTCCCAG | |
| | GAGAGTGTCACAGAGCAGGACAGCAAGGACAGCAC | |
| | CTACAGCCTCAGCAGCACCCTGACGCTGAGCAAAGC | |
| | AGACTACGAGAAACACAAAGTCTACGCCTGCGAAGT | |
| | CACCCATCAGGGCCTGAGCTCGCCCGTCACAAAGAG | |
| | CTTCAACAGGGGAGAGTGTTAGGAATTCCCCGAAGT | |
| | AACTTAGAAGCTGTAAATCAACGATCAATAGCAGGT | |
| | GTGGCACACCAGTCATACCTTGATCAAGCACTTCTGT | |
| | TTCCCCGGACTGAGTATCAATAGGCTGCTCGCGCGG | |
| | CTGAAGGAGAAAACGTTCGTTACCCGACCAACTACT | |
| | TCGAGAAGCTTAGTACCACCATGAACGAGGCAGGGT | |
| | GTTTCGCTCAGCACAACCCCAGTGTAGATCAGGCTG | |
| | ATGAGTCACTGCAACCCCATGGGCGACCATGGCAG | |
| | TGGCTGCGTTGGCGGCCTGCCCATGGAGAAATCCAT | |
| | GGGACGCTCTAATTCTGACATGGTGTGAAGTGCCTAT | |
| | TGAGCTAACTGGTAGTCCTCCGGCCCTGATTGCGGC | |
| | TAATCCTAACTGCGGAGCACATGCTCACAAACCAGT | |
| | GGGTGGTGTGTCGTAACGGGCAACTCTGCAGCGGAA | |
| | CCGACTACTTTGGGTGTCCGTGTTTCCTTTTATTCCTA | |
| | TATTGGCTGCTTATGGTGACAATCAAAAAGTTGTTAC | |
| | CATATAGCTATTGGATTGGCCATCCGGTGTGCAACA | |
| | GGGCAACTGTTTACCTATTTATTGGTTTTGTACCATT | |
| | ATCACTGAAGTCTGTGATCACTCTCAAATTCATTTTG | |
| | ACCCTCAACACAATCAAACGCCACCATGGGATGGAG | |
| | CTGTATCATCCTCTTCTTGGTAGCAACAGCTACCGGT | |
| | GTGCACTCCGAGGTGAAGCTGCTGGAGAGCGGCGGC | |
| | GGCCTGGTGCAGCCCGGCGGCAGCCTGAAGCTGAGC | |
| | TGCGCCGCCAGCGGCTTCGACTTCAGCAGGTACTGG | |
| | ATGAACTGGGTGAGGCAGGCCCCCGGCAAGGGTCTG | |
| | GAGTGGATCGGCGAGATCACCCCCGACAGCAGCACC | |
| | ATCAACTACACCCCCAGCCTGAAGGACAAGTTCATC | |
| | ATCAGCAGGGACAACGCCAAGAACACCCTGTACCTG | |
| | CAGATGATCAAGGTGAGGAGCGAGGACACCGCCCTG | |
| | TACTACTGCGTGAGGCCCTACGACTACGGCGCCTGG | |
| | TTCGCCAGCTGGGGCCAGGGCACCCTGGTGACCGTG | |
| | AGCGCCGCTAGCACCAAGGGCCCCTCCGTGTTCCCC | |
| | CTGGCCCCCAGCAGCAAGAGCACCAGCGGCGGCACA | |
| | GCCGCTCTGGGCTGCCTGGTCAAGGACTACTTCCCCG | |
| | AGCCCGTGACCGTGTCCTGGAACAGCGGAGCCCTGA | |
| | CCTCCGGCGTGCACACCTTCCCCGCCGTGCTGCAGAG | |
| | TTCTGGCCTGTATAGCCTGAGCAGCGTGGTCACCGTG | |
| | CCTTCTAGCAGCCTGGGCACCCAGACCTACATCTGCA | |
| | ACGTGAACCACAAGCCCAGCAACACCAAGGTGGACA | |
| | AGAAGGTGGAGCCCAAGAGCTGCGGAGGGGCGGA | |
| | TCCTTCTGGGTGCTGGTGGTGGTGGGCGGCGTGCTGG | |
| | CCTGCTACAGCCTGCTGGTGACCGTGGCCTTCATCAT | |
| | CTTCTGGGTGAGGAGCAAGAGGAGCAGGCTGCTGCA | |
| | CAGCGACTACATGAACATGACCCCCAGGAGGCCCGG | |
| | CCCCACCAGGAAGCACTACCAGCCCTACGCCCCCCC | |
| | CAGGGACTTCGCCGCCTACAGGAGCAGGGTGAAGTT | |
| | CAGCAGGAGCGCCGACGCCCCCGCCTACCAGCAGGG | |
| | CCAGAACCAGCTGTATAACGAGCTGAACCTGGGCAG | |
| | GAGGGAGGAGTACGACGTGCTGGACAAGAGGAGGG | |
| | GCAGGGACCCCGAGATGGGCGGCAAGCCCAGGAGG | |
| | AAGAACCCCCAGGAGGGCCTGTATAACGAGCTGCAG | |
| | AAGGACAAGATGGCCGAGGCCTACAGCGAGATCGG | |
| | CATGAAGGGCGAGAGGAGGAGGGGCAAGGGCCACG | |
| | ACGGCCTGTACCAGGGCCTGAGCACCGCCACCAAGG | |
| | ACACCTACGACGCCCTGCACATGCAGGCCCTGCCCC | |
| | CCAGGTCCGGAGAGGGCAGAGGAAGTCTTCTAACAT | |
| | GCGGTGACGTGGAGGAGAATCCCGGCCCTAGGGTGA | |
| | GCAAGGGCGAGGAGCTGTTCACCGGGGTGGTGCCCA | |
| | TCCTGGTCGAGCTGGACGGCGACGTAAACGGCCACA | |
| | AGTTCAGCGTGTCCGGCGAGGGCGAGGGCGATGCCA | |
| | CCTACGGCAAGCTGACCCTGAAGTTCATCTGCACCA | |
| | CCGGCAAGCTGCCCGTGCCCTGGCCCACCCTCGTGA | |
| | CCACCCTGACCTACGGCGTGCAGTGCTTCAGCCGCTA | |
| | CCCCGACCACATGAAGCAGCACGACTTCTTCAAGTC | |
| | CGCCATGCCCGAAGGCTACGTCCAGGAGCGCACCAT | |
| | CTTCTTCAAGGACGACGGCAACTACAAGACCCGCGC | |
| | CGAGGTGAAGTTCGAGGGCGACACCCTGGTGAACCG | |
| | CATCGAGCTGAAGGGCATCGACTTCAAGGAGGACGG | |

TABLE 9-continued

Anti-P329G-Fab DNA sequences:

| Construct | DNA Sequenz | SEQ ID NO |
|---|---|---|
| | CAACATCCTGGGGCACAAGCTGGAGTACAACTACAA<br>CAGCCACAACGTCTATATCATGGCCGACAAGCAGAA<br>GAACGGCATCAAGGTGAACTTCAAGATCCGCCACAA<br>CATCGAGGACGGCAGCGTGCAGCTCGCCGACCACTA<br>CCAGCAGAACACCCCCATCGGCGACGGCCCCGTGCT<br>GCTGCCCGACAACCACTACCTGAGCACCCAGTCCGC<br>CCTGAGCAAAGACCCCAACGAGAAGCGCGATCACAT<br>GGTCCTGCTGGAGTTCGTGACCGCCGCCGGGATCAC<br>TCTCGGCATGGACGAGCTGTACAAGTGA | |

TABLE 10

Anti-AAA-scFv amino acid sequences

| Construct | Amino acid sequence | SEQ ID NO |
|---|---|---|
| Anti-AAA CDR H1 Kabat | SYGMS | 53 |
| Anti-AAA CDR H2 Kabat | SSGGSY | 54 |
| Anti-AAA CDR H3 Kabat | LGMITTGYAMDY | 55 |
| Anti-AAA CDR L1 Kabat | RSSQTIVHSTGHTYLE | 56 |
| Anti-AAA CDR L2 Kabat | KVSNRFS | 57 |
| Anti-AAA CDR L3 Kabat | FQGSHVPYT | 58 |
| Anti-AAA-scFv-CD28ATD-CD28CSD-CD3zSSD fusion | MNFGLSLVFLALILKGVQCEVQLVESGGDLVKPGGSLK<br>LSCAASGFTFSSYGMSWVRQTPDKRLEWVATISSGGSY<br>IYYPDSVKGRFTISRDNAKNTLYLQMSSLKSEDTAMYY<br>CARLGMITTGYAMDYWGQGTSVTVSSGGGGSGGGGS<br>GGGGSGGGGSDVLMTQTPLSLPVSLGDQASISCRSSQTI<br>VHSTGHTYLEWFLQKPGQSPKLLIYKVSNRFSGVPDRF<br>SGSGSGTDFTLKISRVEAEDLGVYYCFQGSHVPYTFGG<br>GTKLEIKGGGGSFWVLVVVGGVLACYSLLVTVAFIIFW<br>VRSKRSRLLHSDYMNMTPRRPGPTRKHYQPYAPPRDF<br>AAYRSRVKFSRSADAPAYQQGQNQLYNELNLGRREEY<br>DVLDKRRGRDPEMGGKPRRKNPQEGLYNELQKDKMA<br>EAYSEIGMKGERRRGKGHDGLYQGLSTATKDTYDALH<br>MQALPPR | 59 |
| Anti-AAA-scFv | MNFGLSLVFLALILKGVQCEVQLVESGGDLVKPGGSLK<br>LSCAASGFTFSSYGMSWVRQTPDKRLEWVATISSGGSY<br>IYYPDSVKGRFTISRDNAKNTLYLQMSSLKSEDTAMYY<br>CARLGMITTGYAMDYWGQGTSVTVSSGGGGSGGGGS<br>GGGGSGGGGSDVLMTQTPLSLPVSLGDQASISCRSSQTI<br>VHSTGHTYLEWFLQKPGQSPKLLIYKVSNRFSGVPDRF<br>SGSGSGTDFTLKISRVEAEDLGVYYCFQGSHVPYTFGG<br>GTKLEIK | 60 |
| Anti-AAA VH | MNFGLSLVFLALILKGVQCEVQLVESGGDLVKPGGSLK<br>LSCAASGFTFSSYGMSWVRQTPDKRLEWVATISSGGSY<br>IYYPDSVKGRFTISRDNAKNTLYLQMSSLKSEDTAMYY<br>CARLGMITTGYAMDYWGQGTSVTVSS | 61 |
| Anti-AAA VL | DVLMTQTPLSLPVSLGDQASISCRSSQTIVHSTGHTYLE<br>WFLQKPGQSPKLLIYKVSNRFSGVPDRFSGSGSGTDFTL<br>KISRVEAEDLGVYYCFQGSHVPYTFGGGTKLEIK | 62 |

TABLE 11

Anti-AAA-Fab amino acid sequences

| Construct | Protein Sequence | SEQ ID NO |
|---|---|---|
| Anti-AAA CDR H1 Kabat | see Table 10 | 53 |
| Anti-AAA CDR H2 Kabat | see Table 10 | 54 |
| Anti-AAA CDR H3 Kabat | see Table 10 | 55 |
| Anti-AAA CDR L1 Kabat | see Table 10 | 56 |
| Anti-AAA CDR L2 Kabat | see Table 10 | 57 |
| Anti-AAA CDR L3 Kabat | see Table 10 | 58 |
| Anti-AAA-Fab-heavy chain-CD28ATD-CD28CSD-CD3zSSD fusion | MNFGLSLVFLALILKGVQCEVQLVESGGDLVKPGGSLK LSCAASGFTFSSYGMSWVRQTPDKRLEWVATISSGGSY IYYPDSVKGRFTISRDNAKNTLYLQMSSLKSEDTAMYY CARLGMITTGYAMDYWGQGTSVTVSSASTKGPSVFPL APSSKSTSGGTAALGCLVKDYFPEPVTVSWNSGALTSG VHTFPAVLQSSGLYSLSSVVTVPSSSLGTQTYICNVNHK PSNTKVDKKVEPKSCGGGGSFWVLVVVGGVLACYSLL VTVAFIIFWVRSKRSRLLHSDYMNMTPRRPGPTRKHYQ PYAPPRDFAAYRSRVKFSRSADAPAYQQGQNQLYNEL NLGRREEYDVLDKRRGRDPEMGGKPRRKNPQEGLYNE LQKDKMAEAYSEIGMKGERRRGKGHDGLYQGLSTAT KDTYDALHMQALPPR | 63 |
| Anti-AAA-Fab heavy chain | MNFGLSLVFLALILKGVQCEVQLVESGGDLVKPGGSLK LSCAASGFTFSSYGMSWVRQTPDKRLEWVATISSGGSY IYYPDSVKGRFTISRDNAKNTLYLQMSSLKSEDTAMYY CARLGMITTGYAMDYWGQGTSVTVSSASTKGPSVFPL APSSKSTSGGTAALGCLVKDYFPEPVTVSWNSGALTSG VHTFPAVLQSSGLYSLSSVVTVPSSSLGTQTYICNVNHK PSNTKVDKKVEPKSC | 64 |
| Anti-AAA-Fab light chain | DVLMTQTPLSLPVSLGDQASISCRSSQTIVHSTGHTYLE WFLQKPGQSPKLLIYKVSNRFSGVPDRFSGSGSGTDFTL KISRVEAEDLGVYYCFQGSHVPYTFGGGTKLEIKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC | 65 |
| Anti-AAA VL | see Table 10 | 62 |
| CL | see Table 6 | 42 |
| Anti-AAA VH | see Table 10 | 61 |
| CH1 | see Table 6 | 43 |

TABLE 12

| Construct | Amino acid sequence | SEQ ID NO |
|---|---|---|
| Human CD27 | ATGGCGCGCCCGCATCCGTGGTGGCTGTGCGTGCTG GGCACCCTGGTGGGCCTGAGCGCGACCCCGGCGCCG AAAAGCTGCCCGGAACGCCATTATTGGGCGCAGGGC AAACTGTGCTGCCAGATGTGCGAACCGGGCACCTTT CTGGTGAAAGATTGCGATCAGCATCGCAAAGCGGCG CAGTGCGATCCGTGCATTCCGGGCGTGAGCTTTAGCC CGGATCATCATACCCGCCCGCATTGCGAAAGCTGCC GCCATTGCAACAGCGGCCTGCTGGTGCGCAACTGCA CCATTACCGCGAACGCGGAATGCGCGTGCCGCAACG GCTGGCAGTGCCGCGATAAAGAATGCACCGAATGCG ATCCGCTGCCGAACCCGAGCCTGACCGCGCGCAGCA GCCAGGCGCTGAGCCCGCATCCGCAGCCGACCCATC TGCCGTATGTGAGCGAAATGCTGGAAGCGCGCACCG CGGGCCATATGCAGACCCTGGCGGATTTTCGCCAGC TGCCGGCGCGCACCCTGAGCACCCATTGGCCGCCGC | 66 |

TABLE 12-continued

| Construct | Amino acid sequence | SEQ ID NO |
|---|---|---|
| | AGCGCAGCCTGTGCAGCAGCGATTTTATTCGCATTCT<br>GGTGATTTTTAGCGGCATGTTTCTGGTGTTTACCCTG<br>GCGGGCGCGCTGTTTCTGCATCAGCGCCGCAAATAT<br>CGCAGCAACAAAGGCGAAAGCCCGGTGGAACCGGC<br>GGAACCGTGCCATTATAGCTGCCCGCGCGAAGAAGA<br>AGGCAGCACCATTCCGATTCAGGAAGATTATCGCAA<br>ACCGGAACCGGCGTGCAGCCCG | |
| Human CD27 | MARPHPWWLCVLGTLVGLSATPAPKSCPERHYWAQG<br>KLCCQMCEPGTFLVKDCDQHRKAAQCDPCIPGVSFSPD<br>HHTRPHCESCRHCNSGLLVRNCTITANAECACRNGWQ<br>CRDKECTECDPLPNPSLTARSSQALSPHPQPTHLPYVSE<br>MLEARTAGHMQTLADFRQLPARTLSTHWPPQRSLCSS<br>DFIRILVIFSGMFLVFTLAGALFLHQRRKYRSNKGESPV<br>EPAEPCHYSCPREEEGSTIPIQEDYRKPEPACSP | 67 |
| Murine CD27 | ATGGCGTGGCCGCCGCCGTATTGGCTGTGCATGCTG<br>GGCACCCTGGTGGGCCTGAGCGCGACCCTGGCGCCG<br>AACAGCTGCCCGGATAAACATTATTGGACCGGCGGC<br>GGCCTGTGCTGCCGCATGTGCGAACCGGGCACCTTTT<br>TTGTGAAAGATTGCGAACAGGATCGCACCGCGGCGC<br>AGTGCGATCCGTGCATTCCGGGCACCAGCTTTAGCCC<br>GGATTATCATACCCGCCCGCATTGCGAAAGCTGCCG<br>CCATTGCAACAGCGGCTTTCTGATTCGCAACTGCACC<br>GTGACCGCGAACGCGGAATGCAGCTGCAGCAAAAAC<br>TGGCAGTGCCGCGATCAGGAATGCACCGAATGCGAT<br>CCGCCGCTGAACCCGGCGCTGACCCGCCAGCCGAGC<br>GAAACCCCGAGCCCGCAGCCGCCGCCGACCCATCTG<br>CCGCATGGCACCGAAAAACCGAGCTGGCCGCTGCAT<br>CGCCAGCTGCCGAACAGCACCGTGTATAGCCAGCGC<br>AGCAGCCATCGCCCGCTGTGCAGCAGCGATTGCATT<br>CGCATTTTTGTGACCTTTAGCAGCATGTTTCTGATTTT<br>TGTGCTGGGCGCGATTCTGTTTTTTCATCAGCGCCGC<br>AACCATGGCCCGAACGAAGATCGCCAGGCGGTGCCG<br>GAAGAACCGTGCCCGTATAGCTGCCCGCGCGAAGAA<br>GAAGGCAGCGCGATTCCGATTCAGGAAGATTATCGC<br>AAACCGGAACCGGCGTTTTATCCG | 68 |
| Murine CD27 | MAWPPPYWLCMLGTLVGLSATLAPNSCPDKHYWTGG<br>GLCCRMCEPGTFFVKDCEQDRTAAQCDPCIPGTSFSPD<br>YHTRPHCESCRHCNSGFLIRNCTVTANAECSCSKNWQC<br>RDQECTECDPPLNPALTRQPSETPSPQPPPTHLPHGTEK<br>PSWPLHRQLPNSTVYSQRSSHRPLCSSDCIRIFVTFSSW<br>LIFVLGAILFFHQRRNHGPNEDRQAVPEEPCPYSCPREE<br>EGSAIPIQEDYRKPEPAFYP | 69 |
| Human CD28 | ATGCTGCGCCTGCTGCTGGCGCTGAACCTGTTTCCGA<br>GCATTCAGGTGACCGGCAACAAAATTCTGGTGAAAC<br>AGAGCCCGATGCTGGTGGCGTATGATAACGCGGTGA<br>ACCTGAGCTGCAAATATAGCTATAACCTGTTTAGCCG<br>CGAATTTCGCGCGAGCCTGCATAAAGGCCTGGATAG<br>CGCGGTGGAAGTGTGCGTGGTGTATGGCAACTATAG<br>CCAGCAGCTGCAGGTGTATAGCAAAACCGGCTTTAA<br>CTGCGATGGCAAACTGGGCAACGAAAGCGTGACCTT<br>TTATCTGCAGAACCTGTATGTGAACCAGACCGATATT<br>TATTTTTGCAAAATTGAAGTGATGTATCCGCCGCCGT<br>ATCTGGATAACGAAAAAAGCAACGGCACCATTATTC<br>ATGTGAAAGGCAAACATCTGTGCCCGAGCCCGCTGT<br>TTCCGGGCCCGAGCAAACCGTTTTGGGTGCTGGTGGT<br>GGTGGGCGGCGTGCTGGCGTGCTATAGCCTGCTGGT<br>GACCGTGGCGTTTATTATTTTTGGGTGCGCAGCAAA<br>CGCAGCCGCCTGCTGCATAGCGATTATATGAACATG<br>ACCCCGCGCCGCCCGGGCCCGACCCGCAAACATTAT<br>CAGCCGTATGCGCCGCCGCGCGATTTTGCGGCGTATC<br>GCAGC | 70 |
| Human CD28 | MLRLLLALNLFPSIQVTGNKILVKQSPMLVAYDNAVNL<br>SCKYSYNLFSREFRASLHKGLDSAVEVCVVYGNYSQQ<br>LQVYSKTGFNCDGKLGNESVTFYLQNLYVNQTDIYFC<br>KIEVMYPPPYLDNEKSNGTIIHVKGKHLCPSPLFPGPSK<br>PFWVLVVVGGVLACYSLLVTVAFIIFWVRSKRSRLLHS<br>DYMNMTPRRPGPTRKHYQPYAPPRDFAAYRS | 71 |
| Murine CD28 | ATGACCCTGCGCCTGCTGTTTCTGGCGCTGAACTTTT<br>TTAGCGTGCAGGTGACCGAAAACAAATTCTGGTGA<br>AACAGAGCCCGCTGCTGGTGGTGGATAGCAACGAAG<br>TGAGCCTGAGCTGCCGCTATAGCTATAACCTGCTGGC<br>GAAAGAATTTCGCGCGAGCCTGTATAAAGGCGTGAA | 72 |

TABLE 12-continued

| Construct | Amino acid sequence | SEQ ID NO |
|---|---|---|
| | CAGCGATGTGGAAGTGTGCGTGGGCAACGGCAACTT<br>TACCTATCAGCCGCAGTTTCGCAGCAACGCGGAATTT<br>AACTGCGATGGCGATTTTGATAACGAAACCGTGACC<br>TTTCGCCTGTGGAACCTGCATGTGAACCATACCGATA<br>TTTATTTTTGCAAAATTGAATTTATGTATCCGCCGCC<br>GTATCTGGATAACGAACGCAGCAACGGCACCATTAT<br>TCATATTAAAGAAAAACATCTGTGCCATACCCAGAG<br>CAGCCCGAAACTGTTTTGGGCGCTGGTGGTGGTGGC<br>GGGCGTGCTGTTTTGCTATGGCCTGCTGGTGACCGTG<br>GCGCTGTGCGTGATTTGGACCAACAGCCGCCGCAAC<br>CGCCTGCTGCAGAGCGATTATATGAACATGACCCCG<br>CGCCGCCCGGGCCTGACCCGCAAACCGTATCAGCCG<br>TATGCGCCGGCGCGCGATTTTGCGGCGTATCGCCCG | |
| Murine CD28 | MTLRLLFLALNFFSVQVIENKILVKQSPLLVVDSNEVSL<br>SCRYSYNLLAKEFRASLYKGVNSDVEVCVGNGNFTYQ<br>PQFRSNAEFNCDGDFDNETVTFRLWNLHVNHTDIYFCK<br>IEFMYPPPYLDNERSNGTIIHIKEKHLCHTQSSPKLFWAL<br>VVVAGVLFCYGLLVTVALCVIWTNSRRNRLLQSDYMN<br>MTPRRPGLTRKPYQPYAPARDFAAYRP | 73 |
| Human CD137 | ATGGGAAACAGCTGTTACAACATAGTAGCCACTCTG<br>TTGCTGGTCCTCAACTTTGAGAGGACAAGATCATTGC<br>AGGATCCTTGTAGTAACTGCCCAGCTGGTACATTCTG<br>TGATAATAACAGGAATCAGATTTGCAGTCCCTGTCCT<br>CCAAATAGTTTCTCCAGCGCAGGTGGACAAAGGACC<br>TGTGACATATGCAGGCAGTGTAAAGGTGTTTTCAGG<br>ACCAGGAAGGAGTGTTCCTCCACCAGCAATGCAGAG<br>TGTGACTGCACTCCAGGGTTTCACTGCCTGGGGGCA<br>GGATGCAGCATGTGTGAACAGGATTGTAAACAAGGT<br>CAAGAACTGACAAAAAAAGGTTGTAAAGACTGTTGC<br>TTTGGGACATTTAACGATCAGAAACGTGGCATCTGTC<br>GACCCTGGACAAACTGTTCTTTGGATGGAAAGTCTGT<br>GCTTGTGAATGGGACGAAGGAGAGGGACGTGGTCTG<br>TGGACCATCTCCAGCCGACCTCTCCGGGAGCATCC<br>TCTGTGACCCCGCCTGCCCCTGCGAGAGAGCCAGGA<br>CACTCTCCGCAGATCATCTCCTTCTTTCTTGCGCTGA<br>CGTCGACTGCGTTGCTCTTCCTGCTGTTCTTCCTCACG<br>CTCCGTTTCTCTGTTGTTAAACGGGGCAGAAAGAAA<br>CTCCTGTATATATTCAAACAACCATTTATGAGACCAG<br>TACAAACTACTCAAGAGGAAGATGGCTGTAGCTGCC<br>GATTTCCAGAAGAAGAAGAAGGAGGATGTGAACTGT<br>GA | 74 |
| Human CD137 | MGNSCYNIVATLLLVLNFERTRSLQDPCSNCPAGTFCD<br>NNRNQICSPCPPNSFSSAGGQRTCDICRQCKGVFRTRKE<br>CSSTSNAECDCTPGFHCLGAGCSMCEQDCKQGQELTK<br>KGCKDCCFGTFNDQKRGICRPWTNCSLDGKSVLVNGT<br>KERDVVCGPSPADLSPGASSVTPPAPAREPGHSPQIISFF<br>LALTSTALLFLLFFLTLRFSVVKRGRKKLLYIFKQPFMR<br>PVQTTQEEDGCSCRFPEEEEGGCEL | 75 |
| Murine CD137 | ATGGGCAACAACTGCTATAACGTGGTGGTGATTGTG<br>CTGCTGCTGGTGGGCTGCGAAAAAGTGGGCGCGGTG<br>CAGAACAGCTGCGATAACTGCCAGCCGGGCACCTTT<br>TGCCGCAAATATAACCCGGTGTGCAAAAGCTGCCCG<br>CCGAGCACCTTTAGCAGCATTGGCGGCCAGCCGAAC<br>TGCAACATTTGCCGCGTGTGCGCGGGCTATTTTCGCT<br>TTAAAAAATTTTGCAGCAGCACCCATAACGCGGAAT<br>GCGAATGCATTGAAGGCTTTCATTGCCTGGGCCCGC<br>AGTGCACCCGCTGCGAAAAAGATTGCCGCCCGGGCC<br>AGGAACTGACCAAACAGGGCTGCAAAACCTGCAGCC<br>TGGGCACCTTTAACGATCAGAACGGCACCGGCGTGT<br>GCCGCCCGTGGACCAACTGCAGCCTGGATGGCCGCA<br>GCGTGCTGAAAACCGGCACCACCGAAAAAGATGTGG<br>TGTGCGGCCCGCCGGTGGTGAGCTTTAGCCCGAGCA<br>CCACCATTAGCGTGACCCCGGAAGGCGCCCGGGCG<br>GCCATAGCCTGCAGGTGCTGACCCTGTTTCTGGCGCT<br>GACCAGCGCGCTGCTGCTGGCGCTGATTTTTATTACC<br>CTGCTGTTTAGCGTGCTGAAATGGATTCGCAAAAAA<br>TTTCCGCATATTTTTAAACAGCCGTTTAAAAAAACCA<br>CCGGCGCGGCGCAGGAAGAAGATGCGTGCAGCTGCC<br>GCTGCCCGCAGGAAGAAGAAGGCGGCGGCGGCGGC<br>TATGAACTG | 76 |
| Murine CD137 | MGNNCYNVVVIVLLLVGCEKVGAVQNSCDNCQPGTF<br>CRKYNPVCKSCPPSTFSSIGGQPNCNICRVCAGYFRFKK<br>FCSSTHNAECECIEGFHCLGPQCTRCEKDCRPGQELTK | 77 |

TABLE 12-continued

| Construct | Amino acid sequence | SEQ ID NO |
|---|---|---|
| | QGCKTCSLGTFNDQNGTGVCRPWTNCSLDGRSVLKTG TTEKDVVCGPPVVSFSPSTTISVTPEGGPGGHSLQVLTL FLALTSALLLALIFITLLFSVLKWIRKKFPHIFKQPFKKTT GAAQEEDACSCRCPQEEEGGGGGYEL | |
| Human OX40 | ATGTGCGTGGGCGCGCGCCGCCTGGGCCGCGGCCCG TGCGCGGCGCTGCTGCTGCTGGGCCTGGGCCTGAGC ACCGTGACCGGCCTGCATTGCGTGGGCGATACCTAT CCGAGCAACGATCGCTGCTGCCATGAATGCCGCCCG GGCAACGGCATGGTGAGCCGCTGCAGCCGCAGCCAG AACACCGTGTGCCGCCCGTGCGGCCCGGGCTTTTATA ACGATGTGGTGAGCAGCAAACCGTGCAAACCGTGCA CCTGGTGCAACCTGCGCAGCGGCAGCGAACGCAAAC AGCTGTGCACCGCGACCCAGGATACCGTGTGCCGCT GCCGCGCGGGCACCCAGCCGCTGGATAGCTATAAAC CGGGCGTGGATTGCGCGCCGTGCCCGCCGGGCCATT TTAGCCCGGGCGATAACCAGGCGTGCAAACCGTGGA CCAACTGCACCCTGGCGGGCAAACATACCCTGCAGC CGGCGAGCAACAGCAGCGATGCGATTTGCGAAGATC GCGATCCGCCGGCGACCCAGCCGCAGGAAACCCAGG GCCCGCCGGCGCGCCCGATTACCGTGCAGCCGACCG AAGCGTGGCCGCGCACCAGCCAGGGCCCGAGCACCC GCCCGGTGGAAGTGCCGGGCGGCCGCGGTGGCGG CGATTCTGGGCCTGGGCCTGGTGCTGGGCCTGCTGG GCCCGCTGGCGATTCTGCTGGCGCTGTATCTGCTGCG CCGCGATCAGCGCCTGCCGCCGGATGCGCATAAAACC GCCGGGCGGCGGCAGCTTTCGCACCCCGATTCAGGA AGAACAGGCGGATGCGCATAGCACCCTGGCGAAAAT T | 78 |
| Human OX40 | MCVGARRLGRGPCAALLLLGLGLSTVTGLHCVGDTYP SNDRCCHECRPGNGMVSRCSRSQNTVCRPCGPGFYND VVSSKPCKPCTWCNLRSGSERKQLCTATQDTVCRCRA GTQPLDSYKPGVDCAPCPPGHFSPGDNQACKPWTNCT LAGKHTLQPASNSSDAICEDRDPPATQPQETQGPPARPI TVQPTEAWPRTSQGPSTRPVEVPGGRAVAAILGLGLVL GLLGPLAILLALYLLRRDQRLPPDAHKPPGGGSFRTPIQ EEQADAHSTLAKI | 79 |
| Murine OX40 | ATGTATGTGTGGGTGCAGCAGCCGACCGCGCTGCTG CTGCTGGCGCTGACCCTGGGCGTGACCGCGCGCCGC CTGAACTGCGTGAAACATACCTATCCGAGCGGCCAT AAATGCTGCCGCGAATGCCAGCCGGGCCATGGCATG GTGAGCCGCTGCGATCATACCCGCGATACCCTGTGC CATCCGTGCGAAACCGGCTTTTATAACGAAGCGGTG AACTATGATACCTGCAAACAGTGCACCCAGTGCAAC CATCGCAGCGGCAGCGAACTGAAACAGAACTGCACC CCGACCCAGGATACCGTGTGCCGCTGCCGCCCGGGC ACCCAGCCGCGCCAGGATAGCGGCTATAAACTGGGC GTGGATTGCGTGCCGTGCCCGCCGGGCCATTTTAGCC CGGGCAACAACCAGGCGTGCAAACCGTGGACCAACT GCACCCTGAGCGGCAAACAGACCCGCCATCCGGCGA GCGATAGCCTGGATGCGGTGTGCGAAGATCGCAGCC TGCTGGCGACCCTGCTGTGGGAAACCCAGCGCCCGA CCTTTCGCCCGACCACCGTGCAGAGCACCACCGTGT GGCCGCGCACCAGCGAACTGCCGAGCCCGCCGACCC TGGTGACCCCGGAAGGCCCGGCGTTTGCGGTGCTGC TGGGCCTGGGCCTGGGCCTGCTGGCGCCGCTGACCG TGCTGCTGGCGCTGTATCTGCTGCGCAAAGCGTGGC GCCTGCCGAACACCCCGAAACCGTGCTGGGGCAACA GCTTTCGCACCCCGATTCAGGAAGAACATACCGATG CGCATTTTACCCTGGCGAAAATT | 80 |
| Murine OX40 | MYVWVQQPTALLLLALTLGVTARRLNCVKHTYPSGH KCCRECQPGHGMVSRCDHTRDTLCHPCETGFYNEAVN YDTCKQCTQCNHRSGSELKQNCTPTQDTVCRCRPGTQ PRQDSGYKLGVDCVPCPPGHFSPGNNQACKPWTNCTL SGKQTRHPASDSLDAVCEDRSLLATLLWETQRPTFRPT TVQSTTVWPRTSELPSPPTLVTPEGPAFAVLLGLGLGLL APLTVLLALYLLRKAWRLPNTPKPCWGNSFRTPIQEEH TDAHFTLAKI | 81 |
| Human ICOS | ATGAAAAGCGGCCTGTGGTATTTTTTTCTGTTTTGCC TGCGCATTAAAGTGCTGACCGGCGAAATTAACGGCA GCGCGAACTATGAAATGTTTATTTTTCATAACGGCGG CGTGCAGATTCTGTGTCAAATATCCGGATATTGTGCAG CAGTTTAAAATGCAGCTGCTGAAAGGCGGCCAGATT CTGTGCGATCTGACCAAAACCAAAGGCAGCGGCAAC | 82 |

TABLE 12-continued

| Construct | Amino acid sequence | SEQ ID NO |
|---|---|---|
| | ACCGTGAGCATTAAAAGCCTGAAATTTTGCCATAGC<br>CAGCTGAGCAACAACAGCGTGAGCTTTTTTCTGTATA<br>ACCTGGATCATAGCCATGCGAACTATTATTTTTGCAA<br>CCTGAGCATTTTTGATCCGCCGCCGTTTAAAGTGACC<br>CTGACCGGCGGCTATCTGCATATTTATGAAAGCCAG<br>CTGTGCTGCCAGCTGAAATTTTGGCTGCCGATTGGCT<br>GCGCGGCGTTTGTGGTGGTGTGCATTCTGGGCTGCAT<br>TCTGATTTGCTGGCTGACCAAAAAAAAATATAGCAG<br>CAGCGTGCATGATCCGAACGGCGAATATATGTTTAT<br>GCGCGCGGTGAACACCGCGAAAAAAAGCCGCCTGAC<br>CGATGTGACCCTG | |
| Human ICOS | MKSGLWYFFLFCLRIKVLTGEINGSANYEMFIFHNGGV<br>QILCKYPDIVQQFKMQLLKGGQILCDLTKTKGSGNTVSI<br>KSLKFCHSQLSNNSVSFFLYNLDHSHANYYFCNLSIFDP<br>PPFKVTLTGGYLHIYESQLCCQLKFWLPIGCAAFVVVCI<br>LGCILICWLTKKKYSSSVHDPNGEYMFMRAVNTAKKS<br>RLTDVTL | 83 |
| Murine ICOS | ATGAAACCGTATTTTTGCCGCGTGTTTGTGTTTTGCTT<br>TCTGATTCGCCTGCTGACCGGCGAAATTAACGGCAG<br>CGCGGATCATCGCATGTTTAGCTTTCATAACGGCGGC<br>GTGCAGATTAGCTGCAAATATCCGGAAACCGTGCAG<br>CAGCTGAAAATGCGCCTGTTTCGCGAACGCGAAGTG<br>CTGTGCGAACTGACCAAAACCAAAGGCAGCGGCAAC<br>GCGGTGAGCATTAAAAACCCGATGCTGTGCCTGTAT<br>CATCTGAGCAACAACAGCGTGAGCTTTTTTCTGAACA<br>ACCCGGATAGCAGCCAGGGCAGCTATTATTTTTGCA<br>GCCTGAGCATTTTTGATCCGCCGCCGTTTCAGGAACG<br>CAACCTGAGCGGCGGCTATCTGCATATTTATGAAAG<br>CCAGCTGTGCTGCCAGCTGAAACTGTGGCTGCCGGT<br>GGGCTGCGCGGCGTTTGTGGTGGTGCTGCTGTTTGGC<br>TGCATTCTGATTATTTGGTTTAGCAAAAAAAAATATG<br>GCAGCAGCGTGCATGATCCGAACAGCGAATATATGT<br>TTATGGCGGCGGTGAACACCAACAAAAAAGCCGCC<br>TGGCGGGCGTGACCAGC | 84 |
| Murine ICOS | MKPYFCRVFVFCFLIRLLTGEINGSADHRMFSFHNGGV<br>QISCKYPETVQQLKMRLFREREVLCELTKTKGSGNAVS<br>IKNPMLCLYHLSNNSVSFFLNNPDSSQGSYYFCSLSIFDP<br>PPFQERNLSGGYLHIYESQLCCQLKLWLPVGCAAFVVV<br>LLFGCILIIWFSKKKYGSSVHDPNSEYMFMAAVNTNKK<br>SRLAGVTS | 85 |
| Human DAP10 | ATGATTCATCTGGGCCATATTCTGTTTCTGCTGCTGC<br>TGCCGGTGGCGGCGGCGCAGACCACCCCGGGCGAAC<br>GCAGCAGCCTGCCGGCGTTTTATCCGGGCACCAGCG<br>GCAGCTGCAGCGGCTGCGGCAGCCTGAGCCTGCCGC<br>TGCTGGCGGGCCTGGTGGCGGCGGATGCGGTGGCGA<br>GCCTGCTGATTGTGGGCGCGGTGTTTCTGTGCGCGCG<br>CCCGCGCCGCAGCCCGGCGCAGGAAGATGGCAAAGT<br>GTATATTAACATGCCGGGCCGCGGC | 86 |
| Human DAP10 | M1HLGHILFLLLLPVAAAQTTPGERSSLPAFYPGTSGSCS<br>GCGSLSLPLLAGLVAADAVASLLIVGAVFLCARPRRSP<br>AQEDGKVYINMPGRG | 87 |
| Murine DAP10 | ATGGATCCGCCGGGCTATCTGCTGTTTCTGCTGCTGC<br>TGCCGGTGGCGGCGAGCCAGACCAGCGCGGGCAGCT<br>GCAGCGGCTGCGGCACCCTGAGCCTGCCGCTGCTGG<br>CGGGCCTGGTGGCGGCGGATGCGGTGATGAGCCTGC<br>TGATTGTGGGCGTGGTGTTTGTGTGCATGCGCCCGCA<br>TGGCCGCCCGGCGCAGGAAGATGGCCGCGTGTATAT<br>TAACATGCCGGGCCGCGGC | 88 |
| Murine DAP10 | MDPPGYLLFLLLLPVAASQTSAGSCSGCGTLSLPLLAGL<br>VAADAVMSLLIVGVVFVCMRPHGRPAQEDGRVYINMP<br>GRG | 89 |
| Human DAP12 | ATGGGGGGACTTGAACCCTGCAGCAGGCTCCTGCTC<br>CTGCCTCTCCTGCTGGCTGTAAGTGGTCTCCGTCCTG<br>TCCAGGCCCAGGCCCAGAGCGATTGCAGTTGCTCTA<br>CGGTGAGCCCGGGCGTGCTGGCAGGATCGTGATGG<br>GAGACCTGGTGCTGACAGTGCTCATTGCCCTGGCCGT<br>GTACTTCCTGGGCCGGCTGGTCCCTCGGGGCCGAGG<br>GGCTGCGGAGGCAGCCGACCCGGAAACAGCGTATCAC<br>TGAGACCGAGTCGCCTTATCAGGAGCTCCAGGGTCA | 90 |

TABLE 12-continued

| Construct | Amino acid sequence | SEQ ID NO |
|---|---|---|
| | GAGGTCGGATGTCTACAGCGACCTCAACACACAGAG<br>GCCGTATTACAAATGA | |
| Human DAP12 | MGGLEPCSRLLLLPLLLAVSGLRPVQAQAQSDCSCSTV<br>SPGVLAGIVMGDLVLTVLIALAVYFLGRLVPRGRGAAE<br>AATRKQRITETESPYQELQGQRSDVYSDLNTQRPYYK | 91 |
| Murine DAP12 | ATGGGGGCTCTGGAGCCCTCCTGGTGCCTTCTGTTCC<br>TTCCTGTCCTCCTGACTGTGGGAGGATTAAGTCCCGT<br>ACAGGCCCAGAGTGACACTTTCCCAAGATGCGACTG<br>TTCTTCCGTGAGCCCTGGTGTACTGGCTGGGATTGTT<br>CTGGGTGACTTGGTGTTGACTCTGCTGATTGCCCTGG<br>CTGTGTACTCTCTGGGCCGCCTGGTCTCCCGAGGTCA<br>AGGGACAGCGGAAGGGACCCGGAAACAACACATTG<br>CTGAGACTGAGTCGCCTTATCAGGAGCTTCAGGGTC<br>AGAGACCAGAAGTATACAGTGACCTCAACACACAGA<br>GGCAATATTACAGATGA | 92 |
| Murine DAP12 | MGALEPSWCLLFLPVLLTVGGLSPVQAQSDTFPRCDCS<br>SVSPGVLAGIVLGDLVLTLLIALAVYSLGRLVSRGQGT<br>AEGTRKQHIAETESPYQELQGQRPEVYSDLNTQRQYYR | 93 |
| Human CD3z | MKWKALFTAAILQAQLPITEAQSFGLLDPKLCYLLDGI<br>LFIYGVILTALFLRVKFSRSADAPAYQQGQNQLYNELN<br>LGRREEYDVLDKRRGRDPEMGGKPQRRKNPQEGLYNE<br>LQKDKMAEAYSEIGMKGERRRGKGHDGLYQGLSTAT<br>KDTYDALHMQALPPR | 94 |
| Human CD3z | ATGAAGTGGAAGGCGCTTTTCACCGCGGCCATCCTG<br>CAGGCACAGTTGCCGATTACAGAGGCACAGAGCTTT<br>GGCCTGCTGGATCCCAAACTCTGCTACCTGCTGGATG<br>GAATCCTCTTCATCTATGGTGTCATTCTCACTGCCTT<br>GTTCCTGAGAGTGAAGTTCAGCAGGAGCGCAGAGCC<br>CCCCGCGTACCAGCAGGGCCAGAACCAGCTCTATAA<br>CGAGCTCAATCTAGGACGAAGAGAGGAGTACGATGT<br>TTTGGACAAGAGACGTGGCCGGGACCCTGAGATGGG<br>GGGAAAGCCGAGAAGGAAGAACCCTCAGGAAGGCC<br>TGTACAATGAACTGCAGAAAGATAAGATGGCGGAGG<br>CCTACAGTGAGATTGGGATGAAAGGCGAGCGCCGGA<br>GGGGCAAGGGGCACGATGGCCTTTACCAGGGTCTCA<br>GTACAGCCACCAAGGACACCTACGACGCCCTTCACA<br>TGCAGGCCCTGCCCCCTCGCTAA | 95 |
| Murine CD3z | MKWKVSVLACILHVRFPGAEAQSFGLLDPKLCYLLDGI<br>LFIYGVIITALYLRAKFSRSAETAANLQDPNQLYNELNL<br>GRREEYDVLEKKRARDPEMGGKQQRRRNPQEGVYNA<br>LQKDKMAEAYSEIGTKGERRRGKGHDGLYQGLSTATK<br>DTYDALHMQTLAPR | 96 |
| Murine CD3z | ATGAAGTGGAAAGTGTCTGTTCTCGCCTGCATCCTCC<br>ACGTGCGGTTCCCAGGAGCAGAGGCACAGAGCTTTG<br>GTCTGCTGGATCCCAAACTCTGCTACTTGCTAGATGG<br>AATCCTCTTCATCTACGGAGTCATCATCACAGCCCTG<br>TACCTGAGAGCAAAATTCAGCAGGAGTGCAGAGACT<br>GCTGCCAACCTGCAGGACCCCAACCAGCTCTACAAT<br>GAGCTCAATCTAGGGCGAAGAGAGGAATATGACGTC<br>TTGGAGAAGAAGCGGGCTCGGGATCCAGAGATGGG<br>AGGCAAACAGCAGAGGAGGAGGAACCCCCAGGAAG<br>GCGTATACAATGCACTGCAGAAAGACAAGATGGCAG<br>AAGCCTACAGTGAGATCGGCACAAAAGGCGAGAGG<br>CGGAGAGGCAAGGGGCACGATGGCCTTTACCAGGGT<br>CTCAGCACTGCCACCAAGGACACCTATGATGCCCTG<br>CATATGCAGACCCTGGCCCCTCGCTAA | 97 |
| Human FCGR3A | MWQLLLPTALLLLVSAGMRTEDLPKAVVFLEPQWYRV<br>LEKDSVTLKCQGAYSPEDNSTQWFHNESLISSQASSYFI<br>DAATVDDSGEYRCQTNLSTLSDPVQLEVHIGWLLLQAP<br>RWVFKEEDPIHLRCHSWKNTALHKVTYLQNGKGRKYF<br>HHNSDFYIPKATLKDSGSYFCRGLFGSKNVSSETVNITI<br>TQGLAVSTISSFFPPGYQVSFCLVMVLLFAVDTGLYFSV<br>KTNIRSSTRDWKDHKFKWRKDPQDK | 98 |
| Human FCGR3A | ATGTGGCAGCTGCTGCTGCCGACCGCGCTGCTGCTGC<br>TGGTGAGCGCGGGCATGCGCACCGAAGATCTGCCGA<br>AAGCGGTGGTGTTTCTGGAACCGCAGTGGTATCGCG<br>TGCTGGAAAAAGATAGCGTGACCCTGAAATGCCAGG<br>GCGCGTATAGCCCGGAAGATAACAGCACCCAGTGGT<br>TTCATAACGAAAGCCTGATTAGCAGCCAGGCGAGCA | 99 |

TABLE 12-continued

| Construct | Amino acid sequence | SEQ ID NO |
|---|---|---|
| | GCTATTTTATTGATGCGGCGACCGTGGATGATAGCG<br>GCGAATATCGCTGCCAGACCAACCTGAGCACCCTGA<br>GCGATCCGGTGCAGCTGGAAGTGCATATTGGCTGGC<br>TGCTGCTGCAGGCGCCGCGCTGGGTGTTTAAAGAAG<br>AAGATCCGATTCATCTGCGCTGCCATAGCTGGAAAA<br>ACACCGCGCTGCATAAAGTGACCTATCTGCAGAACG<br>GCAAAGGCCGCAAATATTTTCATCATAACAGCGATT<br>TTTATATTCCGAAAGCGACCCTGAAAGATAGCGGCA<br>GCTATTTTGCCGCGGCCTGTTTGGCAGCAAAAACGT<br>GAGCAGCGAAACCGTGAACATTACCATTACCCAGGG<br>CCTGGCGGTGAGCACCATTAGCAGCTTTTTTCCGCCG<br>GGCTATCAGGTGAGCTTTTGCCTGGTGATGGTGCTGC<br>TGTTTGCGGTGGATACCGGCCTGTATTTTAGCGTGAA<br>AACCAACATTCGCAGCAGCACCCGCGATTGGAAAGA<br>TCATAAATTTAAATGGCGCAAAGATCCGCAGGATAA<br>A | |
| Murine FCGR3A | MFQNAHSGSQWLLPPLTILLLFAFADRQSAALPKAVVK<br>LDPPWIQVLKEDMVTLMCEGTHNPGNSSTQWFHNGRS<br>IRSQVQASYTFKATVNDSGEYRCQMEQTRLSDPVDLG<br>VISDWLLLQTPQRVFLEGETITLRCHSWRNKLLNRISFF<br>HNEKSVRYHHYKSNFSIPKANHSHSGDYYCKGSLGSTQ<br>HQSKPVTITVQDPATTSSISLVWYHTAFSLVMCLLFAV<br>DTGLYFYVRRNLQTPREYWRKSLSIRKHQAPQDK | 100 |
| Murine FCGR3A | ATGTTTCAGAATGCACACTCTGGAAGCCAATGGCTA<br>CTTCCACCACTGACAATTCTGCTGCTGTTTGCTTTTGC<br>AGACAGGCAGAGTGCAGCTCTTCCGAAGGCTGTGGT<br>GAAACTGGACCCCCCATGGATCCAGGTGCTCAAGGA<br>AGACATGGTGACACTGATGTGCGAAGGGACCCACAA<br>CCCTGGGAACTCTTCTACCCAGTGGTTCCACAACGGG<br>AGGTCCATCCGGAGCCAGGTCCAAGCCAGTTACACG<br>TTTAAGGCCACAGTCAATGACAGTGGAGAATATCGG<br>TGTCAAATGGAGCAGACCCGCCTCAGCGACCCTGTA<br>GATCTGGGAGTGATTTCTGACTGGCTGCTGCTCCAGA<br>CCCCTCAGCGGGTGTTTCTGGAAGGGGAAACCATCA<br>CGCTAAGGTGCCATAGCTGGAGGAACAAACTACTGA<br>ACAGGATCTCATTCTTCCATAATGAAAAATCCGTGA<br>GGTATCATCACTACAAAAGTAATTTCTCTATCCCAAA<br>AGCCAACCACAGTCACAGTGGGACTACTACTGCAA<br>AGGAAGTCTAGGAAGTACACAGCACCAGTCCAAGCC<br>TGTCACCATCACTGTCCAAGATCCAGCAACTACATCC<br>TCCATCTCTCTAGTCTGGTACCACACTGCTTTCTCCCT<br>AGTGATGTGCCTCCTGTTTGCAGTGGACACGGGCCTT<br>TATTTCTACGTACGGAGAAATCTTCAAACCCCGAGG<br>GAGTACTGGAGGAAGTCCCTGTCAATCAGAAAGCAC<br>CAGGCTCCTCAAGACAAGTGA | 101 |
| Human NKG2D | MGWIRGRRSRHSWEMSEFHNYNLDLKKSDFSTRWQK<br>QRCPVVKSKCRENASPFFFCCFIAVAMGIRFIIMVAIWS<br>AVFLNSLFNQEVQIPLIESYCGPCPKNWICYKNNCYQF<br>FDESKNWYESQASCMSQNASLLKVYSKEDQDLLKLVK<br>SYHWMGLVHIPTNGSWQWEDGSILSPNLLTIIEMQKGD<br>CALYASSFKGYIENCSTPNTYICMQRTV | 102 |
| Human NKG2D | ATGGGCTGGATTCGCGGCCGCCGCAGCCGCCATAGC<br>TGGGAAATGAGCGAATTTCATAACTATAACCTGGAT<br>CTGAAAAAAAGCGATTTTAGCACCCGCTGGCAGAAA<br>CAGCGCTGCCCGGTGGTGAAAAGCAAATGCCGCGAA<br>AACGCGAGCCCGTTTTTTTTTTGCTGCTTTATTGCGGT<br>GGCGATGGGCATTCGCTTTATTATTATGGTGGCGATT<br>TGGAGCGCGGTGTTTCTGAACAGCCTGTTTAACCAG<br>GAAGTGCAGATTCCGCTGACCGAAAGCTATTGCGGC<br>CCGTGCCCGAAAAACTGGATTTGCTATAAAAACAAC<br>TGCTATCAGTTTTTTGATGAAAGCAAAAACTGGTATG<br>AAAGCCAGGCGAGCTGCATGAGCCAGAACGCGAGC<br>CTGCTGAAAGTGTATAGCAAAGAAGATCAGGATCTG<br>CTGAAACTGGTGAAAAGCTATCATTGGATGGGCCTG<br>GTGCATATTCCGACCAACGGCAGCTGGCAGTGGGAA<br>GATGGCAGCATTCTGAGCCCGAACCTGCTGACCATT<br>ATTGAAATGCAGAAAGGCGATTGCGCGCTGTATGCG<br>AGCAGCTTTAAAGGCTATATTGAAAACTGCAGCACC<br>CCGAACACCTATATTTGCATGCAGCGCACCGTG | 103 |
| Murine NKG2D | MALIRDRKSHHSEMSKCHNYDLKPAKWDTSQEQQKQ<br>RLALTTSQPGENGIIRGRYPIEKLKISPMFVVRVLAIALA<br>IRFTLNTLMWLAIFKETFQPVLCNKEVPVSSREGYCGPC<br>PNNWICHRNNCYQFFNEEKTWNQSQASCLSQNSSLLKI | 104 |

TABLE 12-continued

| Construct | Amino acid sequence | SEQ ID NO |
|---|---|---|
| | YSKEEQDFLKLVKSYHWMGLVQIPANGSWQWEDGSS LSYNQLTLVEIPKGSCAVYGSSFKAYTEDCANLNTYIC MKRAV | |
| Murine NKG2D | ATGGCGCTGATTCGCGATCGCAAAAGCCATCATAGC GAAATGAGCAAATGCCATAACTATGATCTGAAACCG GCGAAATGGGATACCAGCCAGGAACAGCAGAAACA GCGCCTGGCGCTGACCACCAGCCAGCCGGGCGAAAA CGGCATTATTCGCGGCCGCTATCCGATTGAAAAACT GAAAATTAGCCCGATGTTTGTGGTGCGCGTGCTGGC GATTGCGCTGGCGATTCGCTTTACCCTGAACACCCTG ATGTGGCTGGCGATTTTTAAAGAAACCTTTCAGCCGG TGCTGTGCAACAAAGAAGTGCCGGTGAGCAGCCGCG AAGGCTATTGCGGCCCGTGCCCGAACAACTGGATTT GCCATCGCAACAACTGCTATCAGTTTTTTAACGAAGA AAAAACCTGGAACCAGAGCCAGGCGAGCTGCCTGAG CCAGAACAGCAGCCTGCTGAAAATTTATAGCAAAGA AGAACAGGATTTTCTGAAACTGGTGAAAAGCTATCA TTGGATGGGCCTGGTGCAGATTCCGGCGAACGGCAG CTGGCAGTGGGAAGATGGCAGCAGCCTGAGCTATAA CCAGCTGACCCTGGTGGAAATTCCGAAAGGCAGCTG CGCGGTGTATGGCAGCAGCTTTAAAGCGTATACCGA AGATTGCGCGAACCTGAACACCTATATTTGCATGAA ACGCGCGGTG | 105 |
| CD28 YMNM | YMNM | 106 |
| CD28 PYAP | PYAP | 107 |
| CD28 FMNM | FMNM | 108 |
| CD28 AYAA | AYAA | 109 |
| Signal peptide | ATMGWSCIILFLVATATGVHS | 110 |
| Signal peptide DNA sequence | ATGGGATGGAGCTGTATCATCCTCTTCTTGGTAGCAA CAGCTACCGGTGTGCACTCC | 111 |
| Anti-CD20 (GA101) heavy chain | QVQLVQSGAEVKKPGSSVKVSCKASGYAFSYSWINWV RQAPGQGLEWMGRIFPGDGDTDYNGKFKGRVTITADK STSTAYMELSSLRSEDTAVYYCARNVFDGYWLVYWG QGTLVTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPELLGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALPAPIEKTI SKAKGQPREPQVYTLPPSRDELTKNQVSLTCLVKGFYP SDIAVEWESNGQPENNYKTTPPVLDSDGSFFLYSKLTV DKSRWQQGNVFSCSVMHEALHNHYTQKSLSLSPGK | 112 |
| Anti CD20 (GA101) light chain | DIVMTQTPLSLPVTPGEPASISCRSSKSLLHSNGITYLYW YLQKPGQSPQLLIYQMSNLVSGVPDRFSGSGSGTDFTL KISRVEAEDVGVYYCAQNLELPYTFGGGTKVEIKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC | 113 |
| Anti-FAP (4B9) PGLALA heavy chain | EVQLLESGGGLVQPGGSLRLSCAASGFTFSSYAMSWVR QAPGKGLEWVSAIIGSGASTYYADSVKGRFTISRDNSK NTLYLQMNSLRAEDTAVYYCAKGWFGGFNYWGQGTL VTVSSASTKGPSVFPLAPSSKSTSGGTAALGCLVKDYFP EPVTVSWNSGALTSGVHTFPAVLQSSGLYSLSSVVTVP SSSLGTQTYICNVNHKPSNTKVDKKVEPKSCDKTHTCP PCPAPEAAGGPSVFLFPPKPKDTLMISRTPEVTCVVVDV SHEDPEVKFNWYVDGVEVHNAKTKPREEQYNSTYRV VSVLTVLHQDWLNGKEYKCKVSNKALGAPIEKTISKA KGQPREPQVYTLPPSRDELTKNQVSLTCLVKGFYPSDIA VEWESNGQPENNYKTTPPVLDSDGSFFLYSKLTVDKSR WQQGNVFSCSVMHEALHNHYTQKSLSLSPGK | 114 |
| Anti-FAP (4B9) light chain | EIVLTQSPGTLSLSPGERATLSCRASQSVTSSYLAWYQQ KPGQAPRLLINVGSRRATGIPDRFSGSGSGTDFTLTISRL EPEDFAVYYCQQGIMLPPTFGQGTKVEIKRTVAAPSVFI FPPSDEQLKSGTASVVCLLNNFYPREAKVQWKVDNAL QSGNSQESVIEQDSKDSTYSLSSTLTLSKADYEKHKVY ACEVTHQGLSSPVTKSFNRGEC | 115 |

TABLE 12-continued

| Construct | Amino acid sequence | SEQ ID NO |
|---|---|---|
| Anti-CEA (A5B7) PGLALA heavy chain | EVQLVESGGGLVQPGRSLRLSCAASGFTVSSYWMHWV RQAPGKGLEWVGFIRNKANGGTTEYAASVKGRFTISR DDSKNTLYLQMNSLRAEDTAVYYCARDRGLRFYFDY WGQGTTVTVSSASTKGPSVFPLAPSSKSTSGGTAALGC LVKDYFPEPVTVSWNSGALTSGVHTFPAVLQSSGLYSL SSVVTVPSSSLGTQTYICNVNHKPSNTKVDKKVEPKSC DKTHTCPPCPAPEAAGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALGAPI EKTISKAKGQPREPQVYTLPPSRDELTKNQVSLTCLVK GFYPSDIAVEWESNGQPENNYKTTPPVLDSDGSFFLYS KLTVDKSRWQQGNVFSCSVMHEALHNHYTQKSLSLSP GK | 116 |
| Anti-CEA (A5B7) light chain | QAVLTQPASLSASPGASASLTCTLRRGINVGAYSIYWY QQKPGSPPQYLLRYKSDSDKQQGSGVSSRFSASKDASA NAGILLISGLQSEDEADYYCMIWHSGASAVFGGGTKLT VLRTVAAPSVFIFPPSDEQLKSGTASVVCLLNNFYPREA KVQWKVDNALQSGNSQESVTEQDSKDSTYSLSSTLTLS KADYEKHKVYACEVTHQGLSSPVTKSFNRGEC | 117 |
| Anti-CEA (T84.66LCHA) PGLALA heavy chain | QVQLVQSGAEVKKPGSSVKVSCKASGFNIKDTYMHW VRQAPGQGLEWMGRIDPANGNSKYVPKFQGRVTITAD TSTSTAYMELSSLRSEDTAVYYCAPFGYYVSDYAMAY WGQGTLVTVSSASTKGPSVFPLAPSSKSTSGGTAALGC LVKDYFPEPVTVSWNSGALTSGVHTFPAVLQSSGLYSL SSVVTVPSSSLGTQTYICNVNHKPSNTKVDKKVEPKSC DKTHTCPPCPAPEAAGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALGAPI EKTISKAKGQPREPQVYTLPPSRDELTKNQVSLTCLVK GFYPSDIAVEWESNGQPENNYKTTPPVLDSDGSFFLYS KLTVDKSRWQQGNVFSCSVMHEALHNHYTQKSLSLSP GK | 118 |
| Anti-CEA (T84.66LCHA) light chain | EIVLTQSPATLSLSPGERATLSCRAGESVDIFGVGFLHW YQQKPGQAPRLLIYRASNRATGIPARFSGSGSGTDFTLT ISSLEPEDFAVYYCQQTNEDPYTFGQGTKLEIKRTVAAP SVFIFPPSDEQLKSGTASVVCLLNNFYPREAKVQWKVD NALQSGNSQESVIEQDSKDSTYSLSSTLTLSKADYEKH KVYACEVTHQGLSSPVTKSFNRGEC | 119 |
| Anti-CEA (CH1A1A98/992F1) PGLALA heavy chain | QVQLVQSGAEVKKPGASVKVSCKASGYTFTEFGMNW VRQAPGQGLEWMGWINTKTGEATYVEEFKGRVTFTTD TSTSTAYMELRSLRSDDTAVYYCARWDFAYYVEAMD YWGQGTTVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKKVEPKS CDKTHTCPPCPAPEAAGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALGA PIEKTISKAKGQPREPQVCTLPPSRDELTKNQVSLSCAV KGFYPSDIAVEWESNGQPENNYKTTPPVLDSDGSFFLV SKLTVDKSRWQQGNVFSCSVMHEALHNHYTQKSLSLS PGK | 120 |
| Anti-CEA (CH1A1A98/992F1) light chain | DIQMTQSPSSLSASVGDRVTITCKASAAVGTYVAWYQ QKPGKAPKLLIYSASYRKRGVPSRFSGSGSGTDFTLTISS LQPEDFATYYCHQYYTYPLFTFGQGTKLEIKRTVAAPS VFIFPPSDEQLKSGTASVVCLLNNFYPREAKVQWKVDN ALQSGNSQESVIEQDSKDSTYSLSSTLTLSKADYEKHK VYACEVTHQGLSSPVTKSFNRGEC | 121 |
| Anti-CEA (hMN14) PGLALA heavy chain | EVQLVESGGGVVQPGRSLRLSCSASGFDFTTYWMSWV RQAPGKGLEWIGEIHPDSSTINYAPSLKDRFTISRDNAK NTLFLQMDSLRPEDTGVYFCASLYFGFPWFAYWGQGT PVTVSSASTKGPSVFPLAPSSKSTSGGTAALGCLVKDYF PEPVTVSWNSGALTSGVHTFPAVLQSSGLYSLSSVVTV PSSSLGTQTYICNVNHKPSNTKVDKKVEPKSCDKTHTC PPCPAPEAAGGPSVFLFPPKPKDTLMISRTPEVTCVVVD VSHEDPEVKFNWYVDGVEVHNAKTKPREEQYNSTYR VVSVLTVLHQDWLNGKEYKCKVSNKALGAPIEKTISK AKGQPREPQVYTLPPSRDELTKNQVSLTCLVKGFYPSDI AVEWESNGQPENNYKTTPPVLDSDGSFFLYSKLTVDKS RWQQGNVFSCSVMHEALHNHYTQKSLSLSPGK | 122 |
| Anti-CEA (hMN14) light chain | DIQLTQSPSSLSASVGDRVTITCKASQDVGTSVAWYQQ KPGKAPKLLIYWTSTRHTGVPSRFSGSGSGTDFTFTISSL | 123 |

TABLE 12-continued

| Construct | Amino acid sequence | SEQ ID NO |
|---|---|---|
| | QPEDIATYYCQQYSLYRSFGQGTKVEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC | |
| Anti-TNC (2B10) PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARLYGYAYYGAFDYW GQGTTVTVSSASTKGPSVFPLAPSSKSTSGGTAALGCLV KDYFPEPVTVSWNSGALTSGVHTFPAVLQSSGLYSLSS VVTVPSSSLGTQTYICNVNHKPSNTKVDKKVEPKSCDK THTCPPCPAPEAAGGPSVFLFPPKPKDTLMISRTPEVTC VVVDVSHEDPEVKFNWYVDGVEVHNAKTKPREEQYN STYRVVSVLTVLHQDWLNGKEYKCKVSNKALGAPIEK TISKAKGQPREPQVCTLPPSRDELTKNQVSLSCAVKGF YPSDIAVEWESNGQPENNYKTTPPVLDSDGSFFLVSKL TVDKSRWQQGNVFSCSVMHEALHNHYTQKSLSLSPGK | 124 |
| Anti-TNC (2B10) light chain | DIQMTQSPSSLSASVGDRVTITCRASQGIRNDLGWYQQ KPGKAPKRLIYAASSLQSGVPSRFSGSGSGIEFTLTISSL QPEDFATYYCLQNGLQPATFGQGTKVE1KRTVAAPSVF IFPPSDEQLKSGTASVVCLLNNFYPREAKVQWKVDNAL QSGNSQESV1EQDSKDSTYSLSSTLTLSKADYEKHKVY ACEVTHQGLSSPVTKSFNRGEC | 125 |
| Anti-HER2 (PER) PG LALA heavy chain 1 | EVQLVESGGGLVQPGGSLRLSCAASGFTFTDYTMDWV RQAPGKGLEWVADVNPNSGGSIYNQRFKGRFTLSVDR SKNTLYLQMNSLRAEDTAVYYCARNLGPSFYFDYWG QGTLVTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPEAAGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALGAP1EKT ISKAKGQPREPQVYTLPPSRDELTKNQVSLTCLVKGFYP SDIAVEWESNGQPENNYKTTPPVLDSDGSFFLYSKLTV DKSRWQQGNVFSCSVMHEALHNHYTQKSLSLSPGK | 126 |
| Anti-HER2 (PER) light chain 1 | DIQMTQSPSSLSASVGDRVTITCKASQDVSIGVAWYQQ KPGKAPKLLIYSASYRYTGVPSRFSGSGSGTDFTLTISSL QPEDFATYYCQQYYIYPYTFGQGTKVEIKRTVAAPSVFI FPPSDEQLKSGTASVVCLLNNFYPREAKVQWKVDNAL QSGNSQESVIEQDSKDSTYSLSSTLTLSKADYEKHKVY ACEVTHQGLSSPVTKSFNRGEC | 127 |
| Anti-HER2 (PER) PG LALA heavy chain 2 | EVQLVESGGGLVQPGGSLRLSCAASGFTFTDYTMDWV RQAPGKGLEWVADVNPNSGGSIYNQRFKGRFTLSVDR SKNTLYLQMNSLRAEDTAVYYCARNLGPSFYFDYWG QGTLVTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPEAAGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALGAP1EKT ISKAKGQPREPQVYTLPPSRDELTKNQVSLTCLVKGFYP SDIAVEWESNGQPENNYKTTPPVLDSDGSFFLYSKLTV DKSRWQQGNVFSCSVMHEALHNHYTQKSLSLSPGK | 128 |
| Anti-HER2 (PER) light chain 2 | DIQMTQSPSSLSASVGDRVTITCKASQDVSIGVAWYQQ KPGKAPKLLIYSASYRYTGVPSRFSGSGSGTDFTLTISSL QPEDFATYYCQQYYIYPYTFGQGTKVEIKRTVAAPSVFI FPPSDEQLKSGTASVVCLLNNFYPREAKVQWKVDNAL QSGNSQESVIEQDSKDSTYSLSSTLTLSKADYEKHKVY ACEVTHQGLSSPVTKSFNRGEC | 129 |
| Human IgG1 Fc | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTV LHQDWLNGKEYKCKVSNKALPAP1EKTISKAKGQPREP QVYTLPPSRDELTKNQVSLTCLVKGFYPSDIAVEWESN GQPENNYKTTPPVLDSDGSFFLYSKLTVDKSRWQQGN VFSCSVMHEALHNHYTQKSLSLSPGK | 130 |

What is claimed is:

1. An antigen binding receptor comprising an anchoring transmembrane domain and an extracellular domain comprising an antigen binding moiety, wherein the antigen binding moiety is capable of specific binding to a mutated fragment crystallizable (Fc) domain but not capable of specific binding to the non-mutated parent Fc domain, wherein the mutated Fc domain comprises at least one amino acid substitution compared to the non-mutated parent Fc domain, wherein the mutated Fc domain comprises the amino acid mutation P329G according to EU numbering, wherein the antigen binding moiety is capable of specific binding to the mutated Fc domain comprising the P329G mutation but not capable of specific binding to the non-mutated parent Fc domain, and wherein the antigen binding moiety comprises:
(i) a heavy chain variable region (VH) comprising
 (a) the heavy chain complementarity-determining region (CDR H) 1 amino acid sequence RYWMN (SEQ ID NO:1);
 (b) the CDR H2 amino acid sequence EITPDSSTI-NYTPSLKD (SEQ ID NO:2); and
 (c) the CDR H3 amino acid sequence PYDYGAWFAS (SEQ ID NO:3); and
(ii) a light chain variable region (VL) comprising
 (d) the light chain complementary-determining region (CDR L) 1 amino acid sequence RSST-GAVTTSNYAN (SEQ ID NO:4);
 (e) the CDR L2 amino acid sequence GTNKRAP (SEQ ID NO:5); and
 (f) the CDR L3 amino acid sequence ALWYSNHWV (SEQ ID NO:6).

2. The antigen binding receptor of claim 1, wherein Fc receptor binding of the mutated Fc domain is reduced compared to Fc receptor binding of the non-mutated parent Fc domain.

3. The antigen binding receptor of claim 1, wherein the antigen binding moiety is a scFv, a Fab, a cross Fab, or a scFab.

4. The antigen binding receptor of claim 1, wherein the anchoring transmembrane domain is a transmembrane domain selected from the group consisting of the CD8, the CD3z, the FCGR3A, the NKG2D, the CD27, the CD28, the CD137, the OX40, the ICOS, the DAP10, and the DAP12 transmembrane domain, or a fragment thereof.

5. The antigen binding receptor of claim 1, further comprising at least one stimulatory signaling domain and/or at least one co-stimulatory signaling domain.

6. The antigen binding receptor of claim 5, wherein the at least one stimulatory signaling domain is individually selected from the group consisting of the intracellular domain of CD3z, of FCGR3A, and of NKG2D, or fragments thereof.

7. The antigen binding receptor of claim 5, wherein the at least one co-stimulatory signaling domain is individually selected from the group consisting of the intracellular domain of CD27, of CD28, of CD137, of OX40, of ICOS, of DAP10, and of DAP12, or fragments thereof.

8. The antigen binding receptor of claim 5, wherein the antigen binding receptor comprises one stimulatory signaling domain comprising the intracellular domain of CD3z, or a fragment thereof, and one co-stimulatory signaling domain comprising the intracellular domain of CD28, or a fragment thereof.

9. The antigen binding receptor of claim 1, wherein the antigen binding moiety is a scFv fragment, wherein the scFv fragment is connected at the C-terminus to the N-terminus of the anchoring transmembrane domain.

10. The antigen binding receptor of claim 1, wherein the antigen binding moiety is a Fab or a crossFab fragment, wherein the Fab or crossFab fragment is connected at the C-terminus of the heavy chain to the N-terminus of the anchoring transmembrane domain.

11. The antigen binding receptor of claim 1, wherein the mutated Fc domain further comprises at least one amino acid mutation at a position selected from the group consisting of L234, L235, P331, and N297 according to EU numbering.

12. An antigen binding receptor comprising an anchoring transmembrane domain and an extracellular domain comprising an antigen binding moiety, wherein the antigen binding moiety is capable of specific binding to a mutated Fc domain but not capable of specific binding to the non-mutated parent Fc domain, wherein the mutated Fc domain comprises at least one amino acid substitution compared to the non-mutated parent Fc domain, wherein the mutated Fc domain comprises the amino acid mutations I253A, H310A, and H435A according to EU numbering, wherein the antigen binding moiety is capable of specific binding to the mutated Fc domain comprising the I253A, H310A, and H435A mutations but not capable of specific binding to the non-mutated parent Fc domain, and wherein the antigen binding moiety comprises:
(i) a heavy chain variable region (VH) comprising
 (a) the heavy chain complementarity-determining region (CDR H) 1 amino acid sequence SYGMS (SEQ ID NO:53);
 (b) the CDR H2 amino acid sequence SSGGSY (SEQ ID NO:54); and
 (c) the CDR H3 amino acid sequence LGMITTG-YAMDY (SEQ ID NO:55); and
(ii) a light chain variable region (VL) comprising
 (d) the light chain complementary-determining region (CDR L) 1 amino acid sequence RSSQTIVH-STGHTYLE (SEQ ID NO:56);
 (e) the CDR L2 amino acid sequence KVSNRFS (SEQ ID NO:57); and
 (f) the CDR L3 amino acid sequence FQGSHVPYT (SEQ ID NO:58).

13. The antigen binding receptor of claim 1, wherein the VH comprises the amino acid sequence of SEQ ID NO:8 and the VL comprises the amino acid sequence of SEQ ID NO:9.

14. The antigen binding receptor of claim 1, wherein the antigen binding moiety is humanized.

15. The antigen binding receptor of claim 2, wherein the Fc receptor is a Fcγ receptor.

16. The antigen binding receptor of claim 3, wherein the antigen binding moiety is a scFv.

17. The antigen binding receptor of claim 16, wherein the scFv is humanized.

18. The antigen binding receptor of claim 16, wherein the scFv comprises the amino acid sequence of SEQ ID NO:10.

19. The antigen binding receptor of claim 3, wherein the antigen binding moiety is a Fab fragment.

20. The antigen binding receptor of claim 19, wherein the Fab fragment is humanized.

21. The antigen binding receptor of claim 4, wherein the anchoring transmembrane domain is the CD28 transmembrane domain or a fragment thereof.

22. The antigen binding receptor of claim 6, wherein the at least one stimulatory signaling domain is the CD3z intracellular domain or a fragment thereof.

23. The antigen binding receptor of claim 7, wherein the at least one co-stimulatory signaling domain is the CD28 intracellular domain or a fragment thereof.

24. The antigen binding receptor of claim 9, wherein the scFv fragment is connected to the anchoring transmembrane domain through a peptide linker.

25. The antigen binding receptor of claim 10, wherein the Fab or crossFab fragment is connected to the anchoring transmembrane domain through a peptide linker.

26. The antigen binding receptor of claim 11, wherein the amino acid mutation is L234A, L235A, P331S, and/or N297A.

27. An antigen binding receptor comprising an anchoring transmembrane domain and an extracellular domain comprising an antigen binding moiety, wherein the antigen binding moiety is capable of specific binding to a mutated Fc domain but not capable of specific binding to the non-mutated parent Fc domain, wherein the mutated Fc domain comprises at least one amino acid substitution compared to the non-mutated parent Fc domain, wherein the mutated Fc domain comprises the amino acid mutation P329G according to EU numbering, wherein the antigen binding moiety is capable of specific binding to the mutated Fc domain comprising the P329G mutation but not capable of specific binding to the non-mutated parent Fc domain, wherein the antigen binding moiety is a scFv fragment, wherein the scFv fragment is connected at the C-terminus to the N-terminus of the anchoring transmembrane domain through a peptide linker, wherein the antigen binding moiety comprises:
(i) a VH comprising
(a) the CDR H1 amino acid sequence RYWMN (SEQ ID NO:1);
(b) the CDR H2 amino acid sequence EITPDSSTINYTPSLKD (SEQ ID NO:2); and
(c) the CDR H3 amino acid sequence PYDYGAWFAS (SEQ ID NO:3); and
(ii) a VL comprising
(d) the CDR L1 amino acid sequence RSSTGAVTTSNYAN (SEQ ID NO:4);
(e) the CDR L2 amino acid sequence GTNKRAP (SEQ ID NO:5); and
(f) the CDR L3 amino acid sequence ALWYSNHWV (SEQ ID NO:6);
wherein the anchoring transmembrane domain is the CD28 transmembrane domain or a fragment thereof, and
wherein the antigen binding receptor further comprises:
at least one co-stimulatory signaling domain comprising the CD28 intracellular domain or a fragment thereof; and
at least one stimulatory signaling domain comprising the CD3z intracellular domain or a fragment thereof.

28. The antigen binding receptor of claim 27, wherein the antigen binding receptor comprises the amino acid sequence of SEQ ID NO:7.

29. An antigen binding receptor comprising an anchoring transmembrane domain and an extracellular domain comprising an antigen binding moiety, wherein the antigen binding moiety is capable of specific binding to a mutated Fc domain but not capable of specific binding to the non-mutated parent Fc domain, wherein the mutated Fc domain comprises at least one amino acid substitution compared to the non-mutated parent Fc domain, wherein the mutated Fc domain comprises the amino acid mutation P329G according to EU numbering, wherein the antigen binding moiety is capable of specific binding to the mutated Fc domain comprising the P329G mutation but not capable of specific binding to the non-mutated parent Fc domain, wherein the antigen binding moiety is a Fab fragment, wherein the Fab fragment is connected at the C-terminus of the heavy chain to the N-terminus of the anchoring transmembrane domain, wherein the antigen binding moiety comprises:
(i) a VH comprising
(a) the CDR H1 amino acid sequence RYWMN (SEQ ID NO:1);
(b) the CDR H2 amino acid sequence EITPDSSTINYTPSLKD (SEQ ID NO:2); and
(c) the CDR H3 amino acid sequence PYDYGAWFAS (SEQ ID NO:3); and
(ii) a VL comprising
(d) the CDR L1 amino acid sequence RSSTGAVTTSNYAN (SEQ ID NO:4);
(e) the CDR L2 amino acid sequence GTNKRAP (SEQ ID NO:5); and
(f) the CDR L3 amino acid sequence ALWYSNHWV (SEQ ID NO:6);
wherein the anchoring transmembrane domain is the CD28 transmembrane domain or a fragment thereof; and
wherein the antigen binding receptor further comprises:
at least one co-stimulatory signaling domain comprising the CD28 intracellular domain or a fragment thereof; and
at least one stimulatory signaling domain comprising the CD3z intracellular domain or a fragment thereof.

30. The antigen binding receptor of claim 29, wherein the Fab fragment comprises a heavy chain polypeptide comprising the amino acid sequence of SEQ ID NO:40 and a light chain polypeptide comprising the amino acid sequence of SEQ ID NO:41.

31. The antigen binding receptor of claim 29, wherein the antigen binding receptor comprises a heavy chain polypeptide comprising the amino acid sequence of SEQ ID NO:39 and a light chain polypeptide comprising the amino acid sequence of SEQ ID NO:41.

\* \* \* \* \*

SEQUENCE LISTING

<160> NUMBER OF SEQ ID NOS: 130

<210> SEQ ID NO 1
<211> LENGTH: 5
<212> TYPE: PRT
<213> ORGANISM: Artificial sequence
<220> FEATURE:
<223> OTHER INFORMATION: Anti-P329G CDR H1 Kabat

<400> SEQUENCE: 1

Arg Tyr Trp Met Asn
1               5

<210> SEQ ID NO 2
<211> LENGTH: 17
<212> TYPE: PRT
<213> ORGANISM: Artificial sequence
<220> FEATURE:
<223> OTHER INFORMATION: Anti-P329G CDR H2 Kabat

<400> SEQUENCE: 2

Glu Ile Thr Pro Asp Ser Ser Thr Ile Asn Tyr Thr Pro Ser Leu Lys
1               5                   10                  15

Asp

<210> SEQ ID NO 3
<211> LENGTH: 10
<212> TYPE: PRT
<213> ORGANISM: Artificial sequence
<220> FEATURE:
<223> OTHER INFORMATION: Anti-P329G CDR H3 Kabat

<400> SEQUENCE: 3

Pro Tyr Asp Tyr Gly Ala Trp Phe Ala Ser
1               5                   10

<210> SEQ ID NO 4
<211> LENGTH: 14
<212> TYPE: PRT
<213> ORGANISM: Artificial sequence
<220> FEATURE:
<223> OTHER INFORMATION: Anti-P329G CDR L1 Kabat

<400> SEQUENCE: 4

Arg Ser Ser Thr Gly Ala Val Thr Thr Ser Asn Tyr Ala Asn
1               5                   10

<210> SEQ ID NO 5
<211> LENGTH: 7
<212> TYPE: PRT
<213> ORGANISM: Artificial sequence
<220> FEATURE:
<223> OTHER INFORMATION: Anti-P329G CDR L2 Kabat

<400> SEQUENCE: 5

Gly Thr Asn Lys Arg Ala Pro
1               5

<210> SEQ ID NO 6
<211> LENGTH: 9
<212> TYPE: PRT
<213> ORGANISM: Artificial sequence
<220> FEATURE:
<223> OTHER INFORMATION: Anti-P329G CDR L3 Kabat

<400> SEQUENCE: 6

Ala Leu Trp Tyr Ser Asn His Trp Val
1               5

<210> SEQ ID NO 7
<211> LENGTH: 433
<212> TYPE: PRT
<213> ORGANISM: Artificial sequence
<220> FEATURE:
<223> OTHER INFORMATION: Anti-P329G-ds-scFv-CD28ATM-CD28CSD-CD3zSSD
      fusion pETR17096

<400> SEQUENCE: 7

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Gly Gly Gly Gly Ser Gly Gly Gly Gly
        115                 120                 125

Ser Gly Gly Gly Gly Ser Gly Gly Gly Gly Ser Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Lys Arg Ala Pro Gly Val Pro Ala Arg Phe Ser Gly Ser Leu Ile
        195                 200                 205

Gly Asp Lys Ala Ala Leu Thr Ile Thr Gly Ala Gln Thr Glu Asp Glu
    210                 215                 220

Ala Ile Tyr Phe Cys Ala Leu Trp Tyr Ser Asn His Trp Val Phe Gly
225                 230                 235                 240

Cys Gly Thr Lys Leu Thr Val Leu Gly Gly Gly Ser Phe Trp Val
                245                 250                 255

Leu Val Val Val Gly Gly Val Leu Ala Cys Tyr Ser Leu Leu Val Thr
            260                 265                 270

Val Ala Phe Ile Ile Phe Trp Val Arg Ser Lys Arg Ser Arg Leu Leu
        275                 280                 285

His Ser Asp Tyr Met Asn Met Thr Pro Arg Arg Pro Gly Pro Thr Arg
    290                 295                 300

Lys His Tyr Gln Pro Tyr Ala Pro Pro Arg Asp Phe Ala Ala Tyr Arg
305                 310                 315                 320

Ser Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

-continued

Tyr Asp Val Leu Asp Lys Arg Arg Gly Arg Asp Pro Glu Met Gly Gly
            355                 360                 365

Lys Pro Arg Arg Lys Asn Pro Gln Glu Gly Leu Tyr Asn Glu Leu Gln
370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 8
<211> LENGTH: 119
<212> TYPE: PRT
<213> ORGANISM: Artificial sequence
<220> FEATURE:
<223> OTHER INFORMATION: Anti-P329G-ds VH

<400> SEQUENCE: 8

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala
        115

<210> SEQ ID NO 9
<211> LENGTH: 109
<212> TYPE: PRT
<213> ORGANISM: Artificial sequence
<220> FEATURE:
<223> OTHER INFORMATION: Anti-P329G-ds VL

<400> SEQUENCE: 9

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

-continued

```
His Trp Val Phe Gly Cys Gly Thr Lys Leu Thr Val Leu
            100                 105

<210> SEQ ID NO 10
<211> LENGTH: 248
<212> TYPE: PRT
<213> ORGANISM: Artificial sequence
<220> FEATURE:
<223> OTHER INFORMATION: Anti-P329G-ds-scFv

<400> SEQUENCE: 10

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Gly Gly Gly Gly Ser Gly Gly Gly Gly
        115                 120                 125

Ser Gly Gly Gly Gly Ser Gly Gly Gly Gly Ser Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Lys Arg Ala Pro Gly Val Pro Ala Arg Phe Ser Gly Ser Leu Ile
        195                 200                 205

Gly Asp Lys Ala Ala Leu Thr Ile Thr Gly Ala Gln Thr Glu Asp Glu
    210                 215                 220

Ala Ile Tyr Phe Cys Ala Leu Trp Tyr Ser Asn His Trp Val Phe Gly
225                 230                 235                 240

Cys Gly Thr Lys Leu Thr Val Leu
                245

<210> SEQ ID NO 11
<211> LENGTH: 27
<212> TYPE: PRT
<213> ORGANISM: Artificial sequence
<220> FEATURE:
<223> OTHER INFORMATION: CD28ATM

<400> SEQUENCE: 11

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

```
<210> SEQ ID NO 12
<211> LENGTH: 41
<212> TYPE: PRT
<213> ORGANISM: Artificial sequence
<220> FEATURE:
<223> OTHER INFORMATION: CD28CSD

<400> SEQUENCE: 12

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 13
<211> LENGTH: 112
<212> TYPE: PRT
<213> ORGANISM: Artificial sequence
<220> FEATURE:
<223> OTHER INFORMATION: CD3zSSD

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 180
<212> TYPE: PRT
<213> ORGANISM: Artificial sequence
<220> FEATURE:
<223> OTHER INFORMATION: CD28ATM-CD28-CD3z

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser Arg Val Lys Phe Ser Arg Ser Ala Asp Ala Pro Ala
65                  70                  75                  80

Tyr Gln Gln Gly Gln Asn Gln Leu Tyr Asn Glu Leu Asn Leu Gly Arg
                85                  90                  95

Arg Glu Glu Tyr Asp Val Leu Asp Lys Arg Arg Gly Arg Asp Pro Glu
            100                 105                 110
```

```
Met Gly Gly Lys Pro Arg Arg Lys Asn Pro Gln Glu Gly Leu Tyr Asn
        115                 120                 125

Glu Leu Gln Lys Asp Lys Met Ala Glu Ala Tyr Ser Glu Ile Gly Met
130                 135                 140

Lys Gly Glu Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180
```

<210> SEQ ID NO 15
<211> LENGTH: 238
<212> TYPE: PRT
<213> ORGANISM: Artificial sequence
<220> FEATURE:
<223> OTHER INFORMATION: eGFP

<400> SEQUENCE: 15

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
    115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
    195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235
```

<210> SEQ ID NO 16
<211> LENGTH: 20
<212> TYPE: PRT
<213> ORGANISM: Artificial sequence
<220> FEATURE:
<223> OTHER INFORMATION: (G4S)4 linker

<400> SEQUENCE: 16

Gly Gly Gly Gly Ser Gly Gly Gly Ser Gly Gly Gly Ser Gly
1               5                   10                  15

Gly Gly Gly Ser
            20

<210> SEQ ID NO 17
<211> LENGTH: 5
<212> TYPE: PRT
<213> ORGANISM: Artificial sequence
<220> FEATURE:
<223> OTHER INFORMATION: G4S linker

<400> SEQUENCE: 17

Gly Gly Gly Gly Ser
1               5

<210> SEQ ID NO 18
<211> LENGTH: 19
<212> TYPE: PRT
<213> ORGANISM: Artificial sequence
<220> FEATURE:
<223> OTHER INFORMATION: T2A linker

<400> SEQUENCE: 18

Gly Glu Gly Arg Gly Ser Leu Leu Thr Cys Gly Asp Val Glu Glu Asn
1               5                   10                  15

Pro Gly Pro

<210> SEQ ID NO 19
<211> LENGTH: 1356
<212> TYPE: DNA
<213> ORGANISM: Artificial sequence
<220> FEATURE:
<223> OTHER INFORMATION: Anti-P329G-ds-scFv-CD28ATM-CD28CSD-CD3zSSD
      fusion pETR17096

<400> SEQUENCE: 19

```
atgggatgga gctgtatcat cctcttcttg gtagcaacag ctaccggtgt gcattccgag      60
gtgaagctgc tggagagcgg cggcggcctg gtgcagcccg gcggcagcct gaagctgagc     120
tgcgccgcca gcggcttcga cttcagcagg tactggatga actgggtgag gcaggcccc     180
ggcaagtgtc tggagtggat cggcgagatc accccgaca gcagcaccat caactacacc     240
cccagcctga aggacaagtt catcatcagc aggacaacg ccaagaacac cctgtacctg     300
cagatgatca aggtgaggag cgaggacacc gccctgtact actgcgtgag gccctacgac     360
tacggcgcct ggttcgccag ctggggccag ggcaccctgg tgaccgtgag cgccggaggg     420
ggcggaagtg gtggcggggg aagcggcggg ggtggcagcg aggggggcgg atctcaggcc     480
gtggtgaccc aggagagcgc cctgaccacc agccccggcg agaccgtgac cctgacctgc     540
aggagcagca ccggcgccgt gaccaccagc aactacgcca ctgggtgca ggagaagccc     600
gaccacctgt tcaccggcct gatcggcggc accaacaaga gggcccccgg cgtgcccgcc     660
aggttcagcg gcagcctgat cggcgacaag gccgccctga ccatcaccgg cgcccagacc     720
gaggacgagg ccatctactt ctgcgccctg tggtacagca accactgggt gttcggctgt     780
ggcaccaagc tgaccgtgct gggagggggc ggatccttct gggtgctggt ggtggtgggc     840
ggcgtgctgg cctgctacag cctgctggtg accgtggcct tcatcatctt ctgggtgagg     900
agcaagagga gcaggctgct gcacagcgac tacatgaaca tgaccccag gaggcccggc     960
```

```
cccaccagga agcactacca gccctacgcc ccccccaggg acttcgccgc ctacaggagc    1020
agggtgaagt tcagcaggag cgccgacgcc ccgcctacc agcagggcca gaaccagctg     1080
tataacgagc tgaacctggg caggagggag gagtacgacg tgctggacaa gaggaggggc    1140
agggaccccg agatgggcgg caagcccagg aggaagaacc cccaggaggg cctgtataac    1200
gagctgcaga aggacaagat ggccgaggcc tacagcgaga tcggcatgaa gggcgagagg    1260
aggaggggca agggccacga cggcctgtac cagggcctga gcaccgccac caaggacacc    1320
tacgacgccc tgcacatgca ggccctgccc cccagg                              1356

<210> SEQ ID NO 20
<211> LENGTH: 357
<212> TYPE: DNA
<213> ORGANISM: Artificial sequence
<220> FEATURE:
<223> OTHER INFORMATION: Anti-P329G-ds VH

<400> SEQUENCE: 20
gaggtgaagc tgctggagag cggcggcggc ctggtgcagc ccggcggcag cctgaagctg      60
agctgcgccg ccagcggctt cgacttcagc aggtactgga tgaactgggt gaggcaggcc     120
cccggcaagt gtctggagtg gatcggcgag atcacccccg acagcagcac catcaactac     180
acccccagcc tgaaggacaa gttcatcatc agcagggaca cgccaagaa caccctgtac      240 ctgcagatga tcaaggtgag gagcgaggac accgccctgt actactgcgt gaggccctac     300
gactacggcg cctggttcgc cagctggggc cagggcaccc tggtgaccgt gagcgcc        357

<210> SEQ ID NO 21
<211> LENGTH: 327
<212> TYPE: DNA
<213> ORGANISM: Artificial sequence
<220> FEATURE:
<223> OTHER INFORMATION: Anti-P329G-ds VL

<400> SEQUENCE: 21
caggccgtgg tgacccagga gagcgccctg accaccagcc ccggcgagac cgtgaccctg      60
acctgcagga gcagcaccgg cgccgtgacc accagcaact acgccaactg ggtgcaggag     120
aagcccgacc acctgttcac cggcctgatc ggcggcacca caagagggc ccccggcgtg      180 cccgccaggt tcagcggcag cctgatcggc gacaaggccg ccctgaccat caccggcgcc     240
cagaccgagg acgaggccat ctacttctgc gccctgtggt acagcaacca ctgggtgttc     300
ggctgtggca ccaagctgac cgtgctg                                         327

<210> SEQ ID NO 22
<211> LENGTH: 799
<212> TYPE: DNA
<213> ORGANISM: Artificial sequence
<220> FEATURE:
<223> OTHER INFORMATION: Anti-P329G-ds-scFv

<400> SEQUENCE: 22
atgggatgga gctgtatcat cctcttcttg gtagcaacag ctaccggtgt gcattccgag      60
gtgaagctgc tggagagcgg cggcggcctg gtgcagcccg cggcagcct gaagctgagc      120 tgcgccgcca gcggcttcga cttcagcagg tactggatga actgggtgag gcaggccccc     180
ggcaagtgtc tggagtggat cggcgagatc acccccgaca gcagcaccat caactacacc     240
cccagcctga aggacaagtt catcatcagc agggacaacg ccaagaacac cctgtacctg     300
cagatgatca aggtgaggag cgaggacacc gccctgtact actgcgtgag gccctacgac     360
```

```
tacggcgcct ggttcgccag ctggggccag ggcaccctgg tgaccgtgag cgccggaggg      420
ggcggaagtg gtggcggggg aagcggcggg ggtggcagcg gaggggcgg atctcaggcc       480 gtggtgaccc aggagagcgc cctgaccacc agcccggcg agaccgtgac cctgacctgc       540
aggagcagca ccggcgccgt gaccaccagc aactacgcca actgggtgca ggagaagccc      600
gaccacctgt tcaccggcct gatcggcggc accaacaaga gggcccccgg cgtgcccgcc      660
aggttcagcg gcagcctgat cggcgacaag gccgccctga ccatcaccgg cgcccagacc      720
gaggacgagg ccatctactt ctgcgccctg tggtacagca accactgggt gttcggctgt      780
ggcaccaagc tgaccgtgc                                                   799

<210> SEQ ID NO 23
<211> LENGTH: 647
<212> TYPE: DNA
<213> ORGANISM: Artificial sequence
<220> FEATURE:
<223> OTHER INFORMATION: IRES EV71, internal ribosomal entry side

<400> SEQUENCE: 23
cccgaagtaa cttagaagct gtaaatcaac gatcaatagc aggtgtggca caccagtcat       60
accttgatca agcacttctg tttccccgga ctgagtatca ataggctgct cgcgcggctg      120
aaggagaaaa cgttcgttac ccgaccaact acttcgagaa gcttagtacc accatgaacg      180
aggcagggtg tttcgctcag cacaacccca gtgtagatca ggctgatgag tcactgcaac      240
ccccatgggc gaccatggca gtggctgcgt tggcggcctg cccatggaga aatccatggg      300
acgctctaat tctgacatgg tgtgaagtgc ctattgagct aactggtagt cctccggccc      360
ctgattgcgg ctaatcctaa ctgcggagca catgctcaca accagtgggt ggtgtgtcg       420 taacgggcaa ctctgcagcg gaaccgacta ctttgggtgt ccgtgtttcc ttttattcct      480
atattggctg cttatggtga caatcaaaaa gttgttacca tatagctatt ggattggcca      540
tccggtgtgc aacagggcaa ctgtttacct atttattggt tttgtaccat tatcactgaa      600
gtctgtgatc actctcaaat tcattttgac cctcaacaca atcaaac                    647

<210> SEQ ID NO 24
<211> LENGTH: 81
<212> TYPE: DNA
<213> ORGANISM: Artificial sequence
<220> FEATURE:
<223> OTHER INFORMATION: CD28ATM

<400> SEQUENCE: 24
ttttgggtgc tggtggtggt tgtggagtc ctggcttgct atagcttgct agtaacagtg        60
gcctttatta ttttctgggt g                                                81

<210> SEQ ID NO 25
<211> LENGTH: 123
<212> TYPE: DNA
<213> ORGANISM: Artificial sequence
<220> FEATURE:
<223> OTHER INFORMATION: CD28CSD

<400> SEQUENCE: 25
aggagtaaga ggagcaggct cctgcacagt gactacatga acatgactcc ccgccgcccc       60
gggcccaccc gcaagcatta ccagccctat gccccaccac gcgacttcgc agcctatcgc      120
tcc                                                                    123
```

<210> SEQ ID NO 26
<211> LENGTH: 336
<212> TYPE: DNA
<213> ORGANISM: Artificial sequence
<220> FEATURE:
<223> OTHER INFORMATION: CD3z SSD

<400> SEQUENCE: 26

```
agagtgaagt tcagcaggag cgcagacgcc cccgcgtacc agcagggcca gaaccagctc      60
tataacgagc tcaatctagg acgaagagag gagtacgatg tttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336
```

<210> SEQ ID NO 27
<211> LENGTH: 540
<212> TYPE: DNA
<213> ORGANISM: Artificial sequence
<220> FEATURE:
<223> OTHER INFORMATION: CD28ATM-CD28-CD3z

<400> SEQUENCE: 27

```
ttctgggtgc tggtggtggt gggcggcgtg ctggcctgct acagcctgct ggtgaccgtg      60
gccttcatca tcttctgggt gaggagcaag aggagcaggc tgctgcacag cgactacatg     120
aacatgaccc caggaggcc cggccccacc aggaagcact accagcccta cgcccccccc     180
agggacttcg ccgcctacag gagcagggtg aagttcagca ggagcgccga cgccccgcc     240
taccagcagg gccagaacca gctgtataac gagctgaacc tgggcaggag ggaggagtac     300
gacgtgctgg acaagaggag gggcagggac ccgagatgg gcggcaagcc caggaggaag     360
aaccccagg agggcctgta taacgagctg cagaaggaca gatggccga ggcctacagc     420
gagatcggca tgaagggcga gaggaggagg ggcaagggcc acgacggcct gtaccagggc     480
ctgagcaccg ccaccaagga cacctacgac gccctgcaca tgcaggccct gccccccagg     540
```

<210> SEQ ID NO 28
<211> LENGTH: 63
<212> TYPE: DNA
<213> ORGANISM: Artificial sequence
<220> FEATURE:
<223> OTHER INFORMATION: T2A element

<400> SEQUENCE: 28

```
tccggagagg gcagaggaag tcttctaaca tgcggtgacg tggaggagaa tcccggccct      60
agg                                                                   63
```

<210> SEQ ID NO 29
<211> LENGTH: 717
<212> TYPE: DNA
<213> ORGANISM: Artificial sequence
<220> FEATURE:
<223> OTHER INFORMATION: eGFP

<400> SEQUENCE: 29

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
```

```
gtgaccaccc tgacctacgg cgtgcagtgc ttcagccgct accccgacca catgaagcag    240
cacgacttct tcaagtccgc catgcccgaa ggctacgtcc aggagcgcac catcttcttc    300
aaggacgacg gcaactacaa gacccgcgcc gaggtgaagt tcgagggcga caccctggtg    360
aaccgcatcg agctgaaggg catcgacttc aaggaggacg gcaacatcct ggggcacaag    420
ctggagtaca actacaacag ccacaacgtc tatatcatgg ccgacaagca gaagaacggc    480
atcaaggtga acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccgccct gagcaaagac cccaacgaga gcgcgatca catggtcctg    660 ctggagttcg tgaccgccgc cgggatcact ctcggcatgg acgagctgta caagtga      717
```

<210> SEQ ID NO 30
<211> LENGTH: 2136
<212> TYPE: DNA
<213> ORGANISM: Artificial sequence
<220> FEATURE:
<223> OTHER INFORMATION: Anti-P329G-ds-scFv-CD28ATM-CD28CSD-CD3zSSD-eGFP
      fusion pETR17096

<400> SEQUENCE: 30

```
atgggatgga gctgtatcat cctcttcttg gtagcaacag ctaccggtgt gcattccgag     60
gtgaagctgc tggagagcgg cggcggcctg gtgcagcccg gcggcagcct gaagctgagc    120
tgcgccgcca gcggcttcga cttcagcagg tactggatga actgggtgag gcaggccccc    180
ggcaagtgtc tggagtggat cggcgagatc accccgacag cagcaccat caactacacc    240 cccagcctga aggacaagtt catcatcagc agggacaacg ccaagaacac cctgtacctg    300
cagatgatca aggtgaggag cgaggacacc gccctgtact actgcgtgag gcctacgac    360 tacggcgcct ggttcgccag ctggggccag ggcaccctgg tgaccgtgag cgccggaggg    420
ggcggaagtg gtggcggggg aagcggcggg ggtggcagcg gaggggcgg atctcaggcc    480 gtggtgaccc caggagagcgc cctgaccacc agccccggcg agaccgtgac cctgacctgc    540
aggagcagca ccgcgccgt gaccaccagc aactacgcca ctgggtgca ggagaagccc    600 gaccacctgt tcaccggcct gatcggcggc accaacaaga gggccccgg cgtgcccgcc    660 aggttcagcg gcagcctgat cggcgacaag gccgccctga ccatcaccgg cgcccagacc    720
gaggacgagg ccatctactt ctgcgccctg tggtacagca ccactgggt gttcggctgt    780 ggcaccaagc tgaccgtgct gggagggggc ggatccttct gggtgctggt ggtggtgggc    840
ggcgtgctgg cctgctacag cctgctggtg accgtggcct tcatcatctt ctgggtgagg    900
agcaagagga gcaggctgct gcacagcgac tacatgaaca tgacccccag gaggcccggc    960
cccaccagga agcactacca gccctacgcc cccccaggg acttcgccgc ctacaggagc   1020
agggtgaagt tcagcaggag cgccgacgcc ccgcctacc agcagggcca gaaccagctg   1080
tataacgagc tgaacctggg caggagggag gagtacgacg tgctggacaa gaggagggc   1140 agggaccccg agatgggcgg caagcccagg aggaagaacc ccaggagggg cctgtataac   1200
gagctgcaga aggacaagat ggccgaggcc tacagcgaga tcggcatgaa gggcgagagg   1260
aggaggggca agggccacga cggcctgtac cagggcctga gcaccgccac caaggacacc   1320
tacgacgccc tgcacatgca ggccctgccc ccaggtccgg agagggcag aggaagtctt   1380 ctaacatgcg gtgacgtgga ggagaatccc ggccctaggg tgagcaaggg cgaggagctg   1440
ttcaccgggg tggtgcccat cctggtcgag ctggacggcg acgtaaacgg ccacaagttc   1500
```

```
agcgtgtccg gcgagggcga gggcgatgcc acctacggca agctgaccct gaagttcatc    1560
tgcaccaccg gcaagctgcc cgtgccctgg cccaccctcg tgaccaccct gacctacggc    1620
gtgcagtgct tcagccgcta ccccgaccac atgaagcagc acgacttctt caagtccgcc    1680
atgcccgaag ctacgtcca ggagcgcacc atcttcttca aggacgacgg caactacaag    1740
acccgcgccg aggtgaagtt cgagggcgac accctggtga accgcatcga gctgaagggc    1800
atcgacttca aggaggacgg caacatcctg gggcacaagc tggagtacaa ctacaacagc    1860
cacaacgtct atatcatggc cgacaagcag aagaacggca tcaaggtgaa cttcaagatc    1920
cgccacaaca tcgaggacgg cagcgtgcag ctcgccgacc actaccagca gaacacccccc    1980 atcggcgacg cccccgtgct gctgcccgac aaccactacc tgagcaccca gtccgccctg    2040
agcaaagacc ccaacgagaa gcgcgatcac atggtcctgc tggagttcgt gaccgccgcc    2100
gggatcactc tcggcatgga cgagctgtac aagtga                              2136
```

<210> SEQ ID NO 31
<211> LENGTH: 433
<212> TYPE: PRT
<213> ORGANISM: Artificial sequence
<220> FEATURE:
<223> OTHER INFORMATION: Anti-P329G-scFv- CD28ATM-CD28CSD-CD3zSSD fusion

<400> SEQUENCE: 31

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Gly Gly Gly Ser Gly Gly Gly Gly
        115                 120                 125

Ser Gly Gly Gly Ser Gly Gly Gly Ser Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Thr
            180                 185                 190

Asn Lys Arg Ala Pro Gly Val Pro Ala Arg Phe Ser Gly Ser Leu Ile
        195                 200                 205

Gly Asp Lys Ala Ala Leu Thr Ile Thr Gly Ala Gln Thr Glu Asp Glu
    210                 215                 220

Ala Ile Tyr Phe Cys Ala Leu Trp Tyr Ser Asn His Trp Val Phe Gly
225                 230                 235                 240

Gly Gly Thr Lys Leu Thr Val Leu Gly Gly Gly Gly Ser Phe Trp Val
```

```
                245                 250                 255
Leu Val Val Gly Gly Val Leu Ala Cys Tyr Ser Leu Leu Val Thr
        260                 265                 270

Val Ala Phe Ile Ile Phe Trp Val Arg Ser Lys Arg Ser Arg Leu Leu
        275                 280                 285

His Ser Asp Tyr Met Asn Met Thr Pro Arg Arg Pro Gly Pro Thr Arg
        290                 295                 300

Lys His Tyr Gln Pro Tyr Ala Pro Pro Arg Asp Phe Ala Ala Tyr Arg
305                 310                 315                 320

Ser Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
        340                 345                 350

Tyr Asp Val Leu Asp Lys Arg Arg Gly Arg Asp Pro Glu Met Gly Gly
        355                 360                 365

Lys Pro Arg Arg Lys Asn Pro Gln Glu Gly Leu Tyr Asn Glu Leu Gln
370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
                420                 425                 430

Arg

<210> SEQ ID NO 32
<211> LENGTH: 119
<212> TYPE: PRT
<213> ORGANISM: Artificial sequence
<220> FEATURE:
<223> OTHER INFORMATION: Anti-P329G VH

<400> SEQUENCE: 32

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
                20                  25                  30

Trp Met Asn Trp Val Arg Gln Ala Pro Gly Lys Gly Leu Glu Trp Ile
            35                  40                  45

Gly Glu Ile Thr Pro Asp Ser Ser Thr Ile Asn Tyr Thr Pro Ser Leu
        50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
                100                 105                 110

Thr Leu Val Thr Val Ser Ala
        115

<210> SEQ ID NO 33
<211> LENGTH: 109
<212> TYPE: PRT
<213> ORGANISM: Artificial sequence
<220> FEATURE:
<223> OTHER INFORMATION: Anti-P329G VL
```

<400> SEQUENCE: 33

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
                100                 105

<210> SEQ ID NO 34
<211> LENGTH: 248
<212> TYPE: PRT
<213> ORGANISM: Artificial sequence
<220> FEATURE:
<223> OTHER INFORMATION: Anti-P329G-scFv

<400> SEQUENCE: 34

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
                100                 105                 110

Thr Leu Val Thr Val Ser Ala Gly Gly Gly Ser Gly Gly Gly Gly
            115                 120                 125

Ser Gly Gly Gly Ser Gly Gly Gly Ser Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
                180                 185                 190

Asn Lys Arg Ala Pro Gly Val Pro Ala Arg Phe Ser Gly Ser Leu Ile
            195                 200                 205

Gly Asp Lys Ala Ala Leu Thr Ile Thr Gly Ala Gln Thr Glu Asp Glu
        210                 215                 220

Ala Ile Tyr Phe Cys Ala Leu Trp Tyr Ser Asn His Trp Val Phe Gly
225                 230                 235                 240

Gly Gly Thr Lys Leu Thr Val Leu

<210> SEQ ID NO 35
<211> LENGTH: 1356
<212> TYPE: DNA
<213> ORGANISM: Artificial sequence
<220> FEATURE:
<223> OTHER INFORMATION: Anti-P329G-scFv-CD28ATM-CD28CSD-CD3zSSD fusion

<400> SEQUENCE: 35

```
atgggatgga gctgtatcat cctcttcttg gtagcaacag ctaccggtgt gcattccgag      60
gtgaagctgc tggagagcgg cggcggcctg gtgcagcccg gcggcagcct gaagctgagc     120
tgcgccgcca gcggcttcga cttcagcagg tactggatga actgggtgag gcaggcccc     180
ggcaagggtc tggagtggat cggcgagatc accccgaca gcagcaccat caactacacc     240
cccagcctga aggacaagtt catcatcagc agggacaacg ccaagaacac cctgtacctg     300
cagatgatca aggtgaggag cgaggacacc gccctgtact actgcgtgag gccctacgac     360
tacggcgcct ggttcgccag ctggggccag ggcaccctgg tgaccgtgag cgccggaggg     420
ggcggaagtg gtggcggggg aagcggcggg ggtggcagcg aggggggcgg atctcaggcc     480
gtggtgaccc aggagagcgc cctgaccacc agccccggcg agaccgtgac cctgacctgc     540
aggagcagca ccggcgccgt gaccaccagc aactacgcca actgggtgca ggagaagccc     600
gaccacctgt tcaccggcct gatcggcggc accaacaaga gggccccgg cgtgcccgcc     660
aggttcagcg gcagcctgat cggcgacaag gccgccctga ccatcaccgg cgcccagacc     720
gaggacgagg ccatctactt ctgcgccctg tggtacagca ccactgggt gttcggcggt     780
ggcaccaagc tgaccgtgct gggagggggc ggatccttct gggtgctggt ggtggtgggc     840
ggcgtgctgg cctgctacag cctgctggtg accgtggcct tcatcatctt ctgggtgagg     900
agcaagagga gcaggctgct gcacagcgac tacatgaaca tgaccccag gaggcccggc     960
cccaccagga agcactacca gccctacgcc ccccccaggg acttcgccgc ctacaggagc    1020
agggtgaagt tcagcaggag cgccgacgcc cccgcctacc agcagggcca gaaccagctg    1080
tataacgagc tgaacctggg caggagggag gagtacgacg tgctggacaa gaggaggggc    1140
agggaccccg agatgggcgg caagcccagg aggaagaacc cccaggaggg cctgtataac    1200
gagctgcaga ggacaagat ggccgaggcc tacagcgaga tcggcatgaa gggcgagagg    1260
aggaggggca agggccacga cggcctgtac cagggcctga gcaccgccac caaggacacc    1320
tacgacgccc tgcacatgca ggccctgccc cccagg                              1356
```

<210> SEQ ID NO 36
<211> LENGTH: 357
<212> TYPE: DNA
<213> ORGANISM: Artificial sequence
<220> FEATURE:
<223> OTHER INFORMATION: Anti-P329G VH

<400> SEQUENCE: 36

```
gaggtgaagc tgctggagag cggcggcggc ctggtgcagc ccggcggcag cctgaagctg      60
agctgcgccg ccagcggctt cgacttcagc aggtactgga tgaactgggt gaggcaggcc     120
cccggcaagg gtctggagtg gatcggcgag atcaccccg acagcagcac catcaactac     180
accccccagcc tgaaggacaa gttcatcatc agcagggaca acgccaagaa caccctgtac     240
ctgcagatga tcaaggtgag gagcgaggac accgccctgt actactgcgt gaggccctac     300
gactacggcg cctggttcgc cagctggggc cagggcaccc tggtgaccgt gagcgcc       357
```

<210> SEQ ID NO 37
<211> LENGTH: 327
<212> TYPE: DNA
<213> ORGANISM: Artificial sequence
<220> FEATURE:
<223> OTHER INFORMATION: Anti-P329G VL

<400> SEQUENCE: 37

```
caggccgtgg tgacccagga gagcgccctg accaccagcc ccggcgagac cgtgaccctg      60
acctgcagga gcagcaccgg cgccgtgacc accagcaact acgccaactg ggtgcaggag     120
aagcccgacc acctgttcac cggcctgatc ggcggcacca caagagggc ccccggcgtg     180
cccgccaggt tcagcggcag cctgatcggc gacaaggccg ccctgaccat caccggcgcc     240
cagaccgagg acgaggccat ctacttctgc gccctgtggt acagcaacca ctgggtgttc     300
ggcggtggca ccaagctgac cgtgctg                                         327
```

<210> SEQ ID NO 38
<211> LENGTH: 2136
<212> TYPE: DNA
<213> ORGANISM: Artificial sequence
<220> FEATURE:
<223> OTHER INFORMATION: Anti-P329G-scFv-CD28ATM-CD28CSD-CD3zSSD-eGFP
    fusion

<400> SEQUENCE: 38

```
atgggatgga gctgtatcat cctcttcttg gtagcaacag ctaccggtgt gcattccgag      60
gtgaagctgc tggagagcgg cggcggcctg gtgcagcccg gcggcagcct gaagctgagc     120
tgcgccgcca gcggcttcga cttcagcagg tactggatga actgggtgag gcaggccccc     180
ggcaagggtc tggagtggat cggcgagatc accccgaca gcagcaccat caactacacc     240
cccagcctga aggacaagtt catcatcagc agggacaacg ccaagaacac cctgtacctg     300
cagatgatca aggtgaggag cgaggacacc gccctgtact actgcgtgag gccctacgac     360
tacggcgcct ggttcgccag ctggggccag ggcaccctgg tgaccgtgag cgccggaggg     420
ggcggaagtg gtggcggggg aagcggcggg ggtggcagcg agggggcgg atctcaggcc     480
gtggtgaccc aggagagcgc cctgaccacc agccccggcg agaccgtgac cctgacctgc     540
aggagcagca ccggcgccgt gaccaccagc aactacgcca actgggtgca ggagaagccc     600
gaccacctgt tcaccggcct gatcggcggc accaacaaga gggcccccgg cgtgcccgcc     660
aggttcagcg gcagcctgat cggcgacaag gccgccctga ccatcaccgg cgcccagacc     720
gaggacgagg ccatctactt ctgcgccctg tggtacagca accactgggt gttcggcggt     780
ggcaccaagc tgaccgtgct gggagggggc ggatccttct gggtgctggt ggtggtgggc     840
ggcgtgctgg cctgctacag cctgctggtg accgtggcct tcatcatctt ctgggtgagg     900
agcaagagga gcaggctgct gcacagcgac tacatgaaca tgaccccag gaggcccggc     960
cccaccagga agcactacca gccctacgcc cccccaggg acttcgccgc ctacaggagc    1020
agggtgaagt tcagcaggag cgccgacgcc cccgcctacc agcagggcca gaaccagctg    1080
tataacgagc tgaacctggg caggagggag gagtacgacg tgctggacaa gaggagggc    1140
agggaccccg agatgggcgg caagcccagg aggaagaacc cccaggaggg cctgtataac    1200
gagctgcaga aggacaagat ggccgaggcc tacagcgaga tcggcatgaa gggcgagagg    1260
aggaggggca agggccacga cggcctgtac caggccctga gcaccgccac caaggacacc    1320
tacgacgccc tgcacatgca ggccctgccc cccaggtccg gagagggcag aggaagtctt    1380
```

```
ctaacatgcg gtgacgtgga ggagaatccc ggccctaggg tgagcaaggg cgaggagctg   1440
ttcaccgggg tggtgcccat cctggtcgag ctggacggcg acgtaaacgg ccacaagttc   1500
agcgtgtccg gcgagggcga gggcgatgcc acctacggca agctgaccct gaagttcatc   1560
tgcaccaccg gcaagctgcc cgtgccctgg cccaccctcg tgaccaccct gacctacggc   1620
gtgcagtgct tcagccgcta ccccgaccac atgaagcagc acgacttctt caagtccgcc   1680
atgcccgaag ctacgtcca ggagcgcacc atcttcttca aggacgacgg caactacaag   1740
acccgcgccg aggtgaagtt cgagggcgac accctggtga accgcatcga gctgaagggc   1800
atcgacttca aggaggacgg caacatcctg gggcacaagc tggagtacaa ctacaacagc   1860
cacaacgtct atatcatggc cgacaagcag aagaacggca tcaaggtgaa cttcaagatc   1920
cgccacaaca tcgaggacgg cagcgtgcag ctcgccgacc actaccagca gaacacccc   1980 atcggcgacg gccccgtgct gctgcccgac aaccactacc tgagcaccca gtccgccctg   2040
agcaaagacc ccaacgagaa gcgcgatcac atggtcctgc tggagttcgt gaccgccgcc   2100
gggatcactc tcggcatgga cgagctgtac aagtga                              2136
```

<210> SEQ ID NO 39
<211> LENGTH: 407
<212> TYPE: PRT
<213> ORGANISM: Artificial sequence
<220> FEATURE:
<223> OTHER INFORMATION: Anti-P329G-ds-Fab- heavy chain-CD28ATM-CD28CSD-
      CD3zSSD fusion pETR17100

<400> SEQUENCE: 39

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220
```

-continued

```
Gly Gly Ser Phe Trp Val Leu Val Val Gly Val Leu Ala Cys
225                 230                 235                 240

Tyr Ser Leu Leu Val Thr Val Ala Phe Ile Ile Phe Trp Val Arg Ser
                    245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
            275                 280                 285

Asp Phe Ala Ala Tyr Arg Ser Arg Val Lys Phe Ser Arg Ser Ala Asp
            290                 295                 300

Ala Pro Ala Tyr Gln Gln Gly Gln Asn Gln Leu Tyr Asn Glu Leu Asn
305                 310                 315                 320

Leu Gly Arg Arg Glu Glu Tyr Asp Val Leu Asp Lys Arg Arg Gly Arg
                    325                 330                 335

Asp Pro Glu Met Gly Gly Lys Pro Arg Arg Lys Asn Pro Gln Glu Gly
                340                 345                 350

Leu Tyr Asn Glu Leu Gln Lys Asp Lys Met Ala Glu Ala Tyr Ser Glu
            355                 360                 365

Ile Gly Met Lys Gly Glu Arg Arg Arg Gly Lys Gly His Asp Gly Leu
            370                 375                 380

Tyr Gln Gly Leu Ser Thr Ala Thr Lys Asp Thr Tyr Asp Ala Leu His
385                 390                 395                 400

Met Gln Ala Leu Pro Pro Arg
                405

<210> SEQ ID NO 40
<211> LENGTH: 222
<212> TYPE: PRT
<213> ORGANISM: Artificial sequence
<220> FEATURE:
<223> OTHER INFORMATION: Anti-P329G-ds-Fab heavy chain

<400> SEQUENCE: 40

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
                20                  25                  30

Trp Met Asn Trp Val Arg Gln Ala Pro Gly Lys Cys Leu Glu Trp Ile
            35                  40                  45

Gly Glu Ile Thr Pro Asp Ser Ser Thr Ile Asn Tyr Thr Pro Ser Leu
        50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
            210                 215                 220

<210> SEQ ID NO 41
<211> LENGTH: 216
<212> TYPE: PRT
<213> ORGANISM: Artificial sequence
<220> FEATURE:
<223> OTHER INFORMATION: Anti P329G-ds-Fab light chain

<400> SEQUENCE: 41

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Cys Gly Thr Lys Leu Thr Val Leu Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 42
<211> LENGTH: 107
<212> TYPE: PRT
<213> ORGANISM: Artificial sequence
<220> FEATURE:
<223> OTHER INFORMATION: CL

<400> SEQUENCE: 42

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

```
                35                  40                  45
Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 43
<211> LENGTH: 103
<212> TYPE: PRT
<213> ORGANISM: Artificial sequence
<220> FEATURE:
<223> OTHER INFORMATION: CH1

<400> SEQUENCE: 43

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
                100

<210> SEQ ID NO 44
<211> LENGTH: 2645
<212> TYPE: DNA
<213> ORGANISM: Artificial sequence
<220> FEATURE:
<223> OTHER INFORMATION: Anti-P329G-ds-Fab-heavy chain-CD28ATM-CD28CSD-
      CD3zSSD fusion pETR17100

<400> SEQUENCE: 44
```

| | | |
|---|---|---|
| atgggatgga gctgtatcat cctcttcttg gtagcaacag ctacgggtgt gcattcccag | 60 |
| gccgtggtga cccaggagag cgccctgacc accagccccg gcgagaccgt gaccctgacc | 120 |
| tgcaggagca gcaccggcgc cgtgaccacc agcaactacg ccaactgggt gcaggagaag | 180 |
| cccgaccacc tgttcaccgg cctgatcggc ggcaccaaca gagggcccc cggcgtgccc | 240 |
| gccaggttca gcggcagcct gatcggcgac aaggccgccc tgaccatcac cggcgcccag | 300 |
| accgaggacg aggccatcta cttctgcgcc ctgtggtaca gcaaccactg ggtgttcggc | 360 |
| tgtggcacca agctgaccgt gctgcgtacg gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca agcagactac gagaaacac aaagtctacg cctgcgaagt cacccatcag | 660 |
| ggcctgagct cgcccgtcac aaagagcttc aacaggggag agtgttagga attccccgaa | 720 |

```
gtaacttaga agctgtaaat caacgatcaa tagcaggtgt ggcacaccag tcataccttg      780
atcaagcact tctgtttccc cggactgagt atcaataggc tgctcgcgcg gctgaaggag      840
aaaacgttcg ttacccgacc aactacttcg agaagcttag taccaccatg aacgaggcag      900
ggtgtttcgc tcagcacaac cccagtgtag atcaggctga tgagtcactg caaccccat      960 gggcgaccat ggcagtggct gcgttggcgg cctgcccatg gagaaatcca tgggacgctc     1020
taattctgac atggtgtgaa gtgcctattg agctaactgg tagtcctccg gcccctgatt     1080
gcggctaatc ctaactgcgg agcacatgct cacaaaccag tgggtggtgt gtcgtaacgg     1140
gcaactctgc agcggaaccg actactttgg gtgtccgtgt ttcctttat tcctatattg      1200 gctgcttatg gtgacaatca aaagttgtt accatatagc tattggattg ccatccggt       1260 gtgcaacagg gcaactgttt acctatttat tggttttgta ccattatcac tgaagtctgt     1320
gatcactctc aaattcattt tgaccctcaa cacaatcaaa cgccaccatg ggatggagct     1380
gtatcatcct cttcttggta gcaacagcta ccggtgtgca ctccgaggtg aagctgctgg     1440
agagcggcgg cggcctggtg cagcccggcg gcagcctgaa gctgagctgc cgccagcg       1500 gcttcgactt cagcaggtac tggatgaact gggtgaggca ggccccggc aagtgtctgg      1560 agtggatcgg cgagatcacc cccgacagca gcaccatcaa ctacaccccc agcctgaagg     1620
acaagttcat catcagcagg gacaacgcca gaaacaccct gtacctgcag atgatcaagg     1680
tgaggagcga ggacaccgcc ctgtactact gcgtgaggcc ctacgactac ggcgcctggt     1740
tcgccagctg gggccagggc acctggtga ccgtgagcgc cgctagcacc aagggcccct      1800
ccgtgttccc cctggccccc agcagcaaga gcaccagcgg cggcacagcc gctctgggct     1860
gcctggtcaa ggactacttc cccgagcccg tgaccgtgtc ctggaacagc ggagccctga     1920
cctccggcgt gcacaccttc cccgccgtgc tgcagagttc tggcctgtat agcctgagca     1980
gcgtggtcac cgtgccttct agcagcctgg gcacccagac ctacatctgc aacgtgaacc     2040
acaagcccag caacaccaag gtggacaaga aggtggagcc caagagctgc ggagggggcg     2100
gatccttctg ggtgctggtg gtggtgggcg gcgtgctggc ctgctacagc ctgctggtga     2160
ccgtggcctt catcatcttc tgggtgagga gcaagaggag caggctgctg cacagcgact     2220
acatgaacat gacccccagg aggcccggcc ccaccaggaa gcactaccag ccctacgccc     2280
cccccaggga cttcgccgcc tacaggagca gggtgaagtt cagcaggagc gccgacgccc     2340
ccgcctacca gcagggccag aaccagctgt ataacgagct gaacctgggc aggagggagg     2400
agtacgacgt gctggacaag aggaggggca gggaccccga tgggcggc aagcccagga      2460 ggaagaaccc ccaggagggc ctgtataacg agctgcagaa ggacaagatg gccgaggcct     2520
acagcgagat cggcatgaag ggcgagagga ggaggggcaa gggccacgac ggcctgtacc     2580
agggcctgag caccgccacc aaggacacct acgacgccct gcacatgcag gccctgcccc     2640
ccagg                                                                 2645
```

<210> SEQ ID NO 45
<211> LENGTH: 324
<212> TYPE: DNA
<213> ORGANISM: Artificial sequence
<220> FEATURE:
<223> OTHER INFORMATION: CL

<400> SEQUENCE: 45

```
cgtacggtgg ctgcaccatc tgtcttcatc ttcccgccat ctgatgagca gttgaaatct       60
```

| ggaactgcct ctgttgtgtg cctgctgaat aacttctatc ccagagaggc caaagtacag | 120 |
| tggaaggtgg ataacgccct ccaatcgggt aactcccagg agagtgtcac agagcaggac | 180 |
| agcaaggaca gcacctacag cctcagcagc accctgacgc tgagcaaagc agactacgag | 240 |
| aaacacaaag tctacgcctg cgaagtcacc catcagggcc tgagctcgcc cgtcacaaag | 300 |
| agcttcaaca ggggagagtg ttag | 324 |

<210> SEQ ID NO 46
<211> LENGTH: 309
<212> TYPE: DNA
<213> ORGANISM: Artificial sequence
<220> FEATURE:
<223> OTHER INFORMATION: CH1

<400> SEQUENCE: 46

| gctagcacca agggcccctc cgtgttcccc ctggccccca gcagcaagag caccagcggc | 60 |
| ggcacagccg ctctgggctg cctggtcaag gactacttcc ccgagcccgt gaccgtgtcc | 120 |
| tggaacagcg gagccctgac ctccggcgtg cacaccttcc ccgccgtgct gcagagttct | 180 |
| ggcctgtata gcctgagcag cgtggtcacc gtgccttcta gcagcctggg cacccagacc | 240 |
| tacatctgca acgtgaacca caagcccagc aacaccaagg tggacaagaa ggtggagccc | 300 |
| aagagctgc | 309 |

<210> SEQ ID NO 47
<211> LENGTH: 3425
<212> TYPE: DNA
<213> ORGANISM: Artificial sequence
<220> FEATURE:
<223> OTHER INFORMATION: Anti-P329G-ds-Fab-heavy chain-CD28TM-CD28CSD-
    CD3ZSSD-eGFP fusion pETR17100

<400> SEQUENCE: 47

| atgggatgga gctgtatcat cctcttcttg gtagcaacag ctacgggtgt gcattcccag | 60 |
| gccgtggtga cccaggagag cgccctgacc accagccccg gcgagaccgt gaccctgacc | 120 |
| tgcaggagca gcaccggcgc cgtgaccacc agcaactacg ccaactgggt gcaggagaag | 180 |
| cccgaccacc tgttcaccgg cctgatcggc ggcaccaaca gagggcccc cggcgtgccc | 240 |
| gccaggttca gcggcagcct gatcggcgac aaggccgccc tgaccatcac cggcgcccag | 300 |
| accgaggacg aggccatcta cttctgcgcc ctgtggtaca gcaaccactg ggtgttcggc | 360 |
| tgtggcacca gctgaccgt gctgcgtacg gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca aagcagacta cgagaaacac aaagtctacg cctgcgaagt cacccatcag | 660 |
| ggcctgagct cgcccgtcac aaagagcttc aacaggggag agtgttagga attcccgaa | 720 |
| gtaacttaga agctgtaaat caacgatcaa tagcaggtgt ggcacaccag tcataccttg | 780 |
| atcaagcact tctgtttccc cggactgagt atcaataggc tgctcgcgcg gctgaaggag | 840 |
| aaaacgttcg ttacccgacc aactacttcg agaagcttag taccaccatg aacgaggcag | 900 |
| ggtgtttcgc tcagcacaac cccagtgtag atcaggctga tgagtcactg caaccccat | 960 |
| gggcgaccat ggcagtggct gcgttggcgg cctgccatg gagaaatcca tgggacgctc | 1020 |
| taattctgac atggtgtgaa gtgcctattg agctaactga tagtcctccg gcccctgatt | 1080 |

```
gcggctaatc ctaactgcgg agcacatgct cacaaaccag tgggtggtgt gtcgtaacgg    1140
gcaactctgc agcggaaccg actactttgg gtgtccgtgt ttccttttat tcctatattg    1200
gctgcttatg gtgacaatca aaaagttgtt accatatagc tattggattg gccatccggt    1260
gtgcaacagg gcaactgttt acctatttat tggttttgta ccattatcac tgaagtctgt    1320
gatcactctc aaattcattt tgaccctcaa cacaatcaaa cgccaccatg ggatggagct    1380
gtatcatcct cttcttggta gcaacagcta ccggtgtgca ctccgaggtg aagctgctgg    1440
agagcggcgg cggcctggtg cagcccggcg gcagcctgaa gctgagctgc gccgccagcg    1500
gcttcgactt cagcaggtac tggatgaact gggtgaggca ggcccccggc aagtgtctgg    1560
agtggatcgg cgagatcacc cccgacagca gcaccatcaa ctacaccccc agcctgaagg    1620
acaagttcat catcagcagg gacaacgcca agaacaccct gtacctgcag atgatcaagg    1680
tgaggagcga ggacaccgcc ctgtactact gcgtgaggcc ctacgactac ggcgcctggt    1740
tcgccagctg gggccagggc accctggtga ccgtgagcgc cgctagcacc aagggcccct    1800
ccgtgttccc cctggccccc agcagcaaga gcaccagcgg cggcacagcc gctctgggct    1860
gcctggtcaa ggactacttc cccgagcccg tgaccgtgtc ctggaacagc ggagccctga    1920
cctccggcgt gcacaccttc cccgccgtgc tgcagagttc tggcctgtat agcctgagca    1980
gcgtggtcac cgtgccttct agcagcctgg gcacccagac ctacatctgc aacgtgaacc    2040
acaagcccag caacaccaag gtggacaaga aggtggagcc caagagctgc gaggggggcg    2100
gatccttctg ggtgctggtg gtggtgggcg gcgtgctggc ctgctacagc ctgctggtga    2160
ccgtggcctt catcatcttc tgggtgagga gcaagaggag caggctgctg cacagcgact    2220
acatgaacat gacccccagg aggcccggcc ccaccaggaa gcactaccag ccctacgccc    2280
cccccaggga cttcgccgcc tacaggagca gggtgaagtt cagcaggagc gccgacgccc    2340
ccgcctacca gcagggccag aaccagctgt ataacgagct gaacctgggc aggagggagg    2400
agtacgacgt gctggacaag aggaggggca gggaccccga gatgggcggc aagcccagga    2460
ggaagaaccc ccaggagggc ctgtataacg agctgcagaa ggacaagatg gccgaggcct    2520
acagcgagat cggcatgaag ggcgagagga ggaggggcaa gggccacgac ggcctgtacc    2580
agggcctgag caccgccacc aaggacacct acgacgccct gcacatgcag gccctgcccc    2640
ccaggtccgg agagggcaga ggaagtcttc taacatgcgg tgacgtggag gagaatcccg    2700
gccctagggt gagcaagggc gaggagctgt tcaccggggt ggtgcccatc ctggtcgagc    2760
tggacggcga cgtaaacggc cacaagttca gcgtgtccgg cgagggcgag ggcgatgcca    2820
cctacggcaa gctgaccctg aagttcatct gcaccaccgg caagctgccc gtgccctggc    2880
ccaccctcgt gaccaccctg acctacggcg tgcagtgctt cagccgctac cccgaccaca    2940
tgaagcagca cgacttcttc aagtccgcca tgcccgaagg ctacgtccag gagcgcacca    3000
tcttcttcaa ggacgacggc aactacaaga cccgcgccga ggtgaagttc gagggcgaca    3060
ccctggtgaa ccgcatcgag ctgaagggca tcgacttcaa ggaggacggc aacatcctgg    3120
ggcacaagct ggagtacaac tacaacagcc acaacgtcta tatcatggcc gacaagcaga    3180
agaacggcat caaggtgaac ttcaagatcc gccacaacat cgaggacggc agcgtgcagc    3240
tcgccgacca ctaccagcag aacacccca tcggcgacgg ccccgtgctg ctgcccgaca    3300
accactacct gagcacccag tccgccctga gcaaagaccc caacgagaag cgcgatcaca    3360
tggtcctgct ggagttcgtg accgccgccg ggatcactct cggcatggac gagctgtaca    3420
agtga                                                               3425
```

<210> SEQ ID NO 48
<211> LENGTH: 407
<212> TYPE: PRT
<213> ORGANISM: Artificial sequence
<220> FEATURE:
<223> OTHER INFORMATION: Anti-P329G-Fab-heavy chain-CD28ATM-CD28CSD-
CD3zSSD fusion pETR17594

<400> SEQUENCE: 48

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Phe Trp Val Leu Val Val Val Gly Gly Val Leu Ala Cys
225                 230                 235                 240

Tyr Ser Leu Leu Val Thr Val Ala Phe Ile Ile Phe Trp Val Arg Ser
                245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
        275                 280                 285

Asp Phe Ala Ala Tyr Arg Ser Arg Val Lys Phe Ser Arg Ser Ala Asp
    290                 295                 300

Ala Pro Ala Tyr Gln Gln Gly Gln Asn Gln Leu Tyr Asn Glu Leu Asn
305                 310                 315                 320

Leu Gly Arg Arg Glu Glu Tyr Asp Val Leu Asp Lys Arg Gly Arg
                325                 330                 335

Asp Pro Glu Met Gly Gly Lys Pro Arg Arg Lys Asn Pro Gln Glu Gly
            340                 345                 350

Leu Tyr Asn Glu Leu Gln Lys Asp Lys Met Ala Glu Ala Tyr Ser Glu

-continued

```
                355                 360                 365

Ile Gly Met Lys Gly Glu Arg Arg Gly Lys Gly His Asp Gly Leu
        370                 375                 380

Tyr Gln Gly Leu Ser Thr Ala Thr Lys Asp Thr Tyr Asp Ala Leu His
385                 390                 395                 400

Met Gln Ala Leu Pro Pro Arg
                405

<210> SEQ ID NO 49
<211> LENGTH: 222
<212> TYPE: PRT
<213> ORGANISM: Artificial sequence
<220> FEATURE:
<223> OTHER INFORMATION: Anti-P329G-Fab heavy chain

<400> SEQUENCE: 49

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 50
<211> LENGTH: 216
<212> TYPE: PRT
<213> ORGANISM: Artificial sequence
<220> FEATURE:
<223> OTHER INFORMATION: Anti-P329G-Fab light chain

<400> SEQUENCE: 50

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30
```

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys Leu Thr Val Leu Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
        210                 215

<210> SEQ ID NO 51
<211> LENGTH: 2645
<212> TYPE: DNA
<213> ORGANISM: Artificial sequence
<220> FEATURE:
<223> OTHER INFORMATION: Anti-P329G-Fab-heavy chain-CD28ATM-CD28CSD-
      CD3zSSD fusion pETR17594

<400> SEQUENCE: 51
atgggatgga gctgtatcat cctcttcttg gtagcaacag ctacgggtgt gcattcccag      60
gccgtggtga cccaggagag cgccctgacc accagccccg cgagaccgt gaccctgacc     120 tgcaggagca gcaccggcgc cgtgaccacc agcaactacg ccaactgggt gcaggagaag    180
cccgaccacc tgttcaccgg cctgatcggc ggcaccaaca gagggcccc cggcgtgccc     240 gccaggttca gcggcagcct gatcggcgac aaggccgccc tgaccatcac cggcgcccag    300
accgaggacg aggccatcta cttctgcgcc ctgtggtaca gcaaccactg ggtgttcggc    360
ggtggcacca agctgaccgt gctgcgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacggggag agtgttagga attcccgaa     720 gtaacttaga agctgtaaat caacgatcaa tagcaggtgt ggcacaccag tcataccttg    780
atcaagcact tctgtttccc cggactgagt atcaataggc tgctcgcgcg gctgaaggag    840
aaaacgttcg ttacccgacc aactacttcg agaagcttag taccaccatg aacgaggcag    900
ggtgtttcgc tcagcacaac cccagtgtag atcaggctga tgagtcactg caaccccat    960

```
gggcgaccat ggcagtggct gcgttggcgg cctgcccatg gagaaatcca tgggacgctc      1020
taattctgac atggtgtgaa gtgcctattg agctaactgg tagtcctccg gcccctgatt      1080
gcggctaatc ctaactgcgg agcacatgct cacaaaccag tgggtggtgt gtcgtaacgg      1140
gcaactctgc agcggaaccg actactttgg gtgtccgtgt ttccttttat tcctatattg      1200
gctgcttatg gtgacaatca aaagttgtt accatatagc tattggattg gccatccggt       1260
gtgcaacagg gcaactgttt acctatttat tggttttgta ccattatcac tgaagtctgt      1320
gatcactctc aaattcattt tgaccctcaa cacaatcaaa cgccaccatg ggatggagct      1380
gtatcatcct cttcttggta gcaacagcta ccggtgtgca ctccgaggtg aagctgctgg      1440
agagcggcgg cggcctggtg cagcccggcg gcagcctgaa gctgagctgc gccgccagcg      1500
gcttcgactt cagcaggtac tggatgaact gggtgaggca ggcccccggc aagggtctgg      1560
agtggatcgg cgagatcacc cccgacagca gcaccatcaa ctacaccccc agcctgaagg      1620
acaagttcat catcagcagg gacaacgcca gaaacaccct gtacctgcag atgatcaagg      1680
tgaggagcga ggacaccgcc ctgtactact gcgtgaggcc ctacgactac ggcgcctggt      1740
tcgccagctg gggccagggc accctggtga ccgtgagcgc cgctagcacc aagggcccct      1800
ccgtgttccc cctggccccc agcagcaaga gcaccagcgg cggcacagcc gctctgggct      1860
gcctggtcaa ggactacttc cccgagcccg tgaccgtgtc ctggaacagc ggagccctga      1920
cctccggcgt gcacaccttc cccgccgtgc tgcagagttc tggcctgtat agcctgagca      1980
gcgtggtcac cgtgccttct agcagcctgg gcacccagac ctacatctgc aacgtgaacc      2040
acaagcccag caacaccaag gtggacaaga aggtggagcc caagagctgc gagggggcg       2100 gatccttctg ggtgctggtg gtggtgggcg gcgtgctggc ctgctacagc ctgctggtga      2160
ccgtggcctt catcatcttc tgggtgagga gcaagaggag caggctgctg cacagcgact      2220
acatgaacat gacccccagg aggcccgcc ccaccaggaa gcactaccag ccctacgccc       2280
cccccaggga cttcgccgcc tacaggagca gggtgaagtt cagcaggagc gccgacgccc      2340
ccgcctacca gcagggccag aaccagctgt ataacgagct gaacctgggc aggagggagg      2400
agtacgacgt gctggacaag aggaggggca gggaccccga gatgggcggc aagcccagga      2460
ggaagaaccc ccaggagggc ctgtataacg agctgcagaa ggacaagatg gccgaggcct      2520
acagcgagat cggcatgaag ggcgagagga gagggggcaa gggccacgac ggcctgtacc      2580
agggcctgag caccgccacc aaggacacct acgacgccct gcacatgcag gccctgcccc      2640
ccagg                                                                 2645
```

<210> SEQ ID NO 52
<211> LENGTH: 3425
<212> TYPE: DNA
<213> ORGANISM: Artificial sequence
<220> FEATURE:
<223> OTHER INFORMATION: Anti-P329G-Fab-heavy chain-CD28ATM-CD28CSD-
      CD3zSSD-eGFP fusion pETR17594

<400> SEQUENCE: 52

```
atgggatgga gctgtatcat cctcttcttg gtagcaacag ctacgggtgt gcattcccag       60
gccgtggtga cccaggagag cgccctgacc accagcccccg cgagaccgt gaccctgacc      120 tgcaggagca gcaccggcgc cgtgaccacc agcaactacg ccaactgggt gcaggagaag      180
cccgaccacc tgttcaccgg cctgatcggc ggcaccaaca gaggccccc cggcgtgccc       240 gccaggttca gcggcagcct gatcggcgac aaggccgccc tgaccatcac cggcgcccag      300
```

```
accgaggacg aggccatcta cttctgcgcc ctgtggtaca gcaaccactg ggtgttcggc      360
ggtggcacca agctgaccgt gctgcgtacg gtggctgcac catctgtctt catcttcccg      420
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcaccctg      600
acgctgagca agcagacta cgagaaacac aaagtctacg cctgcgaagt cacccatcag      660
ggcctgagct cgcccgtcac aaagagcttc aacaggggag agtgttagga attccccgaa      720
gtaacttaga agctgtaaat caacgatcaa tagcaggtgt ggcacaccag tcataccttg      780
atcaagcact tctgttccc cggactgagt atcaataggc tgctcgcgcg gctgaaggag      840
aaaacgttcg ttacccgacc aactacttcg agaagcttag taccaccatg aacgaggcag      900
ggtgtttcgc tcagcacaac cccagtgtag atcaggctga tgagtcactg caacccccat      960
gggcgaccat ggcagtggct gcgttggcgg cctgcccatg gagaaatcca tgggacgctc      1020
taattctgac atggtgtgaa gtgcctattg agctaactgg tagtcctccg gcccctgatt      1080
gcggctaatc ctaactgcgg agcacatgct cacaaaccag tgggtggtgt gtcgtaacgg      1140
gcaactctgc agcggaaccg actactttgg gtgtccgtgt ttccttttat tcctatattg      1200
gctgcttatg gtgacaatca aaagttgtt accatatagc tattggattg gccatccggt      1260
gtgcaacagg gcaactgttt acctatttat tggttttgta ccattatcac tgaagtctgt      1320
gatcactctc aaattcattt tgaccctcaa cacaatcaaa cgccaccatg ggatggagct      1380
gtatcatcct cttcttggta gcaacagcta ccggtgtgca ctccgaggtg aagctgctgg      1440
agagcggcgg cggcctggtg cagcccggcg gcagcctgaa gctgagctgc gccgccagcg      1500
gcttcgactt cagcaggtac tggatgaact gggtgaggca ggcccccggc aagggtctgg      1560
agtggatcgg cgagatcacc cccgacagca gcaccatcaa ctacaccccc agcctgaagg      1620
acaagttcat catcagcagg gacaacgcca gaaacacct gtacctgcag atgatcaagg      1680
tgaggagcga ggacaccgcc ctgtactact gcgtgaggcc ctacgactac ggcgcctggt      1740
tcgccagctg gggccagggc accctggtga ccgtgagcgc cgctagcacc aagggcccct      1800
ccgtgttccc cctggccccc agcagcaaga gcaccagcgg cggcacagcc gctctgggct      1860
gcctggtcaa ggactacttc cccgagcccg tgaccgtgtc ctggaacagc ggagccctga      1920
cctccggcgt gcacaccttc cccgccgtgc tgcagagttc tggcctgtat agcctgagca      1980
gcgtggtcac cgtgccttct agcagcctgg gcacccagac ctacatctgc aacgtgaacc      2040
acaagcccag caacaccaag gtggacaaga aggtggagcc caagagctgc gagggggcg      2100 gatccttctg ggtgctggtg gtggtgggcg gcgtgctggc ctgctacagc ctgctggtga      2160
ccgtggcctt catcatcttc tgggtgagga gcaagaggag caggctgctg cacagcgact      2220
acatgaacat gacccccagg aggcccggcc ccaccaggaa gcactaccag ccctacgccc      2280
cccccaggga cttcgccgcc tacaggagca gggtgaagtt cagcaggagc gccgacgccc      2340
ccgcctacca gcagggccag aaccagctgt ataacgagct gaacctgggc aggagggagg      2400
agtacgacgt gctggacaag aggagggca gggaccccga gatgggcggc aagcccagga      2460
ggaagaaccc ccaggagggc ctgtataacg agctgcagaa ggacaagatg gccgaggcct      2520
acagcgagat cggcatgaag ggcgagagga ggaggggcaa gggccacgac ggcctgtacc      2580
agggcctgag caccgccacc aaggacacct acgacgccct gcacatgcag gccctgcccc      2640
ccaggtccgg agagggcaga ggaagtcttc taacatgcgg tgacgtggag gagaatcccg      2700
```

```
gccctagggt gagcaagggc gaggagctgt tcaccggggt ggtgcccatc ctggtcgagc    2760
tggacggcga cgtaaacggc cacaagttca gcgtgtccgg cgagggcgag ggcgatgcca    2820
cctacggcaa gctgaccctg aagttcatct gcaccaccgg caagctgccc gtgccctggc    2880
ccaccctcgt gaccaccctg acctacggcg tgcagtgctt cagccgctac cccgaccaca    2940
tgaagcagca cgacttcttc aagtccgcca tgcccgaagg ctacgtccag agcgcacca     3000 tcttcttcaa ggacgacggc aactacaaga cccgcgccga ggtgaagttc gagggcgaca    3060
ccctggtgaa ccgcatcgag ctgaagggca tcgacttcaa ggaggacggc aacatcctgg    3120
ggcacaagct ggagtacaac tacaacagcc acaacgtcta tatcatggcc gacaagcaga    3180
agaacggcat caaggtgaac ttcaagatcc gccacaacat cgaggacggc agcgtgcagc    3240
tcgccgacca ctaccagcag aacaccccca tcggcgacgg ccccgtgctg ctgcccgaca    3300
accactacct gagcacccag tccgccctga gcaaagaccc caacgagaag cgcgatcaca    3360
tggtcctgct ggagttcgtg accgccgccg ggatcactct cggcatggac gagctgtaca    3420
agtga                                                                3425
```

<210> SEQ ID NO 53
<211> LENGTH: 5
<212> TYPE: PRT
<213> ORGANISM: Artificial sequence
<220> FEATURE:
<223> OTHER INFORMATION: Anti-AAA CDR H1 Kabat

<400> SEQUENCE: 53

Ser Tyr Gly Met Ser
1               5

<210> SEQ ID NO 54
<211> LENGTH: 6
<212> TYPE: PRT
<213> ORGANISM: Artificial sequence
<220> FEATURE:
<223> OTHER INFORMATION: Anti-AAA CDR H2 Kabat

<400> SEQUENCE: 54

Ser Ser Gly Gly Ser Tyr
1               5

<210> SEQ ID NO 55
<211> LENGTH: 12
<212> TYPE: PRT
<213> ORGANISM: Artificial sequence
<220> FEATURE:
<223> OTHER INFORMATION: Anti-AAA CDR H3 Kabat

<400> SEQUENCE: 55

Leu Gly Met Ile Thr Thr Gly Tyr Ala Met Asp Tyr
1               5                   10

<210> SEQ ID NO 56
<211> LENGTH: 16
<212> TYPE: PRT
<213> ORGANISM: Artificial sequence
<220> FEATURE:
<223> OTHER INFORMATION: Anti-AAA CDR L1 Kabat

<400> SEQUENCE: 56

Arg Ser Ser Gln Thr Ile Val His Ser Thr Gly His Thr Tyr Leu Glu
1               5                   10                  15

<210> SEQ ID NO 57
<211> LENGTH: 7
<212> TYPE: PRT
<213> ORGANISM: Artificial sequence
<220> FEATURE:
<223> OTHER INFORMATION: Anti-AAA CDR L2 Kabat

<400> SEQUENCE: 57

Lys Val Ser Asn Arg Phe Ser
1               5

<210> SEQ ID NO 58
<211> LENGTH: 9
<212> TYPE: PRT
<213> ORGANISM: Artificial sequence
<220> FEATURE:
<223> OTHER INFORMATION: Anti-AAA CDR L3 Kabat

<400> SEQUENCE: 58

Phe Gln Gly Ser His Val Pro Tyr Thr
1               5

<210> SEQ ID NO 59
<211> LENGTH: 457
<212> TYPE: PRT
<213> ORGANISM: Artificial sequence
<220> FEATURE:
<223> OTHER INFORMATION: Anti-AAA-scFv-CD28ATM-CD28CSD-CD3zSSD fusion

<400> SEQUENCE: 59

Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Ser Gly Gly Gly Gly Ser
145                 150                 155                 160

Asp Val Leu Met Thr Gln Thr Pro Leu Ser Leu Pro Val Ser Leu Gly
                165                 170                 175

Asp Gln Ala Ser Ile Ser Cys Arg Ser Ser Gln Thr Ile Val His Ser
            180                 185                 190

Thr Gly His Thr Tyr Leu Glu Trp Phe Leu Gln Lys Pro Gly Gln Ser
        195                 200                 205

Pro Lys Leu Leu Ile Tyr Lys Val Ser Asn Arg Phe Ser Gly Val Pro
    210                 215                 220

Asp Arg Phe Ser Gly Ser Gly Ser Gly Thr Asp Phe Thr Leu Lys Ile

```
             225                 230                 235                 240
    Ser Arg Val Glu Ala Glu Asp Leu Gly Val Tyr Tyr Cys Phe Gln Gly
                    245                 250                 255

Ser His Val Pro Tyr Thr Phe Gly Gly Gly Thr Lys Leu Glu Ile Lys
                    260                 265                 270

Gly Gly Gly Gly Ser Phe Trp Val Leu Val Val Gly Val Leu
                    275                 280                 285

Ala Cys Tyr Ser Leu Leu Val Thr Val Ala Phe Ile Ile Phe Trp Val
                290                 295                 300

Arg Ser Lys Arg Ser Arg Leu Leu His Ser Asp Tyr Met Asn Met Thr
    305                 310                 315                 320

Pro Arg Arg Pro Gly Pro Thr Arg Lys His Tyr Gln Pro Tyr Ala Pro
                    325                 330                 335

Pro Arg Asp Phe Ala Ala Tyr Arg Ser Arg Val Lys Phe Ser Arg Ser
                    340                 345                 350

Ala Asp Ala Pro Ala Tyr Gln Gln Gly Gln Asn Gln Leu Tyr Asn Glu
                    355                 360                 365

Leu Asn Leu Gly Arg Arg Glu Glu Tyr Asp Val Leu Asp Lys Arg Arg
            370                 375                 380

Gly Arg Asp Pro Glu Met Gly Gly Lys Pro Arg Arg Lys Asn Pro Gln
    385                 390                 395                 400

Glu Gly Leu Tyr Asn Glu Leu Gln Lys Asp Lys Met Ala Glu Ala Tyr
                    405                 410                 415

Ser Glu Ile Gly Met Lys Gly Glu Arg Arg Arg Gly Lys Gly His Asp
                    420                 425                 430

Gly Leu Tyr Gln Gly Leu Ser Thr Ala Thr Lys Asp Thr Tyr Asp Ala
                435                 440                 445

Leu His Met Gln Ala Leu Pro Pro Arg
                    450                 455

<210> SEQ ID NO 60
<211> LENGTH: 272
<212> TYPE: PRT
<213> ORGANISM: Artificial sequence
<220> FEATURE:
<223> OTHER INFORMATION: Anti-AAA-scFv

<400> SEQUENCE: 60

Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
                20                  25                  30

Pro Gly Gly Ser Leu Lys Leu Ser Cys Ala Ala Ser Gly Phe Thr Phe
            35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
                100                 105                 110

Tyr Tyr Cys Ala Arg Leu Gly Met Ile Thr Thr Gly Tyr Ala Met Asp
            115                 120                 125

Tyr Trp Gly Gln Gly Thr Ser Val Thr Val Ser Ser Gly Gly Gly Gly
```

```
            130                 135                 140
Ser Gly Gly Gly Ser Gly Gly Gly Ser Gly Gly Gly Ser
145                 150                 155                 160

Asp Val Leu Met Thr Gln Thr Pro Leu Ser Leu Pro Val Ser Leu Gly
                165                 170                 175

Asp Gln Ala Ser Ile Ser Cys Arg Ser Ser Gln Thr Ile Val His Ser
                180                 185                 190

Thr Gly His Thr Tyr Leu Glu Trp Phe Leu Gln Lys Pro Gly Gln Ser
            195                 200                 205

Pro Lys Leu Leu Ile Tyr Lys Val Ser Asn Arg Phe Ser Gly Val Pro
        210                 215                 220

Asp Arg Phe Ser Gly Ser Gly Ser Gly Thr Asp Phe Thr Leu Lys Ile
225                 230                 235                 240

Ser Arg Val Glu Ala Glu Asp Leu Gly Val Tyr Tyr Cys Phe Gln Gly
                245                 250                 255

Ser His Val Pro Tyr Thr Phe Gly Gly Gly Thr Lys Leu Glu Ile Lys
            260                 265                 270
```

<210> SEQ ID NO 61
<211> LENGTH: 140
<212> TYPE: PRT
<213> ORGANISM: Artificial sequence
<220> FEATURE:
<223> OTHER INFORMATION: Anti-AAA VH

<400> SEQUENCE: 61

```
Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ser
    130                 135                 140
```

<210> SEQ ID NO 62
<211> LENGTH: 112
<212> TYPE: PRT
<213> ORGANISM: Artificial sequence
<220> FEATURE:
<223> OTHER INFORMATION: Anti-AAA VL

<400> SEQUENCE: 62

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30
```

```
Thr Gly His Thr Tyr Leu Glu Trp Phe Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 63
<211> LENGTH: 428
<212> TYPE: PRT
<213> ORGANISM: Artificial sequence
<220> FEATURE:
<223> OTHER INFORMATION: Anti-AAA-Fab-heavy chain-CD28ATM-CD28CSD-
      CD3zSSD fusion

<400> SEQUENCE: 63

Met Asn Phe Gly Leu Ser Leu Val Phe Leu Ala Leu Ile Leu Lys Gly
 1               5                  10                  15

Val Gln Cys Glu Val Gln Leu Val Glu Ser Gly Gly Asp Leu Val Lys
                20                  25                  30

Pro Gly Gly Ser Leu Lys Leu Ser Cys Ala Ala Ser Gly Phe Thr Phe
            35                  40                  45

Ser Ser Tyr Gly Met Ser Trp Val Arg Gln Thr Pro Asp Lys Arg Leu
 50                  55                  60

Glu Trp Val Ala Thr Ile Ser Ser Gly Gly Ser Tyr Ile Tyr Tyr Pro
 65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
            115                 120                 125

Tyr Trp Gly Gln Gly Thr Ser Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Gly Gly Gly Gly Ser Phe Trp Val Leu Val Val Val Gly
                245                 250                 255

Gly Val Leu Ala Cys Tyr Ser Leu Leu Val Thr Val Ala Phe Ile Ile
            260                 265                 270

Phe Trp Val Arg Ser Lys Arg Ser Arg Leu Leu His Ser Asp Tyr Met
            275                 280                 285
```

```
Asn Met Thr Pro Arg Arg Pro Gly Pro Thr Arg Lys His Tyr Gln Pro
    290                 295                 300

Tyr Ala Pro Pro Arg Asp Phe Ala Ala Tyr Arg Ser Arg Val Lys Phe
305                 310                 315                 320

Ser Arg Ser Ala Asp Ala Pro Ala Tyr Gln Gln Gly Gln Asn Gln Leu
                325                 330                 335

Tyr Asn Glu Leu Asn Leu Gly Arg Arg Glu Glu Tyr Asp Val Leu Asp
                340                 345                 350

Lys Arg Arg Gly Arg Asp Pro Glu Met Gly Gly Lys Pro Arg Arg Lys
                355                 360                 365

Asn Pro Gln Glu Gly Leu Tyr Asn Glu Leu Gln Lys Asp Lys Met Ala
    370                 375                 380

Glu Ala Tyr Ser Glu Ile Gly Met Lys Gly Glu Arg Arg Arg Gly Lys
385                 390                 395                 400

Gly His Asp Gly Leu Tyr Gln Gly Leu Ser Thr Ala Thr Lys Asp Thr
                405                 410                 415

Tyr Asp Ala Leu His Met Gln Ala Leu Pro Pro Arg
                420                 425

<210> SEQ ID NO 64
<211> LENGTH: 243
<212> TYPE: PRT
<213> ORGANISM: Artificial sequence
<220> FEATURE:
<223> OTHER INFORMATION: Anti-AAA-Fab heavy chain

<400> SEQUENCE: 64

Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
                20                  25                  30

Pro Gly Gly Ser Leu Lys Leu Ser Cys Ala Ala Ser Gly Phe Thr Phe
                35                  40                  45

Ser Ser Tyr Gly Met Ser Trp Val Arg Gln Thr Pro Asp Lys Arg Leu
50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
                100                 105                 110

Tyr Tyr Cys Ala Arg Leu Gly Met Ile Thr Thr Gly Tyr Ala Met Asp
                115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
    195                 200                 205

Val Thr Val Pro Ser Ser Ser Leu Gly Thr Gln Thr Tyr Ile Cys Asn
210                 215                 220
```

Val Asn His Lys Pro Ser Asn Thr Lys Val Asp Lys Lys Val Glu Pro
225                 230                 235                 240

Lys Ser Cys

<210> SEQ ID NO 65
<211> LENGTH: 219
<212> TYPE: PRT
<213> ORGANISM: Artificial sequence
<220> FEATURE:
<223> OTHER INFORMATION: Anti-AAA-Fab light chain

<400> SEQUENCE: 65

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Thr Gly His Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 66
<211> LENGTH: 780
<212> TYPE: DNA
<213> ORGANISM: Homo sapiens

<400> SEQUENCE: 66
atggcgcgcc cgcatccgtg gtggctgtgc gtgctgggca ccctggtggg cctgagcgcg         60
accccggcgc cgaaaagctg cccggaacgc cattattggg cgcagggcaa actgtgctgc        120
cagatgtgcg aaccgggcac ctttctggtg aaagattgcg atcagcatcg caaagcggcg        180
cagtgcgatc cgtgcattcc gggcgtgagc tttagcccgg atcatcatac ccgcccgcat        240
tgcgaaagct gccgccattg caacagcggc ctgctggtgc gcaactgcac cattaccgcg        300
aacgcggaat gcgcgtgccg caacggctgg cagtgccgcg ataaagaatg caccgaatgc        360
gatccgctgc cgaacccgag cctgaccgcg cgcagcagcc aggcgctgag cccgcatccg        420

```
cagccgaccc atctgccgta tgtgagcgaa atgctggaag cgcgcaccgc gggccatatg    480
cagaccctgg cggattttcg ccagctgccg gcgcgcaccc tgagcaccca ttggccgccg    540
cagcgcagcc tgtgcagcag cgattttatt cgcattctgg tgattttag cggcatgttt     600 ctggtgttta ccctggcggg cgcgctgttt ctgcatcagc gccgcaaata tcgcagcaac    660
aaaggcgaaa gcccggtgga accggcgaaa ccgtgccatt atagctgccc gcgcgaagaa    720
gaaggcagca ccattccgat tcaggaagat tatcgcaaac cggaaccggc gtgcagcccg    780
```

<210> SEQ ID NO 67
<211> LENGTH: 260
<212> TYPE: PRT
<213> ORGANISM: Homo sapiens

<400> SEQUENCE: 67

```
Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260
```

<210> SEQ ID NO 68
<211> LENGTH: 750
<212> TYPE: DNA
<213> ORGANISM: Mus musculus

<400> SEQUENCE: 68

```
atggcgtggc cgccgccgta ttggctgtgc atgctgggca ccctggtggg cctgagcgcg    60
accctggcgc cgaacagctg cccggataaa cattattgga ccggcggcgg cctgtgctgc   120
cgcatgtgcg aaccgggcac cttttttgtg aaagattgcg aacaggatcg caccgcggcg   180
cagtgcgatc cgtgcattcc gggcaccagc tttagcccgg attatcatac cgcccgcat   240
tgcgaaagct gccgccattg aacagcggc tttctgattc gcaactgcac cgtgaccgcg   300
aacgcggaat gcagctgcag caaaaactgg cagtgccgcg atcaggaatg caccgaatgc   360
gatccgccgc tgaacccggc gctgaccgc cagccgagcg aaaccccgag cccgcagccg   420
ccgccgaccc atctgccgca tggcaccgaa aaaccgagct ggccgctgca tcgccagctg   480
ccgaacagca ccgtgtatag ccagcgcagc agccatcgcc cgctgtgcag cagcgattgc   540
attcgcattt ttgtgaccct tagcagcatg tttctgattt ttgtgctggg cgcgattctg   600
ttttttcatc agcgccgcaa ccatggcccg aacgaagatc gccaggcggt gccggaagaa   660
ccgtgcccgt atagctgccc gcgcgaagaa gaaggcagcg cgattccgat tcaggaagat   720
tatcgcaaac cggaaccggc gttttatccg                                    750
```

<210> SEQ ID NO 69
<211> LENGTH: 250
<212> TYPE: PRT
<213> ORGANISM: Mus musculus

<400> SEQUENCE: 69

```
Met Ala Trp Pro Pro Tyr Trp Leu Cys Met Leu Gly Thr Leu Val
1               5                   10                  15
Gly Leu Ser Ala Thr Leu Ala Pro Asn Ser Cys Pro Asp Lys His Tyr
                20                  25                  30
Trp Thr Gly Gly Gly Leu Cys Cys Arg Met Cys Glu Pro Gly Thr Phe
            35                  40                  45
Phe Val Lys Asp Cys Glu Gln Asp Arg Thr Ala Ala Gln Cys Asp Pro
        50                  55                  60
Cys Ile Pro Gly Thr Ser Phe Ser Pro Asp Tyr His Thr Arg Pro His
65                  70                  75                  80
Cys Glu Ser Cys Arg His Cys Asn Ser Gly Phe Leu Ile Arg Asn Cys
                85                  90                  95
Thr Val Thr Ala Asn Ala Glu Cys Ser Cys Ser Lys Asn Trp Gln Cys
            100                 105                 110
Arg Asp Gln Glu Cys Thr Glu Cys Asp Pro Pro Leu Asn Pro Ala Leu
        115                 120                 125
Thr Arg Gln Pro Ser Glu Thr Pro Ser Pro Gln Pro Pro Thr His
    130                 135                 140
Leu Pro His Gly Thr Glu Lys Pro Ser Trp Pro Leu His Arg Gln Leu
145                 150                 155                 160
Pro Asn Ser Thr Val Tyr Ser Gln Arg Ser Ser His Arg Pro Leu Cys
                165                 170                 175
Ser Ser Asp Cys Ile Arg Ile Phe Val Thr Phe Ser Ser Met Phe Leu
            180                 185                 190
Ile Phe Val Leu Gly Ala Ile Leu Phe Phe His Gln Arg Arg Asn His
        195                 200                 205
Gly Pro Asn Glu Asp Arg Gln Ala Val Pro Glu Glu Pro Cys Pro Tyr
    210                 215                 220
Ser Cys Pro Arg Glu Glu Glu Gly Ser Ala Ile Pro Ile Gln Glu Asp
225                 230                 235                 240
```

```
Tyr Arg Lys Pro Glu Pro Ala Phe Tyr Pro
            245                 250
```

<210> SEQ ID NO 70
<211> LENGTH: 660
<212> TYPE: DNA
<213> ORGANISM: Homo sapiens

<400> SEQUENCE: 70

```
atgctgcgcc tgctgctggc gctgaacctg tttccgagca ttcaggtgac cggcaacaaa      60
attctggtga acagagcccc gatgctggtg gcgtatgata cgcgtgaaa cctgagctgc     120
aaatatagct ataacctgtt tagccgcgaa tttcgcgcga gcctgcataa aggcctggat     180
agcgcggtgg aagtgtgcgt ggtgtatggc aactatagcc agcagctgca ggtgtatagc     240
aaaaccggct ttaactgcga tggcaaactg ggcaacgaaa gcgtgacctt ttatctgcag     300
aacctgtatg tgaaccagac cgatatttat ttttgcaaaa ttgaagtgat gtatccgccg     360
ccgtatctgg ataacgaaaa aagcaacggc accattattc atgtgaaagg caaacatctg     420
tgcccgagcc cgctgtttcc gggcccgagc aaaccgtttt gggtgctggt ggtggtgggc     480
ggcgtgctgg cgtgctatag cctgctggtg accgtggcgt ttattatttt tgggtgcgc     540
agcaaacgca ccgcctgct gcatagcgat tatatgaaca tgaccccgcg ccgcccgggc     600
ccgacccgca acattatca gccgtatgcg ccgccgcgcg attttgcggc gtatcgcagc     660
```

<210> SEQ ID NO 71
<211> LENGTH: 220
<212> TYPE: PRT
<213> ORGANISM: Homo sapiens

<400> SEQUENCE: 71

```
Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
```

Tyr Ala Pro Pro Arg Asp Phe Ala Ala Tyr Arg Ser
    210             215             220

<210> SEQ ID NO 72
<211> LENGTH: 654
<212> TYPE: DNA
<213> ORGANISM: Mus musculus

<400> SEQUENCE: 72
atgaccctgc gcctgctgtt tctggcgctg aactttttta gcgtgcaggt gaccgaaaac      60
aaaattctgg tgaaacagag cccgctgctg gtggtggata gcaacgaagt gagcctgagc     120
tgccgctata gctataacct gctggcgaaa gaatttcgcg cgagcctgta taaggcgtg     180
aacagcgatg tggaagtgtg cgtgggcaac ggcaacttta cctatcagcc gcagtttcgc     240
agcaacgcgg aatttaactg cgatggcgat tttgataacg aaaccgtgac ctttcgcctg     300
tggaacctgc atgtgaacca taccgatatt tattttgca aaattgaatt tatgtatccg     360
ccgccgtatc tggataacga acgcagcaac ggcaccatta ttcatattaa agaaaaacat     420
ctgtgccata cccagagcag cccgaaactg ttttgggcgc tggtggtggt ggcgggcgtg     480
ctgttttgct atggcctgct ggtgaccgtg gcgctgtgcg tgatttggac caacagccgc     540
cgcaaccgcc tgctgcagag cgattatatg aacatgaccc cgcgccgccc gggcctgacc     600
cgcaaaccgt atcagccgta tgcgccggcg cgcgattttg cggcgtatcg cccg          654

<210> SEQ ID NO 73
<211> LENGTH: 218
<212> TYPE: PRT
<213> ORGANISM: Mus musculus

<400> SEQUENCE: 73

Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

```
Thr Pro Arg Arg Pro Gly Leu Thr Arg Lys Pro Tyr Gln Pro Tyr Ala
        195                 200                 205
Pro Ala Arg Asp Phe Ala Ala Tyr Arg Pro
    210                 215
```

<210> SEQ ID NO 74
<211> LENGTH: 768
<212> TYPE: DNA
<213> ORGANISM: Homo sapiens

<400> SEQUENCE: 74

```
atgggaaaca gctgttacaa catagtagcc actctgttgc tggtcctcaa ctttgagagg     60
acaagatcat tgcaggatcc ttgtagtaac tgcccagctg gtacattctg tgataataac   120
aggaatcaga tttgcagtcc ctgtcctcca aatagtttct ccagcgcagg tggacaaagg   180
acctgtgaca tatgcaggca gtgtaaaggt gttttcagga ccaggaagga gtgttcctcc   240
accagcaatg cagagtgtga ctgcactcca gggtttcact gcctgggggc aggatgcagc   300
atgtgtgaac aggattgtaa acaaggtcaa gaactgacaa aaaaaggttg taagactgt    360
tgctttggga catttaacga tcagaaacgt ggcatctgtc gaccctggac aaactgttct   420
ttggatggaa agtctgtgct gtgaatggg acgaaggaga gggacgtggt ctgtggacca    480
tctccagccg acctctctcc gggagcatcc tctgtgaccc cgcctgcccc tgcgagagag   540
ccaggacact ctccgcagat catctccttc tttcttgcgc tgacgtcgac tgcgttgctc   600
ttcctgctgt tcttcctcac gctccgtttc tctgttgtta aacggggcag aaagaaactc   660
ctgtatatat tcaaacaacc atttatgaga ccagtacaaa ctactcaaga ggaagatggc   720
tgtagctgcc gatttccaga agaagaagaa ggaggatgtg aactgtga              768
```

<210> SEQ ID NO 75
<211> LENGTH: 255
<212> TYPE: PRT
<213> ORGANISM: Homo sapiens

<400> SEQUENCE: 75

```
Met Gly Asn Ser Cys Tyr Asn Ile Val Ala Thr Leu Leu Val Leu
1               5                   10                  15
Asn Phe Glu Arg Thr Arg Ser Leu Gln Asp Pro Cys Ser Asn Cys Pro
                20                  25                  30
Ala Gly Thr Phe Cys Asp Asn Asn Arg Asn Gln Ile Cys Ser Pro Cys
            35                  40                  45
Pro Pro Asn Ser Phe Ser Ser Ala Gly Gly Gln Arg Thr Cys Asp Ile
        50                  55                  60
Cys Arg Gln Cys Lys Gly Val Phe Arg Thr Arg Lys Glu Cys Ser Ser
65                  70                  75                  80
Thr Ser Asn Ala Glu Cys Asp Cys Thr Pro Gly Phe His Cys Leu Gly
                85                  90                  95
Ala Gly Cys Ser Met Cys Glu Gln Asp Cys Lys Gln Gly Gln Glu Leu
            100                 105                 110
Thr Lys Lys Gly Cys Lys Asp Cys Cys Phe Gly Thr Phe Asn Asp Gln
        115                 120                 125
Lys Arg Gly Ile Cys Arg Pro Trp Thr Asn Cys Ser Leu Asp Gly Lys
    130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Val Thr Pro Pro Ala
```

```
            165                 170                 175
Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
            245                 250                 255

<210> SEQ ID NO 76
<211> LENGTH: 768
<212> TYPE: DNA
<213> ORGANISM: Mus musculus

<400> SEQUENCE: 76
atgggcaaca actgctataa cgtggtggtg attgtgctgc tgctggtggg ctgcgaaaaa      60
gtgggcgcgg tgcagaacag ctgcgataac tgccagccgg gcaccttttg ccgcaaatat     120
aacccggtgt gcaaaagctg cccgccgagc acctttagca gcattggcgg ccagccgaac     180
tgcaacattt gccgcgtgtg cgcgggctat tttcgcttta aaaattttg cagcagcacc      240 cataacgcgg aatgcgaatg cattgaaggc tttcattgcc tgggcccgca gtgcacccgc     300
tgcgaaaaag attgccgccc gggccaggaa ctgaccaaac agggctgcaa acctgcagc      360 ctgggcaccct ttaacgatca gaacggcacc ggcgtgtgcc gcccgtggac caactgcagc    420
ctggatggcc gcagcgtgct gaaaaccggc accaccgaaa agatgtggt gtgcggcccg      480 ccggtggtga gctttagccc gagcaccacc attagcgtga ccccggaagg cggcccgggc     540
ggccatagcc tgcaggtgct gaccctgttt ctggcgctga ccagcgcgct gctgctggcg    600 ctgatttttta ttaccctgct gtttagcgtg ctgaaatgga ttcgcaaaaa atttccgcat    660
atttttaaac agccgtttaa aaaaaccacc ggcgcggcgc aggaagaaga tgcgtgcagc     720
tgccgctgcc gcaggaaga agaaggcggc ggcggcggct atgaactg                   768

<210> SEQ ID NO 77
<211> LENGTH: 256
<212> TYPE: PRT
<213> ORGANISM: Mus musculus

<400> SEQUENCE: 77

Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
            35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110
```

Lys Gln Gly Cys Lys Thr Cys Ser Leu Gly Thr Phe Asn Asp Gln Asn
            115                 120                 125
Gly Thr Gly Val Cys Arg Pro Trp Thr Asn Cys Ser Leu Asp Gly Arg
        130                 135                 140
Ser Val Leu Lys Thr Gly Thr Thr Glu Lys Asp Val Val Cys Gly Pro
145                 150                 155                 160
Pro Val Val Ser Phe Ser Pro Ser Thr Thr Ile Ser Val Thr Pro Glu
                165                 170                 175
Gly Gly Pro Gly Gly His Ser Leu Gln Val Leu Thr Leu Phe Leu Ala
            180                 185                 190
Leu Thr Ser Ala Leu Leu Leu Ala Leu Ile Phe Ile Thr Leu Leu Phe
            195                 200                 205
Ser Val Leu Lys Trp Ile Arg Lys Lys Phe Pro His Ile Phe Lys Gln
210                 215                 220
Pro Phe Lys Lys Thr Thr Gly Ala Ala Gln Glu Glu Asp Ala Cys Ser
225                 230                 235                 240
Cys Arg Cys Pro Gln Glu Glu Glu Gly Gly Gly Gly Tyr Glu Leu
                245                 250                 255

<210> SEQ ID NO 78
<211> LENGTH: 831
<212> TYPE: DNA
<213> ORGANISM: Homo sapiens

<400> SEQUENCE: 78
atgtgcgtgg gcgcgcgccg cctgggccgc ggcccgtgcg cggcgctgct gctgctgggc      60
ctgggcctga gcaccgtgac cggcctgcat tgcgtgggcg ataccatcc gagcaacgat      120
cgctgctgcc atgaatgccg cccgggcaac ggcatggtga ccgctgcag ccgcagccag      180
aacaccgtgt gccgcccgtg cggcccgggc ttttataacg atgtggtgag cagcaaaccg      240
tgcaaaccgt gcacctggtg caacctcgcg agcggcagcg aacgcaaaca gctgtgcacc      300
gcgacccagg ataccgtgtg ccgctgccgc gcgggcaccc agccgctgga tagctataaa      360
ccgggcgtgg attgcgcgcc gtgcccgccg ggccattta gcccgggcga taaccaggcg      420
tgcaaaccgt ggaccaactg caccctggcg ggcaaacata ccctgcagcc ggcgagcaac      480
agcagcgatg cgatttgcga agatcgcgat ccgccggcga cccagccgca ggaaacccag      540
ggcccgccgg cgcgcccgat taccgtgcag ccgaccgaag cgtggccgcg caccagccag      600
ggcccgagca cccgcccggt ggaagtgccg ggcggccgcg cggtggcggc gattctgggc      660
ctgggcctgg tgctgggcct gctgggcccg ctggcgattc tgctggcgct gtatctgctg      720
cgccgcgatc agcgcctgcc gccggatgcg cataaaccgc cggcggcgg cagctttcgc      780
accccgattc aggaagaaca ggcggatgcg catagcaccc tggcgaaaat t              831

<210> SEQ ID NO 79
<211> LENGTH: 277
<212> TYPE: PRT
<213> ORGANISM: Homo sapiens

<400> SEQUENCE: 79

Met Cys Val Gly Ala Arg Arg Leu Gly Arg Gly Pro Cys Ala Ala Leu
1               5                   10                  15
Leu Leu Leu Gly Leu Gly Leu Ser Thr Val Thr Gly Leu His Cys Val
            20                  25                  30
Gly Asp Thr Tyr Pro Ser Asn Asp Arg Cys Cys His Glu Cys Arg Pro

```
                35                  40                  45
Gly Asn Gly Met Val Ser Arg Cys Ser Arg Ser Gln Asn Thr Val Cys
 50                  55                  60

Arg Pro Cys Gly Pro Gly Phe Tyr Asn Asp Val Val Ser Ser Lys Pro
 65                  70                  75                  80

Cys Lys Pro Cys Thr Trp Cys Asn Leu Arg Ser Gly Ser Glu Arg Lys
                 85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 80
<211> LENGTH: 816
<212> TYPE: DNA
<213> ORGANISM: Mus musculus

<400> SEQUENCE: 80
atgtatgtgt gggtgcagca gccgaccgcg ctgctgctgc tggcgctgac cctgggcgtg     60
accgcgcgcc gcctgaactg cgtgaaacat acctatccga gcggccataa atgctgccgc    120
gaatgccagc cgggccatgg catggtgagc cgctgcgatc ataccgcga taccctgtgc    180 catccgtgcg aaaccggctt ttataacgaa gcggtgaact atgatacctg caaacagtgc    240
acccagtgca accatcgcag cggcagcgaa ctgaaacaga actgcacccc gacccaggat    300
accgtgtgcc gctgccgccc gggcacccag ccgcgccagg atagcggcta taaactgggc    360
gtggattgcg tgccgtgccc gccgggccat tttagcccgg gcaacaacca ggcgtgcaaa    420
ccgtggacca actgcacccc tgagcggcaaa cagacccgcc atccggcgag cgatagcctg    480
gatgcggtgt gcgaagatcg cagcctgctg gcgaccctgc tgtgggaaac ccagcgcccg    540
acctttcgcc cgaccaccgt gcagagcacc accgtgtggc gcgcaccag cgaactgccg    600 agcccgccga ccctggtgac cccggaaggc cggcgtttg cggtgctgct gggcctgggc    660
ctgggcctgc tggcgccgct gaccgtgctg ctggcgctgt atctgctgcg caaagcgtgg    720
```

```
cgcctgccga acaccccgaa accgtgctgg ggcaacagct ttcgcacccc gattcaggaa    780
gaacataccg atgcgcattt taccctggcg aaaatt                              816
```

<210> SEQ ID NO 81
<211> LENGTH: 272
<212> TYPE: PRT
<213> ORGANISM: Mus musculus

<400> SEQUENCE: 81

| Met | Tyr | Val | Trp | Val | Gln | Gln | Pro | Thr | Ala | Leu | Leu | Leu | Ala | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Thr | Leu | Gly | Val | Thr | Ala | Arg | Arg | Leu | Asn | Cys | Val | Lys | His | Thr | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Ser | Gly | His | Lys | Cys | Cys | Arg | Glu | Cys | Gln | Pro | Gly | His | Gly | Met |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Val | Ser | Arg | Cys | Asp | His | Thr | Arg | Asp | Thr | Leu | Cys | His | Pro | Cys | Glu |
|     | 50  |     |     |     |     | 55  |     |     |     |     | 60  |     |     |     |     |

| Thr | Gly | Phe | Tyr | Asn | Glu | Ala | Val | Asn | Tyr | Asp | Thr | Cys | Lys | Gln | Cys |
| 65  |     |     |     |     | 70  |     |     |     |     | 75  |     |     |     |     | 80  |

| Thr | Gln | Cys | Asn | His | Arg | Ser | Gly | Ser | Glu | Leu | Lys | Gln | Asn | Cys | Thr |
|     |     |     |     | 85  |     |     |     |     | 90  |     |     |     |     | 95  |     |

| Pro | Thr | Gln | Asp | Thr | Val | Cys | Arg | Cys | Arg | Pro | Gly | Thr | Gln | Pro | Arg |
|     |     |     | 100 |     |     |     |     | 105 |     |     |     |     | 110 |     |     |

| Gln | Asp | Ser | Gly | Tyr | Lys | Leu | Gly | Val | Asp | Cys | Val | Pro | Cys | Pro | Pro |
|     |     |     | 115 |     |     |     |     | 120 |     |     |     |     | 125 |     |     |

| Gly | His | Phe | Ser | Pro | Gly | Asn | Asn | Gln | Ala | Cys | Lys | Pro | Trp | Thr | Asn |
|     |     |     | 130 |     |     |     |     | 135 |     |     |     |     | 140 |     |     |

| Cys | Thr | Leu | Ser | Gly | Lys | Gln | Thr | Arg | His | Pro | Ala | Ser | Asp | Ser | Leu |
| 145 |     |     |     |     | 150 |     |     |     |     | 155 |     |     |     |     | 160 |

| Asp | Ala | Val | Cys | Glu | Asp | Arg | Ser | Leu | Leu | Ala | Thr | Leu | Leu | Trp | Glu |
|     |     |     |     | 165 |     |     |     |     | 170 |     |     |     |     | 175 |     |

| Thr | Gln | Arg | Pro | Thr | Phe | Arg | Pro | Thr | Thr | Val | Gln | Ser | Thr | Thr | Val |
|     |     |     |     | 180 |     |     |     |     | 185 |     |     |     |     | 190 |     |

| Trp | Pro | Arg | Thr | Ser | Glu | Leu | Pro | Ser | Pro | Pro | Thr | Leu | Val | Thr | Pro |
|     |     |     | 195 |     |     |     |     | 200 |     |     |     |     | 205 |     |     |

| Glu | Gly | Pro | Ala | Phe | Ala | Val | Leu | Leu | Gly | Leu | Gly | Leu | Gly | Leu | Leu |
|     | 210 |     |     |     |     | 215 |     |     |     |     | 220 |     |     |     |     |

| Ala | Pro | Leu | Thr | Val | Leu | Leu | Ala | Leu | Tyr | Leu | Leu | Arg | Lys | Ala | Trp |
| 225 |     |     |     |     | 230 |     |     |     |     | 235 |     |     |     |     | 240 |

| Arg | Leu | Pro | Asn | Thr | Pro | Lys | Pro | Cys | Trp | Gly | Asn | Ser | Phe | Arg | Thr |
|     |     |     |     | 245 |     |     |     |     | 250 |     |     |     |     | 255 |     |

| Pro | Ile | Gln | Glu | Glu | His | Thr | Asp | Ala | His | Phe | Thr | Leu | Ala | Lys | Ile |
|     |     |     |     | 260 |     |     |     |     | 265 |     |     |     |     | 270 |     |

<210> SEQ ID NO 82
<211> LENGTH: 597
<212> TYPE: DNA
<213> ORGANISM: Homo sapiens

<400> SEQUENCE: 82

```
atgaaaagcg gcctgtggta ttttttctg ttttgcctgc gcattaaagt gctgaccggc    60
gaaattaacg gcagcgcgaa ctatgaaatg tttattttc ataacggcgg cgtgcagatt   120
ctgtgcaaat atccggatat tgtgcagcag tttaaaatgc agctgctgaa aggcggccag   180
attctgtgcg atctgaccaa aaccaaaggc agcggcaaca ccgtgagcat taaaagcctg   240
```

```
aaattttgcc atagccagct gagcaacaac agcgtgagct ttttctgta taacctggat    300 catagccatg cgaactatta ttttgcaac ctgagcattt ttgatccgcc gccgtttaaa    360
gtgaccctga ccggcggcta tctgcatatt tatgaaagcc agctgtgctg ccagctgaaa    420
ttttggctgc cgattggctg cgcggcgttt gtggtggtgt gcattctggg ctgcattctg    480
atttgctggc tgaccaaaaa aaaatatagc agcagcgtgc atgatccgaa cggcgaatat    540
atgtttatgc gcgcggtgaa caccgcgaaa aaaagccgcc tgaccgatgt gaccctg       597
```

<210> SEQ ID NO 83
<211> LENGTH: 199
<212> TYPE: PRT
<213> ORGANISM: Homo sapiens

<400> SEQUENCE: 83

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195
```

<210> SEQ ID NO 84
<211> LENGTH: 600
<212> TYPE: DNA
<213> ORGANISM: Mus musculus

<400> SEQUENCE: 84

```
atgaaaccgt atttttgccg cgtgtttgtg ttttgctttc tgattcgcct gctgaccggc    60
gaaattaacg gcagcgcgga tcatcgcatg tttagctttc ataacggcgg cgtgcagatt    120
agctgcaaat atccggaaac cgtgcagcag ctgaaaatgc cctgtttcg cgaacgcgaa    180 gtgctgtgcg aactgaccaa aaccaaaggc agcggcaacg cggtgagcat aaaaacccg    240 atgctgtgcc tgtatcatct gagcaacaac agcgtgagct ttttctgaa caacccggat    300 agcagccagg gcagctatta ttttgcagc ctgagcattt ttgatccgcc gccgtttcag    360
```

```
gaacgcaacc tgagcggcgg ctatctgcat atttatgaaa gccagctgtg ctgccagctg      420
aaactgtggc tgccggtggg ctgcgcggcg tttgtggtgg tgctgctgtt tggctgcatt      480
ctgattattt ggtttagcaa aaaaaaatat ggcagcagcg tgcatgatcc gaacagcgaa      540
tatatgttta tggcggcggt gaacaccaac aaaaaaagcc gcctggcggg cgtgaccagc      600
```

<210> SEQ ID NO 85
<211> LENGTH: 200
<212> TYPE: PRT
<213> ORGANISM: Mus musculus

<400> SEQUENCE: 85

```
Met Lys Pro Tyr Phe Cys Arg Val Phe Val Phe Cys Phe Leu Ile Arg
1               5                   10                  15

Leu Leu Thr Gly Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110

Ile Phe Asp Pro Pro Phe Gln Glu Arg Asn Leu Ser Gly Gly Tyr
        115                 120                 125

Leu His Ile Tyr Glu Ser Gln Leu Cys Cys Gln Leu Lys Leu Trp Leu
    130                 135                 140

Pro Val Gly Cys Ala Ala Phe Val Val Leu Leu Phe Gly Cys Ile
145                 150                 155                 160

Leu Ile Ile Trp Phe Ser Lys Lys Tyr Gly Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Val Thr Ser
        195                 200
```

<210> SEQ ID NO 86
<211> LENGTH: 279
<212> TYPE: DNA
<213> ORGANISM: Homo sapiens

<400> SEQUENCE: 86

```
atgattcatc tgggccatat tctgtttctg ctgctgctgc cggtggcggc ggcgcagacc       60
accccgggcg aacgcagcag cctgccggcg tttatccgg gcaccagcgg cagctgcagc       120
ggctgcggca gcctgagcct gccgctgctg gcgggcctgg tggcggcgga tgcggtggcg      180
agcctgctga ttgtgggcgc ggtgtttctg tgcgcgcgcc cgcgccgcag cccggcgcag      240
gaagatggca aagtgtatat taacatgccg ggccgcggc                              279
```

<210> SEQ ID NO 87
<211> LENGTH: 93
<212> TYPE: PRT
<213> ORGANISM: Homo sapiens

<400> SEQUENCE: 87

Met Ile His Leu Gly His Ile Leu Phe Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
            35                  40                  45

Leu Leu Ala Gly Leu Val Ala Ala Asp Ala Val Ala Ser Leu Leu Ile
        50                  55                  60

Val Gly Ala Val Phe Leu Cys Ala Arg Pro Arg Ser Pro Ala Gln
65                  70                  75                  80

Glu Asp Gly Lys Val Tyr Ile Asn Met Pro Gly Arg Gly
                85                  90

<210> SEQ ID NO 88
<211> LENGTH: 237
<212> TYPE: DNA
<213> ORGANISM: Mus musculus

<400> SEQUENCE: 88
atggatccgc cgggctatct gctgtttctg ctgctgctgc cggtggcggc gagccagacc      60
agcgcgggca gctgcagcgg ctgcggcacc ctgagcctgc cgctgctggc gggcctggtg     120
gcggcggatg cggtgatgag cctgctgatt gtgggcgtgg tgtttgtgtg catgcgcccg     180
catggccgcc cggcgcagga agatggccgc gtgtatatta acatgccggg ccgcggc        237

<210> SEQ ID NO 89
<211> LENGTH: 79
<212> TYPE: PRT
<213> ORGANISM: Mus musculus

<400> SEQUENCE: 89

Met Asp Pro Pro Gly Tyr Leu Leu Phe Leu Leu Leu Pro Val Ala
1               5                   10                  15

Ala Ser Gln Thr Ser Ala Gly Ser Cys Ser Gly Cys Gly Thr Leu Ser
            20                  25                  30

Leu Pro Leu Leu Ala Gly Leu Val Ala Ala Asp Ala Val Met Ser Leu
        35                  40                  45

Leu Ile Val Gly Val Val Phe Val Cys Met Arg Pro His Gly Arg Pro
    50                  55                  60

Ala Gln Glu Asp Gly Arg Val Tyr Ile Asn Met Pro Gly Arg Gly
65                  70                  75

<210> SEQ ID NO 90
<211> LENGTH: 342
<212> TYPE: DNA
<213> ORGANISM: Homo sapiens

<400> SEQUENCE: 90 atgggggggac ttgaaccctg cagcaggctc ctgctcctgc ctctcctgct ggctgtaagt     60
ggtctccgtc ctgtccaggc ccaggcccag agcgattgca gttgctctac ggtgagcccg    120
ggcgtgctgg cagggatcgt gatgggagac ctggtgctga cagtgctcat gccctggcc     180 gtgtacttcc tgggccggct ggtccctcgg gggcgagggg ctgcggaggc agcgacccgg    240
aaacagcgta tcactgagac cgagtcgcct tatcaggagc tccagggtca gaggtcggat    300
gtctacagcg acctcaacac acagaggccg tattacaaat ga                       342

<210> SEQ ID NO 91
<211> LENGTH: 113
<212> TYPE: PRT
<213> ORGANISM: Homo sapiens

<400> SEQUENCE: 91

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys

<210> SEQ ID NO 92
<211> LENGTH: 345
<212> TYPE: DNA
<213> ORGANISM: Mus musculus

<400> SEQUENCE: 92
atgggggctc tggagccctc ctggtgcctt ctgttccttc ctgtcctcct gactgtggga      60
ggattaagtc ccgtacaggc ccagagtgac actttcccaa gatgcgactg ttcttccgtg     120
agccctggtg tactggctgg gattgttctg ggtgacttgg tgttgactct gctgattgcc     180
ctggctgtgt actctctggg ccgcctggtc tcccgaggtc aagggacagc ggaagggacc     240
cggaaacaac acattgctga gactgagtcg ccttatcagg agcttcaggg tcagagacca     300
gaagtataca gtgacctcaa cacacagagg caatattaca gatga                     345

<210> SEQ ID NO 93
<211> LENGTH: 114
<212> TYPE: PRT
<213> ORGANISM: Mus musculus

<400> SEQUENCE: 93

Met Gly Ala Leu Glu Pro Ser Trp Cys Leu Leu Phe Leu Pro Val Leu
1               5                   10                  15

Leu Thr Val Gly Gly Leu Ser Pro Val Gln Ala Gln Ser Asp Thr Phe
            20                  25                  30

Pro Arg Cys Asp Cys Ser Ser Val Ser Pro Gly Val Leu Ala Gly Ile
        35                  40                  45

Val Leu Gly Asp Leu Val Leu Thr Leu Leu Ile Ala Leu Ala Val Tyr
    50                  55                  60

Ser Leu Gly Arg Leu Val Ser Arg Gly Gln Gly Thr Ala Glu Gly Thr
65                  70                  75                  80

Arg Lys Gln His Ile Ala Glu Thr Glu Ser Pro Tyr Gln Glu Leu Gln
                85                  90                  95

Gly Gln Arg Pro Glu Val Tyr Ser Asp Leu Asn Thr Gln Arg Gln Tyr
            100                 105                 110

Tyr Arg

<210> SEQ ID NO 94
<211> LENGTH: 164
<212> TYPE: PRT
<213> ORGANISM: Homo sapiens

<400> SEQUENCE: 94

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 95
<211> LENGTH: 492
<212> TYPE: DNA
<213> ORGANISM: Homo sapiens

<400> SEQUENCE: 95
atgaagtgga aggcgctttt caccgcggcc atcctgcagg cacagttgcc gattacagag     60
gcacagagct ttggcctgct ggatcccaaa ctctgctacc tgctggatgg aatcctcttc    120
atctatggtg tcattctcac tgccttgttc ctgagagtga agttcagcag gagcgcagag    180
ccccccgcgt accagcaggg ccagaaccag ctctataacg agctcaatct aggacgaaga    240
gaggagtacg atgttttgga caagagacgt ggccgggacc ctgagatggg gggaaagccg    300
agaaggaaga accctcagga aggcctgtac aatgaactgc agaaagataa gatggcggag    360
gcctacagtg agattgggat gaaaggcgag cgccggaggg gcaaggggca cgatggcctt    420
taccagggtc tcagtacagc caccaaggac acctacgacg cccttcacat gcaggccctg    480
ccccctcgct aa                                                        492

<210> SEQ ID NO 96
<211> LENGTH: 164
<212> TYPE: PRT
<213> ORGANISM: Mus musculus

<400> SEQUENCE: 96

Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Thr Ala
        35                  40                  45

Leu Tyr Leu Arg Ala Lys Phe Ser Arg Ser Ala Glu Thr Ala Ala Asn
 50                  55                  60

Leu Gln Asp Pro Asn Gln Leu Tyr Asn Glu Leu Asn Leu Gly Arg Arg
 65                  70                  75                  80

Glu Glu Tyr Asp Val Leu Glu Lys Lys Arg Ala Arg Asp Pro Glu Met
                 85                  90                  95

Gly Gly Lys Gln Gln Arg Arg Arg Asn Pro Gln Glu Gly Val Tyr Asn
            100                 105                 110

Ala Leu Gln Lys Asp Lys Met Ala Glu Ala Tyr Ser Glu Ile Gly Thr
        115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Thr
145                 150                 155                 160

Leu Ala Pro Arg

<210> SEQ ID NO 97
<211> LENGTH: 495
<212> TYPE: DNA
<213> ORGANISM: Mus musculus

<400> SEQUENCE: 97
atgaagtgga aagtgtctgt tctcgcctgc atcctccacg tgcggttccc aggagcagag      60
gcacagagct tggtctgct ggatcccaaa ctctgctact tgctagatgg aatcctcttc     120
atctacggag tcatcatcac agccctgtac ctgagagcaa aattcagcag gagtgcagag     180
actgctgcca acctgcagga ccccaaccag ctctacaatg agctcaatct agggcgaaga     240
gaggaatatg acgtcttgga gaagaagcgg gctcgggatc cagagatggg aggcaaacag     300
cagaggagga ggaaccccca ggaaggcgta tacaatgcac tgcagaaaga caagatggca     360
gaagcctaca gtgagatcgg cacaaaaggc gagaggcgga gaggcaaggg cacgatggc      420 ctttaccagg gtctcagcac tgccaccaag gacacctatg atgccctgca tatgcagacc     480
ctggccccct gctaa                                                      495

<210> SEQ ID NO 98
<211> LENGTH: 254
<212> TYPE: PRT
<213> ORGANISM: Homo sapiens

<400> SEQUENCE: 98

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
 50                  55                  60

Ser Leu Ile Ser Ser Gln Ala Ser Ser Tyr Phe Ile Asp Ala Ala Thr
65                  70                  75                  80

-continued

```
Val Asp Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135             140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 99
<211> LENGTH: 762
<212> TYPE: DNA
<213> ORGANISM: Homo sapiens

<400> SEQUENCE: 99

```
atgtggcagc tgctgctgcc gaccgcgctg ctgctgctgg tgagcgcggg catgcgcacc      60
gaagatctgc cgaaagcggt ggtgtttctg gaaccgcagt ggtatcgcgt gctggaaaaa     120
gatagcgtga ccctgaaatg ccagggcgcg tatagcccgg aagataacag cacccagtgg     180
tttcataacg aaagcctgat tagcagccag gcgagcagct atttattga tgcggcgacc      240
gtggatgata gcggcgaata tcgctgccag accaacctga gcaccctgag cgatccggtg     300
cagctggaag tgcatattgg ctggctgctg ctgcaggcgc cgcgctgggt gtttaaagaa     360
gaagatccga ttcatctgcg ctgccatagc tggaaaaaca ccgcgctgca taaagtgacc     420
tatctgcaga acggcaaagg ccgcaaatat tttcatcata acagcgattt ttatattccg     480
aaagcgaccc tgaaagatag cggcagctat ttttgccgcg gcctgtttgg cagcaaaaac     540
gtgagcagcg aaaccgtgaa cattaccatt acccagggcc tggcggtgag caccattagc     600
agcttttttc cgccgggcta tcaggtgagc ttttgcctgg tgatggtgct gctgtttgcg     660
gtggataccg gcctgtattt tagcgtgaaa accaacattc gcagcagcac ccgcgattgg     720
aaagatcata aatttaaatg gcgcaaagat ccgcaggata aa                        762
```

<210> SEQ ID NO 100
<211> LENGTH: 261
<212> TYPE: PRT
<213> ORGANISM: Mus musculus

<400> SEQUENCE: 100

```
Met Phe Gln Asn Ala His Ser Gly Ser Gln Trp Leu Leu Pro Pro Leu
1               5                   10                  15

Thr Ile Leu Leu Leu Phe Ala Phe Ala Asp Arg Gln Ser Ala Ala Leu
```

|  |  |  | 20 |  |  |  | 25 |  |  |  | 30 |  |  |
|---|---|---|---|---|---|---|---|---|---|---|---|---|---|

Pro Lys Ala Val Val Lys Leu Asp Pro Pro Trp Ile Gln Val Leu Lys
        35                  40                  45

Glu Asp Met Val Thr Leu Met Cys Glu Gly Thr His Asn Pro Gly Asn
 50                  55                  60

Ser Ser Thr Gln Trp Phe His Asn Gly Arg Ser Ile Arg Ser Gln Val
 65                  70                  75                  80

Gln Ala Ser Tyr Thr Phe Lys Ala Thr Val Asn Asp Ser Gly Glu Tyr
                 85                  90                  95

Arg Cys Gln Met Glu Gln Thr Arg Leu Ser Asp Pro Val Asp Leu Gly
             100                 105                 110

Val Ile Ser Asp Trp Leu Leu Leu Gln Thr Pro Gln Arg Val Phe Leu
         115                 120                 125

Glu Gly Glu Thr Ile Thr Leu Arg Cys His Ser Trp Arg Asn Lys Leu
     130                 135                 140

Leu Asn Arg Ile Ser Phe Phe His Asn Glu Lys Ser Val Arg Tyr His
145                 150                 155                 160

His Tyr Lys Ser Asn Phe Ser Ile Pro Lys Ala Asn His Ser His Ser
                 165                 170                 175

Gly Asp Tyr Tyr Cys Lys Gly Ser Leu Gly Ser Thr Gln His Gln Ser
             180                 185                 190

Lys Pro Val Thr Ile Thr Val Gln Asp Pro Ala Thr Thr Ser Ser Ile
         195                 200                 205

Ser Leu Val Trp Tyr His Thr Ala Phe Ser Leu Val Met Cys Leu Leu
     210                 215                 220

Phe Ala Val Asp Thr Gly Leu Tyr Phe Tyr Val Arg Arg Asn Leu Gln
225                 230                 235                 240

Thr Pro Arg Glu Tyr Trp Arg Lys Ser Leu Ser Ile Arg Lys His Gln
                 245                 250                 255

Ala Pro Gln Asp Lys
            260

<210> SEQ ID NO 101
<211> LENGTH: 786
<212> TYPE: DNA
<213> ORGANISM: Mus musculus

<400> SEQUENCE: 101

| atgtttcaga | atgcacactc | tggaagccaa | tggctacttc | caccactgac | aattctgctg | 60 |
| ctgtttgctt | ttgcagacag | gcagagtgca | gctcttccga | aggctgtggt | gaaactggac | 120 |
| cccccatgga | tccaggtgct | caaggaagac | atggtgacac | tgatgtgcga | agggacccac | 180 |
| aaccctggga | actcttctac | ccagtggttc | cacaacggga | ggtccatccg | agccaggtc | 240 |
| caagccagtt | acacgtttaa | ggccacagtc | aatgacagtg | gagaatatcg | gtgtcaaatg | 300 |
| gagcagaccc | gcctcagcga | ccctgtagat | ctgggagtga | tttctgactg | gctgctgctc | 360 |
| cagacccctc | agcgggtgtt | tctggaaggg | gaaaccatca | cgctaaggtg | ccatagctgg | 420 |
| aggaacaaac | tactgaacag | gatctcattc | ttccataatg | aaaaatccgt | gaggtatcat | 480 |
| cactacaaaa | gtaatttctc | tatcccaaaa | gccaaccaca | gtcacagtgg | ggactactac | 540 |
| tgcaaaggaa | gtctaggaag | tacacagcac | cagtccaagc | ctgtcaccat | cactgtccaa | 600 |
| gatccagcaa | ctacatcctc | catctctcta | gtctggtacc | acactgcttt | ctccctagtg | 660 |
| atgtgcctcc | tgtttgcagt | ggacacgggc | ctttatttct | acgtacggag | aaatcttcaa | 720 |

-continued

```
accccgaggg agtactggag gaagtccctg tcaatcagaa agcaccaggc tcctcaagac    780
aagtga                                                               786
```

<210> SEQ ID NO 102
<211> LENGTH: 216
<212> TYPE: PRT
<213> ORGANISM: Homo sapiens

<400> SEQUENCE: 102

```
Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Cys Cys Phe Ile Ala Val Ala Met Gly
    50                  55                  60

Ile Arg Phe Ile Ile Met Val Ala Ile Trp Ser Ala Val Phe Leu Asn
65                  70                  75                  80

Ser Leu Phe Asn Gln Glu Val Gln Ile Pro Leu Thr Glu Ser Tyr Cys
            85                  90                  95

Gly Pro Cys Pro Lys Asn Trp Ile Cys Tyr Lys Asn Asn Cys Tyr Gln
        100                 105                 110

Phe Phe Asp Glu Ser Lys Asn Trp Tyr Glu Ser Gln Ala Ser Cys Met
    115                 120                 125

Ser Gln Asn Ala Ser Leu Leu Lys Val Tyr Ser Lys Glu Asp Gln Asp
130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
            165                 170                 175

Asn Leu Leu Thr Ile Ile Glu Met Gln Lys Gly Asp Cys Ala Leu Tyr
        180                 185                 190

Ala Ser Ser Phe Lys Gly Tyr Ile Glu Asn Cys Ser Thr Pro Asn Thr
    195                 200                 205

Tyr Ile Cys Met Gln Arg Thr Val
210                 215
```

<210> SEQ ID NO 103
<211> LENGTH: 648
<212> TYPE: DNA
<213> ORGANISM: Homo sapiens

<400> SEQUENCE: 103

```
atgggctgga ttcgcggccg ccgcagccgc catagctggg aaatgagcga atttcataac    60
tataacctgg atctgaaaaa aagcgatttt agcacccgct ggcagaaaca gcgctgcccg   120
gtggtgaaaa gcaaatgccg cgaaaacgcg agcccgtttt tttttgctg ctttattgcg   180 gtggcgatgg gcattcgctt tattattatg gtggcgattt ggagcgcggt gtttctgaac   240
agcctgttta accaggaagt gcagattccg ctgaccgaaa gctattgcgg cccgtgcccg   300
aaaaactgga tttgctataa aaacaactgc tatcagtttt ttgatgaaag caaaaactgg   360
tatgaaagcc aggcgagctg catgagccag aacgcgagcc tgctgaaagt gtatagcaaa   420
gaagatcagg atctgctgaa actggtgaaa agctatcatt ggatgggcct ggtgcatatt   480
ccgaccaacg gcagctggca gtgggaagat ggcagcattc tgagcccgaa cctgctgacc   540
```

```
attattgaaa tgcagaaagg cgattgcgcg ctgtatgcga gcagctttaa aggctatatt    600
gaaaactgca gcaccccgaa cacctatatt tgcatgcagc gcaccgtg               648
```

<210> SEQ ID NO 104
<211> LENGTH: 232
<212> TYPE: PRT
<213> ORGANISM: Mus musculus

<400> SEQUENCE: 104

```
Met Ala Leu Ile Arg Asp Arg Lys Ser His His Ser Glu Met Ser Lys
1               5                   10                  15

Cys His Asn Tyr Asp Leu Lys Pro Ala Lys Trp Asp Thr Ser Gln Glu
                20                  25                  30

Gln Gln Lys Gln Arg Leu Ala Leu Thr Thr Ser Gln Pro Gly Glu Asn
            35                  40                  45

Gly Ile Ile Arg Gly Arg Tyr Pro Ile Glu Lys Leu Lys Ile Ser Pro
        50                  55                  60

Met Phe Val Val Arg Val Leu Ala Ile Ala Leu Ala Ile Arg Phe Thr
65                  70                  75                  80

Leu Asn Thr Leu Met Trp Leu Ala Ile Phe Lys Glu Thr Phe Gln Pro
                85                  90                  95

Val Leu Cys Asn Lys Glu Val Pro Val Ser Ser Arg Glu Gly Tyr Cys
                100                 105                 110

Gly Pro Cys Pro Asn Asn Trp Ile Cys His Arg Asn Asn Cys Tyr Gln
            115                 120                 125

Phe Phe Asn Glu Glu Lys Thr Trp Asn Gln Ser Gln Ala Ser Cys Leu
        130                 135                 140

Ser Gln Asn Ser Ser Leu Leu Lys Ile Tyr Ser Lys Glu Glu Gln Asp
145                 150                 155                 160

Phe Leu Lys Leu Val Lys Ser Tyr His Trp Met Gly Leu Val Gln Ile
                165                 170                 175

Pro Ala Asn Gly Ser Trp Gln Trp Glu Asp Gly Ser Ser Leu Ser Tyr
                180                 185                 190

Asn Gln Leu Thr Leu Val Glu Ile Pro Lys Gly Ser Cys Ala Val Tyr
            195                 200                 205

Gly Ser Ser Phe Lys Ala Tyr Thr Glu Asp Cys Ala Asn Leu Asn Thr
        210                 215                 220

Tyr Ile Cys Met Lys Arg Ala Val
225                 230
```

<210> SEQ ID NO 105
<211> LENGTH: 696
<212> TYPE: DNA
<213> ORGANISM: Mus musculus

<400> SEQUENCE: 105

```
atggcgctga ttcgcgatcg caaaagccat catagcgaaa tgagcaaatg ccataactat    60
gatctgaaac cggcgaaatg ggataccagc caggaacagc agaaacagcg cctggcgctg   120
accaccagcc agccgggcga aaacggcatt attcgcggcc gctatccgat tgaaaaactg   180
aaaattagcc cgatgtttgt ggtgcgcgtg ctggcgattg cgctggcgat cgctttaccc   240
ctgaacaccc tgatgtggct ggcgattttt aaagaaacct ttcagccggt gctgtgcaac   300
aaagaagtgc cggtgagcag ccgcgaaggc tattgcggcc cgtgcccgaa caactggatt   360
tgccatcgca acaactgcta tcagtttttt aacgaagaaa aacctggaa ccagagccag   420
```

```
gcgagctgcc tgagccagaa cagcagcctg ctgaaaattt atagcaaaga agaacaggat    480
tttctgaaac tggtgaaaag ctatcattgg atgggcctgg tgcagattcc ggcgaacggc    540
agctggcagt gggaagatgg cagcagcctg agctataacc agctgaccct ggtggaaatt    600
ccgaaaggca gctgcgcggt gtatggcagc agctttaaag cgtataccga agattgcgcg    660
aacctgaaca cctatatttg catgaaacgc gcggtg                              696
```

```
<210> SEQ ID NO 106
<211> LENGTH: 4
<212> TYPE: PRT
<213> ORGANISM: Artificial sequence
<220> FEATURE:
<223> OTHER INFORMATION: CD28 YMNM

<400> SEQUENCE: 106

Tyr Met Asn Met
1

<210> SEQ ID NO 107
<211> LENGTH: 4
<212> TYPE: PRT
<213> ORGANISM: Artificial sequence
<220> FEATURE:
<223> OTHER INFORMATION: CD28 PYAP

<400> SEQUENCE: 107

Pro Tyr Ala Pro
1

<210> SEQ ID NO 108
<211> LENGTH: 4
<212> TYPE: PRT
<213> ORGANISM: Artificial sequence
<220> FEATURE:
<223> OTHER INFORMATION: CD28 FMNM

<400> SEQUENCE: 108

Phe Met Asn Met
1

<210> SEQ ID NO 109
<211> LENGTH: 4
<212> TYPE: PRT
<213> ORGANISM: Artificial sequence
<220> FEATURE:
<223> OTHER INFORMATION: CD28 AYAA

<400> SEQUENCE: 109

Ala Tyr Ala Ala
1

<210> SEQ ID NO 110
<211> LENGTH: 21
<212> TYPE: PRT
<213> ORGANISM: Artificial sequence
<220> FEATURE:
<223> OTHER INFORMATION: Signal peptide

<400> SEQUENCE: 110

Ala Thr Met Gly Trp Ser Cys Ile Ile Leu Phe Leu Val Ala Thr Ala
1               5                   10                  15

Thr Gly Val His Ser
            20
```

<210> SEQ ID NO 111
<211> LENGTH: 57
<212> TYPE: DNA
<213> ORGANISM: Artificial sequence
<220> FEATURE:
<223> OTHER INFORMATION: Signal peptide DNA sequence

<400> SEQUENCE: 111
atgggatgga gctgtatcat cctcttcttg gtagcaacag ctaccggtgt gcactcc    57

<210> SEQ ID NO 112
<211> LENGTH: 449
<212> TYPE: PRT
<213> ORGANISM: Artificial sequence
<220> FEATURE:
<223> OTHER INFORMATION: Anti-CD20 (GA101) heavy chain

<400> SEQUENCE: 112

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 113
<211> LENGTH: 219
<212> TYPE: PRT
<213> ORGANISM: Artificial sequence
<220> FEATURE:
<223> OTHER INFORMATION: Anti-CD20 (GA101) light chain

<400> SEQUENCE: 113

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
            85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys

-continued

```
                210                 215
```

<210> SEQ ID NO 114
<211> LENGTH: 447
<212> TYPE: PRT
<213> ORGANISM: Artificial sequence
<220> FEATURE:
<223> OTHER INFORMATION: Anti-FAP(4B9) PGLALA heavy chain

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu

```
                355                 360                 365
Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 115
<211> LENGTH: 215
<212> TYPE: PRT
<213> ORGANISM: Artificial sequence
<220> FEATURE:
<223> OTHER INFORMATION: Anti-FAP(4B9) light chain

<400> SEQUENCE: 115

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
                20                  25                  30

Tyr Leu Ala Trp Tyr Gln Lys Pro Gly Gln Ala Pro Arg Leu Leu
            35                  40                  45

Ile Asn Val Gly Ser Arg Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 116
<211> LENGTH: 451
<212> TYPE: PRT
<213> ORGANISM: Artificial sequence
<220> FEATURE:
<223> OTHER INFORMATION: Anti-CEA (A5B7) PGLALA heavy chain

<400> SEQUENCE: 116
```

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ser Ser Tyr
        20                  25                  30

Trp Met His Trp Val Arg Gln Ala Pro Gly Lys Gly Leu Glu Trp Val
            35                  40                  45

Gly Phe Ile Arg Asn Lys Ala Asn Gly Gly Thr Thr Glu Tyr Ala Ala
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
            210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
```

420                 425                 430
His Glu Ala Leu His Asn His Tyr Thr Gln Lys Ser Leu Ser Leu Ser
            435                 440                 445
Pro Gly Lys
    450

<210> SEQ ID NO 117
<211> LENGTH: 223
<212> TYPE: PRT
<213> ORGANISM: Artificial sequence
<220> FEATURE:
<223> OTHER INFORMATION: Anti-CEA (A5B7) light chain

<400> SEQUENCE: 117

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220

<210> SEQ ID NO 118
<211> LENGTH: 451
<212> TYPE: PRT
<213> ORGANISM: Artificial sequence
<220> FEATURE:
<223> OTHER INFORMATION: Anti-CEA (T84.66LCHA) PGLALA heavy chain

<400> SEQUENCE: 118

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

```
Gly Arg Ile Asp Pro Ala Asn Gly Asn Ser Lys Tyr Val Pro Lys Phe
 50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Pro Phe Gly Tyr Tyr Val Ser Asp Tyr Ala Met Ala Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450
```

-continued

```
<210> SEQ ID NO 119
<211> LENGTH: 218
<212> TYPE: PRT
<213> ORGANISM: Artificial sequence
<220> FEATURE:
<223> OTHER INFORMATION: Anti-CEA (T84.66LCHA) light chain

<400> SEQUENCE: 119

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 120
<211> LENGTH: 451
<212> TYPE: PRT
<213> ORGANISM: Artificial sequence
<220> FEATURE:
<223> OTHER INFORMATION: Anti-CEA (CH1A1A98/992F1) PGLALA heavy chain

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 121
<211> LENGTH: 215
<212> TYPE: PRT
<213> ORGANISM: Artificial sequence
<220> FEATURE:
<223> OTHER INFORMATION: Anti-CEA (CH1A1A98/992F1) light chain

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 122
<211> LENGTH: 449
<212> TYPE: PRT
<213> ORGANISM: Artificial sequence
<220> FEATURE:
<223> OTHER INFORMATION: Anti-CEA (hMN14) PGLALA heavy chain

<400> SEQUENCE: 122

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
50                  55                  60

Lys Asp Arg Phe Thr Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 123
<211> LENGTH: 213
<212> TYPE: PRT
<213> ORGANISM: Artificial sequence
<220> FEATURE:
<223> OTHER INFORMATION: Anti-CEA (hMN14) light chain

<400> SEQUENCE: 123

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly

```
            50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Ser Leu Tyr Arg Ser
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 124
<211> LENGTH: 451
<212> TYPE: PRT
<213> ORGANISM: Artificial sequence
<220> FEATURE:
<223> OTHER INFORMATION: Anti-TNC (2B10) PGLALA heavy chain

<400> SEQUENCE: 124

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
                195                 200                 205
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
    355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys
    450

<210> SEQ ID NO 125
<211> LENGTH: 214
<212> TYPE: PRT
<213> ORGANISM: Artificial sequence
<220> FEATURE:
<223> OTHER INFORMATION: Anti-TNC (2B10) light chain

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys Arg Thr Val Ala Ala
```

```
              100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 126
<211> LENGTH: 449
<212> TYPE: PRT
<213> ORGANISM: Artificial sequence
<220> FEATURE:
<223> OTHER INFORMATION: Anti-HER2 (PER) PG LALA heavy chain 1

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
```

```
                    245                 250                 255
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 127
<211> LENGTH: 214
<212> TYPE: PRT
<213> ORGANISM: Artificial sequence
<220> FEATURE:
<223> OTHER INFORMATION: Anti-HER2 (PER) light chain 1

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 128
<211> LENGTH: 449
<212> TYPE: PRT
<213> ORGANISM: Artificial sequence
<220> FEATURE:
<223> OTHER INFORMATION: Anti-HER2 (PER) PG LALA heavy chain 2

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

```
Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 129
<211> LENGTH: 214
<212> TYPE: PRT
<213> ORGANISM: Artificial sequence
<220> FEATURE:
<223> OTHER INFORMATION: Anti-HER2 (PER) light chain 2

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

-continued

```
Phe Asn Arg Gly Glu Cys
    210

<210> SEQ ID NO 130
<211> LENGTH: 330
<212> TYPE: PRT
<213> ORGANISM: Homo sapiens

<400> SEQUENCE: 130

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

UNITED STATES PATENT AND TRADEMARK OFFICE
CERTIFICATE OF CORRECTION

| | | |
|---|---|---|
| PATENT NO. | : 11,679,127 B2 | |
| APPLICATION NO. | : 16/576546 | |
| DATED | : June 20, 2023 | |
| INVENTOR(S) | : Stubenrauch et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 697 days.

Signed and Sealed this
Twelfth Day of November, 2024

Katherine Kelly Vidal
*Director of the United States Patent and Trademark Office*